US012758311B2

(12) United States Patent
Hijazi et al.

(10) Patent No.: US 12,758,311 B2
(45) Date of Patent: Oct. 13, 2026

(54) PULSED FIELD ABLATION DEVICE AND METHOD

(71) Applicant: BTL Medical Development a.s., Prague (CZ)

(72) Inventors: Ahmad Hijazi, Prague (CZ); Vít Suk, Prague (CZ); Vojtěch Nedvěd, Mariánské Lázně (CZ); Jiří Dašek, Sopřeč (CZ); Martin Hanuliak, Prague (CZ)

(73) Assignee: BTL Medical Development a.s., Prague (CZ)

( * ) Notice: Subject to any disclaimer, the term of this patent is extended or adjusted under 35 U.S.C. 154(b) by 0 days.

(21) Appl. No.: 19/022,820

(22) Filed: Jan. 15, 2025

(65) Prior Publication Data

US 2026/0041484 A1 Feb. 12, 2026

Related U.S. Application Data

(60) Provisional application No. 63/729,121, filed on Dec. 6, 2024, provisional application No. 63/680,814, filed on Aug. 8, 2024.

(51) Int. Cl.
*A61B 18/12* (2006.01)
*A61B 18/14* (2006.01)
(Continued)

(52) U.S. Cl.
CPC .............................. *A61B 18/1492* (2013.01); *A61B 2017/00336* (2013.01); *A61B 2018/00267* (2013.01);
(Continued)

(58) Field of Classification Search
CPC ...... A61B 18/1492; A61B 2018/00267; A61B 2018/00351; A61B 5/6852–6859; A61B 1/00085
See application file for complete search history.

(56) References Cited

U.S. PATENT DOCUMENTS

| | | | |
|---|---|---|---|
| 5,002,041 | A | 3/1991 | Chikama |
| 5,057,092 | A | 10/1991 | Webster, Jr. |

(Continued)

FOREIGN PATENT DOCUMENTS

| | | |
|---|---|---|
| CA | 2765976 | 8/2012 |
| CN | 103285491 B | 12/2014 |

(Continued)

OTHER PUBLICATIONS

J. S. Koruth et al., "Endocardial ventricular pulsed field ablation: a proof-of-concept preclinical evaluation", EP Europace, roč. 22, č. 3, s. 434-439, bře. 2020, doi: 10.1093/europace/euz341.

(Continued)

*Primary Examiner* — Daniel W Fowler
(74) *Attorney, Agent, or Firm* — Riverside Law LLP

(57) ABSTRACT

An ablation system and methods comprising a catheter having an expandable basket and a shaft assembly comprising an outer and inner elongated shaft allowing relative longitudinal movement. The expandable basket comprises filaments braided into a braided mesh including electrodes for ablation, mapping and measurement. An expandable basket at the distal end of the catheter is coupled to both shafts and is deployable from a collapsed to an expanded configuration. The system includes an introducer sheath with a highly abrasion-resistant inner liner designed for smooth catheter deployment. An electrical control circuits regulates the delivery of high-voltage pulses from a pulse generator to the target tissue, enhancing the safety, precision and effectiveness of tissue ablation.

12 Claims, 47 Drawing Sheets

(51) Int. Cl.
*A61B 17/00* (2006.01)
*A61B 18/00* (2006.01)

(52) U.S. Cl.
CPC ............... *A61B 2018/00351* (2013.01); *A61B 2018/00577* (2013.01)

(56) References Cited

U.S. PATENT DOCUMENTS

| | | | |
|---|---|---|---|
| 5,242,441 A | | 9/1993 | Avitall |
| 5,395,329 A | | 3/1995 | Fleischhacker |
| 5,456,664 A | | 10/1995 | Heinzelman |
| 5,462,527 A | | 10/1995 | Stevens-Wright |
| 5,591,137 A | | 1/1997 | Stevens |
| 5,676,653 A | | 10/1997 | Taylor |
| 5,676,659 A | | 10/1997 | McGurk |
| 5,876,336 A | | 3/1999 | Swanson |
| 5,935,079 A | | 8/1999 | Swanson |
| 5,951,929 A | | 9/1999 | Wilson |
| 5,997,526 A | | 12/1999 | Giba |
| 6,004,280 A | | 12/1999 | Buck |
| 6,165,169 A | * | 12/2000 | Panescu ............. A61B 18/1492 606/1 |
| 6,267,746 B1 | | 7/2001 | Bumbalough |
| 6,344,026 B1 | * | 2/2002 | Burbank .......... A61B 17/32056 600/567 |
| 6,458,103 B1 | | 10/2002 | Albert |
| 6,522,930 B1 | | 2/2003 | Schaer |
| 6,546,270 B1 | | 4/2003 | Goldin |
| 6,554,794 B1 | | 4/2003 | Mueller |
| 6,562,022 B2 | | 5/2003 | Hoste |
| 6,569,160 B1 | | 5/2003 | Goldin |
| 6,572,590 B1 | | 6/2003 | Stevens |
| 6,837,886 B2 | | 1/2005 | Collins |
| 6,837,890 B1 | | 1/2005 | Chludzinski |
| 6,841,214 B1 | | 1/2005 | Keith |
| 6,929,635 B2 | | 8/2005 | Shelso |
| 6,942,654 B1 | | 9/2005 | Schaefer |
| 6,979,312 B2 | | 12/2005 | Shimada |
| 7,044,135 B2 | | 5/2006 | Lesh |
| 7,056,314 B1 | | 6/2006 | Florio |
| 7,115,122 B1 | | 10/2006 | Swanson |
| 7,195,628 B2 | | 3/2007 | Falkenberg |
| 7,255,695 B2 | | 8/2007 | Falwell |
| 7,615,044 B2 | | 11/2009 | Scheibe |
| 7,670,297 B1 | | 3/2010 | Hauck |
| 7,674,421 B2 | | 3/2010 | Ross |
| 7,704,245 B2 | | 4/2010 | Dittman |
| 7,718,409 B2 | | 5/2010 | Rubinsky |
| 7,727,229 B2 | | 6/2010 | He |
| 7,824,391 B2 | | 11/2010 | Gesswein |
| 7,824,392 B2 | | 11/2010 | Zhou |
| 7,846,157 B2 | | 12/2010 | Kozel |
| 7,909,798 B2 | | 3/2011 | Osypka |
| 7,918,850 B2 | | 4/2011 | Govari |
| 7,935,108 B2 | | 5/2011 | Baxter |
| 7,972,323 B1 | | 7/2011 | Bencini |
| 7,993,351 B2 | | 8/2011 | Worley |
| 8,007,495 B2 | | 8/2011 | Mcdaniel |
| 8,024,024 B2 | | 9/2011 | Mswanathan |
| 8,109,926 B2 | | 2/2012 | Azure |
| 8,114,070 B2 | | 2/2012 | Rubinsky |
| 8,150,536 B2 | | 4/2012 | Osypka |
| 8,221,411 B2 | | 7/2012 | Francischelli |
| 8,226,639 B2 | | 7/2012 | Podhajsky |
| 8,226,709 B2 | | 7/2012 | Groothuis |
| 8,262,671 B2 | | 9/2012 | Osypka |
| 8,315,696 B2 | | 11/2012 | Schwartz |
| 8,394,087 B2 | | 3/2013 | Willyard |
| 8,409,191 B2 | | 4/2013 | Avitall |
| 8,454,589 B2 | | 6/2013 | Deno |
| 8,489,184 B2 | | 7/2013 | Wilfley |
| 8,500,713 B2 | | 8/2013 | Ferek-Petric |
| 8,504,132 B2 | | 8/2013 | Friedman |
| 8,591,520 B2 | | 11/2013 | Barthold |
| 8,603,087 B2 | | 12/2013 | Rubinsky |
| 8,620,423 B2 | | 12/2013 | Demarais |
| 8,647,338 B2 | | 2/2014 | Chornenky |
| 8,903,478 B2 | | 12/2014 | Macadam |
| 8,903,488 B2 | | 12/2014 | Callas |
| 8,926,606 B2 | | 1/2015 | Davalos |
| 8,945,116 B2 | | 2/2015 | Macadam |
| 9,005,100 B2 | | 4/2015 | Gnanashanmugam |
| 9,060,778 B2 | | 6/2015 | Condie |
| 9,061,120 B2 | | 6/2015 | Osypka |
| 9,089,341 B2 | | 7/2015 | Chomas |
| 9,095,350 B2 | | 8/2015 | Condie |
| 9,168,096 B2 | | 10/2015 | Kreindel |
| 9,198,733 B2 | | 12/2015 | Neal, II |
| 9,308,349 B2 | | 4/2016 | Rezac |
| 9,314,620 B2 | | 4/2016 | Long |
| 9,320,540 B2 | * | 4/2016 | Badie ............... A61B 17/32002 |
| 9,326,815 B2 | | 5/2016 | Watson |
| 9,333,031 B2 | | 5/2016 | Salahieh |
| 9,345,538 B2 | | 5/2016 | Deem |
| 9,351,790 B2 | | 5/2016 | Zemel |
| 9,387,031 B2 | | 7/2016 | Stewart |
| 9,427,167 B2 | | 8/2016 | Maskara |
| 9,498,602 B2 | | 11/2016 | Osypka |
| 9,572,957 B2 | | 2/2017 | Osypka |
| 9,700,699 B2 | | 7/2017 | Morris |
| 9,724,170 B2 | | 8/2017 | Mickelsen |
| 9,788,888 B2 | | 10/2017 | Bakos |
| 9,821,143 B2 | | 11/2017 | Kimmel |
| 9,839,769 B2 | | 12/2017 | Furnish |
| 9,844,644 B2 | | 12/2017 | Osypka |
| 9,861,802 B2 | | 1/2018 | Mickelsen |
| 9,877,781 B2 | | 1/2018 | Grasse |
| 9,913,684 B2 | | 3/2018 | Osypka |
| 9,918,790 B2 | | 3/2018 | Zemlin |
| 9,987,081 B1 | | 6/2018 | Bowers |
| 9,993,178 B2 | | 6/2018 | Panescu |
| 9,999,465 B2 | | 6/2018 | Long |
| 10,080,602 B2 | | 9/2018 | Wittkampf |
| 10,130,423 B1 | | 11/2018 | Raju |
| 10,130,791 B2 | | 11/2018 | Heideman |
| 10,130,819 B2 | | 11/2018 | Callas |
| 10,143,399 B2 | | 12/2018 | Condie |
| 10,143,512 B2 | | 12/2018 | Rubinsky |
| 10,154,876 B2 | | 12/2018 | Callas |
| 10,166,071 B2 | | 1/2019 | Sherman |
| 10,207,078 B2 | | 2/2019 | Whiseant |
| 10,245,098 B2 | | 4/2019 | Davalos |
| 10,258,406 B2 | | 4/2019 | Long |
| 10,278,852 B2 | | 5/2019 | Griffin |
| 10,285,755 B2 | | 5/2019 | Stewart |
| 10,314,649 B2 | | 6/2019 | Bakos |
| 10,335,224 B2 | | 7/2019 | Chornenky |
| 10,342,598 B2 | | 7/2019 | Long |
| 10,342,600 B2 | | 7/2019 | Callas |
| 10,362,956 B2 | | 7/2019 | Chauhan |
| 10,426,545 B2 | | 10/2019 | Asirvatham |
| 10,433,908 B2 | | 10/2019 | Raju |
| 10,470,822 B2 | | 11/2019 | Garcia |
| 10,471,254 B2 | | 11/2019 | Sano |
| 10,493,708 B2 | | 12/2019 | Wilkowske |
| 10,507,057 B2 | | 12/2019 | Harlev |
| 10,531,914 B2 | | 1/2020 | Stewart |
| 10,543,340 B2 | | 1/2020 | Fuentes |
| 10,556,102 B1 | | 2/2020 | Rotman |
| 10,569,081 B2 | | 2/2020 | Howard |
| 10,589,092 B2 | | 3/2020 | Sano |
| 10,617,867 B2 | | 4/2020 | Raju |
| 10,625,044 B2 | | 4/2020 | Heisel |
| 10,625,080 B1 | | 4/2020 | Raju |
| 10,687,892 B2 | | 6/2020 | Long |
| 10,688,300 B2 | | 6/2020 | Paul |
| 10,729,891 B2 | | 8/2020 | Werneth |
| 10,806,897 B2 | | 10/2020 | Furnish |
| 10,842,572 B1 | | 11/2020 | Raju |
| 10,849,677 B2 | | 12/2020 | Fraasch |
| 10,856,936 B2 | | 12/2020 | Willard |
| 10,874,451 B2 | | 12/2020 | Athos |
| 10,874,831 B2 | | 12/2020 | Rosenman |
| 10,881,846 B2 | | 1/2021 | Furnish |

(56) References Cited

U.S. PATENT DOCUMENTS

| | | | | |
|---|---|---|---|---|
| 10,893,903 | B2 | 1/2021 | Koblish | |
| 10,912,923 | B2 | 2/2021 | Heideman | |
| 10,918,833 | B2 | 2/2021 | Appling | |
| 10,980,976 | B2 | 4/2021 | Schultz | |
| 10,987,490 | B2 | 4/2021 | Olson | |
| 10,994,133 | B2 | 5/2021 | Sano | |
| 11,027,100 | B2 | 6/2021 | Appling | |
| 11,033,321 | B2 | 6/2021 | Davalos | |
| 11,052,246 | B2 | 7/2021 | Stewart | |
| 11,065,047 | B2 | 7/2021 | Alan | |
| 11,154,691 | B2 | 10/2021 | Thorstenson | |
| 11,207,512 | B2 | 12/2021 | Furnish | |
| 11,229,478 | B2 | 1/2022 | Howard | |
| 11,235,126 | B2 | 2/2022 | Brannick | |
| 11,253,732 | B2 | 2/2022 | Mayer | |
| 11,298,175 | B2 | 4/2022 | Konings | |
| 11,318,306 | B2 | 5/2022 | Stewart | |
| 11,324,920 | B2 | 5/2022 | Inukai | |
| 11,376,064 | B2 | 7/2022 | Rankin | |
| 11,376,397 | B2 | 7/2022 | Tegg | |
| 11,382,681 | B2 | 7/2022 | Arena | |
| 11,419,673 | B2 | 8/2022 | Kauphusman | |
| 11,446,082 | B2 | 9/2022 | Blanck | |
| 11,452,842 | B2 | 9/2022 | Yamaguchi | |
| 11,484,690 | B2 | 11/2022 | Tegg | |
| 11,511,076 | B2 | 11/2022 | Guo | |
| 11,589,919 | B2 | 2/2023 | Long | |
| 11,607,526 | B2 | 3/2023 | Oren | |
| 11,612,424 | B2 | 3/2023 | Fraasch | |
| 11,617,859 | B2 | 4/2023 | Hsueh | |
| 11,633,121 | B2 | 4/2023 | Howard | |
| 11,654,262 | B2 | 5/2023 | Furnish | |
| 11,701,021 | B2 | 7/2023 | Schmidt | |
| 11,701,171 | B2 | 7/2023 | Schultheis | |
| 11,737,821 | B2 | 8/2023 | Algawi | |
| 11,738,200 | B2 | 8/2023 | Raju | |
| 11,779,733 | B2 | 10/2023 | Feerick | |
| 11,793,565 | B2 | 10/2023 | Govari | |
| 11,819,265 | B2 | 11/2023 | Govari | |
| 11,844,909 | B2 | 12/2023 | Tassoni, Jr. | |
| 11,890,431 | B2 | 2/2024 | Edminster | |
| 11,911,087 | B2 | 2/2024 | Foxall | |
| 11,911,096 | B2 | 2/2024 | Govari | |
| 11,918,280 | B2 | 3/2024 | Sherman | |
| 11,925,774 | B2 | 3/2024 | Bogusky | |
| 11,944,372 | B2 | 4/2024 | Cao | |
| 11,950,840 | B2 | 4/2024 | Govari | |
| 11,951,262 | B2 | 4/2024 | Leeflang | |
| 12,004,804 | B2 | 6/2024 | Govari | |
| 12,016,623 | B2 | 6/2024 | Belalcazar | |
| 12,042,208 | B2 | 7/2024 | Raju | |
| 12,042,215 | B2 | 7/2024 | Govari | |
| 12,048,480 | B2 | 7/2024 | Stewart | |
| 12,070,265 | B2 | 8/2024 | Schweitzer | |
| 12,076,071 | B2 | 9/2024 | Miller-Tait | |
| 12,114,918 | B2 | 10/2024 | Govari | |
| 12,144,541 | B2 | 11/2024 | Raju | |
| 12,150,700 | B2 | 11/2024 | Stewart | |
| 12,239,364 | B2 | 3/2025 | Govari | |
| 12,310,652 | B2 | 5/2025 | Shuros | |
| 12,349,964 | B2 | 7/2025 | Shuros | |
| 12,453,597 | B2 | 10/2025 | Viswanathan | |
| 12,478,424 | B2 | 11/2025 | Govari | |
| 2004/0116965 | A1 | 6/2004 | Falkenberg | |
| 2004/0122360 | A1 | 6/2004 | Waldhauser | |
| 2005/0159728 | A1 | 7/2005 | Armour | |
| 2005/0197623 | A1 | 9/2005 | Leeflang | |
| 2006/0030835 | A1 | 2/2006 | Sherman | |
| 2006/0293731 | A1 | 12/2006 | Rubinsky | |
| 2008/0103445 | A1 | 5/2008 | Blaine | |
| 2009/0198231 | A1 | 8/2009 | Esser | |
| 2009/0247933 | A1 | 10/2009 | Maor | |
| 2009/0312698 | A1 | 12/2009 | Farrell | |
| 2010/0179530 | A1 | 7/2010 | Long | |
| 2012/0130369 | A1 | 5/2012 | Cadossi | |
| 2013/0030425 | A1 | 1/2013 | Stewart | |
| 2015/0066010 | A1 | 3/2015 | Mclawhorn | |
| 2015/0073401 | A1 | 3/2015 | Kreindel | |
| 2015/0216588 | A1 | 8/2015 | Deem | |
| 2015/0250399 | A1 | 9/2015 | Laughner | |
| 2015/0289923 | A1 | 10/2015 | Davalos | |
| 2015/0320481 | A1 | 11/2015 | Cosman, Jr. | |
| 2016/0051324 | A1 | 2/2016 | Stewart | |
| 2016/0058493 | A1 | 3/2016 | Neal, II | |
| 2016/0113709 | A1 | 4/2016 | Maor | |
| 2016/0143686 | A1 | 5/2016 | Tunay | |
| 2016/0278851 | A1 | 9/2016 | Mannion | |
| 2016/0278858 | A1 | 9/2016 | Stewart | |
| 2016/0287136 | A1 | 10/2016 | Condie | |
| 2016/0324573 | A1 | 11/2016 | Mickelson | |
| 2016/0331441 | A1 | 11/2016 | Konings | |
| 2016/0361109 | A1 | 12/2016 | Weaver | |
| 2017/0007157 | A1 | 1/2017 | Gross | |
| 2017/0049508 | A1 | 2/2017 | Long | |
| 2017/0072163 | A1 | 3/2017 | Lim | |
| 2017/0100075 | A1 | 4/2017 | Eliason | |
| 2017/0189106 | A1 | 7/2017 | Schuler | |
| 2017/0202469 | A1 | 7/2017 | Scharf | |
| 2017/0215953 | A1 | 8/2017 | Long | |
| 2017/0224415 | A1 | 8/2017 | Dong | |
| 2017/0348049 | A1* | 12/2017 | Vrba | A61B 18/1492 |
| 2018/0132922 | A1 | 5/2018 | Neal, II | |
| 2018/0193090 | A1 | 7/2018 | De La Rama | |
| 2018/0214202 | A1 | 8/2018 | Howard | |
| 2018/0221085 | A1 | 8/2018 | Blanck | |
| 2018/0296264 | A1 | 10/2018 | Desimone | |
| 2018/0303543 | A1 | 10/2018 | Stewart | |
| 2018/0360534 | A1 | 12/2018 | Teplitsky | |
| 2019/0021620 | A1 | 1/2019 | Olson | |
| 2019/0038171 | A1 | 2/2019 | Howard | |
| 2019/0046791 | A1 | 2/2019 | Ebbers | |
| 2019/0060632 | A1 | 2/2019 | Asirvatham | |
| 2019/0125439 | A1 | 5/2019 | Rohl | |
| 2019/0183561 | A1 | 6/2019 | Hobbs | |
| 2019/0201688 | A1 | 7/2019 | Olson | |
| 2019/0209235 | A1 | 7/2019 | Stewart | |
| 2019/0216538 | A1 | 7/2019 | Wittkampf | |
| 2019/0232048 | A1 | 8/2019 | Latouche | |
| 2019/0254735 | A1 | 8/2019 | Stewart | |
| 2019/0255292 | A1 | 8/2019 | Osypka | |
| 2019/0262071 | A1 | 8/2019 | Thom | |
| 2019/0274757 | A1 | 9/2019 | Mahapatra | |
| 2019/0282294 | A1 | 9/2019 | Davalos | |
| 2019/0321091 | A1 | 10/2019 | Zemel | |
| 2019/0328446 | A1 | 10/2019 | Callas | |
| 2019/0350649 | A1 | 11/2019 | Sutermeister | |
| 2019/0365463 | A1 | 12/2019 | Govari | |
| 2020/0008869 | A1 | 1/2020 | Byrd | |
| 2020/0008870 | A1 | 1/2020 | Gruba | |
| 2020/0015890 | A1 | 1/2020 | To | |
| 2020/0023159 | A1 | 1/2020 | Sutermeister | |
| 2020/0114121 | A1 | 4/2020 | Leeflang | |
| 2020/0146741 | A1 | 5/2020 | Long | |
| 2020/0155838 | A1 | 5/2020 | Howard | |
| 2020/0179046 | A1 | 6/2020 | Wittkampf | |
| 2020/0205890 | A1 | 7/2020 | Harlev | |
| 2020/0275973 | A1 | 9/2020 | O'Brien | |
| 2020/0297418 | A1 | 9/2020 | Stewart | |
| 2020/0298008 | A1 | 9/2020 | Asirvatham | |
| 2020/0360667 | A1 | 11/2020 | Aklog | |
| 2020/0397505 | A1 | 12/2020 | Raju | |
| 2020/0398048 | A1 | 12/2020 | Krimsky | |
| 2021/0022794 | A1 | 1/2021 | Raju | |
| 2021/0031020 | A1 | 2/2021 | Mickelsen | |
| 2021/0045805 | A1 | 2/2021 | Govari | |
| 2021/0077188 | A1 | 3/2021 | Long | |
| 2021/0121660 | A1 | 4/2021 | Osypka | |
| 2021/0121663 | A1 | 4/2021 | Marass | |
| 2021/0137587 | A1 | 5/2021 | Olson | |
| 2021/0137592 | A1 | 5/2021 | Raju | |
| 2021/0161582 | A1 | 6/2021 | Byrd | |
| 2021/0162210 | A1 | 6/2021 | Altmann | |
| 2021/0169421 | A1 | 6/2021 | Govari | |
| 2021/0177491 | A1 | 6/2021 | Onik | |

(56) References Cited

U.S. PATENT DOCUMENTS

| | | | |
|---|---|---|---|
| 2021/0177503 | A1 | 6/2021 | Altmann |
| 2021/0186592 | A1 | 6/2021 | Rubinsky |
| 2021/0186593 | A1 | 6/2021 | Altmann |
| 2021/0220038 | A1 | 7/2021 | Kenneth |
| 2021/0275806 | A1 | 9/2021 | Paul |
| 2021/0282847 | A1 | 9/2021 | Raju |
| 2021/0290172 | A1 | 9/2021 | Raju |
| 2021/0307815 | A1 | 10/2021 | Govari |
| 2021/0322086 | A1 | 10/2021 | Gorzycki |
| 2021/0338305 | A1 | 11/2021 | Chen |
| 2021/0338320 | A1 | 11/2021 | Raju |
| 2021/0369338 | A1 | 12/2021 | Govari |
| 2021/0378734 | A1 | 12/2021 | Govari |
| 2021/0393327 | A1 | 12/2021 | Eyster |
| 2021/0401491 | A1 | 12/2021 | Altmann |
| 2021/0402147 | A1 | 12/2021 | Enerson |
| 2022/0000546 | A1 | 1/2022 | Raju |
| 2022/0000550 | A1 | 1/2022 | Henschel |
| 2022/0008123 | A1 | 1/2022 | Altmann |
| 2022/0008128 | A1 | 1/2022 | Zhou |
| 2022/0022952 | A1 | 1/2022 | Koop |
| 2022/0031385 | A1 | 2/2022 | Govari |
| 2022/0047326 | A1 | 2/2022 | Altmann |
| 2022/0071693 | A1 | 3/2022 | Govari |
| 2022/0071699 | A1 | 3/2022 | Raju |
| 2022/0072269 | A1 | 3/2022 | Leeflang |
| 2022/0087736 | A1 | 3/2022 | Govari |
| 2022/0105313 | A1 | 4/2022 | Humphrey |
| 2022/0111176 | A1 | 4/2022 | Dale |
| 2022/0117655 | A1 | 4/2022 | Govari |
| 2022/0126058 | A1 | 4/2022 | Mihelich |
| 2022/0133389 | A1 | 5/2022 | Howard |
| 2022/0133405 | A1 | 5/2022 | Mickelsen |
| 2022/0161027 | A1 | 5/2022 | Aycock |
| 2022/0168041 | A1 | 6/2022 | Mixter |
| 2022/0168594 | A1 | 6/2022 | Mayer |
| 2022/0175445 | A1 | 6/2022 | Sutermeister |
| 2022/0176076 | A1 | 6/2022 | Keidar |
| 2022/0183750 | A1 | 6/2022 | Bai |
| 2022/0192737 | A1 | 6/2022 | Altmann |
| 2022/0192741 | A1 | 6/2022 | Reinders |
| 2022/0192742 | A1 | 6/2022 | Ozeri |
| 2022/0218915 | A1 | 7/2022 | Bataille |
| 2022/0218944 | A1 | 7/2022 | Tassoni |
| 2022/0249157 | A1 | 8/2022 | Raju |
| 2022/0257196 | A1 | 8/2022 | Massmann |
| 2022/0280022 | A1 | 9/2022 | Rothe |
| 2022/0287764 | A1 | 9/2022 | Govari |
| 2022/0288356 | A1 | 9/2022 | Hiorth |
| 2022/0296881 | A1 | 9/2022 | Asirvatham |
| 2022/0313946 | A1 | 10/2022 | Leeflang |
| 2022/0331560 | A1 | 10/2022 | Subramaniam |
| 2022/0338925 | A1 | 10/2022 | Stewart |
| 2022/0370119 | A1 | 11/2022 | Govari |
| 2022/0370122 | A1 | 11/2022 | Smail |
| 2022/0370128 | A1 | 11/2022 | Altmann |
| 2022/0379079 | A1 | 12/2022 | Richter |
| 2023/0000550 | A1 | 1/2023 | Nedved |
| 2023/0008203 | A1 | 1/2023 | Andrew |
| 2023/0009573 | A1 | 1/2023 | Van Niekerk |
| 2023/0012307 | A1 | 1/2023 | Harlev |
| 2023/0012775 | A1 | 1/2023 | Schaer |
| 2023/0035207 | A1 | 2/2023 | Mixter |
| 2023/0049942 | A1 | 2/2023 | Narayan |
| 2023/0051310 | A1 | 2/2023 | Govari |
| 2023/0052114 | A1 | 2/2023 | Marass |
| 2023/0080273 | A1 | 3/2023 | Winston |
| 2023/0089295 | A1 | 3/2023 | Assaf |
| 2023/0105390 | A1 | 4/2023 | Gutbrod |
| 2023/0126785 | A1 | 4/2023 | Tang |
| 2023/0130692 | A1 | 4/2023 | Wang |
| 2023/0149071 | A1 | 5/2023 | Fraasch |
| 2023/0149701 | A1 | 5/2023 | Liu |
| 2023/0172650 | A1 | 6/2023 | Castellvi |
| 2023/0181242 | A1 | 6/2023 | Govari |
| 2023/0190198 | A1 | 6/2023 | Pederson |
| 2023/0190365 | A1 | 6/2023 | Govari |
| 2023/0200895 | A1 | 6/2023 | Ebrahimi |
| 2023/0200901 | A1 | 6/2023 | Doron |
| 2023/0210437 | A1 | 7/2023 | Beeckler |
| 2023/0218340 | A1 | 7/2023 | Werneth |
| 2023/0218343 | A1 * | 7/2023 | Nedved .............. A61B 18/1492 606/41 |
| 2023/0218863 | A1 | 7/2023 | Sarabia |
| 2023/0218868 | A1 | 7/2023 | Chu |
| 2023/0225790 | A1 | 7/2023 | Okarski |
| 2023/0226638 | A1 | 7/2023 | Datta |
| 2023/0240745 | A1 | 8/2023 | Jan |
| 2023/0248412 | A1 | 8/2023 | Govari |
| 2023/0255684 | A1 | 8/2023 | Schmidt |
| 2023/0264031 | A1 | 8/2023 | Harlev |
| 2023/0284957 | A1 | 9/2023 | Bonyak |
| 2023/0301707 | A1 | 9/2023 | Okarski |
| 2023/0301712 | A1 | 9/2023 | Okarski |
| 2023/0301713 | A1 | 9/2023 | Okarski |
| 2023/0310059 | A1 | 10/2023 | Hirao |
| 2023/0310061 | A1 | 10/2023 | Stewart |
| 2023/0310072 | A1 | 10/2023 | Stewart |
| 2023/0329769 | A1 | 10/2023 | Fischbach |
| 2023/0329772 | A1 | 10/2023 | Byrd |
| 2023/0329780 | A1 | 10/2023 | Liu |
| 2023/0330421 | A1 | 10/2023 | Callas |
| 2023/0338709 | A1 | 10/2023 | Nelson |
| 2023/0346460 | A1 | 11/2023 | Govari |
| 2023/0346467 | A1 | 11/2023 | Altmann |
| 2023/0364396 | A1 | 11/2023 | Arnett |
| 2023/0364397 | A1 | 11/2023 | Balkovec |
| 2023/0371836 | A1 | 11/2023 | Govari |
| 2023/0372005 | A1 | 11/2023 | Ng |
| 2023/0380897 | A1 | 11/2023 | Liu |
| 2023/0389984 | A1 | 12/2023 | Redjebian |
| 2023/0397952 | A1 | 12/2023 | Turovskiy |
| 2023/0404644 | A1 | 12/2023 | Shamis |
| 2023/0404663 | A1 | 12/2023 | Sharma |
| 2023/0414270 | A1 | 12/2023 | Gandionco |
| 2023/0414276 | A1 | 12/2023 | Laske |
| 2023/0414277 | A1 | 12/2023 | Kelly |
| 2024/0016536 | A1 | 1/2024 | Kato |
| 2024/0016540 | A1 | 1/2024 | Sigg |
| 2024/0033482 | A1 | 2/2024 | Wang |
| 2024/0058570 | A1 | 2/2024 | Urbanski |
| 2024/0065758 | A1 | 2/2024 | Chen |
| 2024/0081900 | A1 | 3/2024 | Sakaki |
| 2024/0122646 | A1 | 4/2024 | Wang |
| 2024/0156524 | A1 | 5/2024 | Ebrahimi |
| 2024/0164686 | A1 | 5/2024 | Ghosalker |
| 2024/0164833 | A1 | 5/2024 | Turovskiy |
| 2024/0164834 | A1 | 5/2024 | Olson |
| 2024/0180614 | A1 | 6/2024 | Keyes |
| 2024/0180615 | A1 | 6/2024 | Jenkins |
| 2024/0181211 | A1 | 6/2024 | Zeis |
| 2024/0189016 | A1 | 6/2024 | Organ |
| 2024/0189021 | A1 | 6/2024 | Marziiano |
| 2024/0197391 | A1 | 6/2024 | Okarski |
| 2024/0197392 | A1 | 6/2024 | Van Niekerk |
| 2024/0197393 | A1 | 6/2024 | Kingston |
| 2024/0197394 | A1 | 6/2024 | Hagstrom |
| 2024/0206943 | A1 | 6/2024 | Govari |
| 2024/0206965 | A1 | 6/2024 | Beeckler |
| 2024/0215919 | A1 | 7/2024 | Govari |
| 2024/0216039 | A1 | 7/2024 | Panescu |
| 2024/0216048 | A1 | 7/2024 | Suarez |
| 2024/0216049 | A1 | 7/2024 | Beeckler |
| 2024/0216051 | A1 | 7/2024 | Agnew, V |
| 2024/0216056 | A1 | 7/2024 | Keyes |
| 2024/0216075 | A1 | 7/2024 | Roseberry |
| 2024/0225691 | A1 | 7/2024 | Buck |
| 2024/0225726 | A1 | 7/2024 | Govari |
| 2024/0226546 | A1 | 7/2024 | Olson |
| 2024/0238041 | A1 | 7/2024 | Shuros |
| 2024/0252225 | A1 | 8/2024 | Fraasch |
| 2024/0277398 | A1 | 8/2024 | Zhao |
| 2024/0277404 | A1 | 8/2024 | Shuros |
| 2024/0299073 | A1 | 9/2024 | Jais |

(56) References Cited

U.S. PATENT DOCUMENTS

| | | | |
|---|---|---|---|
| 2024/0315769 | A1 | 9/2024 | Mickelsen |
| 2024/0325066 | A1 | 10/2024 | Syrkin-Nikolau |
| 2024/0335231 | A1 | 10/2024 | Govari |
| 2024/0341843 | A1 | 10/2024 | Hagstrom |
| 2024/0350187 | A1 | 10/2024 | Waldstreicher |
| 2024/0350192 | A1 | 10/2024 | Sharma |
| 2024/0366301 | A1 | 11/2024 | Govari |
| 2024/0374305 | A1 | 11/2024 | Xu |
| 2024/0390053 | A1 | 11/2024 | Melsky |
| 2024/0390056 | A1 | 11/2024 | Agnew, V |
| 2024/0390057 | A1 | 11/2024 | Monti |
| 2024/0398468 | A1 | 12/2024 | Van Niekerk |
| 2024/0407836 | A1 | 12/2024 | Girouard |
| 2025/0025230 | A1 | 1/2025 | Suarez |
| 2025/0025666 | A1 | 1/2025 | Deshmukh |
| 2025/0064429 | A1 | 2/2025 | Manogue |
| 2025/0064498 | A1 | 2/2025 | Kauphusman |
| 2025/0064509 | A1 | 2/2025 | Viswanathan |
| 2025/0065079 | A1 | 2/2025 | Ruiz |
| 2025/0072960 | A1 | 3/2025 | Willoughby |
| 2025/0082383 | A1 | 3/2025 | Berman |
| 2025/0082396 | A1 | 3/2025 | Bar-Tal |
| 2025/0090226 | A1 | 3/2025 | Walker |
| 2025/0099160 | A1 | 3/2025 | Pham |
| 2025/0099168 | A1 | 3/2025 | Pham |
| 2025/0134571 | A1 | 5/2025 | Mittal |
| 2025/0177037 | A1 | 6/2025 | Olson |
| 2025/0177041 | A1 | 6/2025 | Govari |
| 2025/0186097 | A1 | 6/2025 | Sutermeister |
| 2025/0195131 | A1 | 6/2025 | Jimenez |
| 2025/0195132 | A1 | 6/2025 | Garcia |
| 2025/0213294 | A1 | 7/2025 | Kato |
| 2025/0213295 | A1 | 7/2025 | Koop |
| 2025/0221753 | A1 | 7/2025 | Belalcazar |
| 2025/0248758 | A1 | 8/2025 | Oliverius |
| 2025/0288349 | A1 | 9/2025 | Rubinsky |
| 2025/0295448 | A1 | 9/2025 | Nguyen |
| 2025/0302527 | A1 | 10/2025 | Kees |
| 2025/0345114 | A1 | 11/2025 | Kees |
| 2025/0359918 | A1 | 11/2025 | Nuccitelli |

FOREIGN PATENT DOCUMENTS

| | | | |
|---|---|---|---|
| CN | 103750899 | B | 4/2016 |
| CN | 106877729 | A | 6/2017 |
| CN | 104287824 | B | 9/2017 |
| CN | 206992984 | U | 2/2018 |
| CN | 109124759 | | 1/2019 |
| CN | 109124760 | | 1/2019 |
| CN | 109171947 | | 1/2019 |
| CN | 109661210 | | 4/2019 |
| CN | 209316045 | U | 8/2019 |
| CN | 109124759 | B | 12/2019 |
| CN | 109124760 | B | 12/2020 |
| CN | 112022331 | | 12/2020 |
| CN | 112618916 | A | 4/2021 |
| CN | 112618010 | B | 5/2021 |
| CN | 112842518 | A | 5/2021 |
| CN | 113017822 | A | 6/2021 |
| CN | 213465297 | U | 6/2021 |
| CN | 113081241 | A | 7/2021 |
| CN | 113243987 | A | 8/2021 |
| CN | 113349920 | A | 9/2021 |
| CN | 113476136 | A | 10/2021 |
| CN | 113729918 | A | 12/2021 |
| CN | 113952026 | A | 1/2022 |
| CN | 114041873 | A | 2/2022 |
| CN | 114081616 | A | 2/2022 |
| CN | 215914864 | U | 3/2022 |
| CN | 215914865 | U | 3/2022 |
| CN | 113974823 | B | 4/2022 |
| CN | 114271926 | A | 4/2022 |
| CN | 114271931 | A | 4/2022 |
| CN | 114305660 | A | 4/2022 |
| CN | 114343834 | A | 4/2022 |
| CN | 114404035 | A | 4/2022 |
| CN | 114425125 | A | 5/2022 |
| CN | 114469308 | A | 5/2022 |
| CN | 114469327 | A | 5/2022 |
| CN | 114652435 | A | 6/2022 |
| CN | 113729923 | B | 7/2022 |
| CN | 216908099 | U | 7/2022 |
| CN | 114948183 | A | 8/2022 |
| CN | 217138245 | U | 8/2022 |
| CN | 113545841 | B | 11/2022 |
| CN | 115414111 | A | 12/2022 |
| CN | 115462889 | A | 12/2022 |
| CN | 218106029 | U | 12/2022 |
| CN | 115580269 | | 1/2023 |
| CN | 111437513 | B | 5/2023 |
| CN | 115844521 | B | 5/2023 |
| CN | 116115323 | A | 5/2023 |
| CN | 116350339 | A | 6/2023 |
| CN | 112914717 | B | 7/2023 |
| CN | 116407262 | A | 7/2023 |
| CN | 116509533 | A | 8/2023 |
| CN | 116531038 | A | 8/2023 |
| CN | 116672064 | | 9/2023 |
| CN | 116687544 | | 9/2023 |
| CN | 116687551 | | 9/2023 |
| CN | 116887772 | A | 10/2023 |
| CN | 116919415 | A | 10/2023 |
| CN | 116919574 | A | 10/2023 |
| CN | 116919577 | A | 10/2023 |
| CN | 116942290 | A | 10/2023 |
| CN | 116919563 | B | 1/2024 |
| CN | 117752406 | A | 3/2024 |
| CN | 118000888 | A | 5/2024 |
| CN | 118000889 | A | 5/2024 |
| CN | 118000890 | A | 5/2024 |
| CN | 118044871 | A | 5/2024 |
| CN | 118044876 | A | 5/2024 |
| CN | 118319468 | A | 7/2024 |
| CN | 118236143 | B | 8/2024 |
| CN | 118415747 | A | 8/2024 |
| CN | 118593107 | A | 9/2024 |
| CN | 221636006 | U | 9/2024 |
| CN | 118766578 | A | 10/2024 |
| CN | 118787432 | A | 10/2024 |
| CN | 115105188 | B | 11/2024 |
| CN | 114587570 | B | 12/2024 |
| CN | 119097409 | A | 12/2024 |
| CN | 119097410 | A | 12/2024 |
| CN | 119367037 | A | 1/2025 |
| CN | 119385680 | A | 2/2025 |
| CN | 119423952 | A | 2/2025 |
| CN | 119564319 | A | 3/2025 |
| CN | 114870246 | B | 4/2025 |
| CN | 119770160 | A | 4/2025 |
| CN | 118436420 | B | 5/2025 |
| CN | 119950006 | A | 5/2025 |
| CN | 120241233 | A | 7/2025 |
| CN | 120304942 | A | 7/2025 |
| CN | 113317868 | B | 11/2025 |
| CN | 121221122 | A | 12/2025 |
| CN | 121465678 | A | 2/2026 |
| CZ | 33133 | U1 | 8/2019 |
| CZ | 33134 | | 8/2019 |
| CZ | 308415 | | 8/2020 |
| DE | 102021121228 | A1 | 3/2022 |
| EP | 358336 | | 3/1990 |
| EP | 0956878 | A2 | 11/1999 |
| EP | 1613387 | B1 | 1/2008 |
| EP | 1189544 | B1 | 1/2009 |
| EP | 1415608 | B1 | 2/2009 |
| EP | 1284670 | B1 | 6/2009 |
| EP | 0957773 | B1 | 6/2011 |
| EP | 1210023 | B1 | 1/2012 |
| EP | 1971285 | B1 | 1/2012 |
| EP | 2429435 | A1 | 3/2012 |
| EP | 2465568 | A1 | 6/2012 |
| EP | 2720747 | A4 | 12/2014 |
| EP | 2859907 | A1 | 4/2015 |
| EP | 2736432 | B1 | 3/2016 |

(56) References Cited

FOREIGN PATENT DOCUMENTS

| | | | |
|---|---|---|---|
| EP | 1171189 | B1 | 5/2016 |
| EP | 3071137 | A1 | 9/2016 |
| EP | 3086838 | A1 | 11/2016 |
| EP | 3091925 | A1 | 11/2016 |
| EP | 2956197 | B1 | 2/2017 |
| EP | 3142584 | A1 | 3/2017 |
| EP | 2598066 | B1 | 9/2017 |
| EP | 3089687 | B1 | 6/2018 |
| EP | 2937110 | B1 | 8/2018 |
| EP | 3368135 | A1 | 9/2018 |
| EP | 2474281 | B1 | 3/2019 |
| EP | 3456278 | A2 | 3/2019 |
| EP | 3459480 | A1 | 3/2019 |
| EP | 2770930 | B1 | 4/2019 |
| EP | 2629690 | B1 | 7/2019 |
| EP | 3135237 | B1 | 7/2019 |
| EP | 3212270 | B1 | 9/2019 |
| EP | 3534816 | A1 | 9/2019 |
| EP | 3573559 | | 12/2019 |
| EP | 3610788 | A1 | 2/2020 |
| EP | 3378427 | B1 | 9/2020 |
| EP | 3742997 | | 12/2020 |
| EP | 3753516 | A1 | 12/2020 |
| EP | 3758638 | | 1/2021 |
| EP | 2995268 | B1 | 3/2021 |
| EP | 3517031 | B1 | 5/2021 |
| EP | 3841999 | | 6/2021 |
| EP | 3944831 | | 2/2022 |
| EP | 3960105 | | 3/2022 |
| EP | 3984484 | | 4/2022 |
| EP | 3986307 | | 4/2022 |
| EP | 4030992 | A1 | 7/2022 |
| EP | 4039210 | | 8/2022 |
| EP | 4065004 | | 10/2022 |
| EP | 4072454 | | 10/2022 |
| EP | 4151168 | | 3/2023 |
| EP | 4185226 | A1 | 5/2023 |
| EP | 4215141 | | 7/2023 |
| EP | 4215142 | | 7/2023 |
| EP | 4215144 | | 7/2023 |
| EP | 4215145 | | 7/2023 |
| EP | 4268750 | | 11/2023 |
| EP | 4280988 | | 11/2023 |
| EP | 4393400 | | 7/2024 |
| EP | 4412549 | | 8/2024 |
| EP | 4635436 | A1 | 10/2025 |
| ES | 2751156 | | 3/2020 |
| HK | 40060966 | | 3/2023 |
| IL | 299866 | | 8/2023 |
| IL | 299868 | | 8/2023 |
| JP | 2014516657 | A | 7/2014 |
| JP | 5885302 | B2 | 3/2016 |
| JP | 2017140446 | A | 8/2017 |
| JP | 2018089431 | A | 6/2018 |
| JP | 2018161471 | | 10/2018 |
| JP | 2020018606 | | 2/2020 |
| JP | 2023164368 | | 11/2023 |
| JP | 2024084443 | | 6/2024 |
| JP | 2024095491 | | 7/2024 |
| WO | 9406349 | | 3/1994 |
| WO | 1995001751 | A1 | 1/1995 |
| WO | 1996001599 | A1 | 1/1996 |
| WO | 2001007583 | A1 | 2/2001 |
| WO | 2002004062 | A3 | 1/2002 |
| WO | 2003071140 | A2 | 8/2003 |
| WO | 2006128068 | A1 | 11/2006 |
| WO | 2007067628 | A1 | 6/2007 |
| WO | 2007067937 | A2 | 6/2007 |
| WO | 2007067938 | A2 | 6/2007 |
| WO | 2007067939 | A2 | 6/2007 |
| WO | 2007067940 | A2 | 6/2007 |
| WO | 2007067941 | A2 | 6/2007 |
| WO | 2007067943 | A2 | 6/2007 |
| WO | 2007070361 | A2 | 6/2007 |
| WO | 2008063195 | A1 | 5/2008 |
| WO | 2009085457 | A1 | 7/2009 |
| WO | 2009085458 | A1 | 7/2009 |
| WO | 2009134876 | A1 | 11/2009 |
| WO | 2010014480 | A1 | 2/2010 |
| WO | 2010085773 | A1 | 7/2010 |
| WO | 2010091701 | A1 | 8/2010 |
| WO | 2010118387 | A1 | 10/2010 |
| WO | 2010132472 | A1 | 11/2010 |
| WO | 2010151277 | A1 | 12/2010 |
| WO | 2011062653 | A1 | 5/2011 |
| WO | 2011072221 | A1 | 6/2011 |
| WO | 2012067682 | A1 | 5/2012 |
| WO | 2012118659 | A1 | 9/2012 |
| WO | 2012122517 | A2 | 9/2012 |
| WO | 2012088149 | A4 | 1/2013 |
| WO | 2014075415 | A1 | 5/2014 |
| WO | 2014110579 | | 7/2014 |
| WO | 2014157253 | A1 | 10/2014 |
| WO | 2014195933 | A1 | 12/2014 |
| WO | 2015006480 | A1 | 1/2015 |
| WO | 2015085162 | A1 | 6/2015 |
| WO | 2015103574 | A1 | 7/2015 |
| WO | 2015171921 | A2 | 11/2015 |
| WO | 2015187430 | A2 | 12/2015 |
| WO | 2015192018 | A1 | 12/2015 |
| WO | 2015192027 | A1 | 12/2015 |
| WO | 2016007851 | A1 | 1/2016 |
| WO | 2016099774 | A1 | 6/2016 |
| WO | 2016164930 | A1 | 10/2016 |
| WO | 2016178697 | A1 | 11/2016 |
| WO | 2016181315 | A1 | 11/2016 |
| WO | 2016181316 | A1 | 11/2016 |
| WO | 2016181317 | A2 | 11/2016 |
| WO | 2016181318 | A1 | 11/2016 |
| WO | 2016181320 | A1 | 11/2016 |
| WO | 2016201264 | A1 | 12/2016 |
| WO | 2017024056 | A1 | 2/2017 |
| WO | 2017117582 | | 7/2017 |
| WO | 2017119934 | A1 | 7/2017 |
| WO | 2017120169 | A1 | 7/2017 |
| WO | 2017123981 | A1 | 7/2017 |
| WO | 2017155867 | A1 | 9/2017 |
| WO | 2017192477 | A1 | 11/2017 |
| WO | 2017192480 | A2 | 11/2017 |
| WO | 2017192495 | A1 | 11/2017 |
| WO | 2017192510 | A2 | 11/2017 |
| WO | 2017192542 | A2 | 11/2017 |
| WO | 2017212257 | A1 | 12/2017 |
| WO | 2018005511 | A1 | 1/2018 |
| WO | 2018010659 | A1 | 1/2018 |
| WO | 2018037594 | A1 | 3/2018 |
| WO | 2018081323 | A1 | 5/2018 |
| WO | 2018187856 | A1 | 10/2018 |
| WO | 2018191149 | A1 | 10/2018 |
| WO | 2018200800 | A1 | 11/2018 |
| WO | 2018201037 | A1 | 11/2018 |
| WO | 2018236754 | A1 | 12/2018 |
| WO | 2019023280 | A1 | 1/2019 |
| WO | 2019055512 | A1 | 3/2019 |
| WO | 2019083982 | A1 | 5/2019 |
| WO | 2019084442 | A1 | 5/2019 |
| WO | 2019118436 | A1 | 6/2019 |
| WO | 2019133606 | A1 | 7/2019 |
| WO | 2019133608 | A1 | 7/2019 |
| WO | 2019143960 | A1 | 7/2019 |
| WO | 2019157359 | A1 | 8/2019 |
| WO | 2019181612 | A1 | 9/2019 |
| WO | 2019181634 | | 9/2019 |
| WO | 2019181634 | A1 | 9/2019 |
| WO | 2019185331 | A1 | 10/2019 |
| WO | 2019212827 | A1 | 11/2019 |
| WO | 2019217300 | A1 | 11/2019 |
| WO | 2019217317 | A1 | 11/2019 |
| WO | 2019217433 | A1 | 11/2019 |
| WO | 2019226640 | A1 | 11/2019 |
| WO | 2019232358 | A1 | 12/2019 |
| WO | 2019234133 | A1 | 12/2019 |
| WO | 2020026217 | A1 | 2/2020 |
| WO | 2020057155 | A1 | 3/2020 |

(56) References Cited

FOREIGN PATENT DOCUMENTS

| | | | |
|---|---|---|---|
| WO | 2020061192 | A1 | 3/2020 |
| WO | 2020072749 | A1 | 4/2020 |
| WO | 2020131885 | A1 | 6/2020 |
| WO | 2020206328 | A1 | 10/2020 |
| WO | 2020251771 | A1 | 12/2020 |
| WO | 2020252506 | A1 | 12/2020 |
| WO | 2021113463 | A1 | 6/2021 |
| WO | 2021150629 | A1 | 7/2021 |
| WO | 2021207452 | A1 | 10/2021 |
| WO | 2021216515 | A1 | 10/2021 |
| WO | 2022007489 | A1 | 1/2022 |
| WO | 2022007490 | A1 | 1/2022 |
| WO | 2022020478 | A1 | 1/2022 |
| WO | 2022145179 | A1 | 7/2022 |
| WO | 2023280822 | | 1/2023 |
| WO | 2023138275 | | 7/2023 |
| WO | 2023196773 | | 10/2023 |
| WO | 2023205899 | | 11/2023 |
| WO | 2023236402 | | 12/2023 |
| WO | 2023239966 | | 12/2023 |
| WO | 2024007424 | | 1/2024 |
| WO | 2024069495 | | 4/2024 |
| WO | 2024086033 | | 4/2024 |
| WO | 2024099406 | | 5/2024 |
| WO | 2024110800 | | 5/2024 |
| WO | 2024118748 | | 6/2024 |
| WO | 2024127115 | | 6/2024 |
| WO | 2024127133 | | 6/2024 |
| WO | 2024211474 | | 10/2024 |
| WO | 2024261755 | A1 | 12/2024 |
| WO | 2025024366 | A1 | 1/2025 |

OTHER PUBLICATIONS

J. S. Koruth et al., "Feasibility, safety, and durability of porcine atrial ablation using a lattice-tip temperature-controlled radiofrequency ablation catheter", J Cardiovasc Electrophysiol, roč. 31, č. 6, s. 1323-1331, čer. 2020, doi: 10.1111/jce. 14473.

J. S. Koruth et al., "Focal Pulsed Field Ablation for Pulmonary Vein Isolation and Linear Atrial Lesions: A Preclinical Assessment of Safety and Durability", Circ: Arrhythmia and Electrophysiology, roč. 13, č. 6, s. e008716, čer. 2020, doi: 10.1161/CIRCEP. 120. 008716. 15 pages.

J. S. Koruth et al., "Pulsed Field Ablation Versus Radiofrequency Ablation: Esophageal Injury in a Novel Porcine Model", Circ: Arrhythmia and Electrophysiology, roč. 13, č. 3, bře. 2020, doi: 10.1161/CIRCEP.119.008303. 10 pages.

J. S. Koruth, I. Kawamura, S. R. Dukkipati, W. Whang, M. Turagam, a V. Y. Reddy, "B-AB06-03 Preclinical Assessment of the Feasibility, Safety and Lesion Durability of a Novel "Single-Shot" Pulse Field Ablation Catheter for Pulmonary Vein Isolation", Heart Rhythm, roč. 18, č. 8, s. S10-S11, srp. 2021, doi: 10.1016/j.hrthm. 2021.06.038.

J. Song, R. P. Joshi, a K. H. Schoenbach, "Synergistic effects of local temperature enhancements on cellular responses in the context of high-intensity, ultrashort electric pulses", Med Biol Eng Comput, roč. 49, č. 6, s. 713-718, čer. 2011, doi: 10.1007/s11517-011-0745-z.

J.- L. Lin et al., "Electrophysiological Mapping and Histological Examinations of the Swine Atrium with Sustained (≥h) Atrial Fibrillation: A Suitable Animal Model for Studying Human Atrial Fibrillation", CRD, roč. 99, č. 2, s. 78-84, 2003, doi: 10.1159/000069728.

K. C. K. Wong et al., "High incidence of acute sub-clinical circumflex artery 'injury' following mitral isthmus ablation", European Heart Journal, roč. 32, č. 15, s. 1881-1890, srp. 2011, doi: 10.1093/eurheartj/ehr117.

K. H. Schoenbach, R. Joshi, J. Kolb, S. Buescher, a S. Beebe, "Subcellular effects of nanosecond electrical pulses", in The 26th Annual International Conference of the IEEE Engineering in Medicine and Biology Society, San Francisco, CA, USA, 2004, roč. 4, s. 5447-5450. doi: 10.1109/IEMBS.2004.1404522.

K. Kuroki et al., "Ostial dimensional changes after pulmonary vein isolation: Pulsed field ablation vs radiofrequency ablation", Heart Rhythm, roč. 17, č. 9, s. 1528-1535, zář. 2020, doi: 10.1016/j.hrthm. 2020.04.040.

K. P. Charpentier, F. Wolf, L. Noble, B. Winn, M. Resnick, a D. E. Dupuy, "Irreversible electroporation of the liver and liver hilum in swine", HPB, roč. 13, č. 3, s. 168-173, bře. 2011, doi: 10.1111/j. 1477-2574.2010.00261.x.

K. R. Thomson et al., "Investigation of the Safety of Irreversible Electroporation in Humans", Journal of Vascular and Interventional Radiology, roč. 22, č. 5, s. 611-621, kvě. 2011, doi: 10.1016/j.jvir. 2010.12.014.

K. Schultheis et al., "Delineating the Cellular Mechanisms Associated with Skin Electroporation", Hum Gene Ther Methods, roč. 29, č. 4, s. 177-188, srp. 2018, doi: 10.1089/hgtb.2017.105.

K. Yokoyama et al., "Canine Model of Esophageal Injury and Atrial-Esophageal Fistula After Applications of Forward-Firing High-Intensity Focused Ultrasound and Side-Firing Unfocused Ultrasound in the Left Atrium and Inside the Pulmonary Vein", Circ Arrhythm Electrophysiol, roč. 2, č. 1, s. 41-49, úno. 2009, doi: 10.1161/CIRCEP.108.807925.

Kelkar, "Resistance and Laser Welding for Medical Devices," Medical Device and Diagnostics Industry (MDDI), Jun. 2006, 14 pages.

Koruth Jacob et al., "Preclinical Evaluation of Pulsed Field Ablation", Circulation: Arrhythmia and Electrophysiology, roč. 12, č. 12, s. e007781, pro. 2019, doi: 10.1161/CIRCEP.119.007781. 9 pages.

L. F. Cima a L. M. Mir, "Macroscopic characterization of cell electroporation in biological tissue based on electrical measurements", s. 4, 2014.

L. Galluzzi et al., "Essential versus accessory aspects of cell death: recommendations of the NCCD 2015", Cell Death Differ, roč. 22, č. 1, s. 58-73, led. 2015, doi: 10.1038/cdd.2014.137.

L. Schomel, S. Eyerly, a Partick Wolf, "Visualization of Convective Heat Transfer with a Thermal Camera in vivo during Cardiac Radiofrequency Ablation", 2014, doi: 10.13140/RG.2.1.3723.6088. 1 page.

L. V. Chernomordik et al., "The electrical breakdown of cell and lipid membranes: the similarity of phenomenologies", Biochimica et Biophysica Acta (BBA)—Biomembranes, roč. 902, č. 3, s. 360-373, zář. 1987, doi: 10.1016/0005-2736 (87)90204-5.

L. V. Saint-Quentin, "Cryterion Cryoablation System FIM/CE Mark sttudy", s. 73, 2019.

L.-B. Shi, O. Rossvoll, P. Tande, P. Schuster, E. Solheim, a J. Chen, "Cryoballoon vs. radiofrequency catheter ablation: insights from NOrwegian randomized study of PERSistent Atrial Fibrillation (NO-PERSAF study)", EP Europace, roč. 24, č. 2, s. 226-233, úno. 2022, doi: 10.1093/europace/euab281.

Lababidi, "Designing an Intravascular Diagnostic Catheter", Tufts University, 2013. 97 pages.

M. A. Pinkert, R. A. Hortensius, B. M. Ogle, a K. W. Eliceiri, "Imaging the Cardiac Extracellular Matrix", in Cardiac Extracellular Matrix, roč. 1098, E. G. Schmuck, P. Hematti, a A. N. Raval, Ed. Cham: Springer International Publishing, 2018, s. 21-44. doi: 10.1007/978-3-319-97421-7_2.

M. B. Sano et al., "Reduction of Muscle Contractions during Irreversible Electroporation Therapy Using High-Frequency Bursts of Alternating Polarity Pulses: A Laboratory Investigation in an Ex Vivo Swine Model", Journal of Vascular and Interventional Radiology, roč. 29, č. 6, s. 893-898.e4, čer. 2018, doi: 10.1016/j.jvir. 2017.12.019.

M. B. Sano, "Production of Spherical Ablations Using Nonthermal Irreversible Electroporation_ A Laboratory Investigation Using a Single Electrode and Grounding Pad", s. 12. 2016.

M. B. Sano, M. R. DeWitt, S. D. Teeter, a L. Xing, "Optimization of a single insertion electrode array for the creation of clinically relevant ablations using high-frequency irreversible electroporation", Computers in Biology and Medicine, roč. 95, s. 107-117, dub. 2018, doi: 10.1016/j.compbiomed.2018.02.009.

M. Das et al., "Local catheter impedance drop during pulmonary vein isolation predicts acute conduction block in patients with

(56) References Cited

OTHER PUBLICATIONS paroxysmal atrial fibrillation: initial results of the Localize clinical trial", EP Europace, roč. 23, č. 7, s. 1042-1051, vc. 2021, doi: 10.1093/europace/euab004.
M. et al Reichel, "Computer Simulation of Field Distribution and Excitation of Denervated Muscle Fibers Caused by Surface Electrodes", Artif Organs, roč. 23, č. 5, s. 4, 1999.
M. F. Lorenzo, S. P. Bhonsle, C. B. Arena, a R. V. Davalos, "Rapid Impedance Spectroscopy for Monitoring Tissue Impedance, Temperature, and Treatment Outcome During Electroporation-Based Therapies", IEEE Trans. Biomed. Eng., roč. 68, č. 5, s. 1536-1546, kvě. 2021, doi: 10.1109/TBME.2020.3036535.
M. Faroja et al., "Irreversible Electroporation Ablation: Is All the Damage Nonthermal?", Radiology, roč. 266, č. 2, s. 462-470, úno. 2013, doi: 10.1148/radiol.12120609.
M. Grimaldi et al., "Time Course of Irreversible Electroporation Lesion Development Through Short- and Long-Term Follow-Up in Pulsed-Field Ablation-Treated Hearts", Circ: Arrhythmia and Electrophysiology, s. 10.1161/CIRCEP.121.010661, čer. 2022, doi: 10.1161/CIRCEP.121.010661. 8 pages.
M. H. A. Groen et al., "In vivo analysis of the origin and characteristics of gaseous microemboli during catheter-mediated irreversible electroporation", EP Europace, roč. 23, č. 1, s. 139-146, led. 2021, doi: 10.1093/europace/euaa243.
M. H. Ruwald, A. Johannessen, M. L. Hansen, R. Worck, a J. Hansen, "Pulsed field ablation of the cavotricuspid isthmus using a multispline-electrode pulsed field ablation catheter", HeartRhythm Case Reports, roč. 8, č. 3, s. 147-150, bře. 2022, doi: 10.1016/j.hrcr.2021.12.009.
M. Haïssaguerre et al., "Spontaneous Initiation of Atrial Fibrillation by Ectopic Beats Originating in the Pulmonary Veins", N Engl J Med, roč. 339, č. 10, s. 659-666, zář. 1998, doi: 10.1056/NEJM199809033391003.
M. Hwang, J. Kim, B. Lim, J.-S. Song, B. Joung, a E. Shim, "Multiple factors influence the morphology of the bipolar electrogram: An in silico modeling study", PLoS Computational Biology, roč. 15, dub. 2019, doi: 10.1371/journal.pcbi.1006765. 13 pages.
M. Pavlin, T. Kotnik, D. Miklavčič, P. Kramar, a A. Maček Lebar, "Chapter Seven Electroporation of Planar Lipid Bilayers and Membranes", in Advances in Planar Lipid Bilayers and Liposomes, roč. 6, Elsevier, 2008, s. 165-226. doi: 10.1016/S1554-4516(07)06007-3.
M. Pešl, "Epicardial delivery of diversified pulsed field potentials in animal model", 2019, roč. 2019. Viděno: 28. duben 2021. [Online]. 2 pages. Dostupné z: https://www.vutbr.cz/en/rad/results/detail?vav_id=157796#vysledek-157796.
M. Phillips, E. Maor, a B. Rubinsky, "Nonthermal Irreversible Electroporation for Tissue Decellularization", Journal of Biomechanical Engineering, roč. 132, č. 9, s. 091003, zář. 2010, 8 pages, doi: 10.1115/1.4001882.
M. R. Meijerink, H. J. Scheffer, a G. Narayanan, Ed., Irreversible Electroporation in Clinical Practice. Cham: Springer International Publishing, 2018. doi: 10.1007/978-3-319-55113-5. 281 pages.
M. Rehman, A. Adiyaman, J. Smit, B. Manfai, a A. Elvan, "Comparison of safety and efficacy between POLARx and Arctic Front cryoballoon ablation", EP Europace, roč. 24, č. Supplement_1, s. euac053.110, kvě. 2022, doi: 10.1093/europace/euac053.110. 1 page.
M. Rienks, A.-P. Papageorgiou, N. G. Frangogiannis, a S. Heymans, "Myocardial Extracellular Matrix: An Ever-Changing and Diverse Entity", Circ Res, roč. 114, č. 5, s. 872-888, úno. 2014, doi: 10.1161/CIRCRESAHA.114.302533.
M. S. Arruda et al., "A Novel Mesh Electrode Catheter for Mapping and Radiofrequency Delivery at the Left Atrium-Pulmonary Vein Junction: A Single-Catheter Approach to Pulmonary Vein Antrum Isolation", J Cardiovasc Electrophysiol, roč. 18, č. 2, s. 206-211, úno. 2007, doi: 10.1111/j.1540-8167.2007.00720.x.
M. T. Stewart et al., "Intracardiac pulsed field ablation: Proof of feasibility in a chronic porcine model", Heart Rhythm, roč. 16, č. 5, s. 754-764, kvě. 2019, doi: 10.1016/j.hrthm.2018.10.030.
M. T. Stewart et al., "Safety and chronic lesion characterization of pulsed field ablation in a Porcine model", J Cardiovasc Electrophysiol, roč. 32, č. 4, s. 958-969, dub. 2021, doi: 10.1111/jce.14980.
M. Tsivian a T. J. Polascik, "Bilateral focal ablation of prostate tissue using low-energy direct current (LEDC): a preclinical canine study", BJU International, roč. 112, č. 4, s. 526-530, 2013, doi: 10.1111/bju.12227.
M. Yacoub a R. C. Sheppard, "Cryoballoon Pulmonary Vein Catheter Ablation of Atrial Fibrillation", in StatPearls, Treasure Island (FL): StatPearls Publishing, 2021. 10 pages. Viděno: 28. duben 2021. [Online]. Dostupné z: http://www.ncbi.nlm.nih.gov/books/NBK534804/.
Melenka, et al. "Manufacturing Processes for Braided Composite Materials," Handbook of Advances in Braided Composite Materials, 2017, 107 pages.
MWS Wire Industries, "Medical Microwire", 2019, 28 pages.
N. G. dela Paz a P. A. D'Amore, "Arterial versus venous endothelial cells", Cell Tissue Res, roč. 335, č. 1, s. 5-16, led. 2009, doi: 10.1007/s00441-008-0706-5.
T. Nakamura et al., "Incidence and Characteristics of Coronary Artery Spasms Related to Atrial Fibrillation Ablation Procedures—Large-Scale Multicenter Analysis—", Circ J, roč. 85, č. 3, s. 264-271, úno. 2021, doi: 10.1253/circj.CJ-20-1096.
T. Saitoh et al., "Coronary Hyperreactivity to Adrenergic Stimulation and Increased Nocturnal Vagal Tone Trigger Coronary Vasospasm", Jpn Circ J, roč. 62, č. 10, s. 721-726, 1998, doi: 10.1253/jcj.62.721.
T. Zhu et al., "Pulsed Field Ablation of Superior Vena Cava: Feasibility and Safety of Pulsed Field Ablation", Frontiers in Cardiovascular Medicine, roč. 8, 2021, Viděno: 3. březen 2022. [Online]. Dostupné z: https://www.frontiersin.org/article/10.3389/fcvm.2021.698716.
V. J. H. M. van Driel et al., "Pulmonary Vein Stenosis After Catheter Ablation: Electroporation Versus Radiofrequency", Circ Arrhythm Electrophysiol, roč. 7, č. 4, s. 734-738, srp. 2014, doi: 10.1161/CIRCEP.113.001111.
V. J. H. M. van Driel, K. Neven, H. van Wessel, A. Vink, P. A. F. M. Doevendans, a F. H. M. Wittkampf, "Low vulnerability of the right phrenic nerve to electroporation ablation", Heart Rhythm, roč. 12, č. 8, s. 1838-1844, srp. 2015, doi: 10.1016/j.hrthm.2015.05.012.
V. Novickij et al., "High-Pulsed Electromagnetic Field Generator for Contactless Permeabilization of Cells In Vitro", IEEE Trans. Magn., roč. 56, č. 5, s. 1-6, kvě. 2020, doi: 10.1109/TMAG.2020.2979120.
V. P. Nikolski a I. R. Efimov, "Electroporation of the heart", EP Europace, roč. 7, č. s2, s. S146-S154, led. 2005, doi: 10.1016/j.eupc.2005.04.011.
V. Puczok, "Zdroj vysokonapěťových pulzů pro elektroporaci buněk", 2016. 75 pages.
V. van Driel, "Electroporation ablation: a new ablation modality for the ablation of arrhythmogenic cardiac substrate", s. 235, 2016.
V. Viswam, M. E. J. Obien, F. Franke, U. Frey, a A. Hierlemann, "Optimal Electrode Size for Multi-Scale Extracellular-Potential Recording From Neuronal Assemblies", Front. Neurosci., roč. 13, 2019, doi: 10.3389/fnins.2019.00385. 23 pages.
V. Y. Reddy et al., "Ablation of Atrial Fibrillation With Pulsed Electric Fields: An Ultra-Rapid, Tissue-Selective Modality for Cardiac Ablation", JACC: Clinical Electrophysiology, roč. 4, č. 8, s. 987-995, srp. 2018, doi: 10.1016/j.jacep.2018.04.005.
V. Y. Reddy et al., "Lattice-Tip Focal Ablation Catheter That Toggles Between Radiofrequency and Pulsed Field Energy to Treat Atrial Fibrillation: A First-in-Human Trial", Circ: Arrhythmia and Electrophysiology, roč. 13, č. 6, čer. 2020, doi: 10.1161/CIRCEP.120.008718. 13 pages.
V. Y. Reddy et al., "Pulsed Field Ablation for Pulmonary Vein Isolation in Atrial Fibrillation", Journal of the American College of Cardiology, roč. 74, č. 3, s. 315-326, čvc. 2019, doi: 10.1016/j.jacc.2019.04.021.
V. Y. Reddy et al., "Pulsed Field Ablation in Patients With Persistent Atrial Fibrillation", Journal of the American College of Cardiology, roč. 76, č. 9, s. 1068-1080, zář. 2020, doi: 10.1016/j.jacc.2020.07.007.

(56) References Cited

OTHER PUBLICATIONS

V. Y. Reddy et al., "Pulsed Field Ablation of Paroxysmal Atrial Fibrillation", JACC: Clinical Electrophysiology, roč. 7, č. 5, s. 614-627, kvě. 2021, doi: 10.1016/j.jacep.2021.02.014.
V. Y. Reddy et al., "Visually-Guided Balloon Catheter Ablation of Atrial Fibrillation: Experimental Feasibility and First-in-Human Multicenter Clinical Outcome", Circulation, roč. 120, č. 1, s. 12-20, čvc. 2009, doi: 10.1161/CIRCULATIONAHA.108.840587.
W. B. Han, S. J. Kim, H. H. An, H.-S. Kim, Y. Kim, a C. S. Yoon, "Molecular dynamics simulation of interlayer water embedded in phospholipid bilayer", Materials Science and Engineering: C, roč. 36, s. 49-56, bře. 2014, doi: 10.1016/j.msec.2013.11.033.
W. Krassowska a P. D. Filev, "Modeling Electroporation in a Single Cell", Biophysical Journal, roč. 92, č. 2, s. 404-417, led. 2007, doi: 10.1529/biophysj.106.094235.
W. R. Rogers et al., "Strength-Duration Curve for an Electrically Excitable Tissue Extended Down to Near 1 Nanosecond", IEEE Trans. Plasma Sci., roč. 32, č. 4, s. 1587-1599, srp. 2004, doi: 10.1109/TPS.2004.831758.
W. Szlasa et al., "Oxidative Effects during Irreversible Electroporation of Melanoma Cells—In Vitro Study", Molecules, roč. 26, č. 1, s. 154, pro. 2020, doi: 10.3390/molecules26010154.
W. van den Bos et al., "Thermal Energy during Irreversible Electroporation and the Influence of Different Ablation Parameters", Journal of Vascular and Interventional Radiology, roč. 27, č. 3, s. 433-443, bře. 2016, doi: 10.1016/j.jvir.2015.10.020.
W. Yang et al., "Differential Sensitivities of Malignant and Normal Skin Cells to Nanosecond Pulsed Electric Fields", Technol Cancer Res Treat, roč. 10, č. 3, s. 281-286, čer. 2011, doi: 10.7785/tcrt.2012.500204.
Y. Granot, A. Ivorra, E. Maor, a B. Rubinsky, "In vivo imaging of irreversible electroporation by means of electrical impedance tomography", Phys. Med. Biol., roč. 54, č. 16, s. 4927-4943, srp. 2009, doi: 10.1088/0031-9155/54/16/006.
Y. Lv, C. Yao, a B. Rubinsky, "A Conceivable Mechanism Responsible for the Synergy of High and Low Voltage Irreversible Electroporation Pulses", Ann Biomed Eng, roč. 47, č. 7, s. 1552-1563, čvc. 2019, doi: 10.1007/s10439-019-02258-5.
Y. Lv, Y. Zhang, a B. Rubinsky, "Molecular and histological study on the effects of electrolytic electroporation on the liver", Bioelectrochemistry, roč. 125, s. 79-89, úno. 2019, doi: 10.1016/j.bioelechem.2018.09.007.
Y. Nakatani et al., "Pulsed field ablation prevents chronic atrial fibrotic changes and restrictive mechanics after catheter ablation for atrial fibrillation", EP Europace, č. euab155, čvc. 2021, doi: 10.1093/europace/euab155. 10 pages.
Y. Salazar, R. Bragos, a J. Rosell, "Transcatheter measurement of myocardium electrical impedance: 2 versus 3 electrode method", in Proceedings of the 25th Annual International Conference of the IEEE Engineering in Medicine and Biology Society (IEEE Cat. No.03CH37439), Cancun, Mexico, 2003, s. 3102-3105. doi: 10.1109/IEMBS.2003.1280798.
Yanes, et al., "Consistent Repeatability in Tube Welding for Balloon Catheter Manufacturing", http://beta.rodpub.com/uploads/BalloonCatheterWelding_WhitePaper.pdf, 2014, retrieved May 8, 2023.
Yavin Hagai et al., "A Circular Multielectrode Pulsed-Field Ablation Catheter , Lasso PFA': Lesion Characteristics, Durability and Effect on Neighboring Structures", Circulation: Arrhythmia and Electrophysiology, roč. 0, č. 0, 2018, doi:10.1161/CIRCEP.120.009229. 9 pages.
Z. Szabó et al., "Real-time intraoperative visualization of myocardial circulation using augmented reality temperature display", Int J Cardiovasc Imaging, roč. 29, č. 2, s. 521-528, úno. 2013, doi: 10.1007/s10554-012-0094-5.
N. Klauke, G. Smith, a J. M. Cooper, "Regional Electroporation of Single Cardiac Myocytes in a Focused Electric Field", Anal. Chem., roč. 82, č. 2, s. 585-592, led. 2010, doi: 10.1021/ac901886j.
N. M. Fried et al., "Laser ablation of the pulmonary veins by using a fiberoptic balloon catheter: Implications for treatment of paroxysmal atrial fibrillation", Lasers Surg. Med., roč. 28, č. 3, s. 197-203, 2001, doi: 10.1002/Ism.1038.
N. M. Fried, H. Calkins, a A. C. Lardo, "Linear lesions in myocardium created by Nd:YAG laser using diffusing optical fibers: In vitro and in vivo results", s. 10, 2000. 10 pages.
N. Sperelakis a T. Hoshiko, "Electrical Impedance of Cardiac Muscle", Circulation Research, roč. 9, č. 6, s. 1280-1283, lis. 1961, doi: 10.1161/01.RES.9.6.1280.
Na, et al., "Prediction of the braid pattern on arbitrary-shaped mandrels using the minimum path condition," Composites Science and Technology, 2013, 8 pages.
Neven Kars et al., "Acute and Long-Term Effects of Full-Power Electroporation Ablation Directly on the Porcine Esophagus", Circulation: Arrhythmia and Electrophysiology, roč. 10, č. 5, s. e004672, kvě. 2017, doi: 10.1161/CIRCEP.116.004672. 7 pages.
Neven Kars, van Driel Vincent, van Wessel Harry, van Es René, Doevendans Pieter A., a Wittkampf Fred, "Myocardial Lesion Size After Epicardial Electroporation Catheter Ablation After Subxiphoid Puncture", Circulation: Arrhythmia and Electrophysiology, roč. 7, č. 4, s. 728-733, srp. 2014, doi: 10.1161/CIRCEP.114.001659.
Notice of Allowance dated Oct. 17, 2023 for U.S. Appl. No. 18/345,897 (pp. 1-7).
O. N. Pakhomova, B. Gregory, I. Semenov, a A. G. Pakhomov, "Calcium-mediated pore expansion and cell death following nanoelectroporation", Biochimica et Biophysica Acta (BBA)—Biomembranes, roč. 1838, č. 10, s. 2547-2554, říj. 2014, doi: 10.1016/j.bbamem.2014.06.015.
O. Sten-Knudsen, "The ineffectiveness of the 'window field' in the initiation of muscle contraction", J Physiol, roč. 125, č. 2, s. 396-404, srp. 1954, doi: 10.1113/jphysiol.1954.sp005167.
O. Tovar a L. Tung, "Electroporation of Cardiac Cell Membranes with Monophasic or Biphasic Rectangular Pulses", Pacing Clin Electro, roč. 14, č. 11, s. 1887-1892, lis. 1991, doi: 10.1111/j.1540-8159.1991.tb02785.x.
Office Action (Non-Final Rejection) dated Feb. 16, 2023 for U.S. Appl. No. 17/931,975 (pp. 1-13).
Office Action dated Sep. 1, 2023 for U.S. Appl. No. 18/345,897 (pp. 1-8).
P. A. J. Krijnen, R. Nijmeijer, C. J. L. M. Meijer, C. A. Visser, C. E. Hack, a H. W. M. Niessen, "Apoptosis in myocardial ischaemia and infarction", J Clin Pathol, roč. 55, č. 11, s. 801-811, lis. 2002, Viděno: 28. duben 2021. [Online]. Dostupné z: https://www.ncbi.nlm.nih.gov/pmc/articles/PMC1769793/.
P. Jaïs et al., "Prospective Randomized Comparison of Irrigated-Tip Versus Conventional-Tip Catheters for Ablation of Common Flutter", Circulation, roč. 101, č. 7, s. 772-776, úno. 2000, doi: 10.1161/01.CIR.101.7.772.
P. Loh et al., "Pulmonary Vein Isolation With Single Pulse Irreversible Electroporation: A First in Human Study in 10 Patients With Atrial Fibrillation", Circ: Arrhythmia and Electrophysiology, roč. 13, č. 10, říj. 2020, doi: 10.1161/CIRCEP.119.008192. 9 pages.
Q. Hu, R. P. Joshi, a K. H. Schoenbach, "Simulations of nanopore formation and phosphatidylserine externalization in lipid membranes subjected to a high-intensity, ultrashort electric pulse", Phys. Rev. E, roč. 72, č. 3, s. 031902, zář. 2005, doi: 10.1103/PhysRevE.72.031902. 10 pages.
R. Cardona-Guarache et al., "Thoracic Sympathectomy for Severe Refractory Multivessel Coronary Artery Spasm", The American Journal of Cardiology, roč. 117, č. 1, s. 159-161, led. 2016, doi: 10.1016/j.amjcard.2015.10.018.
R. E. Neal, P. A. Garcia, J. L. Robertson, a R. V. Davalos, "Experimental Characterization and Numerical Modeling of Tissue Electrical Conductivity during Pulsed Electric Fields for Irreversible Electroporation Treatment Planning", IEEE Trans. Biomed. Eng., roč. 59, č. 4, s. 1076-1085, dub. 2012, doi: 10.1109/TBME.2012.2182994.
R. G. Muthalaly et al., "Temporal trends in safety and complication rates of catheter ablation for atrial fibrillation", J Cardiovasc Electrophysiol, roč. 29, č. 6, s. 854-860, er. 2018, doi: 10.1111/jce.13484.
R. Gupta a B. Rai, "Electroporation of Skin Stratum Corneum Lipid Bilayer and Molecular Mechanism of Drug Transport: A Molecular

(56) References Cited

OTHER PUBLICATIONS

Dynamics Study", Langmuir, roč. 34, č. 20, s. 5860-5870, kvě. 2018, doi: 10.1021/acs.langmuir.8b00423.
R. Kato et al., "Pulmonary Vein Anatomy in Patients Undergoing Catheter Ablation of Atrial Fibrillation: Lessons Learned by Use of Magnetic Resonance Imaging", Circulation, roč. 107, č. 15, s. 2004-2010, dub. 2003, doi: 10.1161/01.CIR.0000061951.81767.4E.
R. Pavlovi, "Electro-Muscle Stimulation—The Application in Practice", s. 8, 2016.
R. Schilling et al., "Safety, effectiveness, and quality of life following pulmonary vein isolation with a multi-electrode radiofrequency balloon catheter in paroxysmal atrial fibrillation: 1-year outcomes from Shine", Ep Europace, roč. 23, č. 6, s. 851-860, čer. 2021, doi: 10.1093/europace/euaa382.
R. Tung a K. A. Ellenbogen, "Emergence of Multielectrode Mapping: On the Road to Higher Resolution", Circ Arrhythm Electrophysiol, roč. 9, č. 6, čer. 2016, doi: 10.1161/CIRCEP.116.004281. 3 pages.
R. Van Es et al., "216-02: In vitro analysis of gas bubble formation and its effect on impedance during electroporation ablation", EP Europace, roč. 18, č. suppl_1, s. i141-i141, čer. 2016, doi: 10.1093/europace/18.suppl_1.i141c. Downloaded Feb. 2021.
R. van Es et al., "High-frequency irreversible electroporation for cardiac ablation using an asymmetrical waveform", BioMedical Engineering OnLine, roč. 18, č. 1, s. 75, čer. 2019, doi: 10.1186/s12938-019-0693-7.
R. van Es et al., "Novel method for electrode-tissue contact measurement with multi-electrode catheters", EP Europace, roč. 20, č. 1, s. 149-156, led. 2018, doi: 10.1093/europace/euw388.
R. W. Ariss et al., "Contemporary trends and in-hospital outcomes of catheter and stand-alone surgical ablation of atrial fibrillation", EP Europace, roč. 24, č. 2, s. 218-225, úno. 2022, doi: 10.1093/europace/euab198.
S. A. Kirsch a R. A. Bockmann, "Membrane pore formation in atomistic and coarse-grained simulations", Biochimica et Biophysica Acta (BBA)—Biomembranes, roč. 1858, č. 10, s. 2266-2277, říj. 2016, doi: 10.1016/j.bbamem.2015.12.031.
S. Bhonsle et al., "Characterization of Irreversible Electroporation Ablation with a Validated Perfused Organ Model", Journal of Vascular and Interventional Radiology, roč. 27, č. 12, s. 1913-1922.e2, pro. 2016, doi: 10.1016/j.jvir.2016.07.012.
S. Honarbakhsh et al., "PolarX Cryoballoon metrics predicting successful pulmonary vein isolation: targets for ablation of atrial fibrillation", EP Europace, s. euac100, čer. 2022, doi: 10.1093/europace/euac100. 10 pages.
S. Honarbakhsh et al., "Radiofrequency balloon catheter ablation for paroxysmal atrial fibrillation, Radiance Study—a UK experience", EP Europace, roč. 19, č. suppl_1, s. i21-i21, říj. 2017, doi: 10.1093/europace/eux283.004.
S. J. E. Rombouts et al., "Irreversible Electroporation of the Pancreas Using Parallel Plate Electrodes in a Porcine Model: A Feasibility Study", PLoS ONE, roč. 12, č. 1, s. e0169396, led. 2017. 13 pages.
S. M. Narayan a T. Baykaner, "Electroporation: The End of the Thermal Ablation Era?•", Journal of the American College of Cardiology, roč. 74, č. 3, s. 327-329, čvc. 2019, doi: 10.1016/j.jacc.2019.06.013.
S. M. Singh et al., "Clinical outcomes after repair of left atrial esophageal fistulas occurring after atrial fibrillation ablation procedures", Heart Rhythm, roč. 10, č. 11, s. 1591-1597, lis. 2013, doi: 10.1016/j.hrthm.2013.08.012.
S. McBride et al., "Ablation Modalities for Therapeutic Intervention in Arrhythmia-Related Cardiovascular Disease: Focus on Electroporation", JCM, roč. 10, č. 12, s. 2657, čer. 2021, doi: 10.3390/jcm10122657.
S. Narayan a J. Zaman, "Mechanistically-based mapping of human cardiac fibrillation", The Journal of physiology, roč. 594, lis. 2015, doi: 10.1113/JP270513. 17 pages.
S. R. Dukkipati et al., "Pulmonary Vein Isolation Using the Visually Guided Laser Balloon", Journal of the American College of Cardiology, roč. 66, č. 12, s. 1350-1360, zář. 2015, doi: 10.1016/j.jacc.2015.07.036.
S. Tohoku et al., "Pulsed Field Ablation for Persistent Superior Vena Cava", JACC: Case Reports, roč. 4, č. 5, s. 301-305, bře. 2022, doi: 10.1016/j.jaccas.2022.01.015.
Shu Xiao, Siqi Guo, V. Nesin, R. Heller, a K. H. Schoenbach, "Subnanosecond Electric Pulses Cause Membrane Permeabilization and Cell Death", IEEE Trans. Biomed. Eng., roč. 58, č. 5, s. 1239-1245, kvě. 2011, doi: 10.1109/TBME.2011.2112360.
T. Batista Napotnik a D. Miklavčič, "Pulse Duration Dependent Asymmetry in Molecular Transmembrane Transport Due to Electroporation in H9c2 Rat Cardiac Myoblast Cells In Vitro", Molecules, roč. 26, č. 21, Art. č. 21, led. 2021, doi: 10.3390/molecules26216571. 22 pages.
T. Batista Napotnik, T. Polajžer, a D. Miklavčič, "Cell death due to electroporation—A review", Bioelectrochemistry, roč. 141, s. 107871, říj. 2021, doi: 10.1016/j.bioelechem.2021.107871. 18 pages.
T. D. Potter, L. Boersma, A. Babkin, M. Mazor, J. Cox, a S. Antonius, "Novel Linear Cryoablation Catheter to Treat Atrial Fibrillation", s. 1. Date unknown.
T. Harayama a H. Riezman, "Understanding the diversity of membrane lipid composition", Nat Rev Mol Cell Biol, roč. 19, č. 5, s. 281-296, kvě. 2018, doi: 10.1038/nrm.2017.138.
T. J. Buist et al., "Efficacy of multi-electrode linear irreversible electroporation", EP Europace, č. euaa280, lis. 2020, doi: 10.1093/europace/euaa280. 5 pages.
T. J. O'Brien et al., "Effects of internal electrode cooling on irreversible electroporation using a perfused organ model", International Journal of Hyperthermia, roč. 35, č. 1, s. 44-55, pro. 2018, doi: 10.1080/02656736.2018.1473893.
T. J. O'Brien et al., "Experimental High-Frequency Irreversible Electroporation Using a Single-Needle Delivery Approach for Nonthermal Pancreatic Ablation In Vivo", Journal of Vascular and Interventional Radiology, roč. 30, č. 6, s. 854-862.e7, čer. 2019, doi: 10.1016/j.jvir.2019.01.032.
T. Kotnik, L. Rems, M. Tarek, a D. Miklavčič, "Membrane Electroporation and Electropermeabilization: Mechanisms and Models", Annu. Rev. Biophys., roč. 48, č. 1, s. 63-91, kvě. 2019, doi: 10.1146/annurev-biophys-052118-115451.
T. Kurita, "Coronary Artery Spasms and ST-Segment Elevation During Catheter Ablation of Pulmonary Vein Isolation—Cause, Mechanism, and Management-", Circ J, roč. 85, č. 3, s. 272-274, úno. 2021, doi: 10.1253/circj. CJ-20-1238.
A. Anic et al., "Acute safety, efficacy, and advantages of a novel cryoballoon ablation system for pulmonary vein isolation in patients with paroxysmal atrial fibrillation: initial clinical experience", EP Europace, roč. 23, č. 8, s. 1237-1243, srp. 2021, doi: 10.1093/europace/euab018.
A. E. Sowers a M. R. Lieber, "Electropore diameters, lifetimes, Nos., and locations in individual erythrocyte ghosts", FEBS Letters, roč. 205, č. 2, s. 179-184, zář. 1986, doi: 10.1016/0014-5793(86)80893-6.
A. G. Pakhomov, J. F. Kolb, J. A. White, R. P. Joshi, S. Xiao, a K. H. Schoenbach, "Long-lasting plasma membrane permeabilization in mammalian cells by nanosecond pulsed electric field (nsPEF)", Bioelectromagnetics, roč. 28, č. 8, s. 655-663, pro. 2007, doi: 10.1002/bem.20354.
A. G. Pakhomov, S. Grigoryev, I. Semenov, M. Casciola, C. Jiang, a S. Xiao, "The second phase of bipolar, nanosecond-range electric pulses determines the electroporation efficiency", Bioelectrochemistry, roč. 122, s. 123-133, srp. 2018, doi: 10.1016/j.bioelechem.2018.03.014.
A. Golberg a B. Rubinsky, "Towards Electroporation Based Treatment Planning considering Electric Field Induced Muscle Contractions", Technol Cancer Res Treat, roč. 11, č. 2, s. 189-201, dub. 2012, doi: 10.7785/tcrt.2012.500249.
A. Hai a M. E. Spira, "On-chip electroporation, membrane repair dynamics and transient in-cell recordings by arrays of gold mushroom-shaped microelectrodes", Lab Chip, roč. 12, č. 16, s. 2865, 2012, doi: 10.1039/c2lc40091j. 9 pages.

(56) References Cited

OTHER PUBLICATIONS

A. Ivorra a B. Rubinsky, "In vivo electrical impedance measurements during and after electroporation of rat liver", Bioelectrochemistry, roč. 70, č. 2, s. 287-295, kvě. 2007, doi: 10.1016/j.bioelechem.2006.10.005.
A. Meissner et al., "Impact of irrigated energy application on the right coronary artery hemodynamics: FFR measurement in patients who underwent ablation of common type atrial flutter", J Interv Card Electrophysiol, roč. 21, č. 1, s. 35-42, led. 2008, doi: 10.1007/s10840-007-9188-8.
A. Sugrue et al., "Irreversible electroporation for catheter-based cardiac ablation: a systematic review of the preclinical experience", J Interv Card Electrophysiol, roč. 55, č. 3, s. 251-265, zář. 2019, doi: 10.1007/s10840-019-00574-3.
A. Sugrue et al., "Irreversible electroporation for the treatment of cardiac arrhythmias", Expert Review of Cardiovascular Therapy, roč. 16, č. 5, s. 349-360, kvě. 2018, doi: 10.1080/14779072.2018.1459185.
A. T. Feldman a D. Wolfe, "Tissue Processing and Hematoxylin and Eosin Staining", in Histopathology, roč. 1180, C. E. Day, Ed. New York, NY: Springer New York, 2014, s. 31-43. doi: 10.1007/978-1-4939-1050-2_3.
A. Valiūnienė, I. Gabriunaite, M. Poderyte, a A. Ramanavicius, "Electroporation of a hybrid bilayer membrane by scanning electrochemical microscope", Bioelectrochemistry, roč. 136, s. 107617, pro. 2020, doi: 10.1016/j.bioelechem.2020.107617.7 pages.
A. Verma et al., "First-in-Human Experience and Acute Procedural Outcomes Using a Novel Pulsed Field Ablation System: The Pulsed AF Pilot Trial", Circ: Arrhythmia and Electrophysiology, roč. 15, č. 1, s. e010168, led. 2022, doi: 10.1161/CIRCEP.121.010168. 10 pages.
A. Vižintin, J. Vidmar, J. Ščančar, a D. Miklavčič, "Effect of interphase and interpulse delay in high-frequency irreversible electroporation pulses on cell survival, membrane permeabilization and electrode material release", Bioelectrochemistry, roč. 134, s. 107523, srp. 2020, doi: 10.1016/j.bioelechem.2020.107523. 14 pages.
A. Wojtaszczyk, G. Caluori, M. Pešl, K. Melajova, a Z. Stárek, "Irreversible electroporation ablation for atrial fibrillation", J Cardiovasc Electrophysiol, roč. 29, č. 4, s. 643-651, dub. 2018, doi: 10.1111/jce.13454.
B. C. du Pré et al., "Minimal coronary artery damage by myocardial electroporation ablation", EP Europace, roč. 15, č. 1, s. 144-149, led. 2013, doi: 10.1093/europace/eus171.
B. Howard et al., "Characterization of Phrenic Nerve Response to Pulsed Field Ablation", Circ: Arrhythmia and Electrophysiology, roč. 15, č. 6, čer. 2022, doi: 10.1161/CIRCEP.121.010127. 9 pages.
B. K. Martinez et al., "Systematic review and meta-analysis of catheter ablation of ventricular tachycardia in ischemic heart disease", Heart Rhythm, roč. 17, č. 1, s. e206-e219, led. 2020, doi: 10.1016/j.hrthm.2019.04.024.
B. López-Alonso, H. Sarnago, Ó. Lucía, P. Briz, a J. M. Burdío, "Real-Time Impedance Monitoring During Electroporation Processes in Vegetal Tissue Using a High-Performance Generator", Sensors, roč. 20, č. 11, s. 3158, čer. 2020, doi: 10.3390/s20113158. 14 pages.
B. Mercadal, C. B. Arena, R. V. Davalos, a A. Ivorra, "Avoiding nerve stimulation in irreversible electroporation: a numerical modeling study", Phys Med Biol, roč. 62, č. 20, s. 8060-8079, říj. 2017, doi: 10.1088/1361-6560/aa8c53.
B. Mercadal, N. Beitel-White, K. N. Aycock, Q. Castellví, R. V. Davalos, a A. Ivorra, "Dynamics of Cell Death After Conventional IRE and H-FIRE Treatments", Ann Biomed Eng, roč. 48, č. 5, s. 1451-1462, kvě. 2020, doi: 10.1007/s10439-020-02462-8.
B. Rubinsky, G. Onik, a P. Mikus, "Irreversible electroporation: a new ablation modality—clinical implications", Technol Cancer Res Treat, roč. 6, č. 1, s. 37-48, úno. 2007, doi: 10.1177/153303460700600106.
B. Schmidt, S. Chen, S. Tohoku, S. Bordignon, F. Bologna, a K. R. J. Chun, "Single shot electroporation of premature ventricular contractions from the right ventricular outflow tract", EP Europace, roč. 24, č. 4, s. 597-597, dub. 2022, doi: 10.1093/europace/euab212.
Biosense Webster, "Study Protocol SHINE 2018". 2018. [Online]. Dostupné z: https://clinicaltrials.gov/ProvidedDocs/33/NCT03437733/Prot_000.pdf. 86 pages.
Boyle, et al. "Laser Source Selection for Micro-welding Processes", Amada Miyachi Europe, 2015, 28 pages.
C. B. Arena et al., "High-frequency irreversible electroporation (H-FIRE) for non-thermal ablation without muscle contraction", BioMed Eng OnLine, roč. 10, č. 1, s. 102, pro. 2011, doi: 10.1186/1475-925X-10-102. 21 pages.
C. B. Arena, M. B. Sano, M. N. Rylander, a R. V. Davalos, "Theoretical Considerations of Tissue Electroporation With High-Frequency Bipolar Pulses", IEEE Trans. Biomed. Eng., roč. 58, č. 5, s. 1474-1482, kvě. 2011, doi: 10.1109/TBME.2010.2102021.
C. Lyu, J. Wang, M. Powell-Palm, a B. Rubinsky, "Simultaneous electroporation and dielectrophoresis in non-electrolytic micro/nano-electroporation", Sci Rep, roč. 8, č. 1, s. 2481, pro. 2018, doi: 10.1038/s41598-018-20535-6. 13 pages.
C. M. Tschabrunn, S. Roujol, N. C. Dorman, R. Nezafat, M. E. Josephson, a E. Anter, "High-Resolution Mapping of Ventricular Scar: Comparison between Single and Multi-Electrode Catheters", Circ Arrhythm Electrophysiol, roč. 9, č. 6, čer. 2016, doi: 10.1161/CIRCEP.115.003841. 22 pages.
C. M. Witt et al., "Intrapulmonary Vein Ablation Without Stenosis: A Novel Balloon-Based Direct Current Electroporation Approach", JAHA, roč. 7, č. 14, čvc. 2018, doi: 10.1161/JAHA.118.009575. 8 pages.
C. V. DeSimone, "Novel balloon catheter device with pacing, ablating, electroporation, and drug-eluting capabilities for atrial fibrillation treatment-preliminary efficacy and safety studies in a canine model", Translational Research, roč. 164, č. 6, s. 7, 2014. 7 pages.
C. Valdez, M. B. Jirjis, C. C. Roth, R. A. Barnes, a B. L. Ibey, "Nanosecond electric pulses modulate skeletal muscle calcium dynamics and contraction", prezentováno v SPIE BiOS, San Francisco, California, United States, úno. 2017, s. 100660X. doi: 10.1117/12.2253693. 9 pages.
C. Yao et al., "Bipolar Microsecond Pulses and Insulated Needle Electrodes for Reducing Muscle Contractions During Irreversible Electroporation", IEEE transactions on bio-medical engineering, roč. PP, dub. 2017, doi: 10.1109/TBME.2017.2690624. 15 pages.
Carey, et al., "Design of Braided Composite Cardiovascular Catheters Based on Required Axial, Flexural, and Torsional Rigidities", Wiley InterScience, 2004, 9 pages.
D. C. Sweeney a M. Reber, "Quantification of cell membrane permeability induced by monopolar and high-frequency bipolar bursts of electrical pulses", Biochimica et Biophysica Acta, s. 10, 1858. 2016, 10 pages.
D. E. Haines et al., "Microembolism and catheter ablation I: a comparison of irrigated radiofrequency and multielectrode-phased radiofrequency catheter ablation of pulmonary vein ostia", Circ Arrhythm Electrophysiol, roč. 6, č. 1, s. 16-22, úno. 2013, doi: 10.1161/CIRCEP.111.973453.
D. E. Haines, A. R. Strunk, A. Novichenok, N. Kirchhof, a M. Stewart, "The Biophysics of Passive Convective Cooling During Catheter Ablation with Gold versus Platinum Electrodes and Multielectrode Phased Radiofrequency Energy Delivery: Gold versus Platinum Ablation Electrodes", J Cardiovasc Electrophysiol, roč. 26, č. 11, s. 1257-1261, lis. 2015, doi: 10.1111/jce.12752.
D. J. Wilber et al., "Comparison of Antiarrhythmic Drug Therapy and Radiofrequency Catheter Ablation in Patients With Paroxysmal Atrial Fibrillation: A Randomized Controlled Trial", JAMA, roč. 303, č. 4, s. 333, led. 2010, doi: 10.1001/jama.2009.2029. 8 pages.
D. L. Packer et al., "Cryoballoon Ablation of Pulmonary Veins for Paroxysmal Atrial Fibrillation", Journal of the American College of Cardiology, roč. 61, č. 16, s. 1713-1723, dub. 2013, doi: 10.1016/j.jacc.2012.11.064.
D. L. Packer et al., "Effect of Catheter Ablation vs Antiarrhythmic Drug Therapy on Mortality, Stroke, Bleeding, and Cardiac Arrest Among Patients With Atrial Fibrillation: The CABANA Randomized Clinical Trial", JAMA, roč. 321, č. 13, s. 1261, dub. 2019, doi: 10.1001/jama.2019.0693. 14 pages.

(56) References Cited

OTHER PUBLICATIONS

D. Miklavc, "A validated model of in vivo electric eld distribution in tissues for electrochemotherapy and for DNA electrotransfer for gene therapy", Biochimica et Biophysica Acta, s. 11. 2000. 11 pages.
D. Miklavčičet al., "The effect of high frequency electric pulses on muscle contractions and antitumor efficiency in vivo for a potential use in clinical electrochemotherapy", Bioelectrochemistry, roč. 65, č. 2, s. 121-128, úno. 2005, doi: 10.1016/j.bioelechem.2004.07.004.
D. Miklavčič, Ed., Handbook of Electroporation. Cham: Springer International Publishing, 2017. doi: 10.1007/978-3-319-32886-7. 2956 pages.
D. R. Tomlinson a J. Mandrola, "Pulsed Field Ablation for Persistent Atrial Fibrillation (PersAFOne)", Journal of the American College of Cardiology, ročč. 76, . 9, s. 1081-1083, zář. 2020, doi: 10.1016/j.jacc.2020.07.032.
D. W. Hunter, G. Kostecki, J. M. Fish, J. A. Jensen, a H. Tandri, "In Vitro Cell Selectivity of Reversible and Irreversible: Electroporation in Cardiac Tissue", Circ: Arrhythmia and Electrophysiology, roč. 14, č. 4, dub. 2021, doi: 10.1161/CIRCEP. 120.008817. 9 pages.
D. W. Hunter, H. Tandri, H. Halperin, L. Tung, a R. D. Berger, "Tetanizing prepulse: A novel strategy to mitigate implantable cardioverter-defibrillator shock-related pain", Heart Rhythm, roč. 13, č. 5, s. 1142-1148, kvě. 2016, doi: 10.1016/j.hrthm.2015.12.047.
Dukkipati Srinivas R. et al., "Visual Balloon-Guided Point-by-Point Ablation", Circulation: Arrhythmia and Electrophysiology, roč. 3, č. 3, s. 266-273, čer. 2010, doi: 10.1161/CIRCEP.109.933283.
E. Guenther, N. Klein, P. Mikus, M. K. Stehling, a B. Rubinsky, "Electrical breakdown in tissue electroporation", Biochemical and Biophysical Research Communications, roč. 467, č. 4, s. 736-741, lis. 2015, doi: 10.1016/j.bbrc.2015.10.072.
E. Maor, "Pulsed electric fields for cardiac ablation and beyond: A state of the art review", s. 30, 2018.
E. P. Gerstenfeld a J. Michele, "Pulmonary vein isolation using a compliant endoscopic laser balloon ablation system in a swine model", J Interv Card Electrophysiol, roč. 29, č. 1, s. 1-9, říj. 2010, doi: 10.1007/s10840-010-9501-9.
E. P. Gerstenfeld, "Catheter Ablation of Atrial Fibrillation Using Electroporation", JACC: Clinical Electrophysiology, roč. 4,č. 8, s. 996-998, srp. 2018, doi: 10.1016/j.jacep.2018.05.020.
E. W. Lee, C. Chen, V. E. Prieto, S. M. Dry, C. T. Loh, a S. T. Kee, "Advanced Hepatic Ablation Technique for Creating Complete Cell Death: Irreversible Electroporation", Radiology, roč. 255, č. 2, s. 426-433, kvě. 2010, doi: 10.1148/radiol.10090337.
F. Alejandro Gómez, L. E. Ballesteros, L. Stella Cortés, F. Alejandro Gómez, L. E. Ballesteros, a L. Stella Cortés, "Morphological description of great cardiac vein in pigs compared to human hearts", Brazilian Journal of Cardiovascular Surgery, roč. 30, č. 1, s. 63-69, úno. 2015, doi: 10.5935/1678-9741.20140101.
F. Argus, B. Boyd, a S. M. Becker, "Electroporation of tissue and cells: A three-equation model of drug delivery", Computers in Biology and Medicine, roč. 84, s. 226-234, kvě. 2017, doi: 10.1016/j.compbiomed.2017.04.001.
F. Bourier et al., "High-power short-duration versus standard radiofrequency ablation: Insights on lesion metrics", J Cardiovasc Electrophysiol, roč. 29, č. 11, s. 1570-1575, lis. 2018, doi: 10.1111/jce.13724.
F. Bourier, "In-silico analysis of the relation between conventional and high-power short-duration RF ablation settings and resulting lesion metrics", J Cardiovasc Electrophysiol, dub. 2020. 23 pages.
F. D. Ramirez, V. Y. Reddy, R. Viswanathan, M. Hocini, a P. Jaïs, "Emerging Technologies for Pulmonary Vein Isolation", Circ Res, roč. 127, č. 1, s. 170-183, er. 2020, doi: 10.1161/CIRCRESAHA.120.316402.
F. H. M. Wittkampf et al., "Myocardial Lesion Depth With Circular Electroporation Ablation", Circ Arrhythm Electrophysiol, roč. 5, č. 3, s. 581-586, čer. 2012, doi: 10.1161/CIRCEP.111.970079.
F. H. M. Wittkampf, R. van Es, a K. Neven, "Electroporation and its Relevance for Cardiac Catheter Ablation", JACC: Clinical Electrophysiology, roč. 4, č. 8, s. 977-986, srp. 2018, doi: 10.1016/j.jacep.2018.06.005.
F. H. Wittkampf et al., "Feasibility of Electroporation for the Creation of Pulmonary Vein Ostial Lesions", Journal of Cardiovascular Electrophysiology, roč. 22, č. 3, s. 302-309, bře. 2011, doi: 10.1111/j.1540-8167.2010.01863.x.
F. Ren et al., "Electrical and thermal analyses of catheter-based irreversible electroporation of digestive tract", International Journal of Hyperthermia, roč. 36, č. 1, s. 853-866, led. 2019, doi: 10.1080/02656736.2019.1646928.
Farapulse, "Pefcat II , CIP". 2019 . . . [Online]. 70 pages. Dostupné z: https://clinicaltrials.gov/ProvidedDocs/08/NCT04170608/Prot_SAP_000.pdf.
Farapulse, "The IMPULSE Study: A Safety and Feasibility Study of the FARAPULSE Endocardial Ablation System to Treat Atrial Fibrillation—Protocol No. CS0188, Revision D". 2019. 66 pages.
FDA, "SSED P030031B BSW NaviStar/Celsius Thermocool". 2004. Viděno: 28. duben 2021. 22 pages. [Online]. Dostupné z: https://www.accessdata.fda.gov/cdrh_docs/pdf3/P030031B.pdf.
G. C. Ganzenmüller, S. Hiermaier, a M. O. Steinhauser, "Shock-wave induced damage in lipid bilayers: a dissipative particle dynamics simulation study", Soft Matter, roč. 7, č. 9, s. 4307, 2011, doi: 10.1039/c0sm01296c.
G. Caluori et al., "AC Pulsed Field Ablation Is Feasible and Safe in Atrial and Ventricular Settings: A Proof-of-Concept Chronic Animal Study", Front Bioeng Biotechnol, roč. 8, pro. 2020, doi: 10.3389/fbioe.2020.552357. 14 pages.
G. Long et al., "Histological and Finite Element Analysis of Cell Death due to Irreversible Electroporation", Technol Cancer Res Treat, roč. 13, č. 6, s. 561-569, pro. 2014, doi: 10.7785/tcrtexpress.2013.600253.
G. Long, P. K. Shires, D. Plescia, S. J. Beebe, J. F. Kolb, a K. H. Schoenbach, "Targeted Tissue Ablation With Nanosecond Pulses", IEEE Trans. Biomed. Eng., roč. 58, č. 8, s. 2161-2167, srp. 2011, doi: 10.1109/TBME.2011.2113183.
G. O. Hartzler, L. V. GiorgiD, A. M. Diehl, a W. R. Hamaker, "Right coronary spasm complicating electrode catheter ablation of a right lateral accessory pathway", Journal of the American College of Cardiology, roč. 6, č. 1, s. 250-253, čvc. 1985, doi: 10.1016/S0735-1097(85)80285-0.
G. Onik, P. Mikus, a B. Rubinsky, "Irreversible electroporation: implications for prostate ablation", Technol Cancer Res Treat, roč. 6, č. 4, s. 295-300, srp. 2007, doi: 10.1177/153303460700600405.
G. P. Tolstykh, "Activation of intracellular phosphoinositide signaling after a single 600 nanosecond electric pulse", s. 7, 2013.
G. R. Meininger et al., "Initial Experience with a Novel Focused Ultrasound Ablation System for Ring Ablation Outside the Pulmonary Vein", s. 8, 2003.
G. S. Munavalli et al., "Safety and Efficacy of Nanosecond Pulsed Electric Field Treatment of Sebaceous Gland Hyperplasia", Dermatol Surg, roč. 46, č. 6, s. 803-809, čer. 2020, doi: 10.1097/DSS.0000000000002154.
Granot et al., In vivo imaging of irreversible electroporation by measn of EIT, s. 18., 2009.
H. Cochet et al., "Pulsed field ablation selectively spares the oesophagus during pulmonary vein isolation for atrial fibrillation", EP Europace, č. euab090, kvě. 2021, doi: 10.1093/europace/euab090. 9 pages.
H. D. Yavin, K. Higuchi, J. Sroubek, A. Younis, I. Zilberman, a E. Anter, "Pulsed-Field Ablation in Ventricular Myocardium Using a Focal Catheter", Circulation: Arrhythmia and Electrophysiology, roč. 14, č. 9, s. e010375, zář. 2021, doi: 10.1161/CIRCEP.121.010375. 10 pages.
H. Hayashi et al., "Left atrial wall thickness and outcomes of catheter ablation for atrial fibrillation in patients with hypertrophic cardiomyopathy", J Interv Card Electrophysiol, roč. 40, č. 2, s. 153-160, srp. 2014, doi: 10.1007/s10840-014-9894-y.
H. J. Phillips, "Dye Exclusion Tests for Cell Viability", in Tissue Culture, Elsevier, 1973, s. 406-408. doi: 10.1016/B978-0-12-427150-0.50101-7.

(56) References Cited

OTHER PUBLICATIONS

H. Kottkamp et al., “Global multielectrode contact-mapping plus ablation with a single catheter in patients with atrial fibrillation: Global AF study”, J Cardiovasc Electrophysiol, roč. 30, č. 11, s. 2248-2255, lis. 2019, doi: 10.1111/jce.14172.

H. Kottkamp, F. Moser, A. Rieger, D. Schreiber, C. Pönisch, a M. Trofin, “Global multielectrode contact mapping plus ablation with a single catheter: Preclinical and preliminary experience in humans with atrial fibrillation: Kottkamp et al.”, J Cardiovasc Electrophysiol, roč. 28, č. 11, s. 1247-1256, lis. 2017, doi: 10.1111/jce.13310.

H. Lehrmann et al., “Near-Fatal Coronary Artery Spasm During Cryoballoon Pulmonary Vein Isolation: An Unreported Complication”, Circ: Arrhythmia and Electrophysiology, roč. 7, č. 6, s. 1273-1274, pro. 2014, doi: 10.1161/CIRCEP.114.001788.

H. Mori et al., “The influence of the electrodes spacing of a mapping catheter on the atrial voltage substrate map”, Journal of Cardiology, roč. 72, č. 5, s. 434-442, lis. 2018, doi: 10.1016/j.jcc.2018.04.012.

H. T. Tien a A. Ottova, “The Bilayer Lipid Membrane ž BLM/ Under Electrical Fields”, roč. 10, č. 5, s. 11, 2003.

H. Yavin et al., “Circular Multielectrode Pulsed Field Ablation Catheter Lasso Pulsed Field Ablation”, Circulation: Arrhythmia and Electrophysiology, roč. 14, č. 2, s. e009229, úno. 2021, doi: 10.1161/CIRCEP.120.009229. 9 pages.

H. Yavin et al., “Pulsed Field Ablation Using a Lattice Electrode for Focal Energy Delivery: Biophysical Characterization, Lesion Durability, and Safety Evaluation”, Circ: Arrhythmia and Electrophysiology, roč. 13, č. 6, s. e008580, čer. 2020, doi: 10.1161/CIRCEP.120.008580. 10 pages.

HCL Technologies, “An Overview of the Plastic Material Selection Process for Medical Devices,” 2013, 26 pages.

Hoffman, et al., “Radiopacity assessment fo neurovascular implants,” Current Directions in Biomedical Engineering, 2 (1) 533-536, 2016.

Howard Brian et al., “Reduction in Pulmonary Vein Stenosis and Collateral Damage With Pulsed Field Ablation Compared With Radiofrequency Ablation in a Canine Model”, Circulation: Arrhythmia and Electrophysiology, roč. 13, č. 9, s. e008337, zář. 2020, doi: 10.1161/CIRCEP.120.008337.

I. Kaminska et al., “Electroporation-induced changes in normal immature rat myoblasts (H9C2)”, gpb, roč. 31, č. 01, s. 19-25, 2012, doi: 10.4149/gpb_2012_003.

I. Kawamura et al., “Does pulsed field ablation regress over time? A quantitative temporal analysis of pulmonary vein isolation”, Heart Rhythm, s. S154752712100182X, úno. 2021, doi: 10.1016/j.hrthm.2021.02.020.

I. Kawamura et al., “How does the level of pulmonary venous isolation compare between pulsed field ablation and thermal energy ablation (radiofrequency, cryo, or laser)?”, EP Europace, č. euab150, čer. 2021, doi: 10.1093/europace/euab150. 10 pages.

J. A. Berkenbrock, G. Brasil Pintarelli, A. de Castro Antônio Junior, a D. O. H. Suzuki, “Verification of Electroporation Models Using the Potato Tuber as In Vitro Simulation”, J. Med. Biol. Eng., roč. 39, č. 2, s. 224-229, dub. 2019, doi: 10.1007/s40846-018-0408-8.

J. D. Kaufman et al., “High-Frequency Irreversible Electroporation Using 5,000-V Waveforms to Create Reproducible 2- and 4-cm Ablation Zones—A Laboratory Investigation Using Mechanically Perfused Liver”, Journal of Vascular and Interventional Radiology, roč. 31, č. 1, s. 162-168.e7, led. 2020, doi: 10.1016/j.jvir.2019.05.009.

J. Dermol-Černe, T. Batista Napotnik, M. Reberšek, a D. Miklavčič, “Short microsecond pulses achieve homogeneous electroporation of elongated biological cells irrespective of their orientation in electric field”, Sci Rep, roč. 10, č. 1, s. 9149, pro. 2020, doi: 10.1038/s41598-020-65830-3.

J. F. Edd, “In vivo results of a new focal tissue ablation technique irreversible electroporation.pdf”, IEEE Transactions on Biomedical Engineering, roč. 2006, 2006. 7 pages.

J. F. Edd, L. Horowitz, R. V. Davalos, L. M. Mir, a B. Rubinsky, “In Vivo Results of a New Focal Tissue Ablation Technique: Irreversible Electroporation”, IEEE Trans. Biomed. Eng., roč. 53, č. 7, s. 1409-1415, čvc. 2006, doi: 10.1109/TBME.2006.873745.

J. G. Skeate, D. M. Da Silva, E. Chavez-Juan, S. Anand, R. Nuccitelli, a W. M. Kast, “Nano-Pulse Stimulation induces immunogenic cell death in human papillomavirus-transformed tumors and initiates an adaptive immune response”, PLoS One, roč. 13, č. 1, s. e0191311, led. 2018, doi: 10.1371/journal.pone.0191311. 17 pages.

J. Gehl, T. Skovsgaard, a L. M. Mir, “Vascular reactions to in vivo electroporation: characterization and consequences for drug and gene delivery”, Biochimica et Biophysica Acta (BBA)—General Subjects, roč. 1569, č. 1-3, s. 51-58, led. 2002, doi: 10.1016/S0304-4165(01)00233-1.

J. Hughes a G. Gobe, “Identification and quantification of apoptosis in the kidney using morphology, biochemical and molecular markers”, Nephrology, roč. 12, č. 5, s. 452-458, 2007, doi: https://doi.org/10.1111/j.1440-1797.2007.00854.x.

J. M. Lee et al., “Characterization of irreversible electroporation on the stomach: A feasibility study in rats”, Sci Rep, ročč. 9, . 1, s. 9094, pro. 2019, doi: 10.1038/s41598-019-45659-1.

Lu Zhibing, “心房颤动的自主神 经机制研究 (Autonomic Mechanism for Atrial Fibrillation)”, Wuhan University Doctor’s Thesis, Apr. 2009, 204 pages.

Lüderitz, Berndt. ‘Historical Perspectives on Interventional Electrophysiology’. Journal of Interventional Cardiac Electrophysiology, vol. 9, No. 2, Oct. 2003, pp. 75-83, doi: 10.1023/A:1026226816096.

Luke Zhao, Adam Rasko, Christian Drescher, et al., “Preliminary Validation of Electroporation-Electrolysis (E2) for Cardiac Ablation Using a Parameterisable In-Vivo Model”, 2019 (pp. 1-5).

M. M. Scheinman, et al., “Catheter-induced ablation of the atrioventricular junction to control refractory supraventricular arrhythmias”, JAMA, vol. 248, No. 7, p. 852, Aug. 1982.

M2 Presswire, “Research Report on the $6.8 billion U.S. Market for Cardiac Rhythm Managment, Electrophysiology and Ablation”, M2 Presswire, 2013 (pp. 1-1).

Ma Changsheng, “心房颤动导管消 融：挑战与展望 (Catheter ablation of atrial fibrillation: challenges and prospects)”, 2015 (pp. 1-6).

Ma Changsheng, Dong Jianzeng, Liu Xingpeng, 心房颤动的经导管消融治疗 2005 (pp. 1-6).

Ma Fusheng, 犬心外膜与心内 膜侧环肺静脉消融治疗心房颤动的对比研究 Peking Union Medical College Doctoral Thesis, May 2008, 206 pages.

Mali, Barbara, et al. ‘The Effect of Electroporation Pulses on Functioning of the Heart’. Medical & Biological Engineering & Computing, vol. 46, No. 8, Aug. 2008, p. 745, doi: 10.1007/s11517-008-0346-7.

Mao Wei, Chen Junzhu, Shi Weixing, 从心导管介入技术的发展看现代技术革命", 医学哲学 (Medicine and Philosophy), 2001, 6 pages.

Massimo Grimaldi, Antonio Di Monaco, Tara Gomez, et al., “Subchronic Versus Chronic Safety Assessment of a Circular Irreversible Electroporation Catheter Design and a Pulse Field Ablation Generator”, Heart Rhythm, 2021 (pp. 1-1).

Miklavčič, Damijan. ‘Cardiac Ablation by Electroporation’. JACC: Clinical Electrophysiology, vol. 4, No. 11, Nov. 2018, pp. 1481-1482, doi: 10.1016/j.jacep.2018.09.014.

Nakagawa, Hiroshi, and Warren M. Jackman. ‘Electroporation (Revival of Direct Current Ablation): New Approach for Increasing Epicardial Ablation Safety in Close Proximity to a Coronary Artery’. Circulation: Arrhythmia and Electrophysiology, vol. 7, No. 5, Oct. 2014, pp. 779-780, doi: 10.1161/CIRCEP.114.002255.

Nakagawa, Hiroshi, et al. ‘Effects of Contact Force on Lesion Size During Pulsed Field Catheter Ablation: Histochemical Characterization of Ventricular Lesion Boundaries’. Circulation: Arrhythmia and Electrophysiology, vol. 17, No. 1, Jan. 2024, doi: 10.1161/CIRCEP.123.012026 (pp. 1-13).

Neven, K., et al. ‘Preservation of Luminal Coronary Artery Diameter after Epicardial Irreversible Electroporation Ablation’. European Heart Journal, vol. 34, No. suppl 1, Aug. 2013, p. P518-P518, doi: 10.1093/eurheartj/eht307. P518.

(56) References Cited

OTHER PUBLICATIONS

Neven, Kars, Vincent Van Driel, Harry Van Wessel, Rene Van Es, Bastiaan Du Pré, et al. 'Safety and Feasibility of Closed Chest Epicardial Catheter Ablation Using Electroporation'. Circulation: Arrhythmia and Electrophysiology, vol. 7, No. 5, Oct. 2014, pp. 913-919, doi: 10.1161/CIRCEP.114.001607.
Neven, Kars, Vincent Van Driel, Harry Van Wessel, Rene Van Es, Pieter A. Doevendans, et al. 'Epicardial Linear Electroporation Ablation and Lesion Size'. Heart Rhythm, vol. 11, No. 8, Aug. 2014, pp. 1465-1470, doi: 10.1016/j. hrthm.2014.04.031.
Ngo, Linh, et al. 'Utilisation and Safety of Catheter Ablation of Atrial Fibrillation in Public and Private Sector Hospitals'. BMC Health Services Research, vol. 21, No. 1, Dec. 2021, p. 883, doi: 10.1186/s12913-021-06874-7.
Nikolski, Vladimir P., and Igor R. Efimov. 'Electroporation of the Heart'. EP Europace, vol. 7, No. s2, Jan. 2005, pp. S146-S154, doi: 10.1016/j.eupc.2005.04.011.
Ollitrault, Pierre, et al. 'Vascular Entrapment of a Multipolar Basket Catheter (OrionTM ) during Catheter Ablation'. Journal of Cardiovascular Electrophysiology, vol. 32, No. 2, Feb. 2021, pp. 545-546, doi: 10.1111/jce.14780.
Pedretti, Stefano, et al. 'A Case of Premature Ventricular Contractions, Ventricular Tachycardia, and Arrhythmic Storm Induced by Right Ventricular Pacing during Cardiac Resynchronization Therapy: Electrophysiological Mechanism and Catheter Ablation'. Journal of Arrhythmia, vol. 31, No. 6, Dec. 2015, pp. 401-405, doi: 10.1016/j.joa.2015.06.002.
Petr Neuzil, Blake Morrow, Charles Eggert, et al., "Pulsed Field Ablation for Paroxysmal Atrial Fibrillation Using an Optimized Biphasic Waveform: Recurrence of Atrial Arrhythmias", Heart Rhythm, vol. 18, No. 8, pp. S10, Aug. 2021.
Qu Baiming, 三维电场导航系 统非透视引导下导 管消融治疗阵发性 室上性心动过速的 临床研究 (pp. 1-8).
Rong Bing, "Carto 及单根环状电极指 导下导管消融治疗 心房颤动临床疗效 分析 (Carto and Single Circular Mapping Catheter to Guide the Catheter Ablaton of Artial Fibrillation)", Shandong University Master's Thesis, May 2010 (pp. 1-47).
Sánchez Muñoz, Juan José, et al. 'Catheter Ablation of Ventricular Arrhythmias in Left Ventricular Noncompaction Cardiomyopathy'. Heart Rhythm, vol. 18, No. 4, Apr. 2021, pp. 545-552, doi: 10.1016/j.hrthm.2020.12.014.
Tao Hailong and Ma Changsheng, " 房颤器械治疗新 进展 (Advances in the Treatment of AF Devices)", vol. 24, No. 5, pp. 5-7, 2009.
Verma, Atul, Lucas Boersma, et al. 'First-in-Human Experience and Acute Procedural Outcomes Using a Novel Pulsed Field Ablation System: The PULSED AF Pilot Trial'. Circulation: Arrhythmia and Electrophysiology, vol. 15, No. 1, Jan. 2022, p. e010168, doi: 10.1161/CIRCEP.121.010168 (pp. 1-10).
Verma, Atul, Samuel J. Asivatham, et al. 'Primer on Pulsed Electrical Field Ablation: Understanding the Benefits and Limitations'. Circulation: Arrhythmia and Electrophysiology, vol. 14, No. 9, Sep. 2021, doi: 10.1161/CIRCEP.121.010086 (pp. 1-16).
Viswanathan, Karthik, et al. 'Evaluation of a Novel High-Resolution Mapping System for Catheter Ablation of Ventricular Arrhythmias'. Heart Rhythm, vol. 14, No. 2, Feb. 2017, pp. 176-183, doi: 10.1016/j.hrthm.2016.11.018.
Vivek Y. Reddy, Ante Anic, Jacob Koruth, et al., "Pulsed Field Ablation in Patients With Persistent Atrial Fibrillation", J Am Coll Cardiol, vol. 76, No. 9, pp. 1068-1080, Sep. 2020.
Vivek Y. Reddy, Jacob Koruth, Pierre Jais, et al., "Ablation of Atrial Fibrillation With Pulsed Electric Fields: An Ultra-Rapid, Tissue-Selective Modality for Cardiac Ablation", JACC: Clinical Electrophysiology, vol. 4, No. 8, pp. 987-995, Aug. 2018.
Wang Bin, " 快速肺静脉起搏 持续性心房颤动犬 模型的建立及其电 生理学特征的研究 (Establishment of a Canine Model of Persistent Atrial Fibrillation by Chronic Rapid Pulmonary Vein Pacing and the Study of the Electrophysiology about the Model)", Fourth Military Medical University Master's Thesis, May 2008, 132 pages.
Wang Xinhua and Liu Xu, 心房颤动经导管 消融治疗方法的历 史演变概述 , 2005, 6 pages.
Wang Yuru, 经皮冷冻球囊导 管消融治疗阵发性 心房颤动患者的术 中护理 (pp. 1-6).
Wojtaszczyk, Adam, et al. 'Irreversible Electroporation Ablation for Atrial Fibrillation'. Journal of Cardiovascular Electrophysiology, vol. 29, No. 4, Apr. 2018, pp. 643-651, doi: 10.1111/jce.13454.
Xiao Mingyang, 心房颤动导管消融 成功率与肺静脉结 构的关系 Chongqing Medical University Master's Degree Thesis, May 2017 (pp. 1-64).
Xie, Fei, and Christian W. Zemlin. 'Effect of Twisted Fiber Anisotropy in Cardiac Tissue on Ablation with Pulsed Electric Fields'. PLOS ONE, edited by Vladimir E. Bondarenko, vol. 11, No. 4, Apr. 2016, p. e0152262, doi: 10.1371/journal.pone.0152262.
Xie, Fei, et al. 'Ablation of Myocardial Tissue With Nanosecond Pulsed Electric Fields'. PLOS ONE, edited by Diego Fraidenraich, vol. 10, No. 12, Dec. 2015, p. e0144833, doi: 10.1371/journal.pone.0144833.
Xiong Qingsong, "持续性房颤合并 心衰患者导管消融 对比药物治疗对心 功能影响的Meta 分析 (Meta-analysis of the effect of catheter ablation versus medical therapy on cardiac function in patients with persistent atrial fibrillation and heart failure)", Chongqing Medical University Master's Thesis, May 2019 (pp. 1-60).
Xu Kai and Liu Xu, "心房颤动导管消 融治疗进展 (Progress in the treatment of atrial fibrillation by catheter ablation)",上 海医药 (Shanghai Medical & Pharmaceutical Journal), vol. 16, pp. 6-9, 2014.
Yang Pingzhen, "心包压塞的识别 与处理", 江西医药 (Jiangxi Medical Journal), vol. 47, No. 5, May 2012 (pp. 1-6).
Yang Xiaomin, Chen Yao, Guo Qinghua, et al.,"运用磁导航行心 房颤动消融与手动 消融的比较分析及 护理", 护士进 修杂 志 (Journal of Nurses Training), vol. 29, No. 15, pp. 1374-1378, Aug. 2014.
Ye Xuying, "脉冲电场消融治 疗房颤的效应与机 制研究 (Study on effect and mechanism of pulsed electric field ablation for atrial fibrillation)", Tianjin Medical University Doctoral Dissertation, Nov. 2021 (pp. 1-162).
Yue Chen, "VisiTag 指导下持续性房颤 导管消融的临床研 究 (Clinical study on catheter ablation of persistent atrial fibrillation under the guidance of VisiTag)", WanNan Medical College Master's Dissertation, Mar. 2020 (pp. 1-102).
Zager, Yaniv, et al. 'Optimization of Irreversible Electroporation Protocols for In-Vivo Myocardial Decellularization'. PLOS ONE, edited by Maria Rosaria Scarfi, vol. 11, No. 11, Nov. 2016, p. e0165475, doi: 10.1371/journal.pone.0165475 (pp. 1-15).
Zhang Daoliang, "A study on the mechanism of atrial fibrosis: changes of the MAPKs/TGF-β1/TRAF6 signaling pathway in patients with atrial fibrillation", Shanghai Jiao Tong University Doctoral Dissertation, Apr. 2015, 188 pages.
Zhou Yuanfeng, "阵发性房颤的环 肺静脉电隔离单环 消融及双环消融术 比较 (Comparison of circumferential pulmonary vein bicyclo-ablation with monocyclic ablation in paroxysmal atrial fibrillation therapy)", Nanchang University Master's Thesis, Jun. 2011 (pp. 1-64).
佚名.联合左心耳封 堵与导管消融治疗 卒中高危的阵发性 心房颤动[J].中国心 脏起搏与心电生理 杂志 2016(3):5, doi: 10.13333/j.cnki.cjcpe.2016.03.004.
刘启明. '器质性心 脏病室性心动过速 导管消融治疗进展'. 心血管病学进展 vol. 32, No. 03, 2011, p. 297, doi: 10.3969/j.issn.1004-3934.2011.03.002.
吴立群.心房颤动的 现代诊断及导管消 融治疗进展认识[J]. 诊断学理论与实践 2015(3):3, doi: 10.16150/j.1671-2870.2015.03.002.
Abdulsalam, Nashwa, and Nazem Akoum. 'Esophageal Injury and Progression to Atrial-Esophageal Fistula in Catheter Ablation for

(56) References Cited

OTHER PUBLICATIONS

Atrial Fibrillation'. Current Cardiovascular Risk Reports, vol. 15, No. 10, Oct. 2021, p. 20, doi: 10.1007/s12170-021-00681-9.
Aguilar, Martin, et al. 'Catheter Ablation of Ventricular Tachycardia in Patients with Prior Cardiac Surgery: An Analysis from the International VT Ablation Center Collaborative Group'. Journal of Cardiovascular Electrophysiology, vol. 32, No. 2, Feb. 2021, pp. 409-416, doi: 10.1111/jce.14849.
Althoff, Till F., and Lluís Mont. 'Novel Concepts in Atrial Fibrillation Ablation—Breaking the Trade-off between Efficacy and Safety'. Journal of Arrhythmia, vol. 37, No. 4, Aug. 2021, pp. 904-911, doi: 10.1002/joa3.12592.
Anic, Ante, et al. 'Pulsed Field Ablation: A Promise That Came True'. Current Opinion in Cardiology, vol. 36, No. 1, Jan. 2021, pp. 5-9, doi: 10.1097/HCO.0000000000000810.
Avazzadeh, Sahar, et al. 'Establishing Irreversible Electroporation Electric Field Potential Threshold in A Suspension In Vitro Model for Cardiac and Neuronal Cells'. Journal of Clinical Medicine, vol. 10, No. 22, Nov. 2021, p. 5443, doi: 10.3390/jcm10225443.
Barnett, Adam S., et al. 'Recent Advances in Lesion Formation for Catheter Ablation of Atrial Fibrillation'. Circulation: Arrhythmia and Electrophysiology, vol. 9, No. 5, May 2016, p. e003299, doi: 10.1161/CIRCEP.115.003299.
Belalcazar, Andres. 'Safety and Efficacy Aspects of Pulsed Field Ablation Catheters as a Function of Electrode Proximity to Blood and Energy Delivery Method'. Heart Rhythm O2, vol. 2, No. 6, Dec. 2021, pp. 560-569, doi: 10.1016/j.hroo.2021.10.004.
Boersma, L., et al. 'Therapeutic Options for Patients with Advanced Atrial Fibrillation: From Lifestyle and Medication to Catheter and Surgical Ablation'. Netherlands Heart Journal, vol. 28, No. S1, Aug. 2020, pp. 13-18, doi: 10.1007/s12471-020-01447-5.
Brian Howard, David E. Haines, Atul Verma, et al., "Reduction in Pulmonary Vein Stenosis and Collateral Damage With Pulsed Field Ablation Compared With Radiofrequency Ablation in a Canine Model", Circulation: Arrhythmia and Electrophysiology, 2020 (pp. 1-11).
Cao Wancai, Tian Yanfang, Huang Minghui, et al., Lasso "Lasso环状标测电极导管指导 心房颤动持续过程 中心脏大静脉电隔 离", 临床心血管病杂志 (Journal of Clinical Cardiology), vol. 21, No. 5, May 2005 (pp. 1-6).
Chance Witt, Christopher Li, Tyra A. Witt, et al., "Electroporative Myocardial Ablation Utilizing a Non-contact, Virtual Electrode: Proof of Concept in Ex-vivo and In-vivo Canine Hearts", Heart Rhythm Society Conference, Chicago, May 2017, 1 page.
Chen Jianhua, Lin Chaogui, Zhang Feilong, Chen Lianglong, 电解剖标测系统加 单环状电极导管指 导环肺静脉 前庭线性消融电隔离肺静脉 治疗心房颤动 2007, pp. 234-238.
Chen Xuewen, Chao Jiangang, Zhang Yan, et al., "基于人在回路感知的房颤导管消融训 练器研究 (Training Simulator of Catheter Ablation for Atrial Fibrillation Based on Perception of Human in Loop)", 航天医学与医学工程 (Space Medicine & Medical Engineering), vol. 26, No. 2, pp. 109-114, Apr. 2013.
Cirasa, Arianna, et al. 'Catheter Ablation of Atrial Fibrillation in Heart Failure: From Evidences to Guidelines'. Current Heart Failure Reports, vol. 18, No. 3, Jun. 2021, pp. 153-162, doi: 10.1007/s11897-021-00508-z.
Deng Jiaqiang, Zhong Guoqiang, Zhu Liguang, et al., 心房扑动经导管消融治疗的临 床分析 2008 (pp. 1-4).
Deodhar, Ajita, et al. 'Irreversible Electroporation Near the Heart: Ventricular Arrhythmias Can Be Prevented With ECG Synchronization'. American Journal of Roentgenology, vol. 196, No. 3, Mar. 2011, pp. W330-W335, doi: 10.2214/AJR. 10.4490.
DeSimone, Christopher V., et al. 'Electroporation: Past and Future of Catheter Ablation'. Circulation: Arrhythmia and Electrophysiology, vol. 7, No. 4, Aug. 2014, pp. 573-575, doi: 10.1161/CIRCEP.114.001999.
Dong Jianzeng, 心房颤动的 导管消融 (2011) 6 pages.
Dong Jianzeng, et al., "Catheter for Atrial Fibrillation", 2010 (pp. 1-6).
Dong Jianzeng, Ma Changsheng, Liu Xingpeng, et al., 三维标测系统和 单环状标测导管 指示下环肺静脉线性消融电学隔 离肺静脉 方法学评价 2005 (pp. 1-10).
Dukkipati, Srinivas R., et al. 'Catheter Ablation of Ventricular Tachycardia in Structurally Normal Hearts'. Journal of the American College of Cardiology, vol. 70, No. 23, Dec. 2017, pp. 2909-2923, doi: 10.1016/j.jacc.2017.10.031.
Eyal Heller, Tomas Garcia-Sanchez, Yonatan Moshkovits, et al., "Comparing High-Frequency With Monophasic Electroporation Protocols in an In Vivo Beating Heart Model", JACC: Clinical Electrophysiology, vol. 7, No. 8, pp. 959-964, Aug. 2021.
Folprecht, Martin, et al. 'Compact High-Voltage AC Generator with Pulse Transformer for High-Frequency Irreversible Electroporation (H-FIRE)'. Electronics, vol. 10, No. 23, Nov. 2021, p. 2898, doi: 10.3390/electronics10232898.
Gerry C. Kaye (Translated by Tang Kai, Zhang Jiexiao), 介入心脏病学知识(一)__经皮 介入电生理学 英国医学杂志中 文版 (British Medical Journal Chinese Edition) 8 pages.
Guang Xuefeng, "慢性持续 性房颤导管消融 评价", 中国医刊 (Chinese Journal of Medicine), vol. 50, No. 10, pp. 51, 2015.
Gunawardene, Melanie A., et al. 'Coronary Spasm During Pulsed Field Ablation of the Mitral Isthmus Line'. JACC: Clinical Electrophysiology, vol. 7, No. 12, Dec. 2021, pp. 1618-1620, doi: 10.1016/j.jacep.2021.08.016.
Hagai D. Yavin, Koji Higuchi, Jakub Sroubek, et al., "Pulsed-Field Ablation in Ventricular Myocardium Using a Focal Catheter: The Impact of Application Repetition on Lesion Dimensions", Circulation: Arrhythmia and Electrophysiology, 2021 (pp. 1-10).
Han Bing, Luo Bingshuan, Li Weidong, et al., "网篮电极导管临床使用的初步经验", 中华心律失 常学杂志 (Chinese Journal of Cardiac Arrhythmias), vol. 5, No. 6, p. 361, Dec. 2001.
Hou Yuemei, 临床心脏电 生理标测技 术及应用现状 新疆医科大学第一临床学院心血 管病专科医院 (Cardiovascular Hospital, The First Hospital of Xinjiang Medical University), 2004 (pp. 1-16).
Hsu J., Gibson D., Banker R., et al., "Characterization of atrial lesion safety and efficacy utilizing a circular catheter and the IRE generator with an in vivo porcine model", Europace, vol. 23, Supplement 3, pp. iii103, 2021.
Huang Congxin, Wang Fangzheng, Zhang Yi, et al., "中国经导管消融治疗心房颤动注册 研究", 中华医学 会心电生理和起 搏分会 (Chinese Society of Pacing and Electrophysiology) 14 pages.
Huang Dejia, Jiang Jian, Wen Shan, et al., "经冠状窦消融后间隔房室旁路 (Radiofrequency ablation of posteroseptal accessory pathway using coronary sinus approach)", 1996 (pp. 1-8).
Huang Qiang, 心房颤动经导管 消融: 新技术带来的 转变 中国心脏起搏与心 电生理杂志 (Chinese Journal of Cardiac Pacing and Electrophysiology), vol. 25, No. 6, 2011 (pp. 1-8).
Ilaria Cazzoli, Clara Gunturiz-Beltran, Silvia Guarguagli, et al., "Catheter ablation for patients with end-stage complex congenital heart disease or cardiomyopathy considered for transplantation: Trials and tribulations", International Journal of Cardiology, vol. 301, pp. 127-134, 2020.
Jacob S. Koruth, Iwanari Kawamura, Srinivas R. Dukkipati, et al., "Preclinical Assessment of the Feasibility, Safety and Lesion Durability of a Novel "Single-Shot" Pulse Field Ablation Catheter for Pulmonary Vein Isolation", Heart Rhythm, vol. 18, No. 8, Aug. 2021 (pp. 1-2).
Jinback Hong, Mark T. Stewart, Daniel S. Cheek, et al., "Cardiac ablation via electroporation", 31st Annual International Conference of the IEEE EMBS, pp. 3381-3384, Sep. 2009.
Jones, David G., et al. 'Biomarkers in Persistent AF and Heart Failure: Impact of Catheter Ablation Compared with Rate Control'. Pacing and Clinical Electrophysiology, vol. 39, No. 9, Sep. 2016, pp. 926-934, doi: 10.1111/pace.12919.
K. L. Hong, O. Amirana, T. Ransbury, B. Glover, "Acute detection of optical tissue changes in real-time during pulsed field ablation (PFA)", ESC Congress 2020—The Digital Experience, 2020 (pp. 1-1).

(56) References Cited

OTHER PUBLICATIONS

Kang Ningning, 导电球囊电极导管经食管心室起搏的临床应用 Qingdao University Master's Thesis, May 2004 (pp. 1-92).

Koruth, Jacob S., et al. 'Endocardial Ventricular Pulsed Field Ablation: A Proof-of-Concept Preclinical Evaluation'. EP Europace, vol. 22, No. 3, Mar. 2020, pp. 434-439, doi: 10.1093/europace/euz341.

Kuroki, Kenji, et al. 'Ostial Dimensional Changes after Pulmonary Vein Isolation: Pulsed Field Ablation vs Radiofrequency Ablation'. Heart Rhythm, vol. 17, No. 9, Sep. 2020, pp. 1528-1535, doi: 10.1016/j.hrthm.2020.04.040.

L. Maizels, E. Heller, M. Landesberg, et al., "Study and modulation of cardiac electroporation with a novel model utilizing human induced pluripotent stem cells", ESC Congress 2021—The Digital Experience, 2021 (pp. 1-1).

Lavee Jacob, Onik Gary, Mikus Paul, Rubinsky Boris, "A novel nonthermal energy source for surgical epicardial atrial ablation: irreversible electroporation", The Heart Surgery Forum, vol. 10, No. 2, pp. E162-71, 2007.

Li Teng, 接触压力导管在心房颤动导管消融中的应用 国际心血管病杂志 (Int J Cardiovasc Dis), vol. 40, No. 6, Nov. 2013 (pp. 1-6).

Li Teng. 'PentaRay 电极高密度基质标测指导持续性心房颤动导管消融的疗效'.'. 临床内科杂志 vol. 37, No. 06, 2020, p. 433, doi: 10.3969/j.issn.1001-9057.2020.06.012.

Li Yifu, "Hybrid Ablation Therapy for Persistent Atrial Fibrillation", 2015 (pp. 1-2).

Li Zhongjie, 临床心脏电生理检查基础知识 浙江省人民医院心脏电生理室 (pp. 1-24).

Liu Shangzhong, "脉冲电场消融对心肌组织的消融效果实验研究 (Experimental study on the ablation effect of pulsed field ablation on myocardial tissue)", Tianjin Medical University Master's Dissertation, May 2021 (pp. 1-118).

Liu Zheng 流出道室性心律失常的心电图特点和导管消融 Peking Union Medical College Doctoral Dissertation, May 2016 (pp. 1-190).

Loh P., Groen Mha, Taha K., et al., "Pulmonary vein isolation by irreversible electroporation: an efficacy and safety study in 20 patients with atrial fibrillation", Europace, vol. 23, Supplement 3, pp. iii104, 2021.

周一坤. '不可逆电穿孔技术联合导管电极用于组织消融的研究进展'. 中国医疗器械杂志 vol. 44, No. 02, 2020, p. 172, doi: 10.3969/j.issn. 1671-7104.2020.02.016.

孟 旭. '房颤的外科消融治疗进展'. 医学与哲学 vol. 37, No. 12B, 2016, p. 10, doi: 10.12014/j.issn.1002-0772.2016.12b.04.

巢胜吾,樊济海 心室翼状电极缠绕右房内"纤维小梁"一例[J].中国心脏起搏与心电生理杂志, 2014(2):1, doi: 10.13333/j.cnki.cjcpe.2014.02.024.

徐剑刚,唐闽,梁 明,等.脉冲电场消融与细胞电穿孔:从基础到临床[J].中国心脏起搏与心电生理杂志 2022, doi: 10.13333/j.cnki.cjcpe.2022.05.002 (pp. 1-6).

晏彪. '消融导管在起搏器心房电极导线复位中应用价值的探讨'. 中国循环杂志 vol. 00, No. 10, 2015, p. 993, doi: 10.3969/j.issn.1000-3614.2015.10.016.

朱俊. '压力监测导管在心房颤动导管消融治疗中的应用'. 中国介入心脏病学杂志, vol. 23, No. 04, 2015, p. 229, doi: 10.3969/j.issn.1004-8812.2015.04.011.

王传慧. '对心房颤动电复律治疗的认识'. 中国介入心脏病学杂志 vol. 24, No. 04, 2016, p. 221, doi: 10.3969/j.issn.1004-8812.2016.04.009.

王炎. '脉冲电场消融多源性房性心动过速合并心房颤动一例'. 临床内科杂志 vol. 38, No. 11, 2021, p. 776, doi: 10.3969/j.issn.1001-9057.2021.11.017.

聂晶. '不同类型心房颤动导管消融治疗的对比研究'. 中国全科医学杂志 vol. 15, No. 20, 2012, p. 1821, doi: 10.3969/j.issn.1007-9572.2012.06.014.

蒋晨曦. '心房颤动导管消融术后复发峡部依赖折返的电生理特点和成因分析'. 中国介入心脏病学杂志 vol. 00, No. 05, 2014, p. 273, doi: 10.3969/j.issn. 1004-8812.2014.05.001.

袁佳栎,李瑛泽, 莫斌峰,等.脉冲电场对人心室肌细胞的影响[J].中国心脏起搏与心电生理杂志 2021, doi: 10.13333/j.cnki.cjcpe.2021.05.012 (pp. 1-10).

谢瑞芹.心房颤动导管消融的地位和进展[J].临床荟萃 2016, 31(1):4, doi: 10.3969/j.issn.1004-583X.2016.01.005.

谭红伟. '压力感知导管消融治疗心房颤动的效果观察'. 山东医药 vol. 56, No. 17, 2016, p. 44, doi: 10.3969/j.issn.1002-266X.2016.17.015.

赵志宏. '快速心律失常脉冲电场不可逆电穿孔消融治疗研究进展'. 中国医疗器械杂志 vol. 45, No. 05, 2021, p. 517, doi: 10.3969/j.issn.1671-7104.2021.05.010.

路桥,张先林,王洪巨.脉冲场消融在房颤中的应用进展[J].实用心电学杂志 2021, 30(5):6, doi: 10.13308/j.issn.2095-9354.2021.05.005.

郑亚如,王利宏.持续性房颤导管消融治疗研究进展[J].心电与循环 2020, 39(5):7, doi: 10.12124/j.issn.2095-3933.2020.5.2020-4129.

郭雪原,马长生 房颤导管消融新技术和新器械[J].中国医疗设备 2020,35(12):4, doi: 10.3969/j.issn.1674-1633.2020.12.003.

马正科,何智余,姚亚丽.心房颤动脉冲电场消融的研究进展[J].心血管病学进展 2021年42卷2期 114-117页 ISTIC CA, 2021, doi: 10.16806/j.cnki.issn.1004-3934.2021.02.005.

鲁志兵,江洪,黄鹤 et al. 心房颤动消融时图像融合技术再评价[J].中国心脏起搏与心电生理杂志 2015, 29(5):4, doi: 10.13333/j.cnki.cjcpe.2015.05.006.

黄从新. '中国房颤导管消融现状'. 医学与哲学 vol. 37, No. 11B, 2016, p. 10, doi: 10.12014/j.issn.1002-0772.2016.11b.04.

* cited by examiner

PULSED FIELD ABLATION DEVICE AND METHOD

CROSS-REFERENCE TO RELATED APPLICATIONS

This application claims priority to US Provisional Ser. No. 63/729,121, filed on Dec. 6, 2024, and to US Provisional Ser. No. 63/680,814, filed on Aug. 8, 2024, each of which is incorporated herein by reference in their entirety.

FIELD OF THE INVENTION

This invention relates to a medical device that may be used, for example, for an ablation, mapping, measurement or a signal acquisition from a part of a human or an animal body and a method of operating and manufacturing of such a device.

BACKGROUND OF THE INVENTION

Medical devices, for example for ablation or mapping, often include catheters with some type of electrode or electrodes. The electrode or electrodes may, for example, be placed on the body of the catheter, or the catheter may include a structure at its distal end that supports the electrode or electrodes. The structure may be, for example, a type of basket comprising filaments. At least a portion of the electrodes may be positioned on such a basket and coupled to the filaments. The electrodes may have different shapes, for example, the electrodes may be in the form of flexible printed circuit boards, wires, coils, meshes, helixes, or other shapes known in the art. A common form of electrodes used on the basket at the distal end of a catheter are ring-shaped electrodes that are coupled to the filaments, thereby forming a filament assembly.

Patient safety is an important consideration for a medical device including a catheter having a basket with ring-shaped electrodes. For example, a catheter is to be inserted into a human or animal body, often, for example, into a body cavity. Among other things, the catheter, especially the distal end of the catheter, should be as atraumatic as possible. This means, for example, that when the catheter is manipulated inside the body, it should not inadvertently damage surrounding tissue, e.g. by scratching. To avoid this risk, the catheter should not have any sharp edges that could cause such tissue damage. A possible limitation in existing ablation catheters is the integration of functional components, such as electrodes and expandable basket assemblies, into compact and maneuverable designs. Achieving a reliable coupling between electrodes and supporting filaments, while ensuring uniform energy delivery and preventing exposure of sharp edges, may be technically challenging.

Another potential issue may be the configuration of the distal tip and expandable basket assembly. Traditional designs may suffer from uneven electrode distribution or inadequate mechanical properties, resulting in suboptimal ablation patterns. In addition, the transition mechanisms that allow deployment and retraction of the expandable baskets must balance reliability with minimal operational complexity to support effective procedures in complex anatomical structures.

Pulsed field energy ablation catheters are a promising technology due to their ability to selectively ablate target tissue while minimizing damage to surrounding structures.

Despite these advances, significant challenges remain in improving the precision, safety, and efficiency of these systems.

Thus, there is a need for an ablation device that addresses these limitations by improving the integration of innovative materials, ensuring safety through enhanced structural stability, and providing reliable electrode coupling methods. The present invention seeks to address these needs by introducing a catheter system with superior mechanical properties, improved safety features, and optimized energy delivery capabilities.

SUMMARY OF THE INVENTION

Disclosed herein are devices and methods according to the description.

Disclosed herein is a device and method of an ablation system, in particular an ablation method and device for pulsed field ablation by electric fields according to the description, which can address and solve the above-mentioned problems, and which would be more gentle and safer for the patient, with reduced time and technical complexity and with enhanced quality, efficacy and reliability of the system, method and device itself.

BRIEF DESCRIPTION OF THE DRAWINGS

An exemplary aspect of the present disclosure is illustrated by way of example in the accompanying drawings in which like reference numbers indicate the same or similar elements and in which.

DETAILED DESCRIPTION

Figure 1:
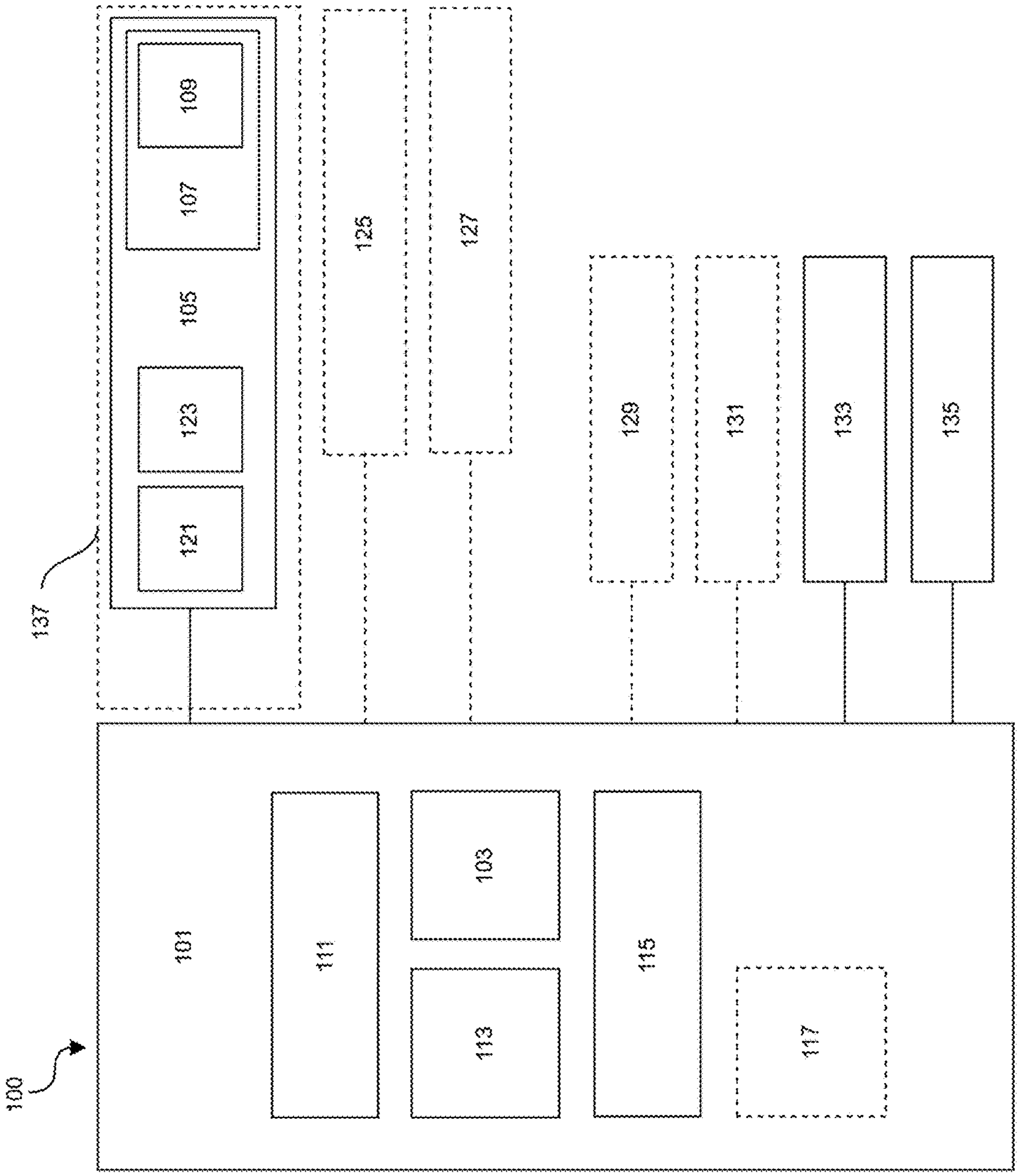
FIG. 1 is a block diagram of an exemplary ablation system.

FIG. 1 illustrates an ablation system (100) for pulsed field ablation of target tissue. The ablation system (100) described herein includes a pulsed field ablation device (101). The ablation system (100) may include or be coupled to other parts or devices suitable for performing or assisting in performing a method of pulsed field ablation described herein. The other parts or devices may be, for example, a control unit (111), a graphical user interface (GUI) unit (113), electrical control circuits (115), electrocardiogram (ECG) trigger circuits (117), an ECG recording device (129), ECG electrodes (125), a pacing device (131), an introducer sheath (137), and/or an electrophysiology (EP) display device (133), which may include an EP recording system. The EP display device may display and/or record data from one or more other devices connected to the ablation system (100). Further, the ablation system (100) may include a mapping device (135), such as a three-dimensional (3D) mapping device or a real position measurement (RPM) device, and/or indifferent electrodes (127). The mapping device (135) records EGMs (intracardial electrograms) for a location in a space measured, for example, by a catheter and produces a map of a heart surface. It may also show a position and orientation of the catheter. Other possible methods for measuring the actual position of a catheter may be via a sensor in a catheter (e.g. position measurement based on magnetics), or for example using impedance measurements on the electrodes of a catheter, or a measurement based on radio frequency, or a combination thereof. Advantageously, in some examples, the catheter used for the position measurements is the same catheter used for the ablation.

The pulsed field ablation device (101) may include a pulse generator (103) for generating short, high-voltage electrical pulses, and a catheter (105) suitable for insertion into a cavity of a patient's body having a catheter distal tip (107) suitable for performing pulsed field ablation of target tissue by pulsed electrical fields with a set of electrodes (109) wherein the catheter (105) is electrically coupled to the pulse generator (103). The distal tip (107) of the catheter may include an expandable basket.

The catheter (105) may further include a handle assembly (123) and a connection assembly (121). The catheter (105) may be steerable or non-steerable and may be inserted into its position via, for example, an introducer sheath (137) and with or without the aid of a guidewire (not shown).

The connection assembly (121) of the catheter (105) may serve to couple the catheter (105) to other parts of the ablation system (100). The connection assembly (121) may include a single connection portion or multiple spatially separated connection portions. The connection assembly (121) may be positioned on the proximal portion of the catheter (105) and/or, for example, may be part of a handle assembly (123). The connection assembly (121) portion may include, for example, one or more electrical connections, mechanical connections, fluid connections, and/or an input for a guidewire.

The connection assembly may include at least one connector, such as an electrical connector, a fluid connector, a data connector, an optical connector, etc. The connector may serve to connect and disconnect the catheter (105) to and from other parts of the ablation system (100).

Figure 2:
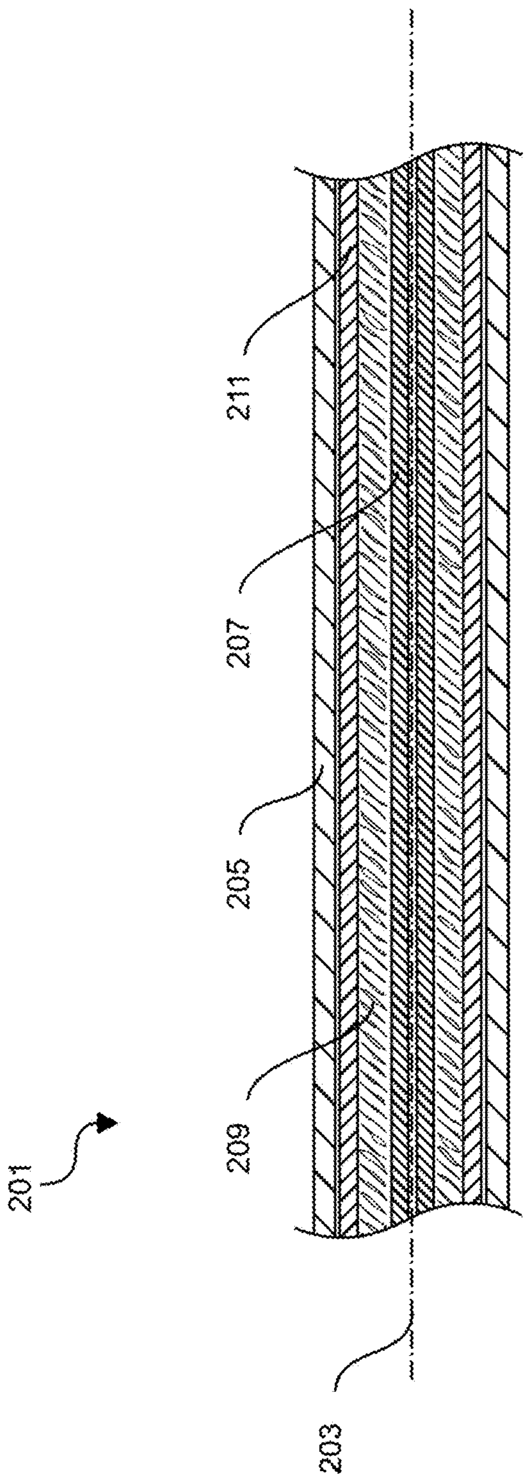
FIG. 2 is a cross-section of a portion of a catheter shaft assembly.

The catheter (105) may include a shaft assembly (201) and a catheter distal tip (107) disposed adjacent a distal portion of the catheter (105). A cross-section of an exemplary shaft assembly is shown in FIG. 2. The shaft assembly (201) defines a longitudinal central axis (203) of the catheter (105). The shaft assembly may include two concentric tubes, the outer tube being the outer elongated shaft (205) and the inner tube being the inner elongated shaft (207). The shafts may translate relative to each other in a longitudinal direction along the longitudinal central axis (203). This translation can allow, for example, the deployment/retraction of an expandable basket i.e. the distal tip of the catheter from a collapsed configuration to an expanded configuration and back.

The outer elongated shaft may comprise a proximal portion adjacent a proximal end of the outer elongated shaft, a distal portion adjacent a distal end of the outer elongated shaft, and a body extending between the proximal and distal ends of the outer elongated shaft. The outer elongated shaft may be coupled to a handle assembly adjacent its proximal portion and to the distal tip of the catheter adjacent its distal portion.

The body of the outer elongated shaft may include one or more lumens (209) extending, for example, along its entire length between the proximal and distal ends. The lumens may be adapted, for example, for passage of wires or fluids, for example, an irrigation fluid. One or more of the lumens may be configured to receive one or more of the inner elongated shafts. The body of the outer elongated shaft may, for example, be further defined by a proximal portion and a midsection. The midsection of the body may be configured with a flexible jacket relative to the proximal section to allow bending and increase flexibility of the outer elongated shaft. For example, the proximal section includes a stiffer material jacket to increase the torque and stiffness of the body of the outer elongated shaft. Suitable materials for the construction of the jacket include, but are not limited to, nylon, TPU, HDPE or PEBA.

Inner Elongated Shaft

In some aspects, the inner elongated shaft may be configured to slide along the longitudinal central axis relative to the outer elongated shaft. Therefore, for example, one or more of the lumens of the outer elongated shaft may comprise a low friction liner, such as a liner comprising a polytetrafluoroethylene (PTFE) material or other low friction material. In another example, the inner elongated shaft may slide along an irrigation shaft (211) contained within the outer elongated shaft.

Rigidity and torque are important characteristics that the outer elongated shaft should have, therefore laterally over/around the low friction liner, the outer elongated shaft may include, for example, a braid of a metal or rigid polymer wire wrapped around the inner layer of the body, which in some aspects is embedded within the outer jacket of the body, or may comprise a rigid polymer including, but not limited to, polyimide, polyamide, polyether ether ketone (PEEK) or any other suitable material contained within the outer elongated shaft.

The outer layer of the outer elongated shaft may comprise a laminated polymer to provide a seamless, smooth and soft surface. Note that, as mentioned above, the outermost layers of the intermediate section and the proximal section may be formed from different polymers, e.g., a nylon material could be used on the proximal section, while e.g., a PEBA, which is more flexible compared to nylon, could be used on the outermost layer of the intermediate section. However, both sections may have the same innermost layers. The outer elongated shaft may have a substantially constant outer diameter along its length.

In some aspects, the inner elongated shaft may have at least two portions. The first portion may include a layer comprising a braid. The second portion may not include a layer comprising a braid. In some aspects, the second portion may be in the distal end of the inner elongated shaft. The inner elongated shaft may include a plurality of protrusions generally disposed, for example, adjacent to the distal end of the inner elongated shaft. One of the protrusions may, for example, be included at the boundary of the first and second portions of the inner elongated shaft. An electrode may be at least partially disposed on one of the protrusions and/or at least a portion of one of the protrusions may include an electrode.

In some examples, the outer diameter (OD) dimension of the outer elongated shaft may conform to the French catheter scale, which is commonly used to standardize catheter sizes. The diameter in this scale is defined in French (FR), where 1 mm=3 FR. The scale typically ranges from a 3 FR catheter to a 34 FR catheter. In some examples, the diameter of the outer elongated shaft may range from 5 FR to 20 FR. In other examples, the outer elongated shaft range may be from 7 FR to 16 FR. In further examples, the outer elongated shaft range may be from 9 FR to 15 FR. The diameter of the central lumen of the outer elongated shaft may be approximately between 0.1 mm to 5 mm. In some examples, the diameter range of the central lumen may fall within the 0.1 mm to 5 mm diameter range. For example, the diameter range of the central lumen may be one of either 1 mm to 4 mm, 2 mm to 3.5 mm, or 2.5 mm to 3 mm.

The inner elongated shaft may comprise a proximal end, a distal end, and a body extending between the proximal and distal ends. The body of the inner elongated shaft may comprise one or more lumens, for example, extending along an entire length between the proximal and distal ends of the inner elongated shaft. Further, the body of the inner elongated shaft may not comprise a lumen. The one or more lumens of the inner elongated shaft may be configured, for example, to receive a standard guidewire (not shown) and/or to conduct a fluid, for example an irrigation fluid. The diameter of the one or more lumens may be from 0.1 mm to 3 mm, or from 0.5 mm to 1.5 mm, or from 0.9 mm to 1 mm, or from 0.94 mm to 0.99 mm.

The proximal end of the inner elongated shaft may, for example, terminate within the handle assembly or may extend even further proximally through the handle assembly and terminate proximally outside the handle assembly. The proximal end of the inner elongated shaft may be coupled to a valve, port, or connection to an irrigation system.

The inner elongated shaft may include a plurality of protrusions. The protrusions may, for example, be disposed adjacent the distal and/or proximal end of the inner elongated shaft.

The inner elongated shaft may be coupled to a basket deployment mechanism, e.g. included in the handle assembly. The basket deployment mechanism may be configured to move the inner elongated shaft laterally forward (in a direction of a distal end) and back ward (in a direction of a proximal end) along a longitudinal central axis against the outer elongated shaft, irrigation shaft and/or a handle assembly. The basket deployment mechanism may be configured to translate rotational motion to linear motion, e.g. rotational motion of a control wheel, to linear motion of the inner elongated shaft and/or it may be configured to translate linear motion of a control knob to linear motion of the inner elongated shaft. The basket deployment mechanism may be manipulated manually by an operator or automatically. The basket deployment mechanism may include, for example, at least one of a rack and pinion mechanism, a stepper motor, an electric motor and so on. It may also be coupled to the control circuits, for example.

Figure 3:
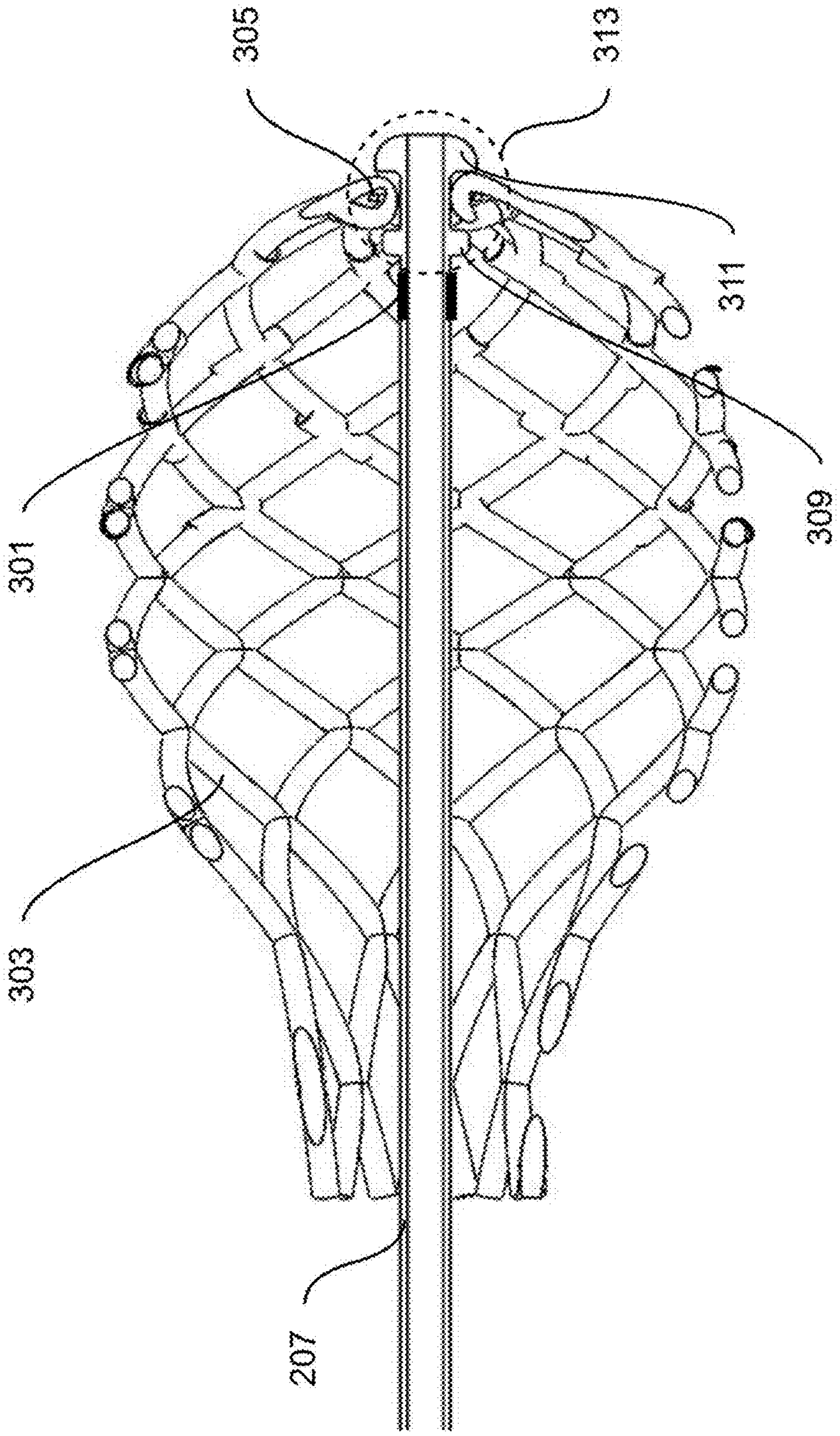
FIG. 3 is a cross-section of an exemplary distal tip of the catheter.

The inner elongated shaft may include an inner shaft electrode and/or a sensor (301) as seen in FIG. 3. The inner shaft electrode and/or a sensor (301) may be disposed in a portion of the inner elongated shaft extending distally from the distal end of the outer elongated shaft. The inner shaft electrode and/or a sensor may be disposed in a portion of the inner elongated shaft that extends distally from the distal end of the outer elongated shaft. An exemplary configuration may be one in which the expandable basket (303) is deployed in at least one of its expanded configurations. Some non-limiting examples of the expandable basket's expanded configurations may include when the expandable basket is deployed in its fully expanded configuration, or when the expandable basket is in a partially expanded configuration. Such a position allows the electrode to be inside of the expandable basket when the basket is deployed in at least one of its expanded configurations. The inner shaft electrode and/or a sensor may be coupled to the pulse generator and/or other parts of the apparatus via an electrical lead disposed at least partially on and/or in the inner elongated shaft. The inner shaft electrode disposed on the inner elongated shaft may serve, for example, as an ablation electrode, a mapping electrode, and/or a measurement electrode—for example, an ECG measuring electrode. The inner shaft electrode disposed on the inner elongated shaft may serve, for example, as a ground electrode.

The sensor included on the inner elongated shaft may be, for example, a position sensor, temperature sensor, magnetic sensor, electronic sensor, or another type of sensor.

The inner shaft electrode and/or a sensor (301) and/or other device placed on the catheter, for example on the outer elongated shaft, inner elongated shaft, distal tip, terminal assembly and/or expandable basket, may include, or be coupled to either a passive or active radio frequency identification (RFID) tag. It can store and transmit information from the catheter to an RFID reader, e.g. placed outside the patient.

The shaft assembly (201) may further include an irrigation shaft (211). The irrigation shaft may be positioned in one of the lumens (209) of the body of the outer elongated shaft and may be configured to conduct a fluid, for example, an irrigation fluid. However, in addition to the irrigation fluid, the irrigation shaft (211) may be further configured to guide another structure, for example, a wire. In one example, the irrigation shaft (211) may be positioned in one of the lumens (209) configured to receive one or more of the inner elongate shafts (207). In this example, the inner elongated shaft (207) may lead within the irrigation shaft (211), and the irrigation shaft (211) may be configured to lead the irrigation fluid and the inner elongated shaft (207). Suitable materials for the construction of the irrigation shaft (211) include, but are not limited to, nylon, TPU, HDPE or PEBA.

The irrigation shaft may be made as a tube of one material (for example a polymer tube, nylon, TPU, HDPE or PEBA . . . ), or may be made of multiple layers that may include, for example, a low-friction liner in its lumen, where the low-friction liner may include a PTFE or other low friction material or additive. A braided sheath may be woven along the length of the low-friction liner. Another aspect may include a cut hypotube in place of the braid. A polymer sheath may be melted and/or laminated laterally over the braided layer or the hypotube layer to increase the softness of the tube and provide a seamless surface. A variety of polymers can be used for the jacket, such as NYLON, polyether block amide (PEBA), polyether ether ketone (PEEK), or polyimide.

The irrigation shaft may be placed within the body of the outer elongated shaft and may extend from its proximal end to its distal end. However, the irrigation shaft need not be the same length as the outer elongated shaft. For example, the irrigation shaft may overlap the outer elongated shaft in a proximal direction—e.g., it may extend further proximally in the handle assembly, or it may extend even further proximally through the handle assembly and begin proximally outside the handle assembly. The proximal end of the irrigation shaft may be coupled, for example, to a valve, port, or connection to an irrigation system.

The distal end of the irrigation shaft may terminate in the region of the distal end of the outer elongated shaft body or may extend distally beyond the distal end of the outer elongated shaft body. The irrigation fluid from the irrigation shaft may, for example, help with irrigating a basket assembly coupled adjacent to the distal end of the outer elongated shaft.

Figure 4:
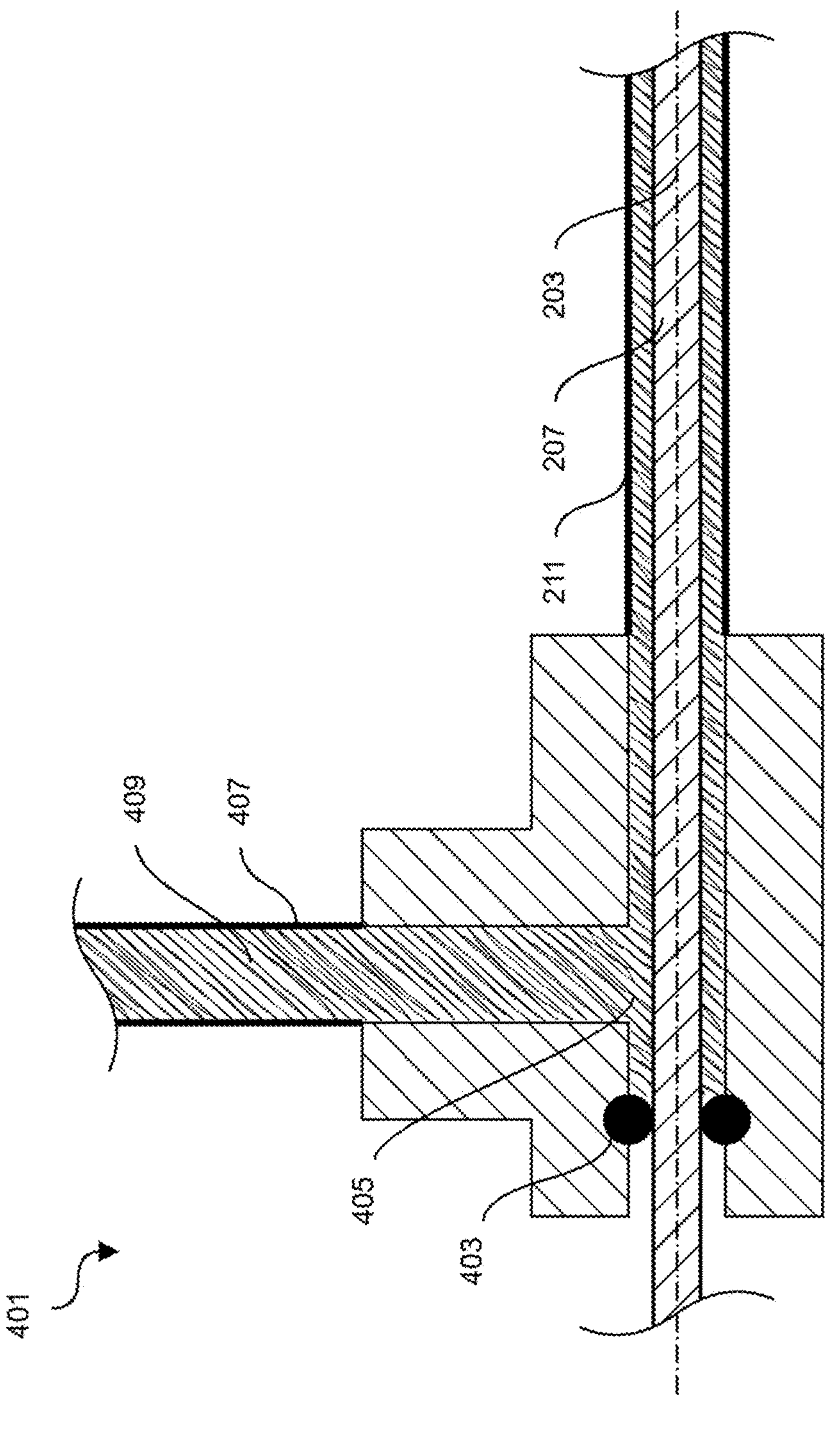
FIG. 4 is a cross-section of an exemplary valve.

The handle assembly may include one or more valves coupled to the inner elongated shaft. The valve (401), as shown in FIG. 4, may include at least one seal (403), such as an O-ring, and a valve cavity (405). The inner elongated shaft (207) may extend through at least a portion of the valve cavity and be movable against the valve in a direction along the longitudinal central axis (203). The valve cavity may include the seal and the inner elongated shaft may extend through the seal, wherein the seal seals an irrigation fluid within at least a portion of the valve cavity. The valve cavity may be coupled to a valve inlet (407). The valve inlet may introduce the irrigation fluid (409) into at least a portion of the valve cavity. The valve cavity may further be coupled to the irrigation shaft (211) by a fluid coupling.

The dimensions of the inner elongated shaft may be chosen to match the diameter of the intended lumen of the outer elongated shaft, but the two structures must still allow for their smooth relative translation. That is, the outer dimensions of the inner elongated shaft may be from 0.1 mm to 4.9 mm, or from 0.5 mm to 3.5 mm, or from 1 mm to 3 mm, or from 1.28 mm to 2.8 mm. Since the inner elongated shaft can be suitable for accommodation of a guidewire inside its lumen, a low-friction liner, for example a PTFE liner, of the inner lumen can be used.

As mentioned above, the inner elongated shaft may be translated relative to the outer elongated shaft to deploy the basket assembly/expandable basket, and may for example include a braided sleeve along the length of the low friction liner to form a body of the inner elongated shaft. Another aspect may include a cut hypotube in place of a braid in a body of the inner elongated shaft to improve its flexibility and torque.

A polymer jacket can be melted and/or laminated laterally over the braid or hypotube layer to increase the softness of the tube and provide a seamless surface. A variety of polymers can be used for the jacket, including NYLON, polyether block amide (PEBA), polyether ether ketone (PEEK), or polyimide.

At least a portion of the outer elongated shaft, e.g. at least a portion of the body of the outer elongated shaft, may comprise a flexible printed circuit board (FPCB). The FPCB may, for example, be in the form of a flat FPCB rolled into a shaped tube. It may be included in one of the layers and/or one of the portions of the body of the outer elongated shaft. The FPCB may include a stretchable material, for example in its substrate.

The outer shaft of the catheter may be made entirely or partially of flexible/stretchable circuit board (PCB). At the distal end, the shaft may branch into filaments forming the basket. The flexible/stretchable PCB used in the shaft may be rolled into a tubular shape and either bonded or welded to form the shaft. In addition, the outer elongated shaft can consist of multiple layers of flexible/stretchable PCB. Each layer can bifurcate at the distal end, resulting in multiple filaments forming the basket, providing a more intricate and reinforced structure.

The body of the outer elongated shaft may include conductive wires. The conductive wires may pass through the lumen (209) of the outer elongated shaft, or the outer elongated shaft may include a plurality of other lumens such that one or more of the wires may pass through one or more of the other lumens. In some aspects, the number of other lumens may correspond to the number of filaments of a braided mesh on the distal tip of the catheter, e.g., if 20 filaments are used in the construction of the distal tip of the catheter, 20 other lumens may be used.

Figure 5:
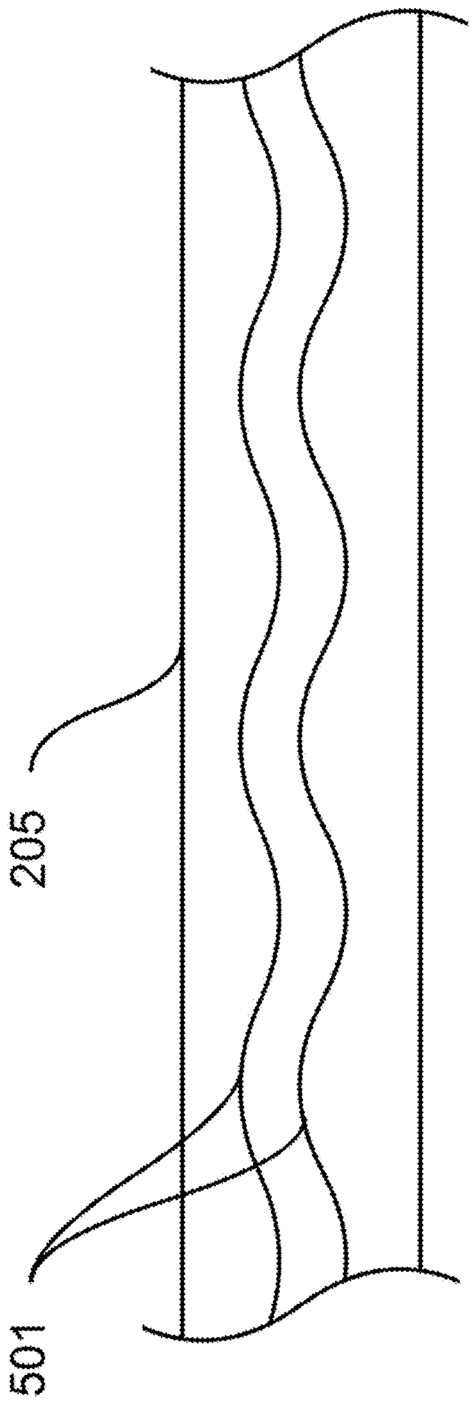
FIG. 5 shows a portion of an outer catheter shaft with conductive leads.

A body of the outer elongated (205) shaft may include at least one conductive lead, for example, in the case where the elongated body comprises the FPCB as shown in FIG. 5. The conductive lead (501) may be part of a conductive layer of the FPCB and may be coupled to the substrate of the FPCB. The conductive leads and/or the conductive wires included in the elongated shaft may be configured to conduct an electrical signal between the proximal and distal ends of the outer elongated shaft, e.g. between a connection assembly (e.g. connector) coupled to the proximal side of the outer elongated shaft and at least one electrode coupled to the distal end of the outer elongated shaft. The electrode may be placed directly on the outer elongated shaft, or may be placed on the expandable basket or other structure coupled to the distal end of the outer elongated shaft, either directly, via the conductive leads, or indirectly, e.g. via an electrical connection. Examples of suitable electrical connections include, but are not limited to, a connector, a solder connection, a clamp, and so on.

The distal tip (107) of the catheter (105) may include a basket assembly comprising an expandable basket (303). The proximal portion of the basket assembly may include an attachment of the proximal portion of the expandable basket adjacent to the distal end of the outer elongated shaft. The distal portion of the basket assembly may include an attachment of the distal portion of the expandable basket adjacent to the distal end of one or more of the inner elongated shafts forming a terminal assembly.

The expandable basket may be coupled to the inner elongated shaft and/or to the outer elongated shaft by, for example, gluing, welding, lamination, or mechanical means. When the expandable basket includes FPCB, e.g., in the case at least a portion of the filaments included in the expandable basket includes FPCB in their structure, the coupling may include connectors, soldering connections between the FPCB and conductive wires and/or conductive leads comprised in the outer elongated shaft. In examples where the expandable basket includes FPCB, e.g. in case at least portion of the filaments included in the expandable basket includes FPCB in their structure and where the catheter shaft, e.g. outer elongated shaft includes the FPCB in its structure, the coupling of the expandable basket to the inner elongated shaft and/or to the outer elongated shaft may include coupling via FPCB. The FPCB comprised in the one of the elongated shafts may, for example, continue longitudinally beyond a distal end of one of the elongated shafts and may be included in the expandable basket, e.g. in the at least portion of the filaments creating the expandable basket.

For example, the expandable basket may be configured to transition (deploy/retract) between a collapsed configuration and one or more expanded configurations. The transition (deployment/retraction) may be caused by a pretensioned shape of the expandable basket and/or by a linear displacement of the inner elongated shaft against the outer elongated shaft along a longitudinal central axis of the catheter, or by combinations thereof. Another way to deploy/retract the expandable basket can be by tensioning an additional support structure, such as an inner coil or balloon.

The expandable basket may comprise filaments braided into a braided mesh or may comprise a molded mesh. In the collapsed configuration, the cross-section of the expandable basket may be equal to or dimensionally close to the cross-section of the outer elongated shaft. In one aspect, the cross-section of the expandable basket may be smaller than the cross-section of the outer elongated shaft, and may depend on the dimensions of the outer elongated shaft. In the expanded configuration, the cross-section of the expandable basket may be significantly larger than the cross-section of the outer elongated shaft. For example, a fully expanded expandable basket may have a maximum cross-sectional diameter of from 20 mm to 40 mm, or from 22 mm to 38 mm, or from 25 mm to 35 mm. Such dimensions of a fully expanded expandable basket may be suitable, for example, for placement in cardiac cavities.

For larger body cavities, the expandable basket may, for example, have larger dimensions, such as from 30 mm to 150 mm, or from 40 mm to 120 mm, or from 50 mm to 100 mm.

In other situations, a fully expanded expandable basket having smaller dimensions may be suitable for smaller body cavities. Such a smaller expandable basket may have dimensions in its fully expanded state of, for example, 3 mm to 25 mm, or 5 mm to 15 mm, or 7 mm to 10 mm.

The fully expanded configuration of the basket may mean a configuration of the expandable basket in which the expandable basket has the largest circumference at a location of the highest circumference of the basket as compared to other configurations in which the basket has a smaller circumference at a location of the highest circumference of the basket. The location of the basket with the highest circumference may be defined by a circumference of the expandable basket in a plane perpendicular to the longitudinal central axis including at least one point of the expandable basket having the largest radial distance from the inner elongated shaft or from the longitudinal central axis. In examples where linear displacement of the inner elongated shaft against the outer elongated shaft along a longitudinal central axis of the catheter provides expansion of the expandable basket, it may mean that the distal end of the inner elongated shaft, i.e., a distal end of the expandable basket, i.e., an end assembly of the distal tip, is in the closest possible position to the distal end of the outer elongated shaft allowed by the ablation device. The fully expanded configuration, expanded configurations and collapsed configuration are defined in a free space outside the human body under standard environmental conditions.

In some aspects, the filaments braided into the braided mesh are not cut adjacent to the distal portion of the expandable basket, but rather the filaments may be bent at the distal portion and attached adjacent to the distal portion of the inner elongated shaft to form a terminal assembly. The bent filaments may then be returned to the expandable basket or outer elongated shaft where they may be terminated.

The expandable basket made of the braided mesh has advantages over a prior art solution with unbraided struts in that the expandable basket has greater mechanical stability while using comparatively thinner filaments. More filaments in the structure may also allow more electrodes to be used. The electrodes placed on the filaments can also be better distributed, i.e. they can be placed closer together or create a desired pattern on the expandable basket. Another advantage of the braided mesh expandable basket is the increased mechanical stability of the structure, which can provide stable and predictable electrode spacing.

The braided mesh may be heat treated, which may provide for deformations and fixation of such deformations of the filaments. Such deformed filaments then ensure that during expansion and collapse of the basket assembly (expandable basket), the crossing points of the filaments (points where the filaments cross each other) remain relatively stable with respect to a filament length. This means that the filament crossing points remain at relatively the same filament length distances in the collapsed configuration, as well as in all expanded states of the basket assembly (expandable basket). What changes is a mutual angle of the individual filaments creating the crossing points (for example, from about 2 degrees to 178 degrees or vice versa). A certain amount of longitudinal movement of the crossing points can't be completely avoided by this process, but it remains within limits where it doesn't affect the dimensional and/or mechanical stability of the braided mesh. This feature can then be used, for example, to place the electrodes at the crossing points of the filaments and/or to ensure stable, predictable, desired mutual positions of the electrodes and/or their mutual spacing.

The expandable basket (e.g., placement of the electrodes on the expandable basket) may allow the ablation device to ablate based on, for example, the placement of the electrodes on the expandable basket. In some aspects, the electrodes may deliver ablation energy (e.g., high-voltage electrical pulses) in either the expanded state of the expandable basket and/or in a collapsed configuration of the expandable basket. The delivery of the ablation pulses may allow, for example, a circular, linear, or point-like pattern to be created in either the expanded state of the expandable basket and/or a linear or point-like pattern of ablated target tissue in the treatment site with the basket in its collapsed configuration.

An example of the attachment of the distal portion of the expandable basket (303) adjacent to the distal end of the inner elongated shaft (207), hence the terminal assembly (313) can be found in FIG. 3. In this particular example, the distal end of the expandable basket (303) may be formed using a ring (305) to which the filaments (307) of the expandable basket (303) are attached and/or bent. The distal portion of the expandable basket (303) may be attached to the inner elongated shaft (207) by a mechanical locking mechanism. In order to lock the basket to the inner elongated shaft (207), two protrusions—proximal protrusion (309), distal protrusion (311)—are created on the inner elongated shaft (207) so as to hold both sides (proximal and distal) of the distal end of the expandable basket (303), for example including the ring (305) which will lock the expandable basket (303) to the inner elongated shaft (207).

In one of the examples, the attachment may be created by pushing the inner elongated shaft (207) with the prepared proximal protrusion (309) distally through the opening in a distal part of the expandable basket, for example through a hole of the ring (305), until the proximal protrusion (309) on the shaft reaches the distal part of the expandable basket from the proximal side. The distal end of the inner elongated shaft, which may protrude distally from the basket, may be then tipped/heated on a bullet-shaped mold to create the distal protrusion (311) with an atraumatic bullet-shaped end that will prevent the inner elongated shaft (207) from moving proximally relative to the expandable basket (303).

Figure 6:
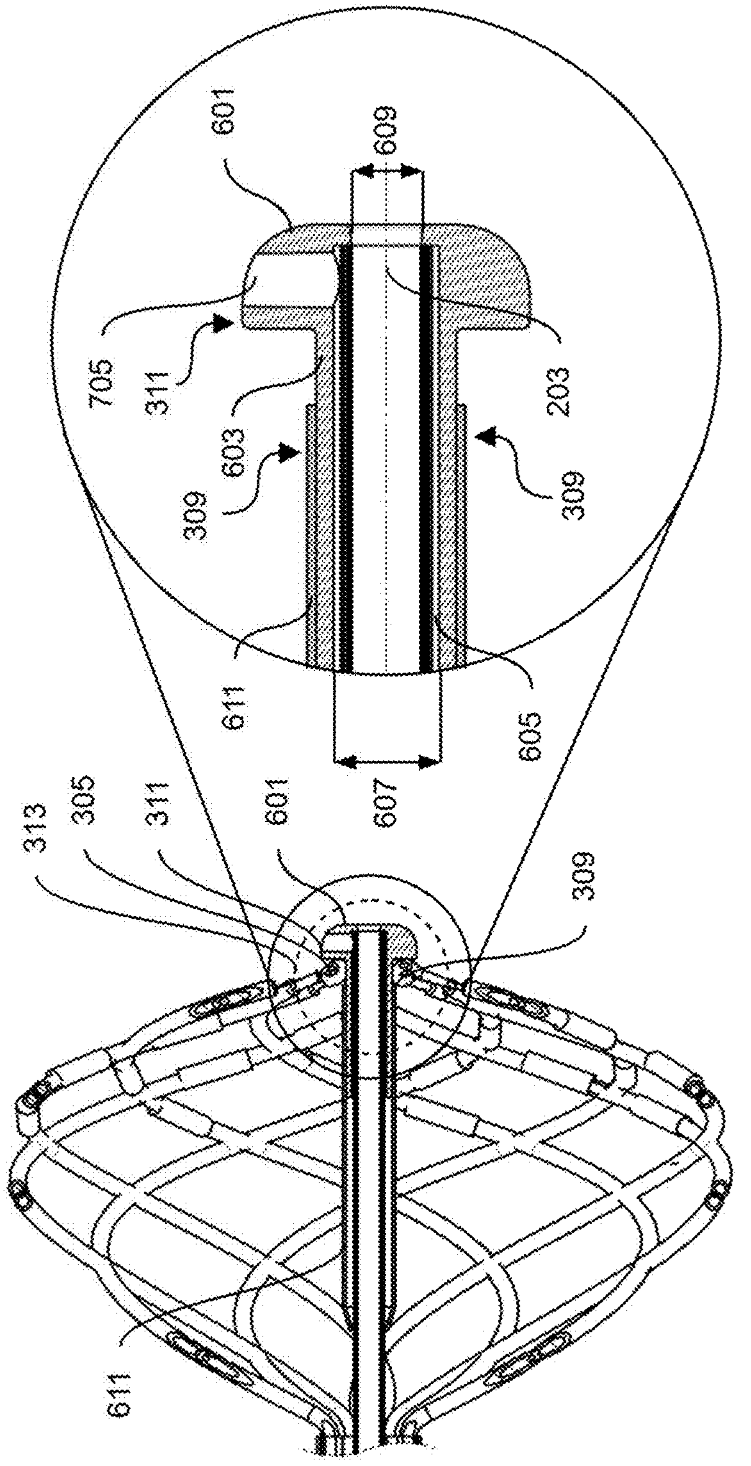
FIG. 6 is a cross-section of an exemplary distal tip.

The proximal protrusion (309) and/or the distal protrusion (311) may be formed on the inner elongated shaft by other techniques as well. One particular example is shown in FIG. 6. The distal protrusion (311) may be, in this example, formed by a distal additional member (601) coupled to the inner elongated shaft (207). The distal additional member (601) may be, for example, in a form of toroidal, cylindrical, conical, truncated conical, or hollow tubular body with, for example, an atraumatic shape (e.g. bullet shape, flange shape) formed on its distal end which may ensure the terminal assembly (313) will not mechanically injure a patient. The distal additional member (601) may, for example, be made out of plastic or metal. The distal additional member (601) may include a tubular structure (603) protruding proximally from the distal protrusion (311) parallel with the inner elongated shaft (207). The distal additional member (601) may include a cavity (605) that is, for example, adapted to receive at least a portion of the inner elongated shaft (207) and a guidewire. The tubular structure (603) may include a body and a cavity (605) in the body, wherein the cavity (605) may be configured, for example, to receive at least a portion of the inner elongated shaft (207) and a guidewire.

The cavity (605) may have two internal diameters: a first diameter (607) formed proximally in the distal additional member (601) and large enough to fit the at least a portion of the inner elongated shaft (207), and a second diameter (609) formed distally from the first diameter (607) and having a smaller diameter than the first diameter (607).

Figure 7:
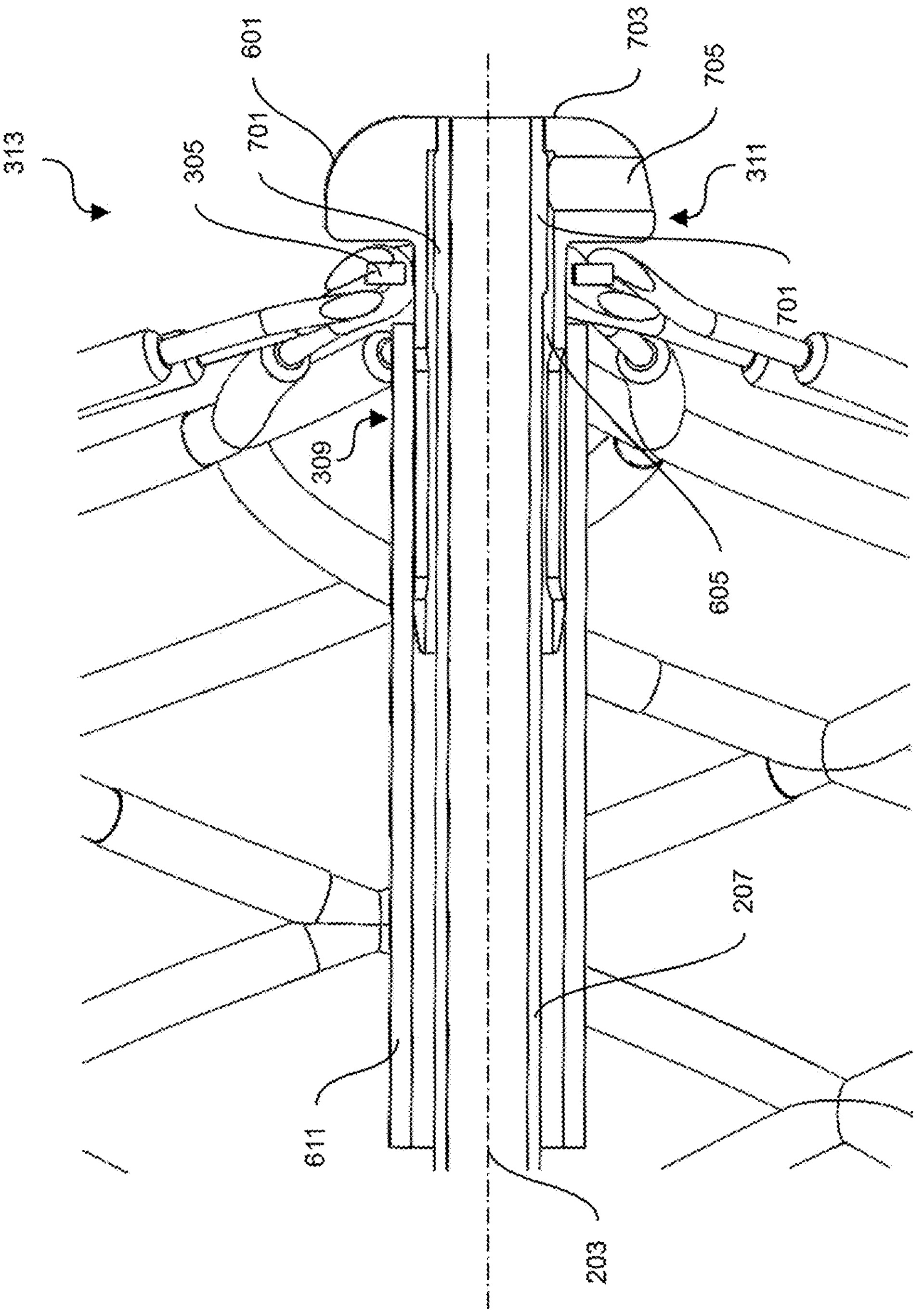
FIG. 7 is a cross section of another example of distal tip.

The second diameter may be smaller than an outer diameter of the inner elongated shaft (207) configured, for example, for a guidewire to pass therethrough, or it may be large enough for the outer diameter of the outer elongated shaft but smaller than a diameter of the third protrusion (701) of the inner elongated shaft (207) as shown in FIG. 7. With such a configuration of the cavity (605), the distal additional member (601) can act as a distal stopper for the inner elongated shaft (207) in the direction of the longitudinal central axis (203) while also preventing possible sharp edges of a distal end of the inner elongated shaft (207) from being exposed distally of the distal additional member (601) and potentially causing tissue damage upon contact in a configuration where the second diameter (609) is smaller than the diameter of the inner elongated shaft (as in example on the FIG. 6).

In an example where the second diameter (609) is large enough for the outer diameter of the inner elongated shaft (207) but smaller than the diameter of the third protrusion (701) on the inner elongated shaft (207) (as shown in FIG. 7), at least a portion of the inner elongated shaft (207), for example at least a portion of the second portion of the inner elongated shaft (207) not including a layer comprising a braid, may be allowed to protrude distally beyond the distal additional member (601). In such a case, the portion of the inner elongated shaft (207) extending beyond the distal additional member (601) may be cut off in a manufacturing step at the additional member distal edge (703). An advantage of this solution may be that a portion of a distal portion of the inner elongated shaft remains within the cavity (605) and may ensure that a potential guidewire that would be positioned within the cavity (605) of the inner elongated shaft (207) and protruding beyond the additional member distal edge (703) and/or distal end of the inner elongated shaft (207) does not come into direct contact with the distal additional member (601). This solution can help to protect the guidewire, for example, when the distal additional member (601) is made of a hard material, such as a metal.

The distal additional member (601) may be coupled to the inner elongated shaft (207), and the coupling may include, for example, a crimp, a weld, a screw, a thread, molten plastic, or an adhesive such as a hot melt adhesive or a glue.

In a particular example, the distal additional member (601) may be coupled to the inner elongated shaft (207) by, for example, a fused plastic or an adhesive. The distal additional member (601) may include a cavity (605) having a diameter that is greater than an outer diameter of the inner elongated shaft (207), for example greater by 0.1% to 50%, or 0.5% to 40%, or 1% to 25%.

The inner elongated shaft may be inserted into the cavity (605), and the resulting space between the inner elongated shaft (207) and the walls of the cavity (605) may be filled with an adhesive, such as hot melt adhesive or glue. In an example with the third protrusion (701) on the inner elongated shaft, the third protrusion (701) may act as a seal for the adhesive to prevent the adhesive from spilling distally from the cavity (605) of the additional member (601).

The distal additional member (601) may include a glue opening (705) connecting an outer surface of the additional member (601) with the cavity (605). The glue opening (705) may serve as an access for the adhesive into the cavity (605), for example, into the resulting space between the inner elongated shaft (207) and the walls of the cavity (605).

Figure 8:
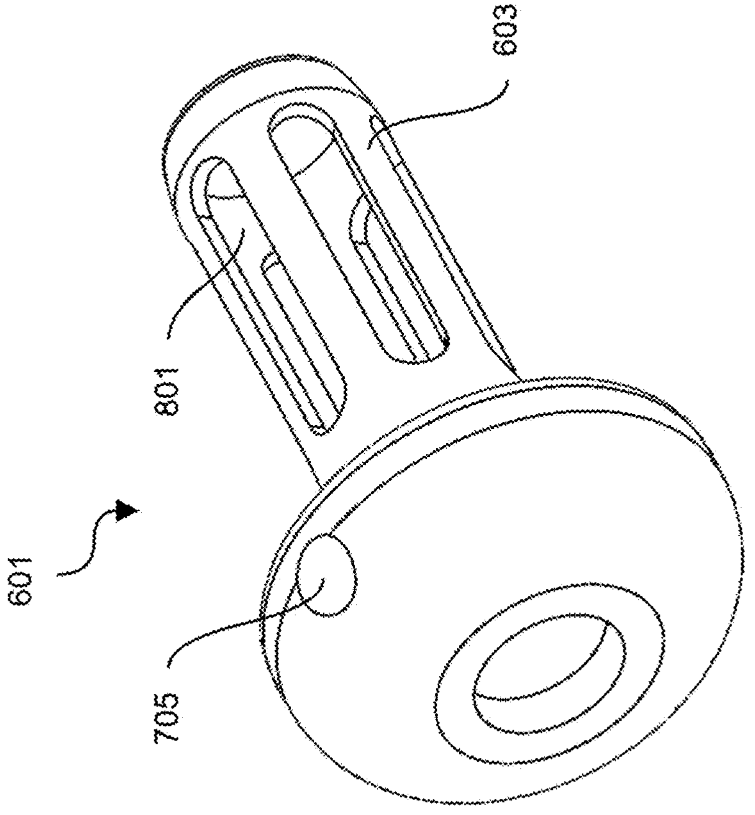
FIG. 8 is a view of an exemplary distal additional member.

After the glue is filled into the cavity (605), the glue opening (705) may be closed and sealed, for example, by a plug, a melted plastic, or an adhesive such as a hot melt adhesive or glue. The same adhesive used to couple the distal additional member (601) to the inner elongated shaft (207) may be used here. The tubular structure (603) may include at least one aperture (801) in its body, as shown in FIG. 8. The aperture (801) may be configured to be filled with the adhesive during this process, thereby assisting in the strength of the adhesive connection between the inner elongated shaft and the distal additional member (601). The aperture (801) may also be configured to allow an ultraviolet light to better reach at least a portion of the adhesive when an ultraviolet curing adhesive is used.

The proximal protrusion (309), as shown in an example in FIGS. 6 and 7, may be formed, for example, by a tubular proximal additional member (611) coupled to the inner elongated shaft (207). The proximal additional member (611) may be directly coupled to the inner elongated shaft (207), or it may be coupled, for example, via the distal additional member (601), to the inner elongated shaft (207) by way of the, for example, tubular structure (603). In another example, the proximal additional member (611) may be coupled to the inner elongated shaft (207) both directly and indirectly, for example, via the distal additional member (601). The coupling of the proximal additional member (611) to the inner elongated shaft (207) and/or to the distal additional member (601) may include, for example, a crimp, a weld, a screw, a thread, molten plastic, an adhesive such as a hot melt adhesive or a glue, or another fixation member (not shown) placed proximally of the distal additional member (601) on the inner elongated shaft (207). The proximal protrusion (309), i.e., the proximal additional member (611), may have a shape or include, for example, a plastic tube.

The ring (305) to which the filaments (307) are attached may be coupled to the inner elongated shaft (207) directly or, for example, via the distal additional member (601) or the proximal additional member (611). An example of the ring (305) coupled to the inner elongated shaft (207) via the distal additional member (601) is shown in FIGS. 6 and 7. In this particular example, the distal additional member (601) includes the tubular structure (603) protruding proximally from the distal protrusion (311) parallel to the inner elongated shaft, and the ring (305) may surround the tubular structure (603).

Figure 9A:
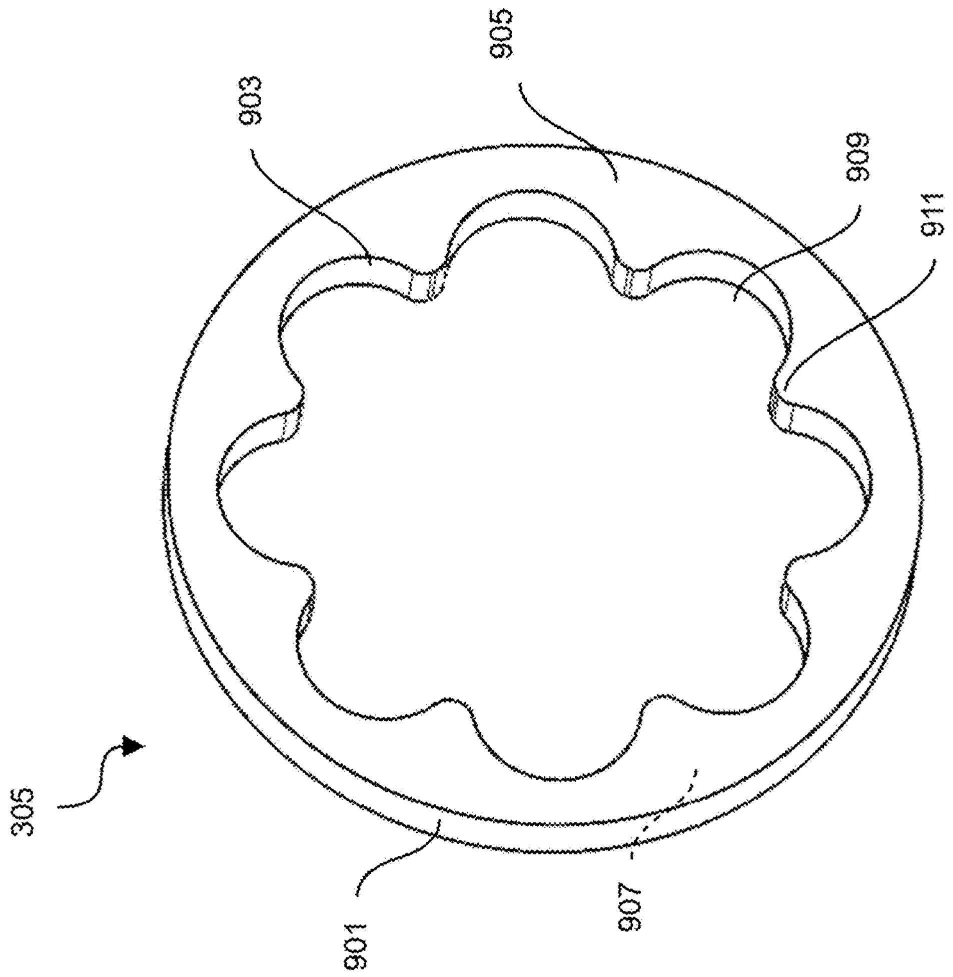
FIG. 9*a* shows a view of a ring.

The ring (305), as shown in a FIG. 9, may have an outer edge (901), an inner edge (903), a proximal edge (905), and a distal edge (907) opposite the proximal edge (905). The edges can be understood as boundaries of the ring (305). The outer edge (901) represents the outer boundary of the ring (305), the inner edge (903) refers to the boundary closest to the shaft, the distal edge (907) is the most distal boundary, and the proximal edge (905) is the proximal boundary of the ring (305). The ring (305) may have different types of cross-sections, such as circular, elliptical, rectangular, square, or other shaped cross-sections. The inner edge (903) of the ring (305) may comprise a plurality of notches (909) and/or projections (911). Notches (909) and/or projections (911) may be understood as recesses, grooves, or indentations along the inner edge (903) of the ring (305). An advantage of this arrangement may be that these notches (909) and/or projections (911) may serve to securely hold the filaments in place by preventing lateral movement along the ring (305). This arrangement may ensure that the filaments maintain their intended position and configuration. The notches (909) and/or projections (911) need not be on the inner edge (903), but may be on the distal edge (907), the outer edge (901), or the proximal edge (905). The notches (909) and/or projections (911) may be separate on each edge, or they may be continuous from one edge to the other, thus forming ridges on a surface of the ring (305).

Each of the said notches may have an inner radius that may be equal to or greater than the outer radius of the filament surface, corresponding to the cross-sectional diameter of at least a portion of the filament in contact with the ring. For example, the radius may be from 0.01 mm to 2 mm, or from 0.03 mm to 1.5 mm, from 0.05 mm to 1.2 mm, or from 0.08 mm to 1 mm, or from 0.1 mm to 0.8 mm, or from 0.2 mm to 0.7 mm.

Figure 9B:
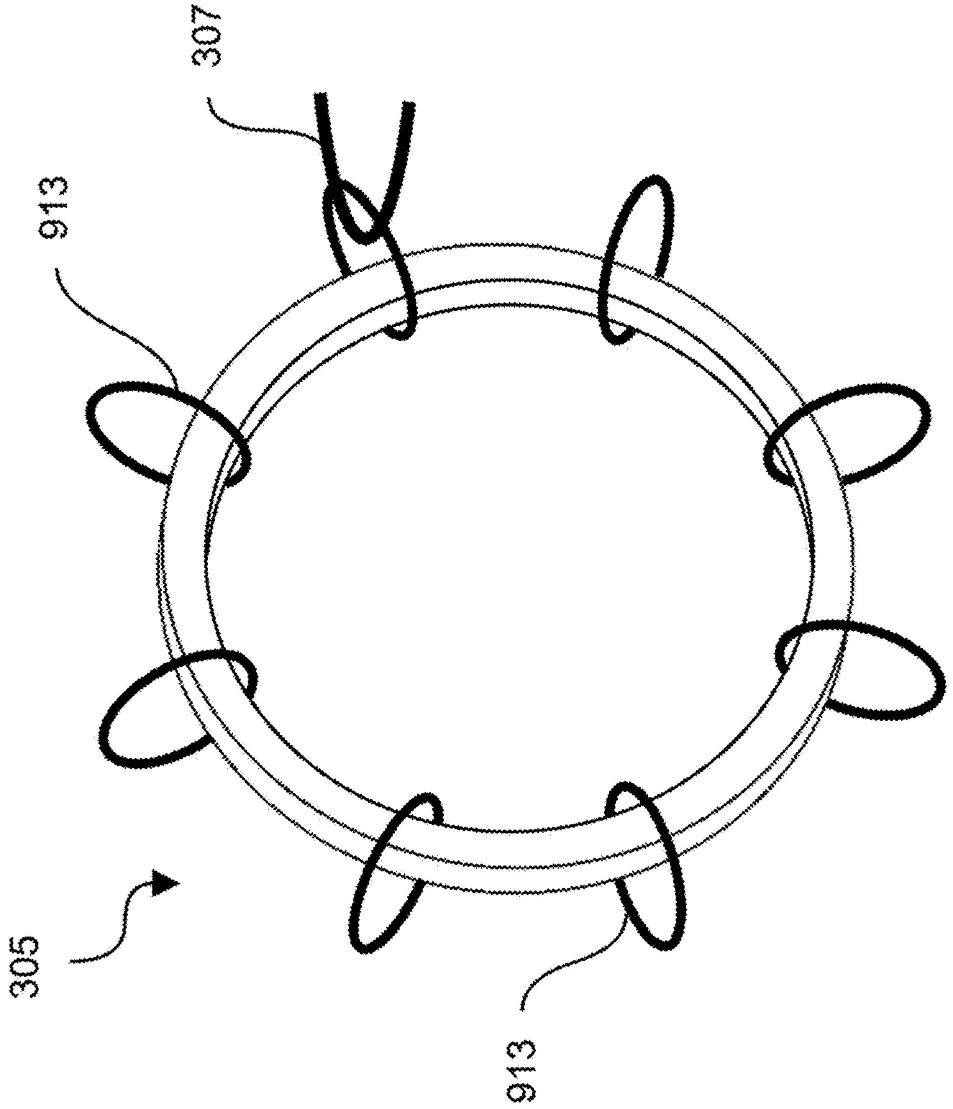
FIG. 9*b* shows a ring including retaining members.
Figure 9C:
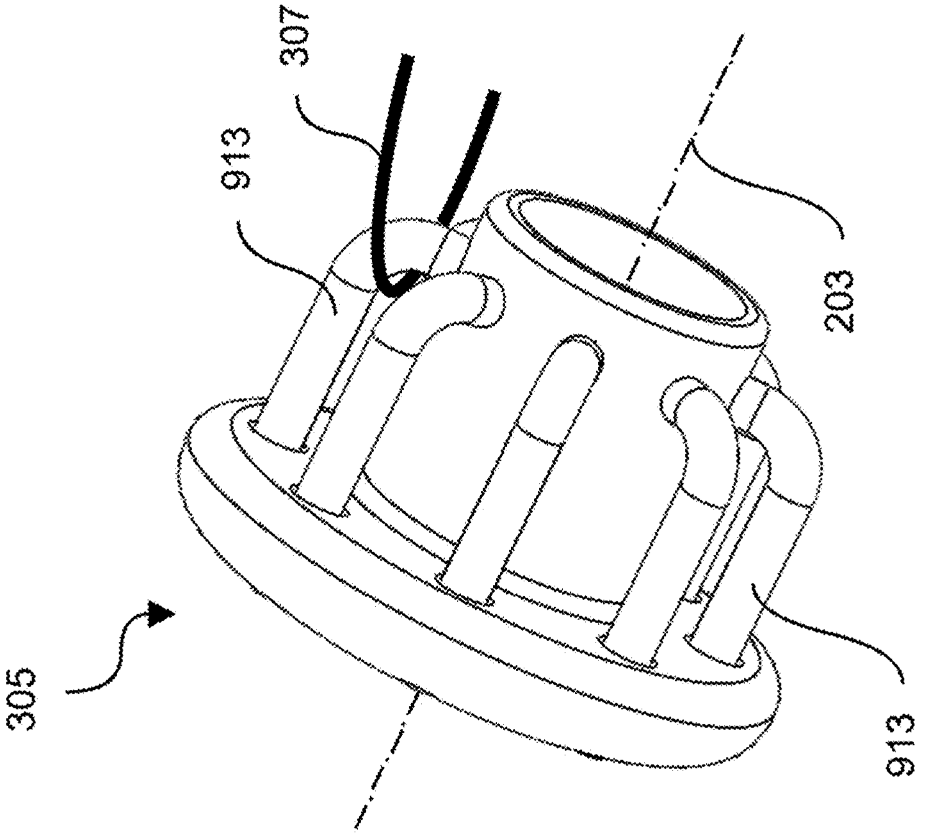
FIG. 9*c* shows an exemplary ring including retaining members.

The ring may include at least one retaining member coupled to the ring, which may serve to couple the filament to the ring. Examples of a ring having similar retaining members are shown in FIGS. 9*b* and 9*c*. The retaining member (913) may be oriented such that at least a portion of the retaining member (913) does not lie in a plane perpendicular to the longitudinal central axis (203). Additionally, the retaining member (913) may be oriented such that at least a portion of the retaining member (913) lies in a plane having an angle of 1° to 89°, or 5° to 88°, or 10° to 85°, or 15° to 80° relative to the plane perpendicular to the longitudinal central axis (203). The retaining member (913) may also be oriented such that at least a portion of the retaining member (913) lies in a structure plane parallel to the longitudinal central axis (203). The structure plane may be parallel to the longitudinal central axis (203), and the longitudinal central axis (203) may or may not pass through the structure plane. In another example, the structure plane may not be parallel to the longitudinal central axis (203). Further, the retaining member (913) may define at least one opening (gap, recess, cutout . . . ) configured to receive at least a portion of a filament (307), and the opening and the retaining member (913) may be configured such that the at least a portion of the filament (307) received in the opening may be bent around at least a portion of the retaining member (913).

The ring may include a plurality of the retaining members, for example, arranged around a circumference of the ring. The retaining members may be rigidly coupled to the ring, for example by bonding, welding, screwing, or other techniques known in the art, or the retaining members may be part of the ring and, for example, made as a part of the ring during a production of the ring, for example by injection molding, molding, cutting, milling, drilling, or other similar techniques. An example of a ring having such rigidly coupled retaining members is shown in FIG. 9*c*. In another example, the retaining members may be coupled to the ring, but the coupling need not be rigid, but may allow mutual movement of the ring and the retaining members. An example of such a ring with non-rigidly coupled retaining members is shown in FIG. 9*b*, for example.

The ring need not be limited to an exact ring, but may be included in or replaced by a coupling structure, such as an annular structure, for example similar to a cylinder, cage or other structure. It may even be a portion of the inner elongated shaft. The retaining members may be coupled to the coupling structure or in one example, directly to the inner elongated shaft.

The coupling of the filament to the retaining member and/or to the ring may allow rotational movement of the filament in a coupling region of the filament about at least a portion of the ring or at least a portion of the retaining member at least during deployment or retraction of the expandable basket. Thus, the coupling between the filament and the ring and/or the retaining member may provide rotational engagement of the filament with the inner elongated shaft in the terminal assembly.

Figure 10A:
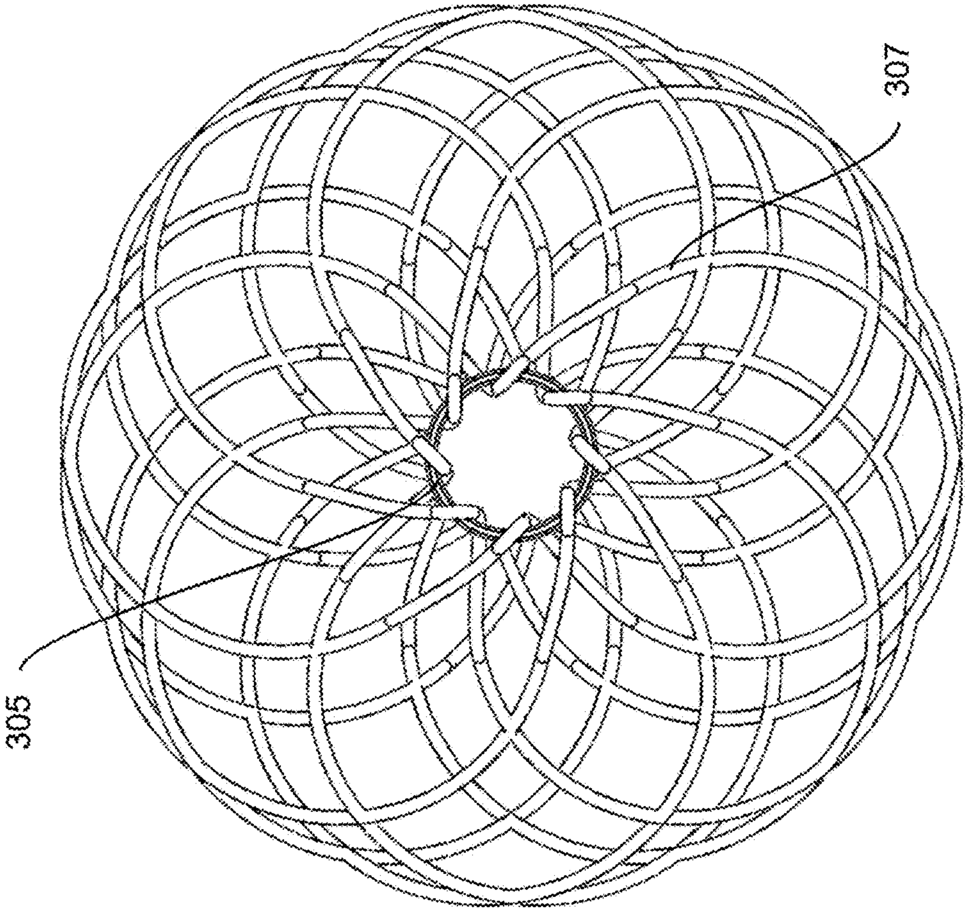
FIG. 10*a* is a front view of a portion of an expandable basket with a ring.
Figure 10B:
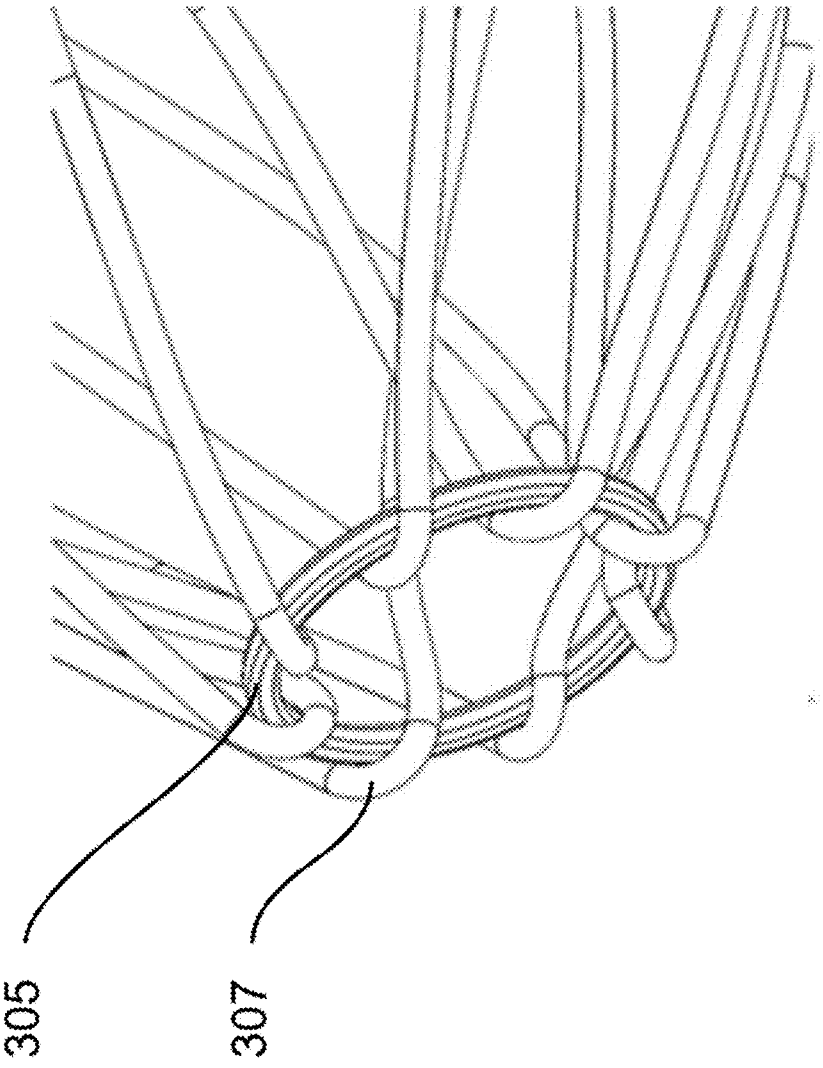
FIG. 10*b* is a detail of a ring with filaments bent around the ring.
Figure 11A:
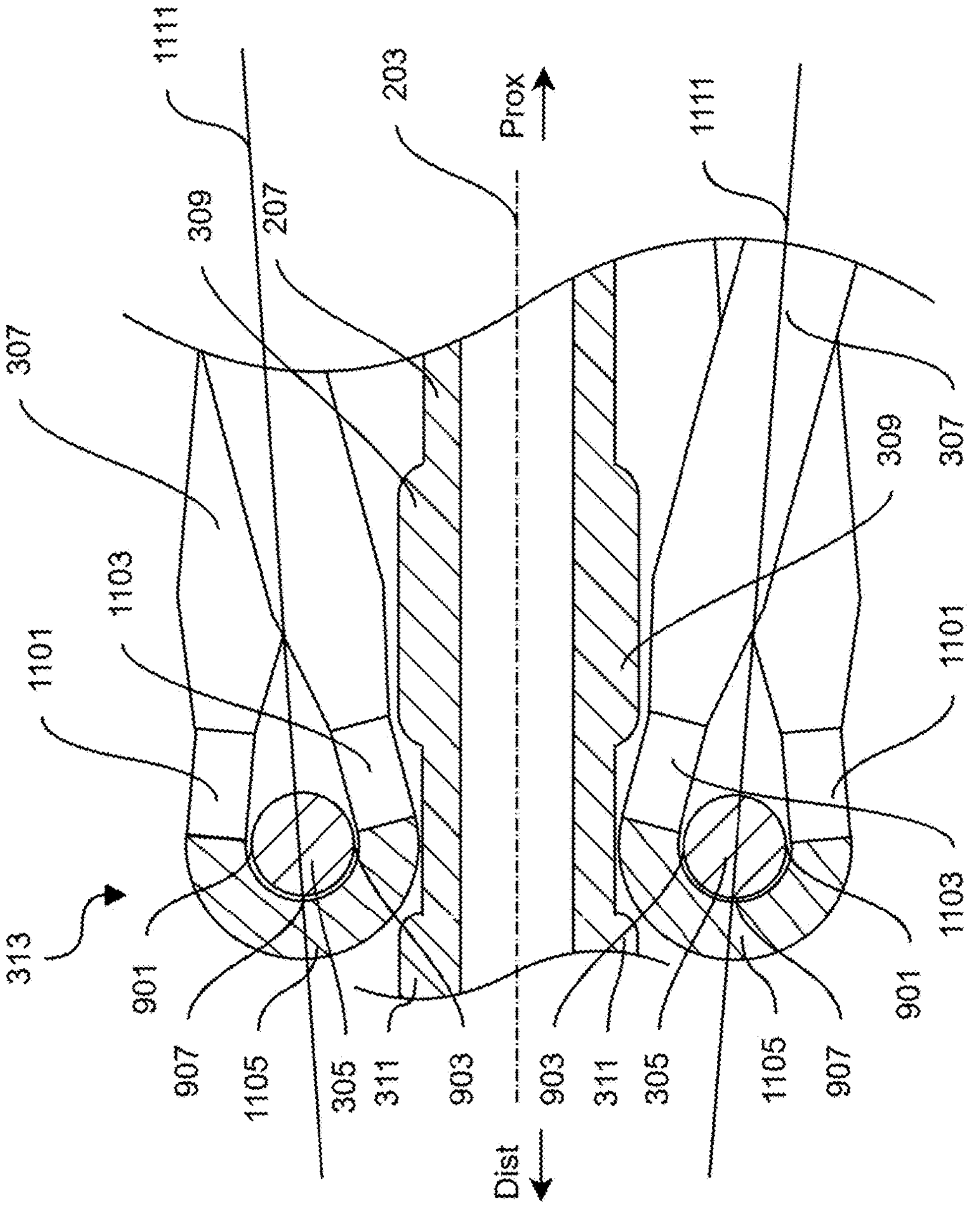
FIG. 11*a* is a cross-section of a detail of a ring with filaments and inner elongated shaft.

At least one filament (307) of the plurality of filaments (307) may be bent around the ring (305) as shown in FIGS. 10*a* and 10*b*. The filament (307) may be bent around the ring (305) such that a first portion (1101) of each filament (307) extends approximately from a proximal direction approximately parallel to a parallel plane (1111) approximately parallel to a longitudinal central axis (203) over the outer edge (901) of the ring (305), a second portion (1103) of the filament (307) extends over the inner edge (903) from an approximately proximal direction approximately parallel to a parallel plane (1111) approximately parallel to the longitudinal central axis, and a third portion (1105) of the filament (307) is bent around a distal edge (907) of the ring (305) as shown in FIG. 11*a*. Such a configuration is described when the expandable basket is in a retracted configuration.

The coupling region of the filament may include the first portion (1101), the second portion (1103) and the third portion (1105) of the filament (307).

Figure 11B:
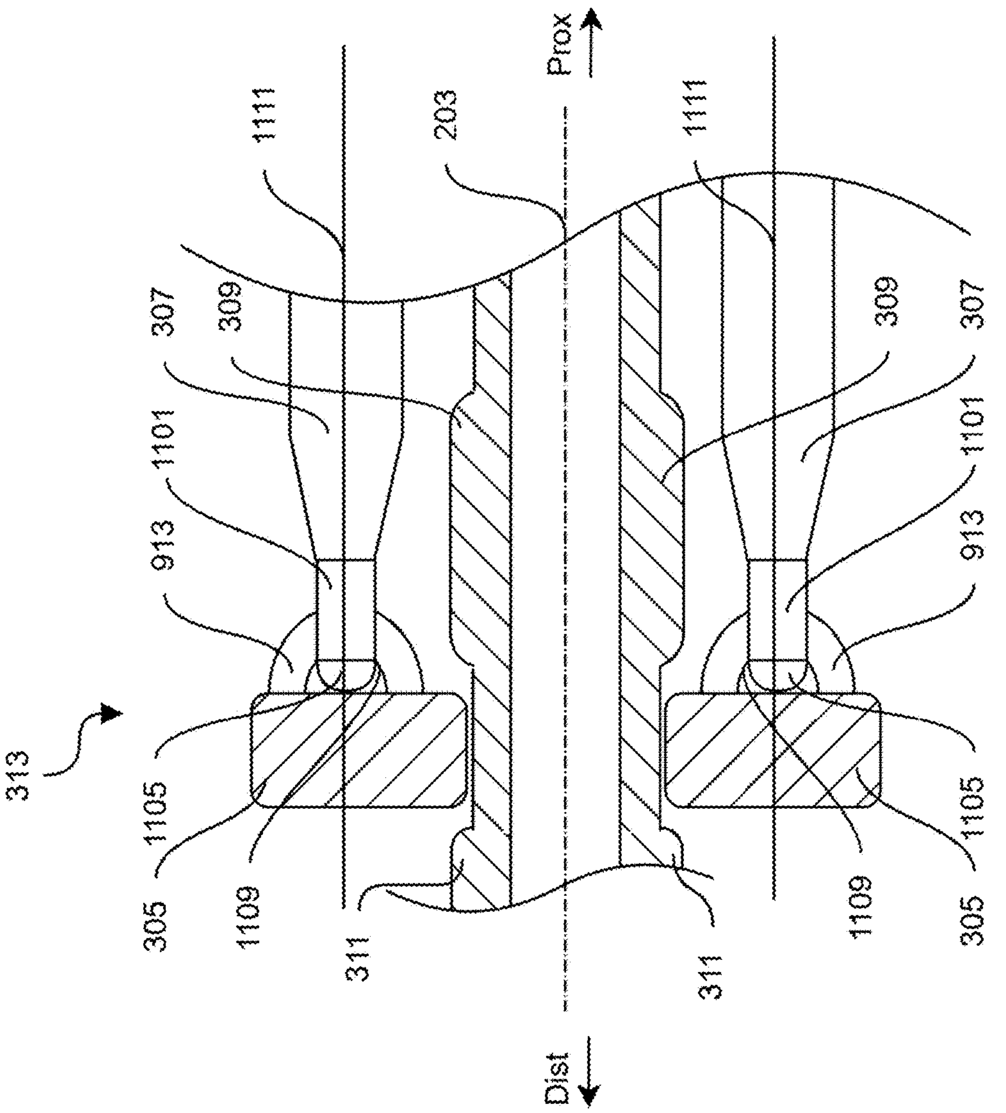
FIG. 11*b* is a cross-section of a detail of a ring with exemplary retaining members, filaments and inner elongated shaft.

FIG. 11*b* shows an example of the coupling of the filament (307) to the ring, but this time via the retaining member (913). The filament (307) may be bent around the retaining member (913) such that a first portion (1101) of each filament (307) extends approximately from a proximal direction approximately parallel to a parallel plane (1111) approximately parallel to a longitudinal central axis (203) over a first edge of the retaining member (913), a second portion of the filament (307) extends over a second edge of the retaining member (913) from an approximately proximal direction approximately parallel to a parallel plane (1111) approximately parallel to the longitudinal central axis (203), and a third portion (1105) of the filament (307) is bent about an inner edge (1109) of the retaining member (913). Such a configuration is described when the expandable basket is in a retracted configuration.

Figure 12A:
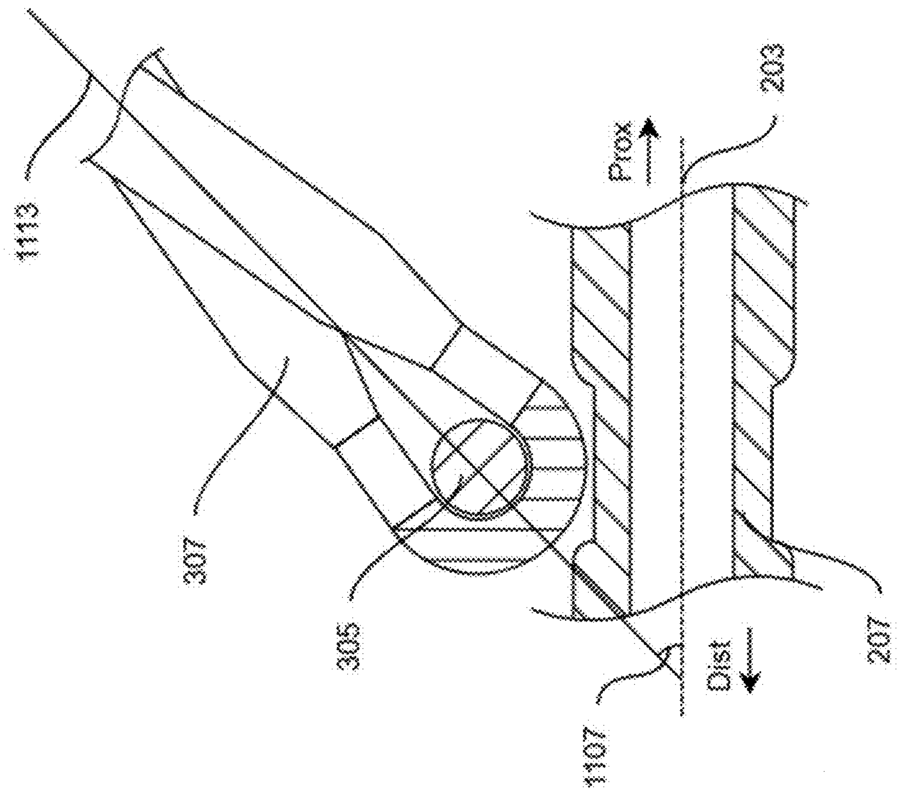
FIG. 12*a* is a cross-section of a detail of a ring, inner elongated shaft and filaments in different deployment state.
Figure 12B:
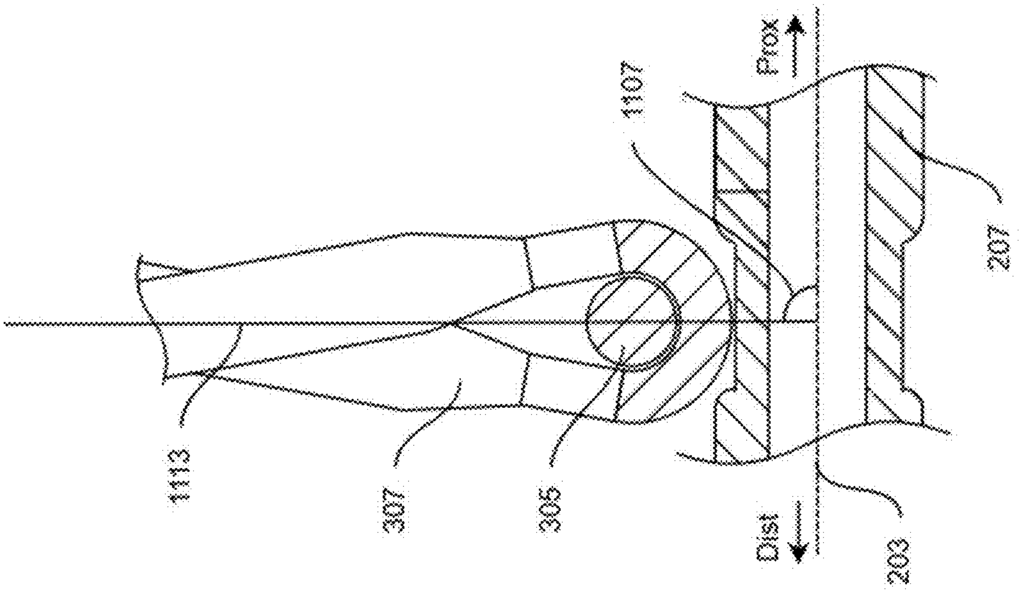
FIG. 12*b* is a cross-section of a detail of a ring, inner elongated shaft and filaments in another deployment state.
Figure 12C:
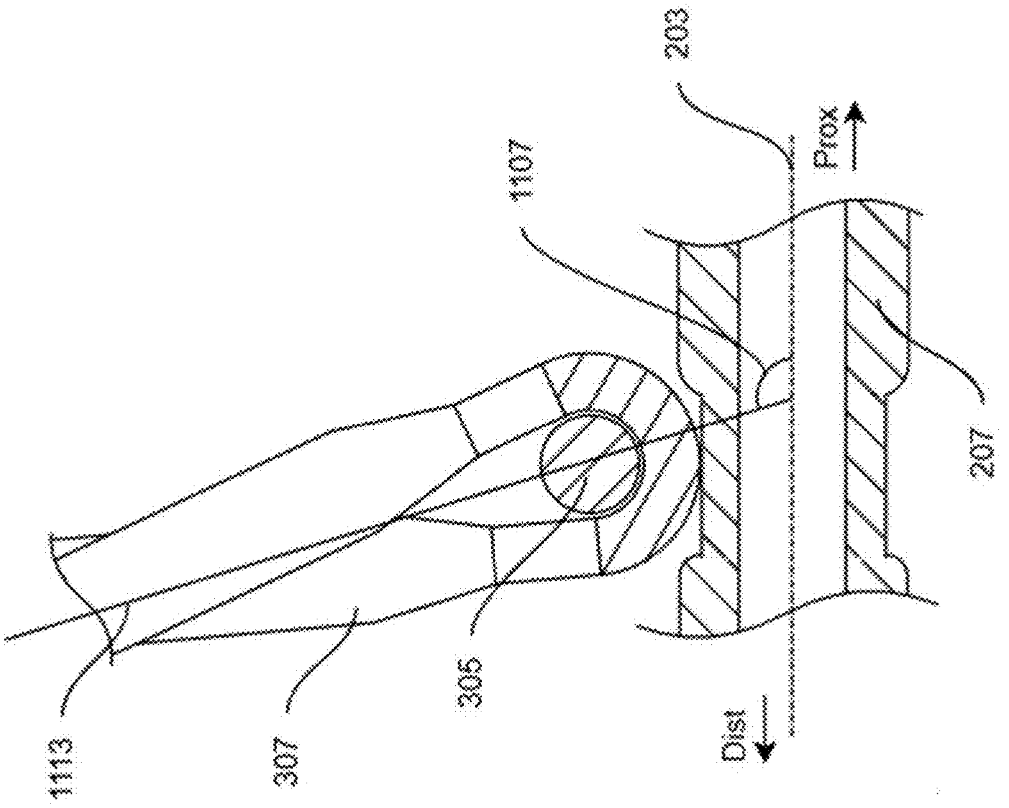
FIG. 12*c* is a cross-section of a detail of a ring, inner elongated shaft and filaments in yet another deployment state.

In an example, when the filament (307) is coupled to the ring (305) by the bending, only the filament (307) or the first, second, and third portions of the filament (307) may move radially relative to the cross-sectional surface of the ring (305) when the expandable basket is deployed to one of its expanded configurations. The position of the first, second, and third portions relative to the cross-sectional surface of the ring (305) is dependent upon the state of deployment of the basket, as shown in FIGS. 12*a* through 12*c*. In these cases, the first portion (1101) and second portion (1103) of the filament (307) are no longer approximately parallel to the parallel plane (1111) approximately parallel to the longitudinal central axis (203), but are approximately parallel to a plane (1113) having an angle (1107) to the longitudinal central axis (203). However, the FIGS. 12*a* through 12*c* show an example, where the filament is bent around the ring, the same is true for the examples, where the filaments are coupled to the retaining members (913).

The angle (1107) depends on the state of expandable basket deployment and can range from 0°—when the expandable basket is in a retracted configuration (in this example the plane (1113) corresponds to the parallel plane (1111))—to 25° to 120°, or 35° to 110°, or 40% to 100%, or 45% to 95%, when the expandable basket is in its fully expanded configuration. The term "approximately" in this particular example, in this particular paragraph, may mean the value +−30%.

This may correspond to the rotational movement of the coupling of the filament which may have a direction radially outwards with respect to the longitudinal central axis about at least a portion of the ring or at least a portion of the retaining member at least during the deployment or retraction of the expandable basket from the collapsed configuration to at least one expanded configuration and may have a maximum angle of the rotation between 0° to 120°, or between 0° to 110°, or between 0° to 100°, or between 0° to 90°.

The first, second or third portion of the filament may be disposed in the notch. Bending may be understood as the act of curving or angling a component, and in this context, it refers to the way the filaments are positioned relative to the ring. One advantage of this arrangement is that the three distinct portions of the filament ensure secure attachment to the ring while allowing controlled (radial) movement of the filaments when the catheter is deployed or retracted. By extending portions of the filaments over both the outer and inner edges of the ring and bending the third portion around the distal edge, the structure ensures that the filaments are not displaced under stress. One advantage of this design is that by securing the filament in the notch, the structure enhances the stability and accuracy of the filament's positioning during catheter use. This ensures that the filament remains in its intended position, particularly during the expansion and contraction of the catheter's basket. The notches help maintain the overall geometry of the filament array, ensuring effective and consistent contact with the tissue during ablation, thus improving procedural outcomes.

The first, second, or third portions of the filament may have a different outer diameter than the remaining portion of the filament, e.g., the outer diameter in these areas may be smaller than the outer diameter of the remaining portion of the filament. A smaller diameter refers to a reduced thickness compared to other portions of the filament. For example, the reduced outer diameter may correspond to the inner diameter of the remainder of the filament. This configuration can allow for increased flexibility in the thinner portion while maintaining strength in the thicker portions. One advantage of this arrangement may be that it allows the ring to have smaller outer dimensions compared to the solution without the diameter reduction in these portions of the filament, or the ring may retain more filaments with the same outer dimensions compared to the solution without the diameter reduction in these portions of the filament.

The diameter of the filament in the first, second or third portion of the filament may be reduced by 10% to 95%, or by 15% to 90%, or by 15% to 85%, or by 20% to 80%, or by 25% to 75%, or by 30% to 70% compared to the remainder of the filament.

The diameter of the filament in the first, second, or third portion of the filament may be, for example, from 0.1 mm to 0.7 mm, or from 0.15 mm to 0.6 mm, or from 0.2 mm to 0.5 mm, or from 0.25 mm to 0.45 mm.

The total length of the first, second and third portions of the filament may be, for example, from 1% to 50%, or from 1% to 40%, or from 1% to 30%, or from 1% to 20%, or from 1% to 15% of the total length of the filament.

The number of notches may correspond to the number of filaments coupled to the ring. For example, the number of notches may be from 1 to 60, from 2 to 30, from 3 to 20, from 4 to 15, or from 5 to 12.

This design contributes to the consistent expansion and contraction of the filaments, which increases the reliability of the catheter during ablation procedures by maintaining the intended shape of the expandable basket and ensuring an even distribution of force across the filaments.

In examples where a design of the terminal assembly includes metal parts, they may be used, for example, as electrodes, either for ablation, for sensing or mapping, or for a combination thereof.

Figure 13A:
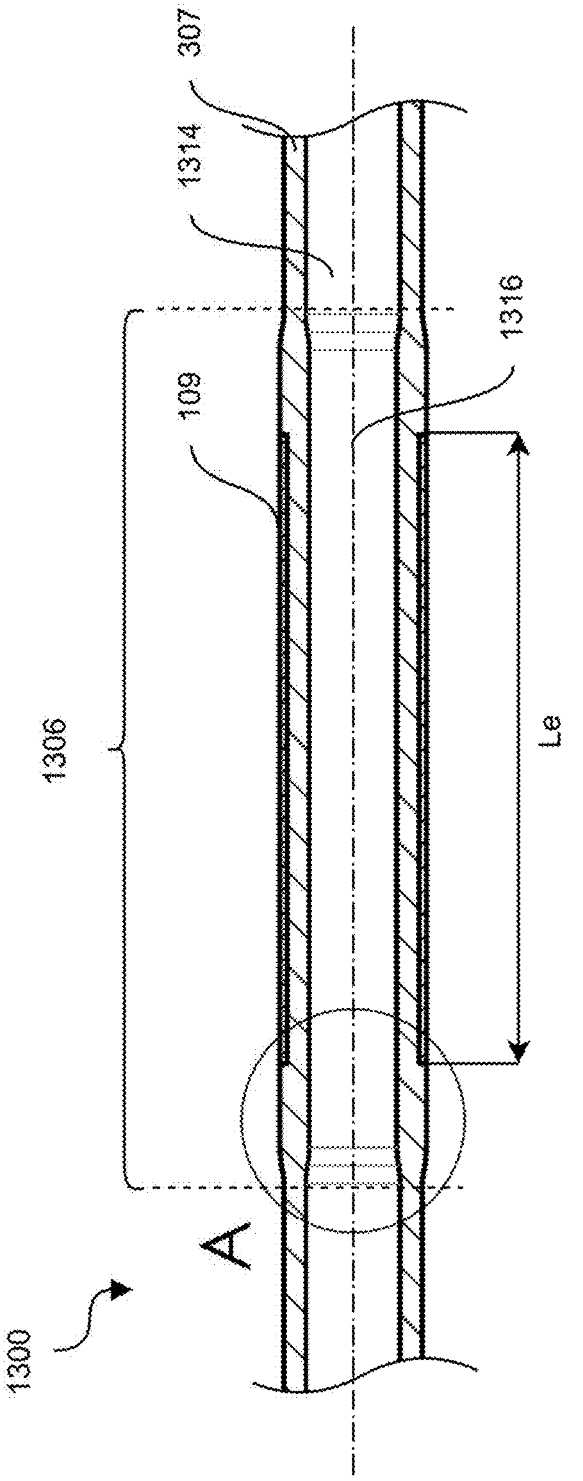
FIG. 13*a* is a cross-section of an exemplary filament assembly.
Figure 13B:
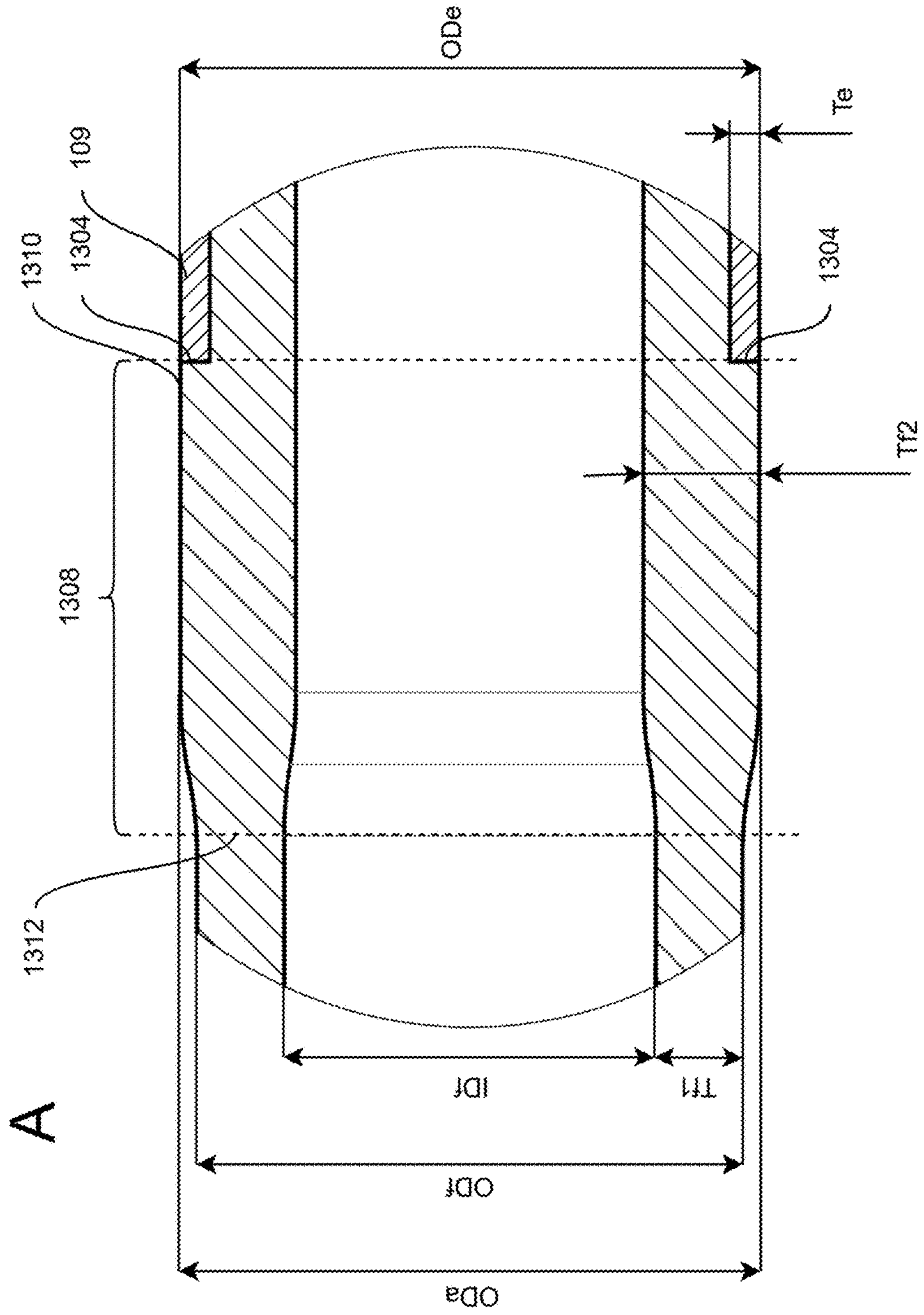
FIG. 13*b* is a detail of a cross-section of a portion of a filament assembly.

The distal tip of the catheter may comprise an expandable basket including at least one filament, which may comprise a filament assembly (1300). The filament assembly (1300), as shown in FIGS. 13*a* and 13*b*, comprises at least one filament (307) having a longitudinal axis (1316) of the filament and at least one electrode (109). The filament may have, for example, a structure of a hollow tube with a lumen (1314). The filament may have the lumen along its entire length or, for example, the lumen may be present only in a portion of the length of the filament. The filament may have an outer diameter (ODf) and a length. In the case where the filament is a hollow structure, for example, a tube, it has an inner diameter (IDf) and filament wall thickness (Tf1). The outer diameter of the filament may be from 0.2 mm to 8 mm, from 0.3 mm to 5 mm, from 0.4 mm to 2 mm, or from 0.5 mm to 1 mm.

When the filament includes a lumen (filament is a hollow structure, for example a tube), the filament wall thickness (Tf1) may be, for example, from 0.01 mm to 2 mm, from 0.02 mm to 1.5 mm, from 0.05 mm to 1 mm, from 0.07 mm to 0.5 mm, or from 0.08 mm to 0.5 mm. The filament wall thickness may be uniform throughout the whole circumference (all angular directions from a central longitudinal axis of the filament) of the filament, or may differ in different angular directions from the central longitudinal axis of the filament. The wall thickness as well as the outer diameter (ODf) and/or inner diameter (IDf) may be uniform or may differ through the length of the filament as well.

The filament may include fusible material, for example, a plastic material or, for example, a thermoplastic. The material may include, for example, polymers or thermoplastic elastomers like Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET). The material may be further reinforced, for example, by glass fibers.

The cross-section of the filament may be circular, or, alternatively, other cross-section shapes are possible, for example but not limited to oval, round, semicircular, rectangular, square, or flat. Some or all of the filaments can be hollow along their entire length or, for example, the lumen may be present only in a portion of the length of one or more filaments.

Figure 14A:
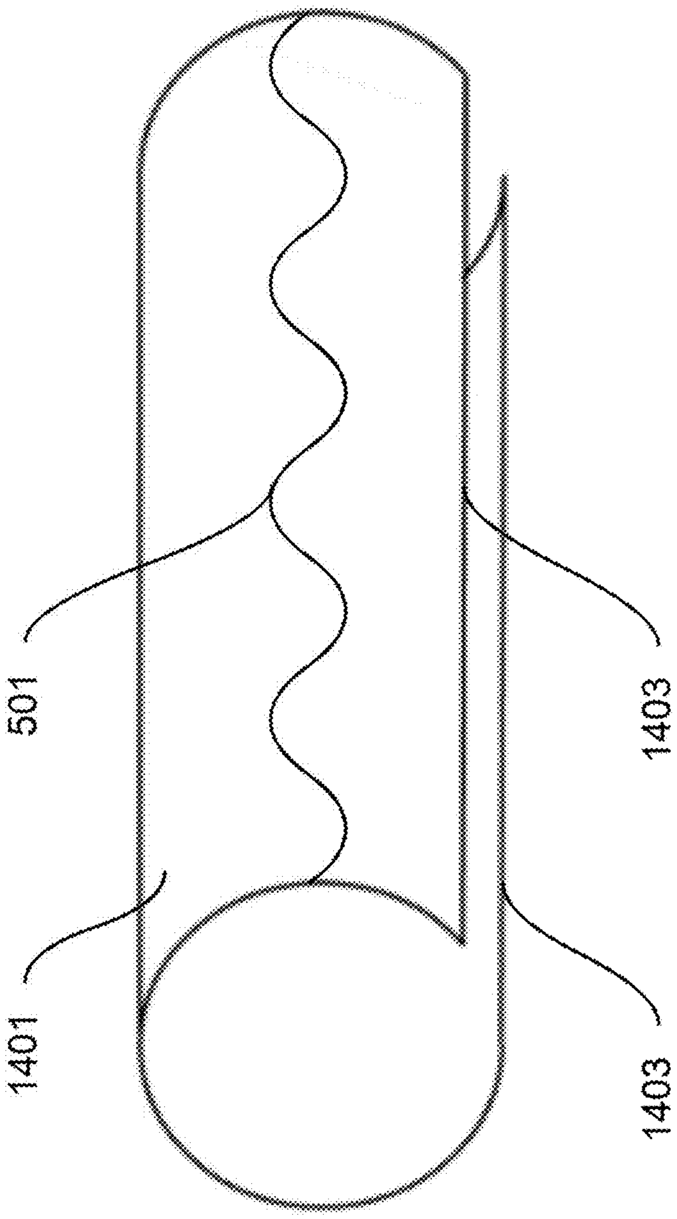
FIG. 14*a* is an example of a flexible printed circuit board.
Figure 14B:
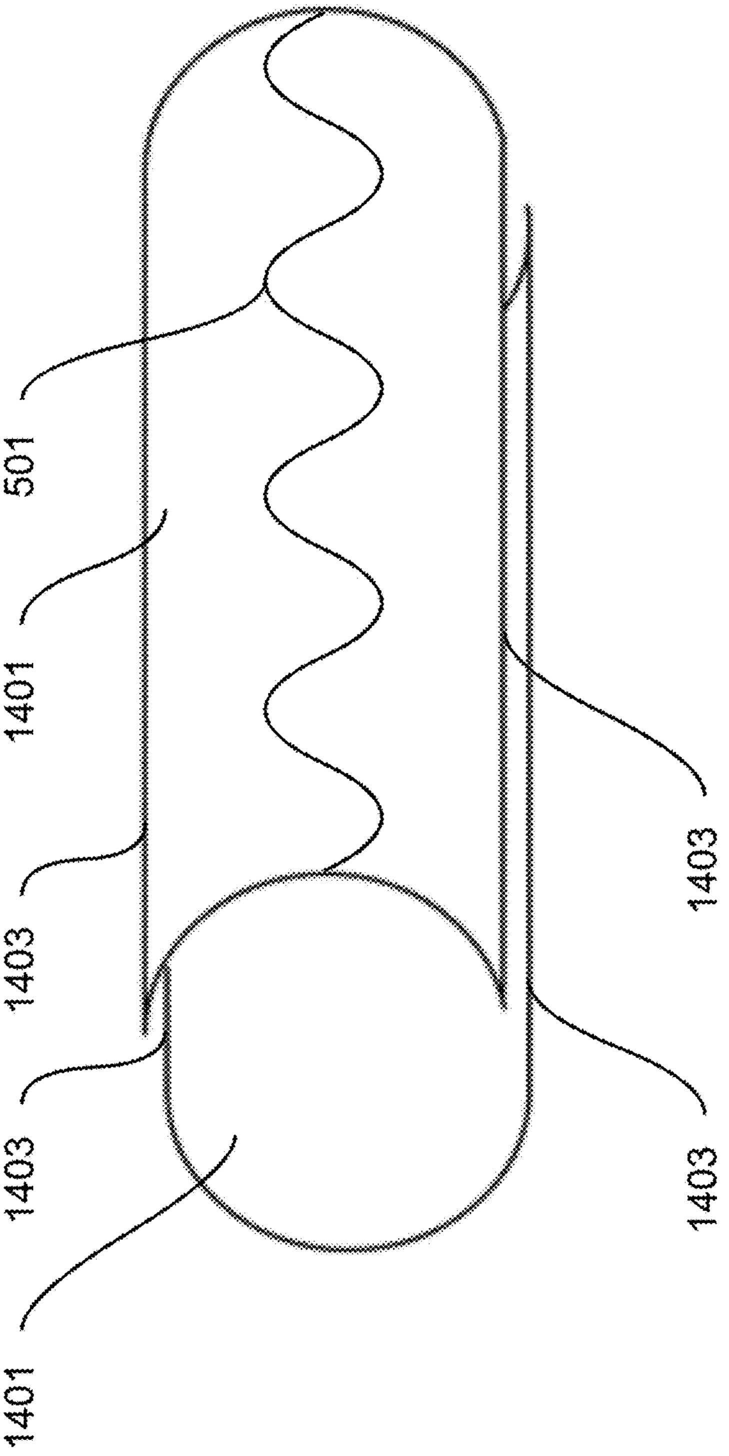
FIG. 14*b* is another example of a flexible printed circuit board.

The filament may include a flexible circuit board (FPCB), which may also be stretchable. A substrate of the FPCB may include stretchable material. The filament comprising the flexible/stretchable printed circuit board may be formed from a flat FPCB (1401) rolled into a tube of circular cross-section as shown in FIGS. 14*a* and 14*b*. The filament may be formed, for example, from one sheet of the FPCB (1401), as shown in FIG. 14*a*, or from multiple sheets of the FPCB (1401), as shown, for example, in FIG. 14*b*. The edges (1403) of the rolled FPCB (1401) may be joined by either bonding or welding to form a tubular structure. Such filaments may then be braided into a braided mesh to form the catheter basket at the distal end of the catheter.

The substrate of the FPCB may be a single layer or may include a plurality of layers of the same or different materials. The substrate may consist of an electrically insulating material, e.g. in the form of a flexible and/or stretchable film, and may include a polymer layer, e.g. polyimide or a cycloaliphatic polyolefin. The substrate may serve as a support for a conductive layer, which may include, for example, conductive leads (501) and/or other components, for example electrodes, sensors, various electronic components and so on. The conductive layer may be at least partially coupled to the at least one side of the substrate. The conductive layer may be at least partially coupled to the at least two sides of the substrate. The substrate may include transverse conductive portions in its thickness, which may electrically connect one side of the substrate to the other side of the substrate or one side of the substrate layer to the other side of the respective substrate layer. The transverse conductive portion may be in the form of a through-hole, e.g. a conductor (e.g. copper) plated through-hole. The conductive layer may be coupled between two substrate layers. The FPCB may comprise multiple layers of the substrate and/or conductive layers.

The FPCB, the substrate and/or the conductive layer may include another layer of material, e.g. a coating, e.g. a biocompatible coating, an insulating coating, an anti-corrosion coating, a low-friction coating, and so on.

The conductive layer, e.g. the conductive leads, may be adapted to withstand substantial flexing, bending, and stretching of the conductive layer, i.e. the substrate, without changing its mechanical properties (braking, tearing, disintegrating) and/or without changing its electrical conductivity, especially in a case where the flexible substrate is also stretchable, e.g. comprises or consists of a stretchable material. The conductive layer may comprise or be made of a material that is electrically conductive while still being flexible or stretchable enough to adapt to the flexing, stretching, and bending of the substrate. The conductive layer, e.g. the conductive leads, may also create a special pattern, e.g. on a surface of the substrate, which can minimize or eliminate an influence of the stretching, bending or flexing of the substrate on the mechanical properties of the conductive leads.

Figure 15A:
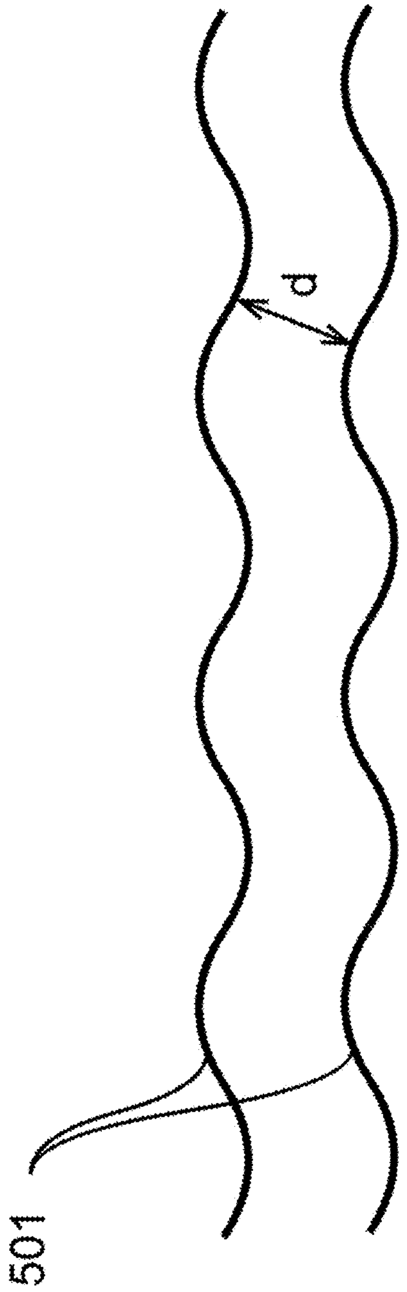
FIG. 15*a* shows a meandering pattern of conductive leads.
Figure 15B:
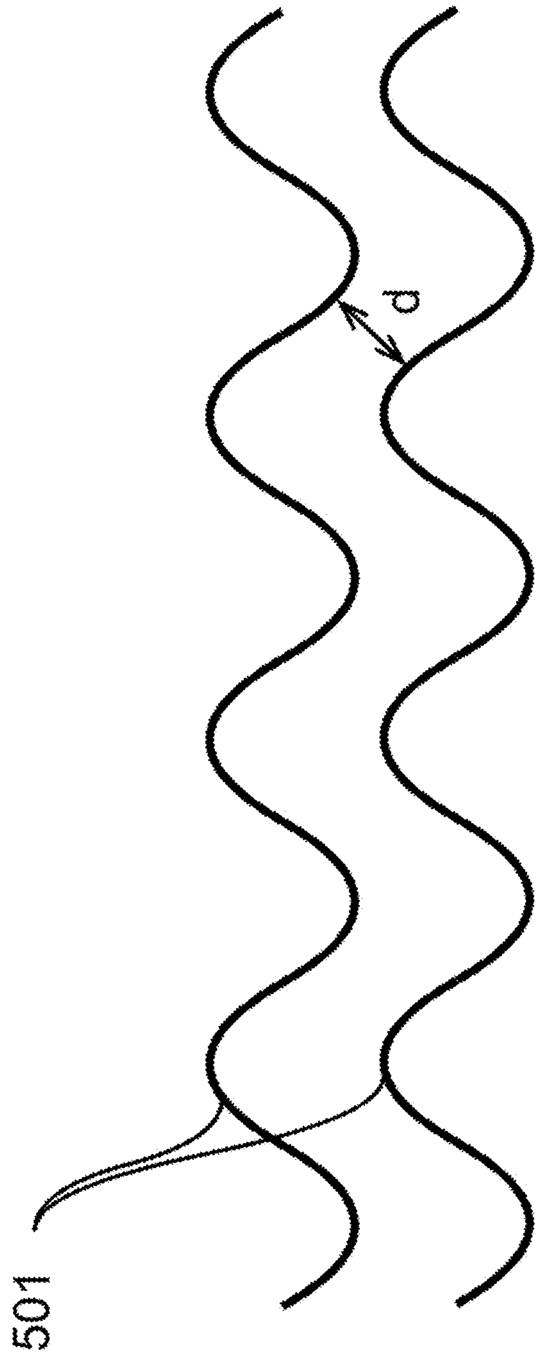
FIG. 15*b* shows another meandering pattern of conductive leads.
Figure 15C:
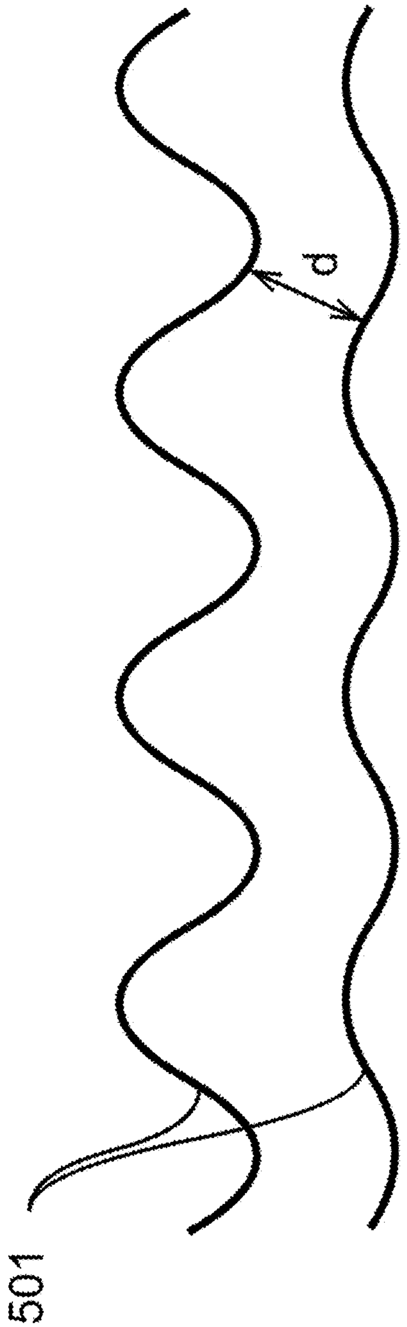
FIG. 15*c* shows an exemplary meandering pattern of conductive leads.

The conductive leads (501) within the filaments can be designed with specific patterns to accommodate the flexing of the expandable basket. The pattern on the filaments may be meandering or zigzagging to allow for flexibility. An exemplary meandering pattern of the conductive leads (501) is shown in FIGS. 15*a* through 15*c*. However, this pattern could introduce unwanted inductance when used in the catheter shaft or the filament. Therefore, the pattern on the outer shaft of the catheter or the filament may be different, being either straight or having a flatter zigzag or meandering pattern with reduced angles between turns.

The conductive leads within the filaments may be configured for specific voltage requirements. For example, conductive leads adapted for connection to, for example, a sensor requiring a low voltage and/or current may have different parameters than conductive leads required for transfer of ablative energy to an electrode. The conductive lead (hence the FPCB) adapted for transfer of ablative energy, e.g. for transfer of an electrical signal from a pulse generator to an electrode configured for generation of a pulsed electric field, must be configured to withstand and safely deliver (transfer) a voltage of hundreds or thousands of volts without negative effects of breakage, melting, disintegration, or short circuiting.

The FPCB (conductive layer, conductive leads) for electrical signals for pulsed field ablation can be configured to transmit more than 5000V. When a filament has only one conductive lead, the electrical insulation of the lead may not be too difficult, especially if the conductive lead is straight. However, when more than one wire is required on a filament, it may be advantageous to keep a minimum required distance (d) between the closest points of the conductive leads on the filament as far apart as possible to provide the best electrical insulation between them. For example, if there are two leads on a filament, they can be placed on opposite sides of the filaments.

For example, a minimum required distance (d) between a closest point of two adjacent conductive leads configured to transmit electrical signals for pulsed field ablation may be, for example, from 0.01 mm to 2 mm, or from 0.05 mm to 1.5 mm, or from 0.08 mm to 1.1 mm, or from 0.09 mm to 1 mm, or from 0.1 mm to 0.8 mm, or from 0.11 mm to 0.6 mm, or from 0.12 mm to 0.4 mm.

The conductive lead configured to transmit electrical signals for pulsed field ablation may have a particular minimum path width to withstand electrical signals for pulsed field ablation without risk of breakage of the conductive lead. For example, the required minimum path width may be from 0.01 mm to 1 mm, or from 0.02 mm to 0.8 mm, or from 0.015 mm to 0.5 mm, or from 0.02 mm to 0.3 mm, or from 0.025 mm to 0.1 mm, or from 0.03 mm to 0.09 mm.

The catheter may include one filament or a plurality of filaments. One filament may include one electrode or a plurality of electrodes. One filament may include one electrode fitting area or a plurality of electrode fitting areas.

The filament may be further mechanically reinforced, for example, by inserting a mechanical support into a lumen of the filament. Such mechanical support may, for example, be in the form of a strut inserted into the lumen of the filament. The strut may be placed in the entire length of the filament, or in a full length of the filament lumen in the event that the filament does not have a lumen along its entire length. Another possible option would be to place the strut in only a portion of the length of the lumen, leaving a portion of the filament reinforced with a strut and another portion without strut reinforcement.

The strut may be made of e.g. nitinol, e.g. with an electrical insulating layer, and/or e.g. polyamide (PA), polyimide (PI) or PTFE. Other possible materials for the strut may be polymers or thermoplastics, such as nylon, fluorinated ethylene propylene (FEP), polyethylene (PE), PEBA, PEEK, polyimide (PI), polypropylene (PP), PTFE, polyurethane (PU), polyethylene terephthalate (PET), or silicon. Another option suitable for further reinforcing the filaments is to fill at least part of the lumen of the filament with adhesive or molten polymer or thermoplastic material.

The reinforcement struts (struts), e.g. nitinol struts, may be pre-formed prior to an assembly of the expandable basket to define the final shape of the respective filaments, i.e. the braided expandable basket. In one example, the final shape of the expandable basket is achieved by threading the filaments, e.g. filaments in the form of non-conductive e.g. thermoplastic tubes, or filaments comprising and/or made of FPCB onto the preformed nitinol struts, which are then braided together to form a durable structure.

In one example, the pre-forming of the nitinol struts may allow the struts in the expandable basket to be pre-formed to the shape of the expandable basket in one of the expanded states. In this example, omitting the coupling of the expandable basket to the inner elongated shaft could be one of the possible design solutions, as the expandable basket could expand by pre-tensioning force and no external force would be required during deployment from the collapsed to the expanded configuration of the expandable basket. The configuration without coupling the expandable basket to the inner shaft may allow the distal end of the basket to be flat without any distally protruding structures, thereby improving tissue contact.

However, the expandable basket comprising pre-formed struts may be coupled to the inner elongated shaft at its distal end as well as to the outer elongated shaft. The pre-forming of the struts may not only assist in pre-forming the expandable basket to one of its expanded states, but the pre-forming of the struts may even assist in coupling the expandable basket, particularly in coupling the basket to the inner elongated shaft adjacent to the terminal assembly. As noted above, the coupling of the expandable basket to the inner elongated shaft may include a ring around which the filaments are bent.

In examples where the strut is included in the filament, e.g. in the filament lumen, the strut may be pre-formed in the region of the expandable basket. If, in some aspects, the strut does not terminate adjacent to the terminal assembly but is continuous, it may be pre-formed (pre-bent) adjacent to the terminal assembly and/or in the region where the filament is bent around the ring.

In the example, when the strut does not terminate adjacent to the distal end region, it may be pre-formed, for example, in the manner as we can see in FIGS. 16*a* to 16*e*. The strut (1601) may include at least a first elongated portion (1603) and a second elongated portion (1605) and a bent portion (1607). The first and/or second elongated portion may be pre-formed such that the strut follows an envelope (outer shape) of the expandable basket, for example, deployed in one of its expanded configurations or in the collapsed configuration. Within this envelope, the strut may be pre-formed into a helical shape about the longitudinal central axis of the catheter but within the envelope of the basket. The pre-form corresponds, for example, to the path of a filament braided into a braided mesh contained within the expandable basket in the particular expanded configuration. The first end of the helix (spiral) may begin at the proximal end of the expandable basket, for example at the distal end of the outer elongated shaft, and the second end of the helix may be located at the distal end of the expandable basket, for example, in the area of the terminal assembly adjacent the ring. The number of turns of the helix may depend on several factors, such as a number of filaments contained in the expandable basket. For example, the number of turns may be from 0.05 to 10, or from 0.1 to 8, or from 0.15 to 5, or from 0.2 to 3, or from 0.25 to 2, or from 0.3 to 1, or from 0.35 to 0.8. One turn may mean completing a full circle around the shape of the expandable basket deployed in one of its expanded configurations or in a collapsed configuration, observed from the front view. For example, it may mean that the proximal portion of the helix may begin at the outer shaft of the catheter, for example, at the distal end of the outer shaft at a point on a plane intersected by the longitudinal central axis and in a radial direction from the longitudinal central axis, and the distal portion of the helix terminates adjacent to the terminal assembly, for example, adjacent to the ring at the point on the same plane intersected by the longitudinal central axis in the same radial direction from the longitudinal central axis.

Figure 16A:
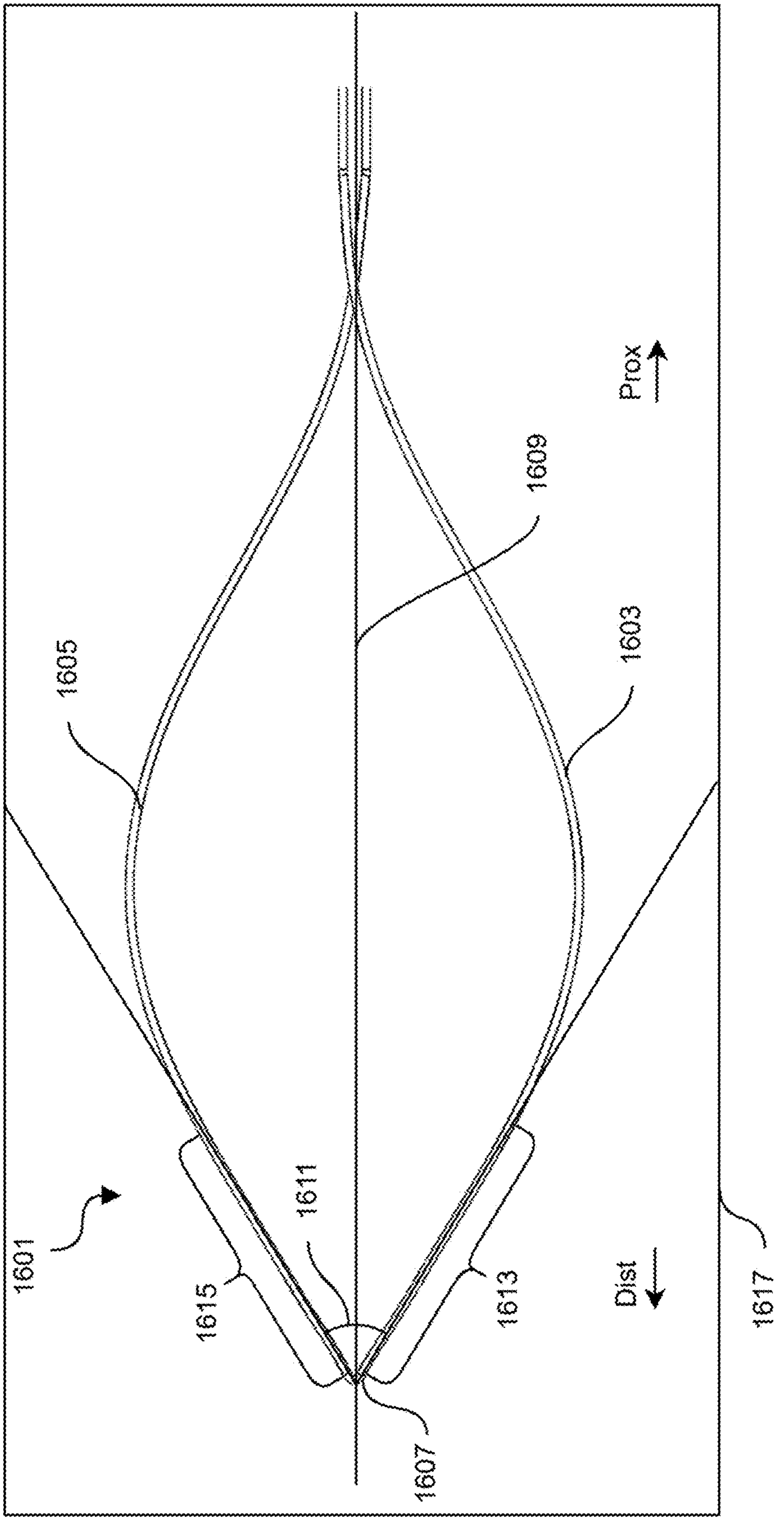
FIG. 16*a* is a top view of a preformed strut.
Figure 16B:
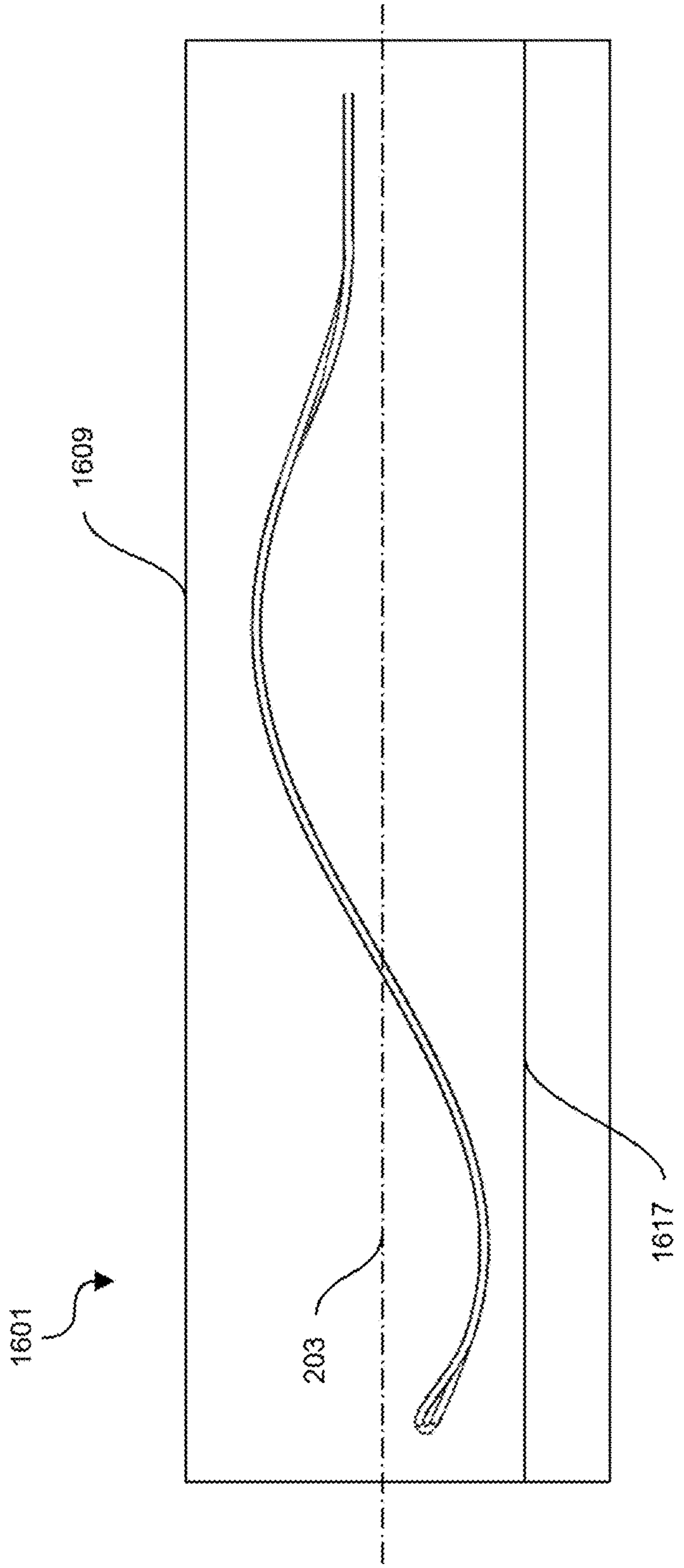
FIG. 16*b* is a side view of a preformed strut.

The first elongated portion (1603) and second elongated portion (1605) may be coupled by the bent portion (1607) and may or may not mirror symmetrically about a plane of symmetry (1609) therebetween, as seen in FIG. 16*a*, which is a top view of the preformed strut, and in FIG. 16*b*, which is a side view of the preformed strut. The plane of symmetry (1609) may be substantially parallel to the longitudinal central axis of the catheter. A distal portion (1613) of the first elongated portion (1603) and a distal portion (1615) of the second elongated portion (1605) coupled to the bent portion (1607) may maintain an angle (1611) with each other. The angle (1611) may be measured on the projection of the distal portion (1613) of the first elongated portion (1603) and the distal portion (1615) of the second elongated portion (1605) coupled to the bent portion (1607) to the maximum angle plane (1617) which is one of the planes substantially parallel to the longitudinal central axis (203) of the catheter and in which the projection has the highest angle (1611) compared to angles of the projections in other planes substantially parallel to the longitudinal central axis (203). The distal portions of the first elongated portion (1603) and the second elongated portion (1605) may be from 0.1% to 50%, or from 0.3% to 40%, or from 0.5% to 35%, or from 0.75% to 30%, or from 1% to 25% of the length of the first elongated portion (1603) and the second elongated portion (1605) of the strut measured from the coupling to the bent portion (1607).

The angle (1611) may be from 0.5° to 90°, or from 1° to 85°, or from 1.5° to 80°, or from 2° to 75°, or from 3° to 70°, or from 4° to 65°, or from 5° to 60°.

Figure 17:
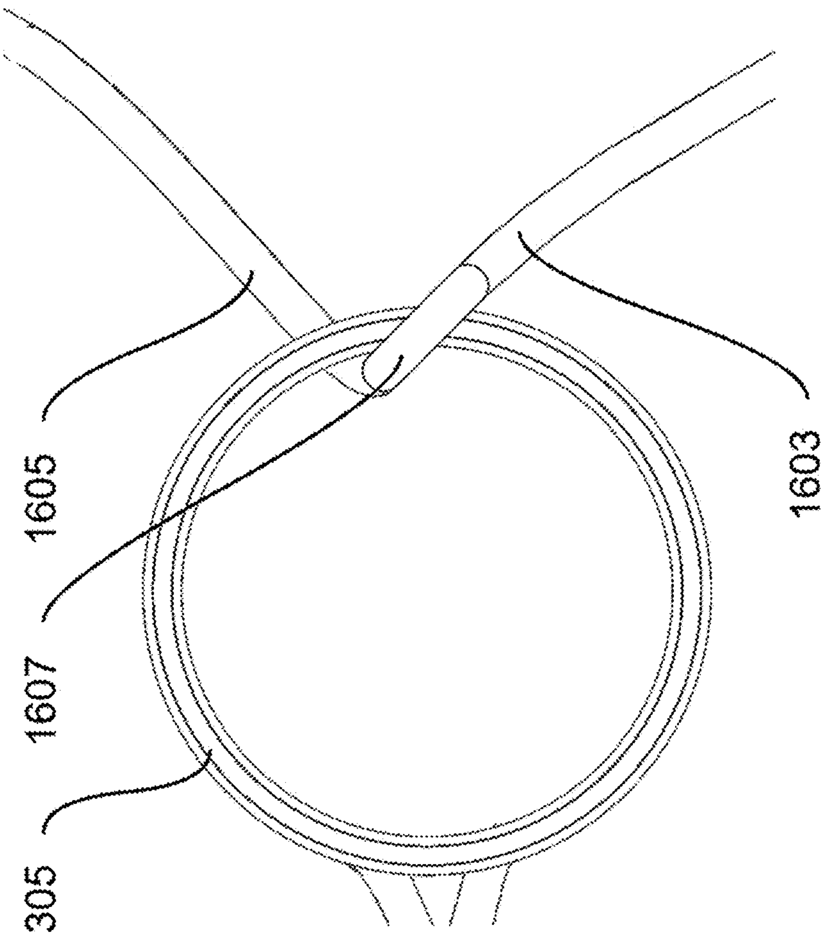
FIG. 17 is a view of a ring and a preformed strut.

The bent portion (1607) may include a bend. In the finished assembly of the basket assembly, the bend may be in a region of the terminal assembly; in particular, the bend may pass around the ring. For example, a terminal end of the first elongated portion (1603) may lie in the filament outside of the ring, while the terminal portion of the second elongated portion may lie in the filament inside of the ring, while the bent portion connects both terminal portions around the ring which we can see in FIG. 17, which is a frontal view of a detail of the distal end of the strut (1601) with a ring.

Figure 18:
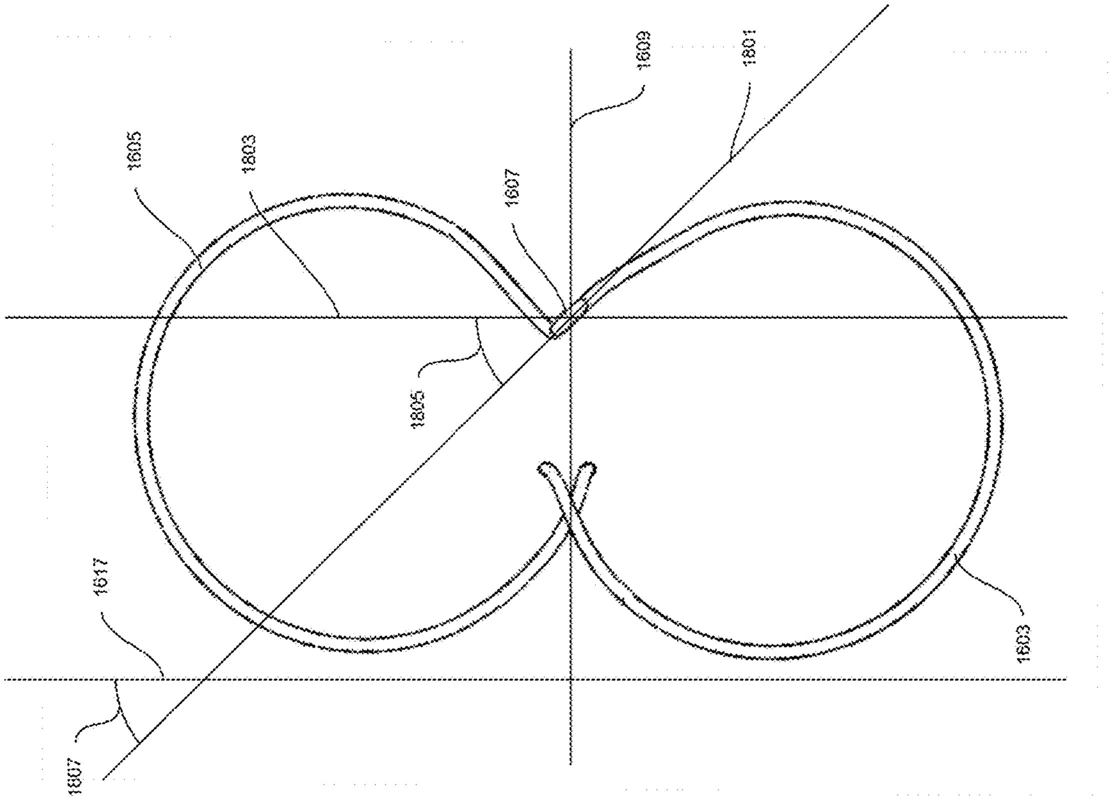
FIG. 18 is a front view of a preformed strut.

FIG. 18 is a front view of the strut (1601). Bending of the bent portion (1607) may occur in a bending plane (1801). The bending plane (1801) may not correspond to or be parallel to either a plane (1803) perpendicular to the plane of symmetry (1609) separating the first and second elongated portions in mirror symmetry or the maximum angle plane (1617), but may be rotated with respect to at least one of the plane (1803) perpendicular to the plane of symmetry (1609) or the maximum angle plane (1617) by an angle of rotation (1805) other than a right angle. For example, the bending plane (1801) may be rotated at the first rotational angle (1805) with respect to the plane (1803) perpendicular to the plane of symmetry from 0.1° to 8990°, or from 30.5° to 85°, from 51° to 80°, from 102° to 75°, from 153° to 70°, from 204° to 65°, or from 255° to 60°, or from 306° to 55°, or from 357° to 53°, or from 388° to 50°.

The bending plane (1801) may be rotated by a second angle of rotation (1807) with respect to the maximum angle plane (1617). For example, the second angle of rotation (1807) may be from 0.1° to 90°, or from 0.5° to 85°, from 1° to 80°, from 2° to 75°, from 3° to 70°, from 4° to 65°, or from 5° to 60°, or from 6° to 55°, or from 7° to 53°, or from 8° to 50°.

Figure 19:
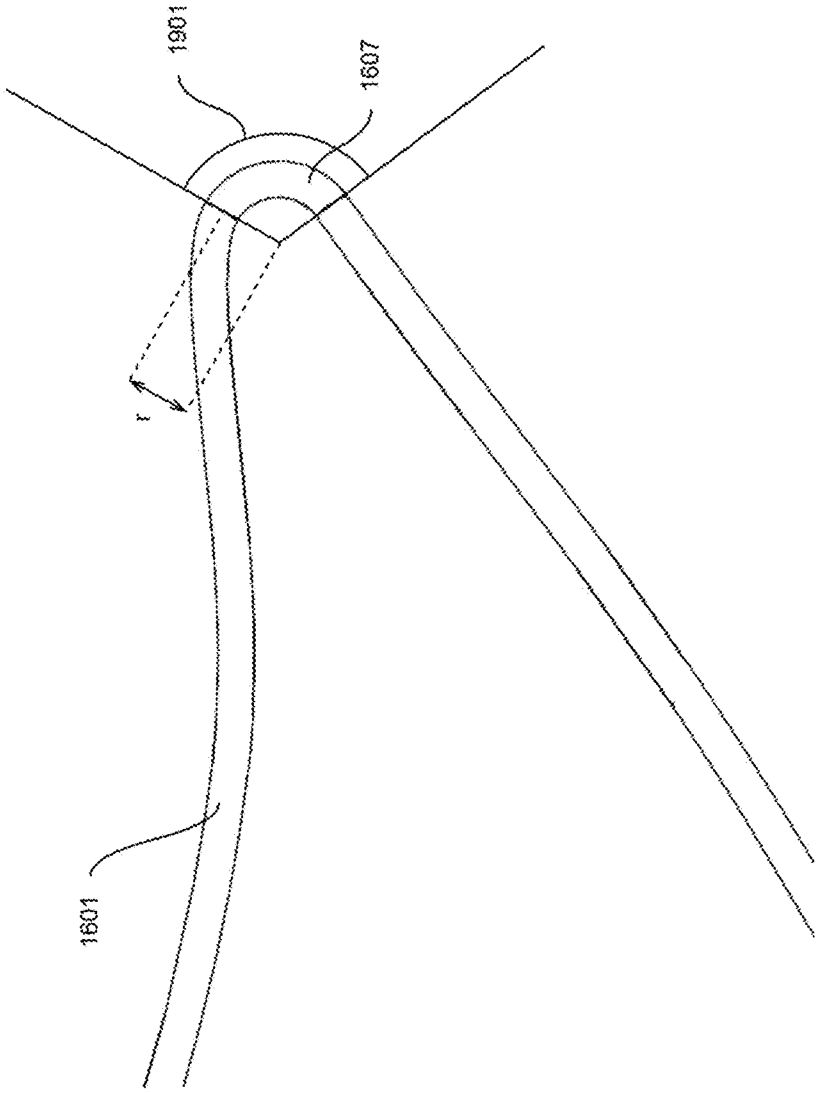
FIG. 19 is a detail of a bent portion of a preformed strut.

A peak bending angle (1901) of the bend in the bent portion (1607) of the strut (1601), as shown in FIG. 19, may depend on a plurality of factors. The factors may include the number of struts (1601), the filaments included in the expandable basket, and/or the braiding pattern of the filaments, which results in struts (1601) braided into a braided mesh within the expandable basket. In some aspects, the peak bending angle (1901) of the bend in the bent portion (1607) performed in a bending plane may be in a range of from 95° to 160°, or from 100° to 150°, or from 105° to 140°, or from 110° to 130°.

The strut (1601) may have a center radius (r) of the bend (measured at the center of the cross-section of the reinforcing strut) in the range of, for example, from 0.2 mm to 0.7 mm from 0.25 mm to 0.6 mm or from 0.3 mm to 0.5 mm. The required radius may depend, for example, on the cross-sectional dimensions of the ring and/or a cross-section of the strut.

As previously mentioned, at least one of the plurality of filaments may be bent around the ring such that a first portion of each filament extends from a proximal direction over the outer edge, a second portion of the filament extends from a proximal direction over the inner edge, and a third portion of the filament is bent around a distal edge of the ring. The strut may be pre-formed (bent) in an area comprising the first, second, and/or third portion of the filament. For example, the strut may be pre-formed (bent) in a region of the third portion of the filament. However, if the strut is bent around the ring during an assembly of the filaments to the ring, the pre-forming of the strut may assist in the assembly of the filaments to the ring, e.g. it may assist in determining a correct area on the filament comprising the first, second, and third portions of the filament. It may also help to make the final shape of the basket assembly, i.e. the expandable basket, i.e. the final assembly of the expandable basket, more predictable and/or according to the specific requirements of the basket assembly.

In one example, the filaments may not include the strut, or at least a portion of the filaments may not include the strut. The filaments themselves may be pre-formed in the same manner as described above with the struts, whether or not they include the strut. In such a case, the preforming would be applied directly to the filament. In examples where the filament includes the strut, the pre-forming of the strut is transferred to the filament, i.e. the filament is pre-formed according to the strut included in the filament.

The electrode (109) coupled to the filament, as shown in FIGS. 13*a* and 13*b*, may be, for example, a ring electrode. The electrode comprises electrically conductive material, for example, a metal, for example, copper, gold, steel, titanium, platinum, platinum-iridium, and so on. The electrode coupled to the filament may have an outer diameter (ODe), inner diameter, and/or length (Le). The outer diameter (ODe) of the electrode may be from 0.2 mm to 8 mm, from 0.3 mm to 5 mm, from 0.4 mm to 2 mm, or from 0.5 mm to 1 mm.

The length (Le) of the electrode may be between 0.1 mm to 15 mm, between 0.2 mm to 10 mm, between 0.3 mm to 6 mm, or between 0.4 mm to 4 mm.

The electrode may include a wall having an electrode wall thickness (Te), electrode cavity (lumen), and at least one electrode edge (1304). The electrode wall thickness (Te) may be from 0.001 mm to 1 mm, or from 0.005 mm to 0.3 mm, or from 0.01 mm to 0.1 mm, or from 0.015 mm to 0.075 mm.

The electrode may be coupled to the particular filament, for example, by way of mechanical attachment, swagging, crimping, gluing, lamination, deposition and/or soldering. The portion of the filament including the electrode may be called an electrode fitting area (1306). The electrode fitting area includes an area of the filament lying between electrode edges (1304) with length corresponding to the length (Le) of the electrode, and an electrode adjacent area (1308), which is an area of the filament lying adjacent to the electrode. The electrode fitting area may include two electrode adjacent areas (1308) on each side of the electrode. The length of the electrode adjacent area (1308) may correspond to the outer diameter (ODe) of the electrode and may be, for example, in a range from 0.1×ODe to 2×ODe, from 0.3×ODe to 1.5×ODe, from 0.5×ODe to 1.3×ODe, from 0.7×ODe to 1.1×ODe, or from 0.8×ODe to 1×ODe.

The length of the electrode adjacent area (1308) may correspond to the length (Le) of the electrode and may be for example in a range from 0.05×Le to 2×Le, or from 0.08×Le to 1.5×Le, or from 0.1×Le to 1.1×Le, or from 0.2×Le to 1×Le, or from 0.3×Le to 0.8×Le.

The electrode fitting area (1306) may have different properties compared to the rest of the filament or at least a portion of the filament lying outside of the electrode fitting area. For example, the diameter of at least a portion of the filament in the electrode fitting area (1306) may be approximately equal to the outer diameter of the electrode, at least at the electrode proximal end (1310), which is an end of the electrode adjacent area (1308) which neighbors the edge (1304) of the electrode. While the diameter of the rest of the filament, or at least portion of the filament lying outside of the electrode fitting area (1306), may have a diameter which is smaller. The material of the filament may be in direct contact with the edge (1304) of the electrode, with at least a portion of the edge (1304), or with the whole edge (1304).

Filament wall thickness (Tf2) in at least a portion of the electrode adjacent area (1308) of the filament may be different compared to the filament wall thickness (Tf1) of the rest of the filament, or at least different compared to the filament thickness of the portion of the filament outside of the electrode fitting area. The filament wall thickness (Tf2) in at least a portion of the electrode adjacent area may be, for example, larger than the filament wall thickness (Tf1) of the rest of the filament and may approximately equal (Tf1+Te)±40%, (Tf1+Te)±30%, (Tf1+Te)±20%, or (Tf1+Te)±10%.

The outer diameter of the filament in at least a portion of the electrode adjacent area (1308), the electrode adjacent area outer diameter (ODa), may be greater than the outer diameter (ODf) of the filament or at least a portion of the filament lying outside of the electrode adjacent area and/or in the electrode fitting area and may be approximately the same as or larger than the outer diameter (ODe) of the electrode. The average diameter of the filament in the electrode adjacent area (1308) (electrode adjacent area outer diameter (ODa)) may be higher than an average diameter of the filament lying outside of the electrode adjacent area. The inner diameter (IDf) of the filament in the electrode adjacent area and/or in the electrode fitting area may be the same as, or smaller than, the inner diameter (IDf) of the filament lying outside of the electrode fitting area.

The outer diameter of the filament in at least portion of the electrode adjacent area (1308), the electrode adjacent area outer diameter (ODa), may be, for example, from 0.9×ODe to 2×ODe, from 1×ODe to 1.5×ODe, from 1×ODe to 1.3×ODe, from 1×ODe to 1.2×ODe, or from 1×ODe to 1.1×ODe.

The wall thickness, electrode adjacent area outer diameter, and/or the inner diameter in the electrode adjacent area may not be uniform. It may have, for example, the smallest wall thickness at the electrode adjacent area (1308) in an area (1312) with the furthest distance from the electrode (109) and the highest wall thickness at the electrode proximal end (1310) of the electrode adjacent area (1308) lying next to the edge (1304) of the electrode (109). The same may be true for the electrode adjacent area outer diameter (ODa) of the filament. The electrode adjacent area outer diameter (ODa) may be different, for example, smaller in the area (1312) at the furthest distance from the electrode compared to the electrode adjacent area outer diameter (ODa) at the electrode proximal end (1310) of the electrode adjacent area. The inner diameter (IDf) of the filament in the electrode adjacent area (1308) may be different in the area (1312) with the furthest distance from the electrode compared to the inner diameter (IDf) of the filament at electrode proximal end (1310) as well. For example, the inner diameter (IDf) may be higher in the area (1312) with the furthest distance from the electrode and smaller in the electrode adjacent area (1308), however the inner diameter may also stay the same in the whole electrode fitting area (1306). The above-mentioned parameters may, for example, progressively change from one side of the electrode adjacent area (e.g., area with the furthest distance from the electrode) to the other side of the electrode adjacent area (e.g., electrode proximal end).

The electrode may include coupling to another device, for example, to a pulse generator or another device capable of sending electrical signals to the electrode or receiving electrical signals from the electrode. The coupling may be carried out by a conducting wire (lead) coupled to the electrode, for example to the inner or outer surface of the electrode or to the edge of the electrode.

The wire may lead towards the electrode, for example, in the cavity (lumen) of the filament, along the outer surface of the filament, or from another direction. The material used for conductive wire may be any electrically conductive material for example copper, stainless steel, steel, nitinol, aluminum, gold, platinum, silver, and so on. The conductive wires may be insulated or uninsulated. The wire may be insulated using any suitable material, for example polyimide, polyurethane, polyester, polyvinyl chloride (PVC), rubber, rubber-like polymers, nylon, polyethylene, polypropylene, silicone, fiberglass, ethylene propylene diene monomer (EPDM), different fluoropolymers like polytetrafluoroethylene (PTFE) and so on. The wire may be made of a single conductor or with a group of conductors, whereas a wire made of a group of conductors is sometimes called "cable". In the case when the wire is insulated a minimum breakdown voltage of the wire insulation should be at least 100V, at least 500V, at least 1000V, at least 4000V, or at least 10000V.

The diameter of the wire with insulation may be limited by the dimensions of other structures of the device such as, for example, the filaments. The diameter of the wire with insulation may also be limited by the minimum voltage it must carry without risk of breakdown. Typical diameter of the wire with or without insulation may be between 0.05 mm and 0.7 mm, between 0.07 mm and 0.5 mm, between 0.1 mm to 0.3 mm, between 0.11 mm to 0.2 mm, or between 0.12 mm to 0.18 mm.

The described filament assembly may help to avoid an exposure of sharp edges of the electrodes which may be helpful, for example, in medical devices applied inside or outside of a body and medical devices that contact a tissue of the body, for example in the distal tip of a catheter device. Edges of the electrodes in the filament assembly (1300) may be covered by a material of the filament and/or the sharp edges of the electrodes may be eliminated. When a filament wall thickness is increased and/or when the filament has a higher diameter in at least portion of the electrode adjacent area, the electrode fitting area may become more rigid compared to the rest of the filament or at least portion of the filament lying outside of the electrode fitting area. When the filament assembly needs to be bent, the bending point of the filament assembly hence the point of bending of the filament assembly with the smallest radius may be moved away from the electrode and/or electrode fitting area along a longitudinal axis of the filament. Exposure of the electrode edges caused by a bending of the filament assembly may be eliminated or reduced.

An exemplary method of a manufacturing of the filament assembly may involve the assembly of the filament, constructed of fusible, for example, plastic material, and an electrode, for example a ring shape electrode coupled to the filament. The electrode may be configured to fit to the outer diameter of the filament. The method may include coupling of the electrode securely to the filament, fitting a mandrel into the cavity of the filament, and/or fitting an additional die at least over edges of the electrode and a portion of the filament adjacent to the electrode. The electrode fitting area of the filament then may be heated up, for example, via a heating of the electrode at least to the melting temperature of the filament material and the heating causes melting of a portion of the filament under the electrode and adjacent the electrode in the electrode fitting area. Melting of the filament material adjacent and under the electrode causes conforming the filament material adjacent to electrode to the edge of the electrode.

FIGS. 20-23 show a cross section of the filament assembly (1300) in particular exemplary steps of the method of manufacturing of the filament assembly. FIG. 20*a* shows an initial setup with portion of the filament (307) and the electrode (109). The electrode is, in this example, coupled to the filament, but is not secured.

Figure 20A:
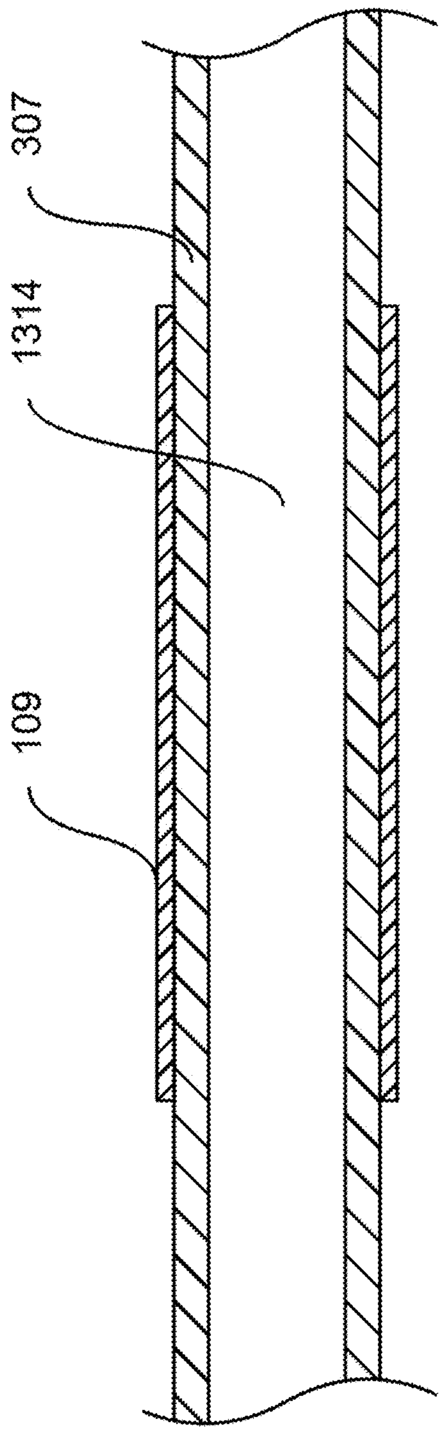
FIG. 20*a* is a cross-section of a portion of a filament with an electrode.
Figure 20B:
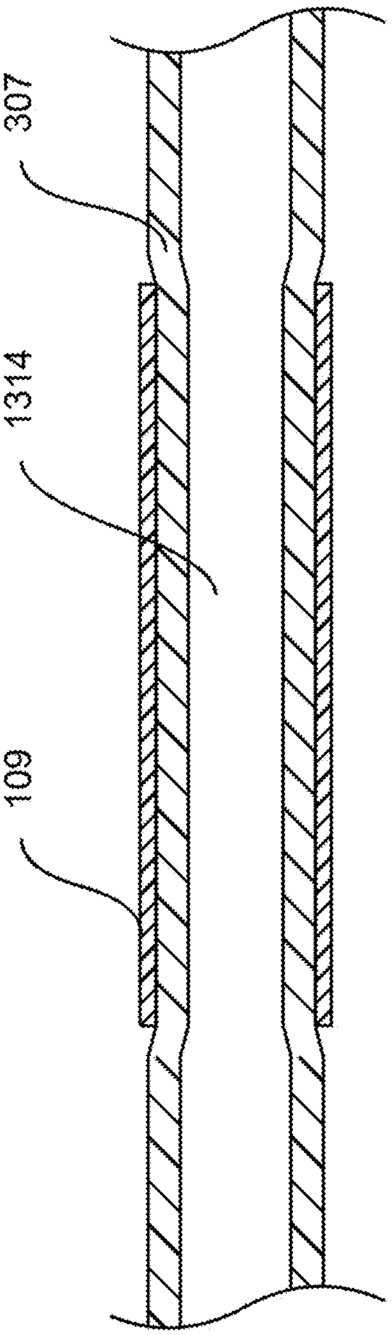
FIG. 20*b* is a cross-section of a portion of a filament with an electrode secured to the filament.

FIG. 20*b* shows a cross-section of the filament (307) with the electrode (109) already coupled and secured to the filament, for example, by way of mechanical attachment, swagging, crimping, gluing, lamination, deposition and/or soldering.

During, before, or after the steps shown in FIGS. 20*a* and 20*b*, a wire (not shown) may already be coupled to the electrode and placed, for example, into the lumen (1314) of the filament or to another possible location, for example, on the outer surface of the filament.

Figure 21:
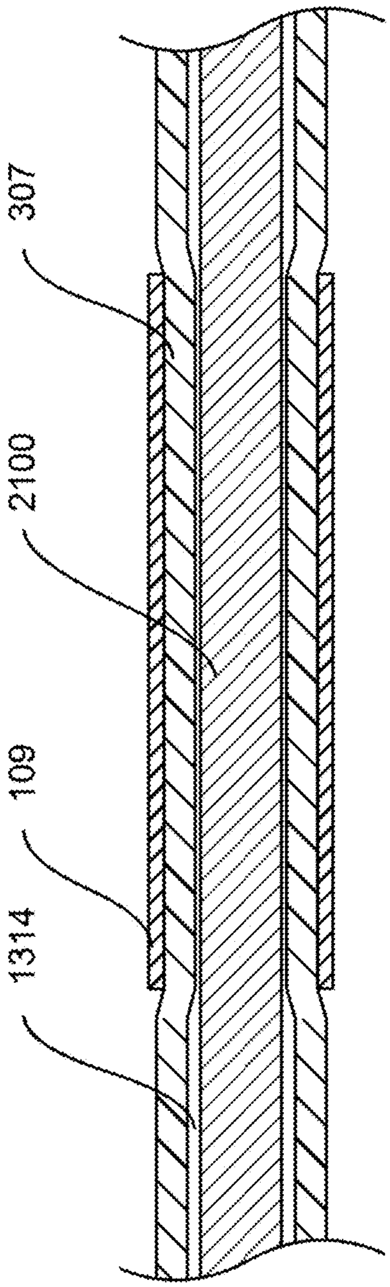
FIG. 21 is a cross-section of a portion of an exemplary filament with an electrode and a mandrel.

FIG. 21 shows a portion of the filament (307) with the electrode (109) where the filament already includes a mandrel (2100). The mandrel (2100) may be placed into the lumen (1314) of the filament. The mandrel (2100) may be, for example, in the form of a tube, filament, or strut made, for example, out of a material with a higher melting point compared to the melting point of the material of the filament. The mandrel may be made out of a metal, for example, copper, stainless steel, steel, nitinol, aluminum, gold, platinum, silver, and so on. It may also be made out of, or may include, a coating on its surface made out of, for example, Nylon, Fluorinated ethylene propylene (FEP), Polyethylene (PE), PEBA, PEEK, Polyimide (PI), Polypropylene (PP), PTFE, Polyurethane (PU), Polyethylene terephthalate (PET) or Silicon and so on.

Figure 22A:
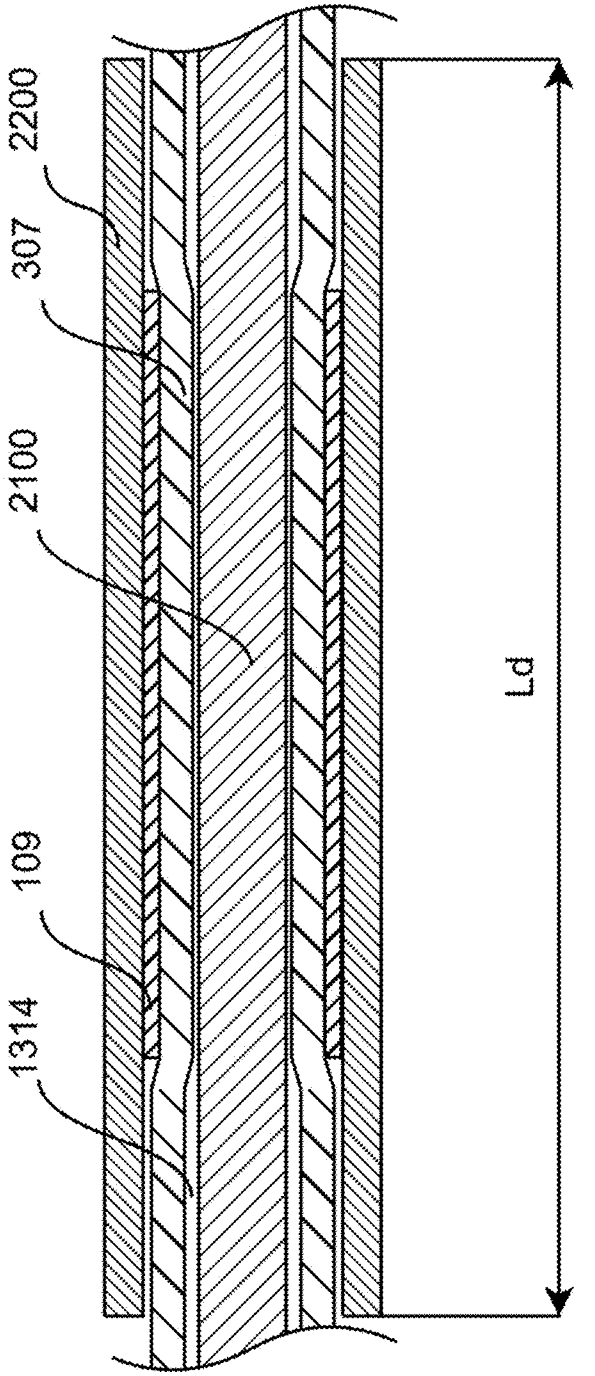
FIG. 22*a* is a cross-section of a portion of an exemplary filament with an example of a die.
Figure 22B:
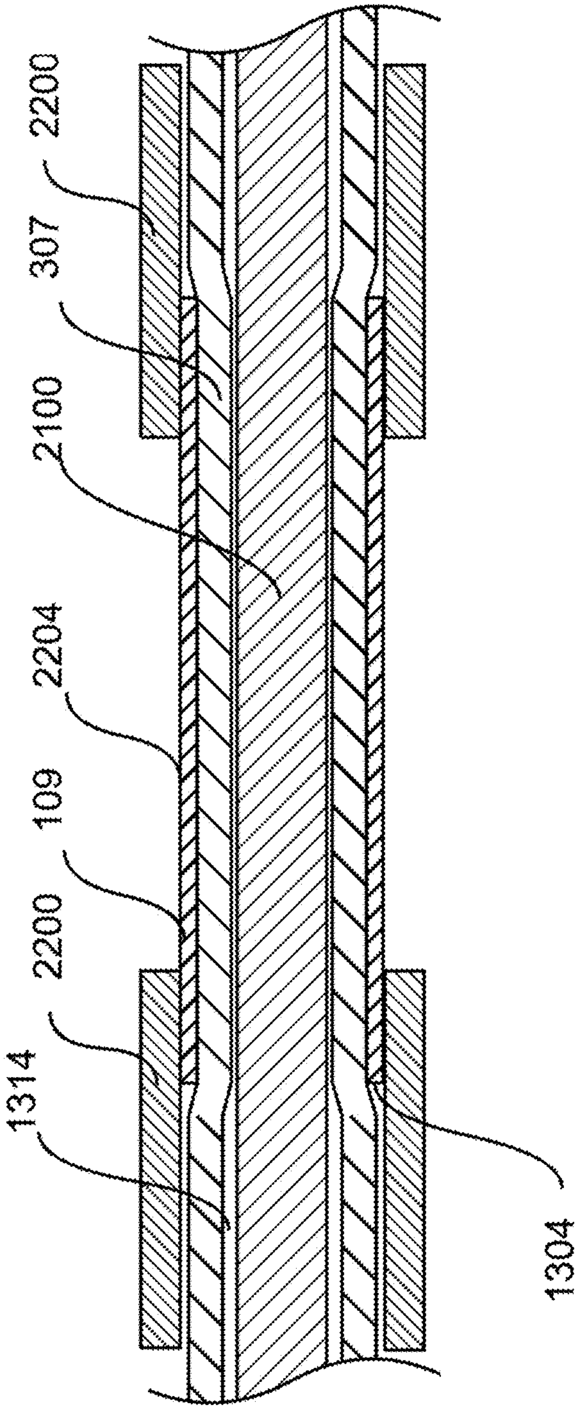
FIG. 22*b* is a cross-section of a portion of a filament with an example of a different die.

FIGS. 22*a* and 22*b* show a die (2200) being placed over the filament assembly. The die may have, for example, a form of a split die or cast, but may also have a different form, for example, a tube. In the FIG. 22*a*, the die (2200) is placed over the whole outer surface (2204) and the length of the electrode (109). The die, when placed on the assembly, may take the shape of a tubular object with an inner cross-section and diameter corresponding to the outer shape (cross-section and/or diameter) of the electrode already coupled to the filament. The length of the die (Ld) may be longer than the length of the electrode and may be at least equal to or longer than the length of the electrode fitting area. The whole electrode fitting area preferably lies within the length of the die.

FIG. 22*b* shows another example of the die (2200). In this particular case, the die (2200) comprises two parts. Both parts may be coupled to the opposite ends of the electrode and may cover at least a portion of the electrode comprising the edge (1304) and at least the electrode adjacent area of the filament. At least a portion of the electrode is exposed.

Figure 22C:
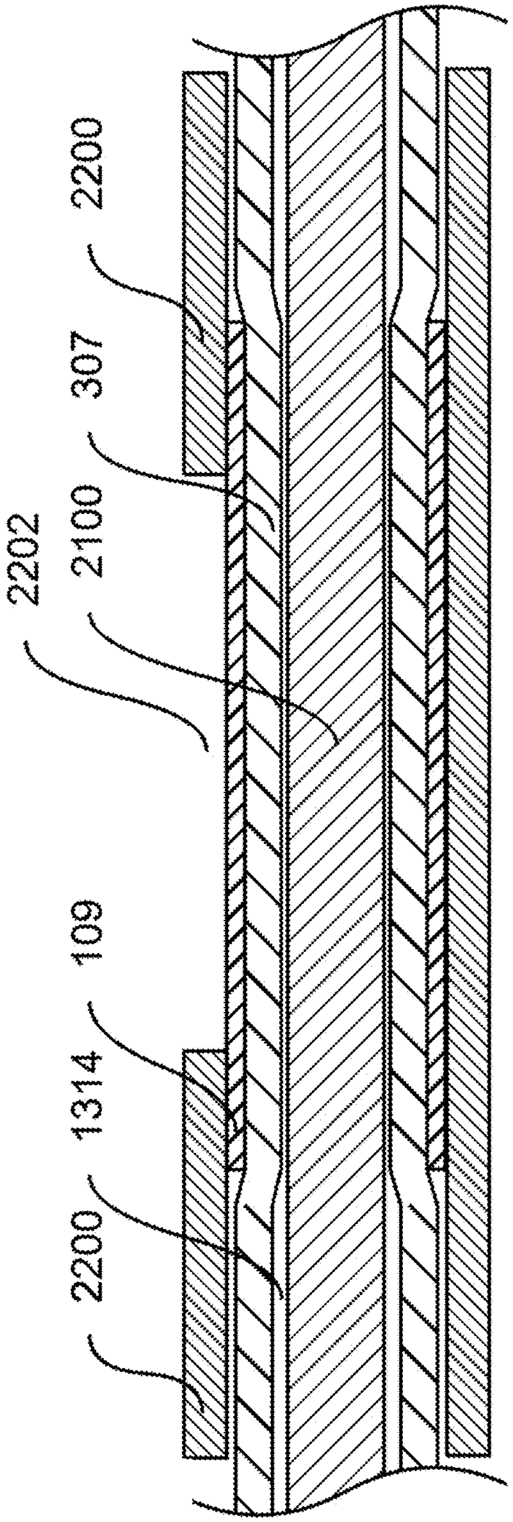
FIG. 22*c* is a cross-section of an example of a portion of a filament with an example of another die.

Another option to keep a portion of the electrode exposed while the die is coupled to the filament assembly would be to make the die with an opening (2202) as shown in the example in the FIG. 22*c*.

The die may include other structures or may be coupled to other devices. For example, the cast may include venting means, for example, venting holes or cavities, for example, adjacent to the electrode edge, for example, to allow the escape of trapped air or gas between the die and filament, for example, before, during, or after the heating step. The die may be coupled, for example, to a heating or cooling device and may be heated or cooled. It may include means for cooling, heating, for example cavities for heating or cooling fluid or fins adapted to radiate heat. It may also include thermoelectric heating or cooling.

A portion of the assembly adjacent to the electrode may be heated up at least to a melting temperature of the material of the filament. The heating may be realized by the die or by other means for example by radiation heating, conduction heating, convection heating, induction heating, thermoelectric heating, laser, phase change, vibration, and so on by a radiation, conduction, convection, induction, thermoelectric, laser, vibration, phase change heater, heating element, or hot medium for example air, gas or fluid. The heat may be produced by the die, may be transferred via or through the die, and/or may be delivered to the electrode, for example, via the exposed part of the electrode or via the opening in the die. Part of the heat may also be delivered from the inside of the filament, for example via the mandrel, which may be coupled to the heat source and may include means for transferring the heat to the electrode fitting area. The mandrel may be coupled or may include a heating source and the heating may be realized, for example, by conduction heating, convection heating, induction heating, laser, vibration, and so on.

Figure 23:
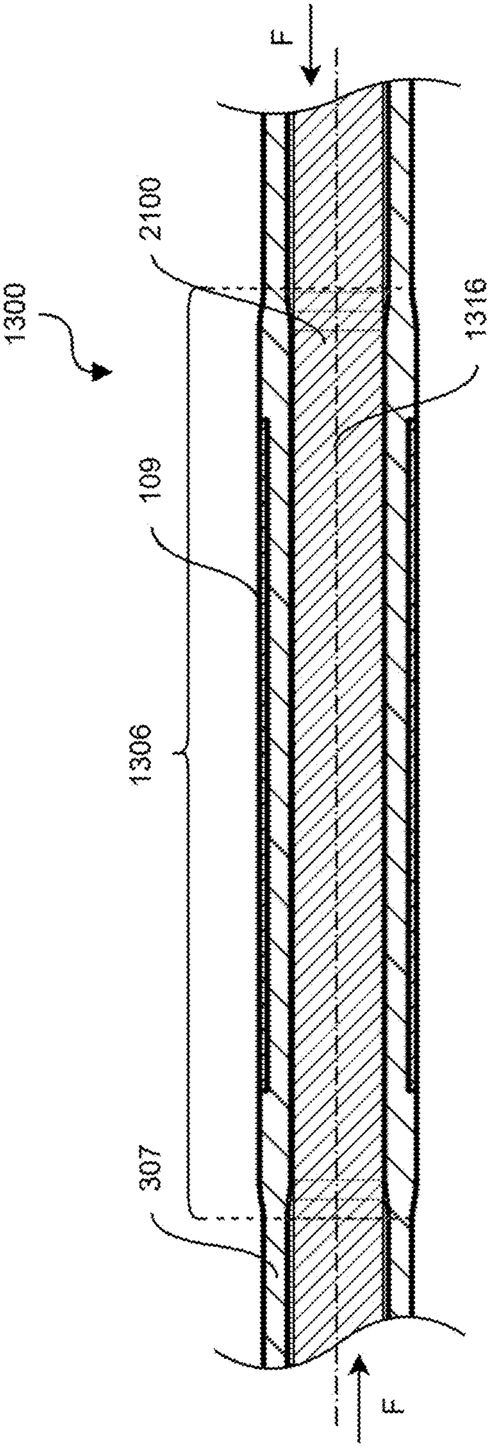
FIG. 23 is a cross-section of a portion of a filament with a filament assembly after a manufacturing process.

Before, after, and/or during the heating and/or the melting of the filament material, it is possible to further include a step of applying a force (F) to the filament, for example, a pushing force to the filament along its longitudinal axis (1316) of the filament as shown in FIG. 23. The pushing force may be applied, for example, on a portion of the filament outside of the electrode fitting area along the longitudinal axis (1316) of the filament in the direction towards the electrode, hence the electrode fitting area. Such a pushing force may help with forming the electrode fitting area, particularly the electrode adjacent area. It may help the melted material to expand to the higher filament wall thickness and higher filament diameter in the electrode adjacent area and to conform to the edge of the electrode. The force (F) may be applied to the filament manually by hand or by a force applying device for example a hydraulic, pneumatic or electromechanical device. The force applying device may include a piston, a cylinder, an electric motor, a lever, a cogwheel, a chain and so on. The force (F) may be, for example, measured by a mechanical (e.g. spring scale) or an electrical (e.g. load cell) force gauge.

After the heating of the at least portion of the filament included in the electrode fitting area, the material of the filament may be melted and may fill at least a space between the filament surface and the inner surface of the die that is at least adjacent to the electrode edge. The diameter of the filament expands in at least a portion of the electrode adjacent area to the substantially same diameter as a diameter of the electrode. Therefore, the exposed edge of the electrode is eliminated. The filament wall thickness in at least a portion of the electrode adjacent area may be increased during the melting process as well.

FIG. 23 shows a filament assembly (1300) after melting and forming the portion of the filament assembly in the electrode fitting area (1306). The assembly may be cooled, and the die may be removed. The mandrel (2100) may be removed as well or may stay in the filament (307) and may become a part of the filament assembly, for example, as a part of reinforcement, for example, as a reinforcement strut.

Figure 24:
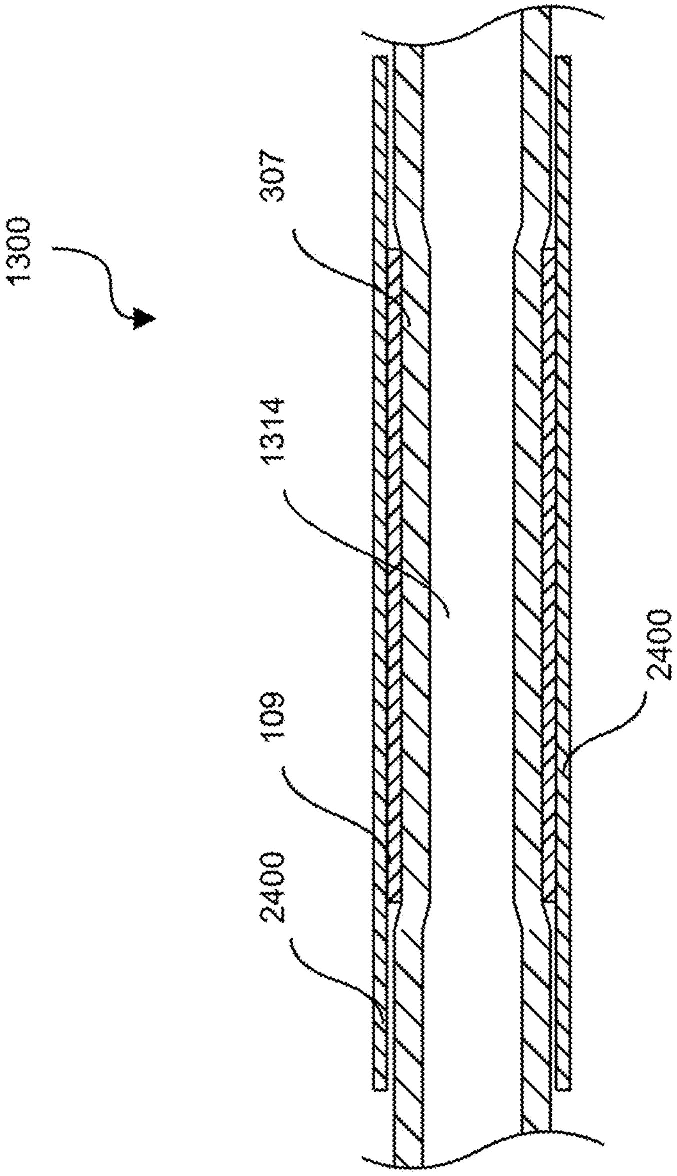
FIG. 24 is a cross-section of a portion of a filament with an example of a tube fitted over the electrode.
Figure 25:
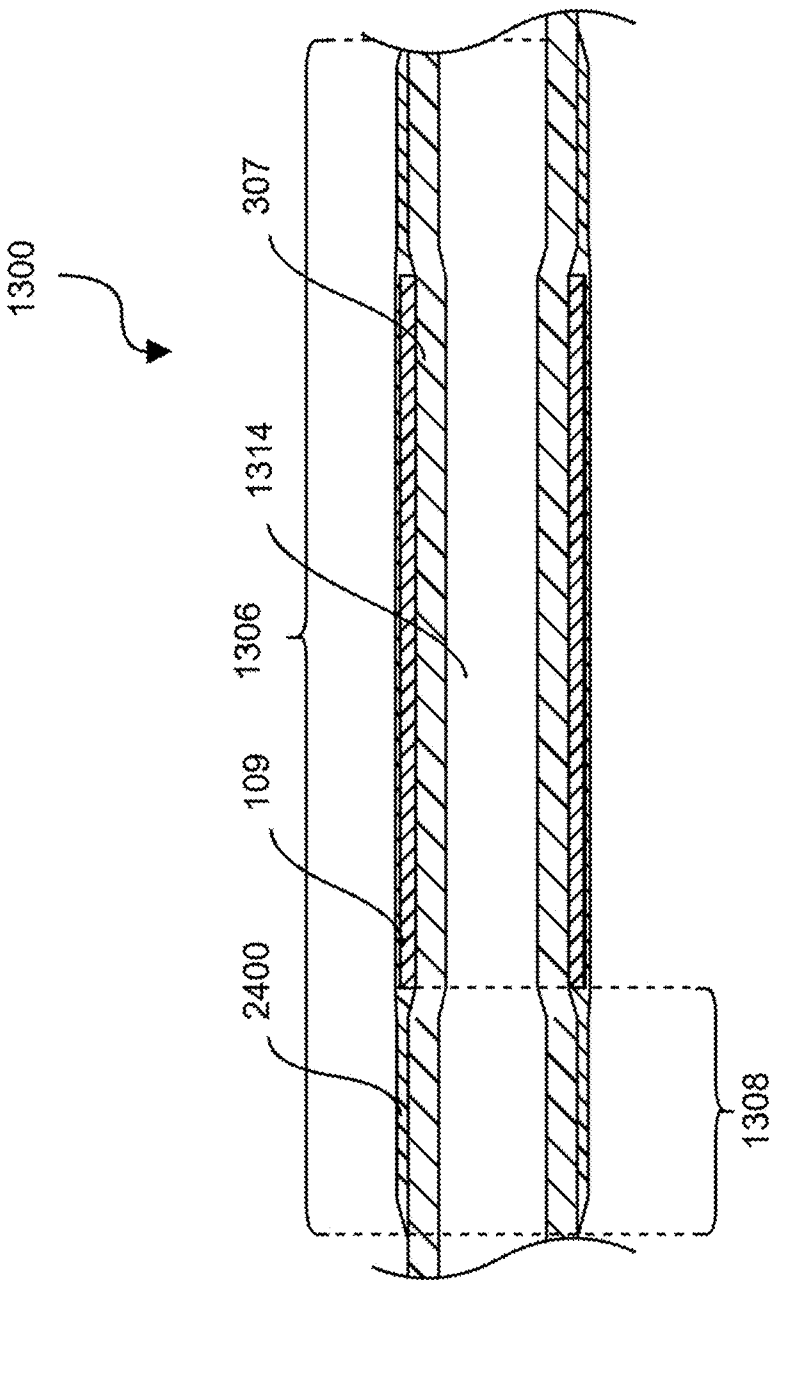
FIG. 25 is a cross-section of a portion of a filament with an example of a melted material of tube after a manufacturing step.
Figure 26:
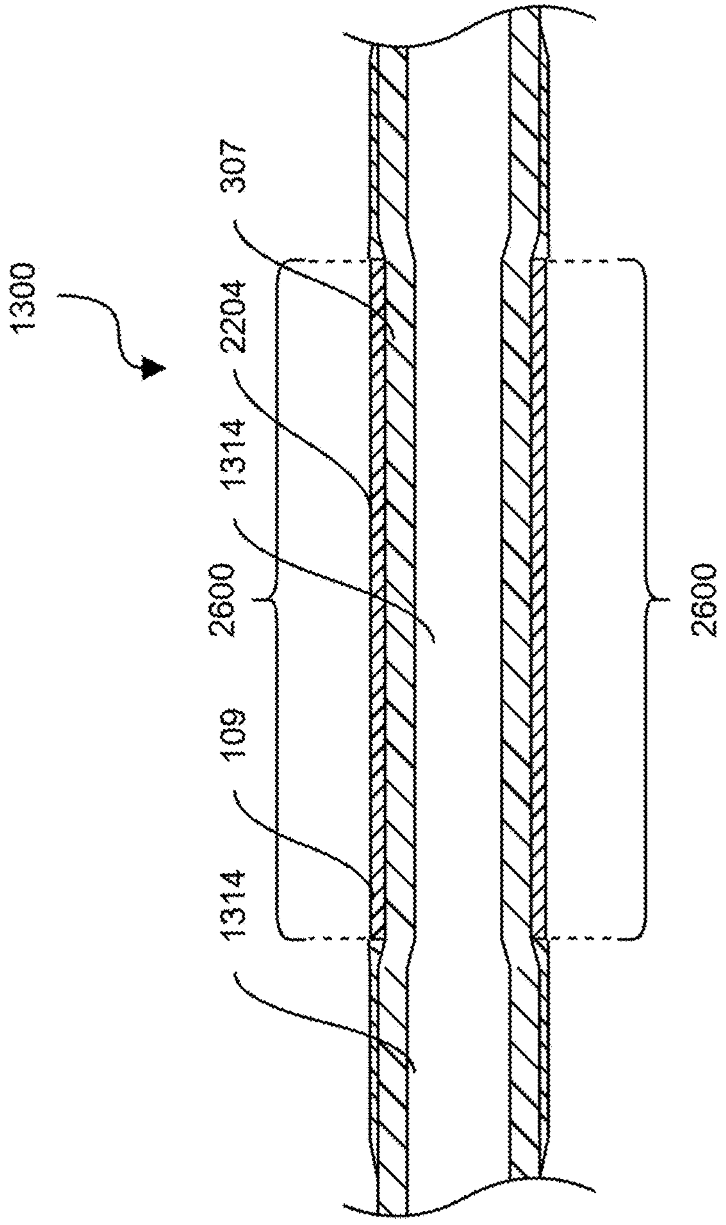
FIG. 26 is a cross-section of a portion of a filament after another manufacturing step with removed portion of a melted material.

FIGS. 24-26 show another possible way to create the filament assembly (1300) including the electrode fitting area (1306) and at least one electrode adjacent area (1308).

FIG. 24 shows the filament assembly (1300) where the electrode (109) may be coupled to the filament (307) in the electrode fitting area, for example, in the same way as described in FIGS. 20*a* and 20*b*. In the next step, a tubular object, for example a tube, a tube made of a fusible material, or a thermoplastic tube, is fitted over at least portion of the electrode fitting area of the filament assembly. The length of the tube (2400) may be longer than or may correspond with the length of the electrode fitting area. The tube (2400) may also be longer than an electrode, and a portion of the tube may correspond or at least partially cover at least one electrode adjacent area. The tube (2400) may cover the whole electrode or may cover just a portion of the electrode and at least a portion of at least one electrode adjacent area. A mandrel may or may not be placed in a cavity of the filament.

There may be only one tube fitted to the filament assembly or there may be a plurality of tubes fitted to the filament assembly. In the case of only one tube, it may, for example, cover the whole length of the electrode and at least a portion of at least one electrode adjacent area. In the case of a plurality of tubes, there may be, for example, two tubes; each one can, for example, cover a portion of the electrode and a portion of the electrode's adjacent area.

The tube may be made out of the same material as the filament, or it may be made out of a different material. The tube material may have, for example, the same or a lower melting point temperature compared to the melting temperature (Mf) of the material of the filament. The melting temperature (Mt) of the tube material may be, for example, from 30% to 100% of the Mf, from 30% to 100% of the Mf, from 50% to 100% of the Mf, from 60% to 100% of the Mf, from 70% to 100% of the Mf, from 80% to 100% of the Mf, from 90% to 100% of the Mf, or from 95% to 100% of the Mf.

The inner diameter of the tube may correspond to the outer diameter (ODe) of the electrode or may be smaller than the outer diameter of the electrode, for example, in cases where the tube is made out of flexible material and in cases where it is still possible to fit the tube over the filament assembly. In these cases, the inner diameter of the tube may be from 50%×ODe to 100%×ODe, from 60%×ODe to 100%×ODe, from 70%×ODe to 100%×ODe, from 80%×ODe to 100%×ODe, or from 90%×ODe to 100%×ODe.

The inner diameter of the tube may correspond to the outer diameter (ODe) of the electrode or may be larger. In this case, the inner diameter of the tube may be from 100%×ODe to 250%×ODe, from 100%×ODe to 200%×ODe, from 100%×ODe to 150%×ODe, from 100%×ODe to 130%×ODe, or from 100%×ODe to 120%×ODe.

The inner diameter of the tube may correspond to or may be smaller than the outer diameter (ODf) of the filament, for example, in cases where the tube is made out of flexible material and in cases where it is still possible to fit the tube over the filament assembly. In these cases, the inner diameter of the tube may be from 50%×ODf to 100%×ODf, from 60%×ODf to 100%×ODf, from 70%×ODf to 100%×ODf, from 80%×ODf to 100%×ODf, or from 90%×ODf to 100%×ODf.

The inner diameter of the tube may correspond to or may be larger than the outer diameter (ODf) of the filament. In this case, the inner diameter of the tube may be from 100%×ODf to 250%×ODf, from 100%×ODf to 200%×ODf, from 100%×ODf to 150%×ODf, from 100%×ODf to 130%×ODf, or from 100%×ODf to 120%×ODf.

At least a portion of the filament assembly, including the tube (2400), may then be heated up to at least the melting temperature of the material of the tube. The result of such a step may be seen in FIG. 25. The heating may be realized, for example, by radiation, conduction heating, convection heating, induction heating, thermoelectric heating, laser, vibration, phase change and so on by a radiation, conduction, convection, induction, thermoelectric, laser, vibration, and/or phase change heater or heating element, and/or a hot medium, for example, hot air, gas, or fluid.

After the heating of the at least a portion of the filament assembly, including the at least one tube, the material of the tube may be melted, may conform to outer surfaces of the filament, may conform to the outer surface (2204) of the electrode and/or may conform to the electrode edge. The melted tube material may cover and/or help to create at least a portion of the electrode adjacent area adjacent to the electrode edge with the parameters described earlier.

The electrode adjacent area outer diameter (ODa) may be increased thanks to the additional melted material of the tube. The outer diameter of the filament plus the melted tube material in at least a portion of the electrode adjacent area, the electrode adjacent area outer diameter (ODa), may have substantially the same or a higher diameter as the diameter of the electrode (ODe), for example from 0.9×ODe to 2×ODe, from 1×ODe to 1.5×ODe, from 1×ODe to 1.3×ODe, from 1×ODe to 1.2×ODe, or from 1×ODe to 1.1×ODe. The exposed edge of the electrode may be eliminated.

The filament wall thickness (TF2) in at least a portion of the electrode adjacent area may be increased during the melting process and/or by adding the melted material of the tube on top of the material of the filament. That means the filament wall thickness (TF2) in the electrode adjacent area may be calculated as a filament wall thickness (TF1) plus the thickness of the melted tube material.

The filament assembly, or at least a portion of the filament assembly, including the material of the tube, is then cooled down at least below the tube material melting temperature. The cooling may be done naturally by an ambient environment (ambient air) and/or may be carried out by a cooling device, for example, a cooler. The cooler may be a radiation, conduction and/or convection cooler. The cooling device may include a cooling medium, for example, a gas or a liquid. The cooling device may include a fan or a pump.

FIG. 26 shows the filament assembly (1300) after another step of the manufacturing process. In this last step, at least a portion of the previously melted tube material is removed from at least a portion of an outer surface (2204) of the electrode (109). The tube material melted in previous steps may fill a space between material of the filament and the edge (1304) of the electrode and even out at least a portion of outer surfaces of the filament assembly (1300), thus preventing any sharp edge of the electrode from being exposed. However, during the melting and cooling step, a portion of the tube material may stay at the outer surface (2204) of the electrode as well. For the electrode to work properly at least a portion of the outer surface of the electrode should be exposed. To achieve this, at least a portion of the tube material covering the outer surface (2204) of the electrode should be removed, creating an exposed electrode surface (2600). Preferably the exposed electrode surface (2600) wholly or mostly comprises the outer surface (2204) of the electrode lying between the edges (1304) of the electrode. The exposed electrode surface (2600) may comprise from 50% to 100%, from 60% to 100%, from 70% to 100%, from 80% to 100%, from 90% to 100%, or from 95% to 100% of the outer surface (2204) of the electrode.

The tube material may be removed from the electrode, thus the exposed electrode surface may be created, for example, by mechanically removing the tube material. Tube material can removed by, for example, scratching, cutting, grinding, scrubbing, brushing, sanding and so on.

The tube material may be removed from the electrode, thus the exposed electrode surface may be created, for example, by applying an energy. The energy may be, for example, electromagnetic energy such as but not limited to laser, heat, burning and so on.

The tube material may be removed from the electrode, thus the exposed electrode surface may be created for example by applying an energy. The energy may be from a chemical reaction. A non-limiting example of a chemical reaction includes cleaning the surface with a solvent that dissolves the tube material by chemical processes.

The exposed electrode surface (2600) may start at the edge of the electrode, or on the outer surface of the electrode close to the edge of the electrode, for example in a distance from 0 mm to 1.5 mm, from 0 mm to 1 mm, from 0 mm to 0.8 mm, from 0 mm to 0.5 mm, or from 0 mm to 0.3 mm from the edge of the electrode.

Electrodes can be integrated into the flexible/stretchable PCB that forms the filaments, or which are included on the filaments of the expandable basket. These electrodes may be pre-fabricated on the flexible/stretchable PCB during manufacturing of the flexible/stretchable PCB or added after the expandable basket's assembly.

In some configurations, longer electrodes on the filaments may be divided into several shorter electrodes. This segmentation may allow the basket, i.e. the filaments to be shaped into shapes or bends with sharper angles or tighter curves, which may facilitate better shaping and contact with the target tissue. These shorter electrodes may be interconnected to the same potential using a single conductor, for example a wire or a conductive lead.

The shape of the electrodes is not limited to a ring; they can be designed in various forms according to the specific needs of the procedure.

Additional structures, such as sensors (e.g., ECG, pH, positioning, electrical, or temperature sensors), may also be integrated into the filaments or the expandable basket. These sensors could be embedded during the flexible/stretchable PCB manufacturing or attached post-assembly.

Furthermore, a distal electrode may be placed at the distal tip of the expandable basket for point ablation or measurement purposes. This electrode could be pre-integrated into the flexible/stretchable PCB or coupled to the basket via prepared contact points on the PCB. Electrical leads for this electrode can be integrated into the flexible/stretchable PCB during manufacturing.

Figure 27A:
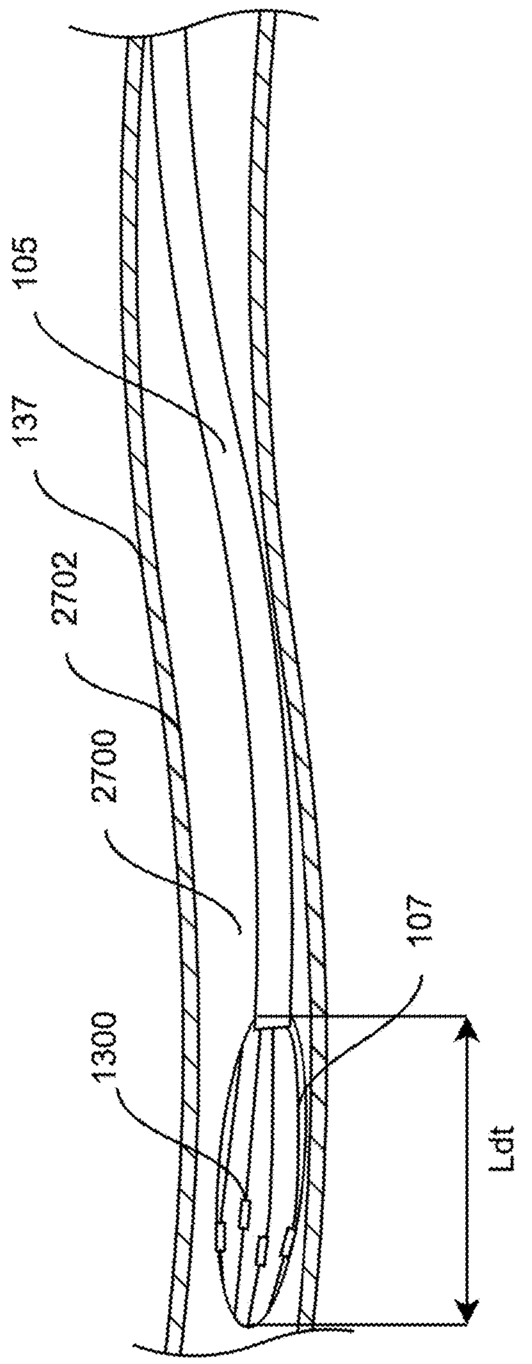
FIG. 27*a* is a cross-section of a portion of an introducer sheath with a catheter comprising a filament assembly.

FIG. 27*a* shows a system of an assembly of an introducer sheath (137) and a catheter (105) comprising the filament assembly (1300). The introducer sheath (137) includes a lumen (2700) with an inner liner (2702). For example, the inner liner (906) of the introducer sheath may be compatible with the filament assembly (1300). The compatibility may include a high resistance against mechanical damage, for example against a scratching by at least portion of the filament assembly (1300), for example during an introduction of the catheter (105) comprising the filament assembly into the introducer sheath (137) or via the introducer sheath (137) into a body of a patient (high abrasion resistance).

The inner liner of the introducer sheath may, for example, include a material with a high abrasion resistance. The inner liner may include a material with a low friction coefficient as well. The material may be, for example, a thermoplastic, a thermoplastic elastomer, a synthetic polymer and/or an organic polymer in at least a portion of the inner liner. The material may be, for example, a Polyethylene (PE), for example, Ultra high molecular weight polyethylene (UHMW, UHMWPE), High-modulus polyethylene (HMPE), and/or High-density polyethylene (HDPE), Polyether block amide (PEBA), Nylon, and/or Polyether ether ketone (PEEK).

A standard material often used in the inner liner is Polytetrafluoroethylene (PTFE). It has excellent friction characteristics, but it has low resistance against abrasion. Compared to the PTFE, the inner liner may, for example, include a material with an abrasion resistance from 2 times to 20 times, from 2.5 times to 15 times, from 3 times to 10 times, from 3.5 times to 8 times, or from 4 times to 7 times higher compared to the PTFE, for example, according to standard ASTM G75.

The inner liner may, for example, include a material with friction coefficient from 0.01 to 0.8, from 0.01 to 0.75, from 0.01 to 0.7, from 0.01 to 0.65, from 0.01 to 0.6, from 0.01 to 0.55, from 0.01 to 0.5, from 0.01 to 0.45, from 0.1 to 0.4, from 0.01 to 0.35, or from 0.01 to 0.3 according to dynamic pin-on-disk test according to ASTM G99.

The inner liner may, for example, include a material with Shore hardness according to ASTM D2240 from Shore D 56 to D 120, from D 57 to D 110, from D 58 to D 100, from D 58 to D 90, from D59 to D 80, or from D 60 to D 70.

At least a portion of the inner liner may, for example, include an additive and/or a reinforcement with high abrasion resistance and/or low friction coefficient. The additive and/or the reinforcement may be included in the material of the inner liner. The additive and/or the reinforcement may include filaments. The additive and/or the reinforcement may create a protective layer, for example, on top of the inner liner material, for example, from the side of the lumen of the introducer sheath. The additive and/or the reinforcement may, for example, include a thermoplastic, a thermoplastic elastomer, a synthetic polymer, an organic polymer, and/or a metal material, for example, a Polyethylene (PE), for example, Ultra high molecular weight polyethylene (UHMW, UHMWPE), High-modulus polyethylene (HMPE), and/or High-density polyethylene (HDPE), Polyether block amide (PEBA), Nylon, and/or Polyether ether ketone (PEEK).

The additive and/or reinforcement may for example include a material with an abrasion resistance from 2 times to 20 times, from 2.5 times to 15 times, from 3 times to 10 times, from 3.5 times to 8 times, or from 4 times to 7 times higher compared to the PTFE, for example according to standard ASTM G75.

The additive and/or reinforcement may for example include a material with friction coefficient from 0.01 to 0.8, from 0.01 to 0.75, from 0.01 to 0.7, from 0.01 to 0.65, from 0.01 to 0.6, from 0.01 to 0.55, from 0.01 to 0.5, from 0.01 to 0.45, from 0.1 to 0.4, from 0.01 to 0.35, or from 0.01 to 0.3 according to dynamic pin-on-disk test according to ASTM G99.

The additive and/or reinforcement may, for example, include a material with Shore hardness according to ASTM D2240 from Shore D 55 to D 120, or from D 57 to D 110, or from D 58 to D 100, or from D 58 to D 90, or from D59 to D 80, or from D 60 to D 70.

The introducer sheath, and hence, the inner liner, may be specifically configured to be scratch-resistant in combination with the catheter comprising the filament assembly. The introducer sheath, and hence, the inner liner, may be configured to be scratch-resistant in combination with a different catheter or a catheter comprising a different filament assembly.

The introducer sheath may further comprise a jacket (an outer layer, an outer jacket) and a reinforcement layer between the inner liner and the jacket. The reinforcement layer may comprise, for example, a braid and/or a coil. The jacket may be made of a flexible material, such as thermoplastic. The braid and/or the coil in the reinforcement layer may be made of plastic or metal, for example, metal wire having different types of cross-sections, for example, circular, elliptical, rectangular, or other shaped cross-sections. In one aspect, the inner liner and the jacket may be made of mutually compatible materials. Material compatibility in this context means that the material of the jacket and the material of the inner liner may be fusible. The two materials may be fusible in a similar temperature range and may be able to bond together by thermal fusion. In this process, the two materials are heated to a molten state and then fused together so that at least a portion of the inner liner and the sheath solidify into a single continuous material upon cooling, forming a strong bond layer. In one example, when the introducer sheath comprises the braid and/or coil between the inner liner and the jacket, the molten material from either the jacket, the inner liner, or both may penetrate through the wire braid or coil. When the molten material solidifies into a single, continuous material upon cooling, the braid or coil may lie in this solidified layer of material, thereby forming a portion of the bond layer.

The compatible materials may be selected from, for example, a thermoplastic elastomer, a synthetic polymer, and/or an organic polymer in at least a portion of the liner. The material may be, for example, a polyethylene (PE), such as ultra-high molecular weight polyethylene (UHMW, UHMWPE), high modulus polyethylene (HMPE), and/or high-density polyethylene (HDPE), polyether block amide (PEBA), nylon, and/or polyether ether ketone (PEEK).

The introducer sheath (137) may be steerable and may include a plurality of sections having different degrees of flexibility to safely receive a catheter having an expandable basket with a plurality of electrodes of the examples described above as shown in FIG. 27*b*. The sheath may include a proximal rigid section (2703), a flexible section (2704) disposed distally of the proximal rigid section (2703), and a distal rigid section (2701) disposed distally of the flexible section (2704). The flexible section (2704) may be flexed by an operator, for example, by actuating an actuator (2705) included in the operating handle (2706) of the introducer sheath (137). The actuator may actuate a pull wire (2707) included in the introducer sheath, e.g., in the jacket and/or in the reinforcement layer of the introducer sheath (137), extending longitudinally from the operating handle (2706) to the distal rigid section (2701). The length (Ldrs) of the distal rigid section (2701) of the introducer sheath may be, for example, from 20% to 200%, or from 30% to 175%, or from 35% to 150%, or from 40% to 140%, or from 45% to 130%, or from 50% to 125% of a length (Ldt) of the distal tip (107) of the catheter (105) deployed in a collapsed configuration (which means that an expandable basket included in the distal tip is not expanded but is deployed in a collapsed configuration).

Figure 27B:
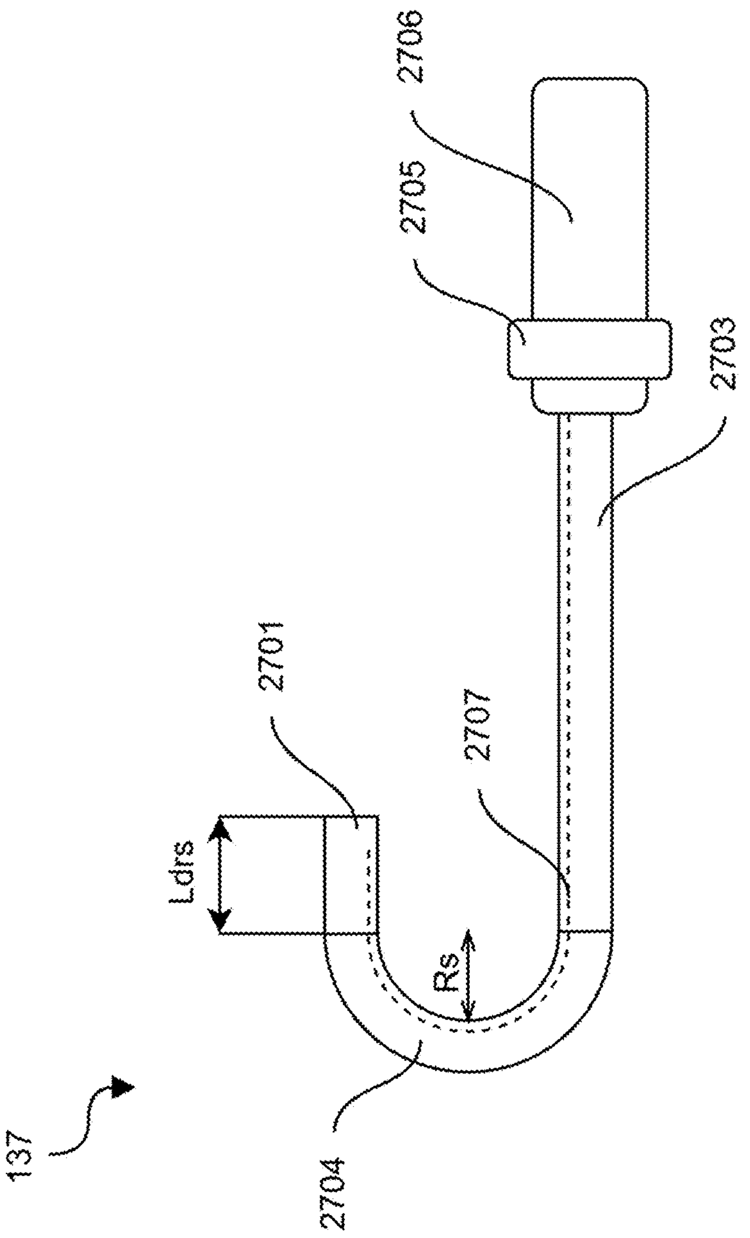
FIG. 27*b* is a cross-section of an introducer sheath.

The maximum bending radius (Rs) of the flexible section (2704) during bending must be limited such that the inner cross-section of the lumen (2700) of the introducer sheath is not deformed into an oval shape, i.e. remains circular at least up to a bending angle of 180° as shown in FIG. 27*b*.

The pulsed field ablation device comprises a pulse generator for generating short high voltage electrical pulses and a catheter adapted for insertion into a cavity of a patient's body having a catheter distal tip adapted for performing pulsed field ablation of target tissue by pulsed electric fields with a set of electrodes. The catheter is electrically coupled to the pulse generator.

The generator (103) can be configured to generate high voltage electrical pulses, for example at a frequency of 0.1 Hz to 10 Hz, wherein the amplitude of the monophasic pulses varies from 100 V to 5 kV and the peak-to-peak amplitude of the biphasic pulses varies from 200 V to 10 kV. The pulse duration can range from nanoseconds to milliseconds.

Figure 28:
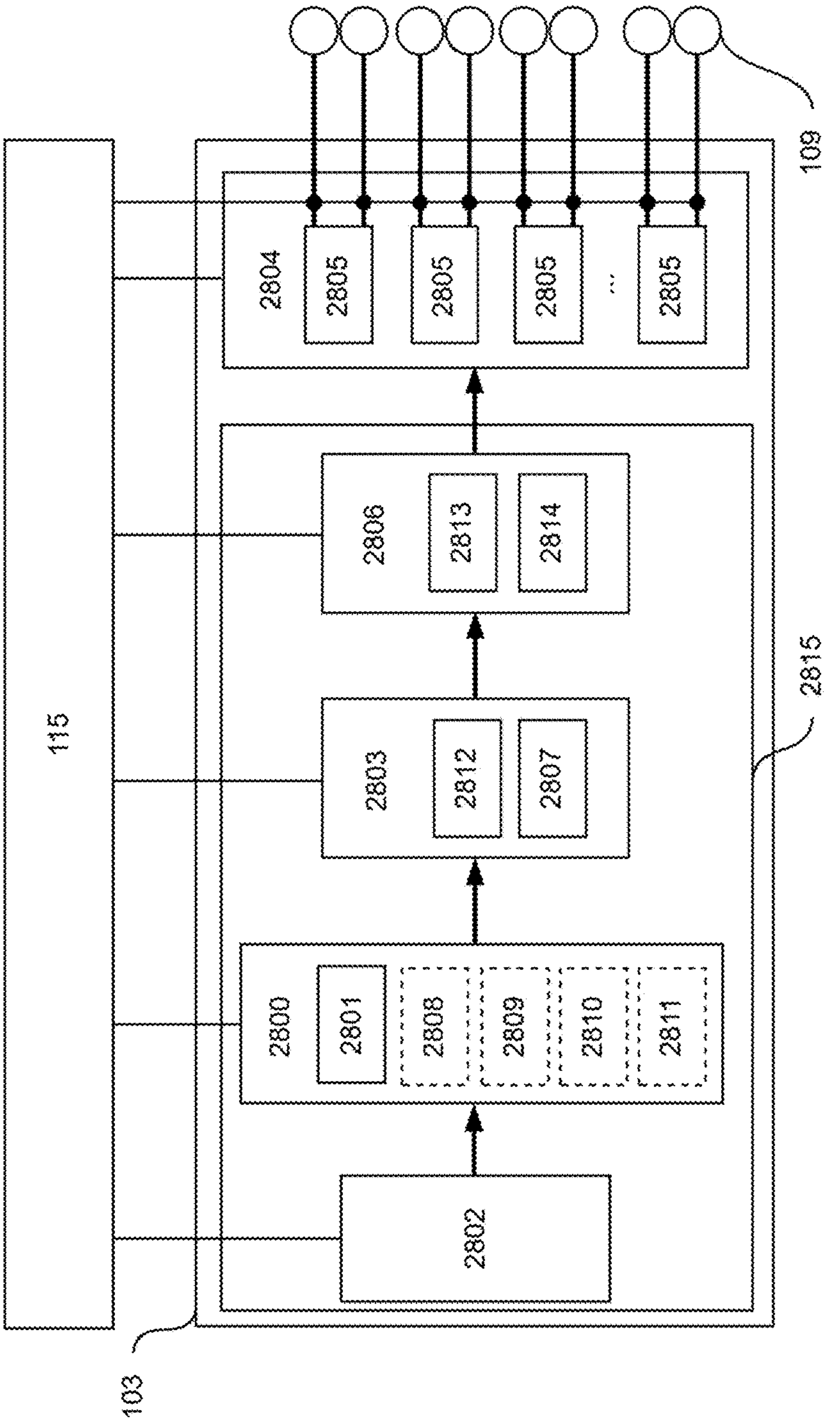
FIG. 28 is a block diagram of a pulse generator.

An exemplary simplified schematic of the pulse generator (103) is shown in FIG. 28. The pulse generator (103) may comprise a power supply unit (2800) which may produce at its output a working voltage of, for example, 100 V to 5000 V or 250 V to 2000 V or 500 V to 1000 V. The power supply unit (2800) may also, for example, transfer an alternating current from a current source (2802), for example from a plug, to a direct current in the output of the power supply unit (2800).

The power supply unit (2800) may have an output power of from 100 W to 5000 W, or from 200 W to 3000 W, or from 500 W to 1000 W. The power supply unit (2800) may include a regulator (2801) that regulates the generation of the operating voltage. The operating voltage may be regulated, for example, turned on and off in response to feedback from the output of the power supply unit (2800). The power supply unit (2800) may comprise a switched mode power supply (2808), a safety transformer (2809) (e.g., an AC to DC transformer), a power factor correction (PFC) block (2810), e.g., configured to change the voltage coming from the current source (2802), e.g., to change it from about 230V to about 400V; and/or at least one DC to DC converter (2811). The power supply unit (2800) may also be coupled to electrical control circuits (115) and may be regulated, for example turned on and off, in accordance with a signal from the electrical control circuits (115).

The output of the power supply unit (2800) may be coupled to a capacitor unit (2803) including at least one capacitor (2812). The capacitance of the capacitor unit (2803) may be, for example, from 50 μF to 1500 μF, or from 80 μF to 1000 μF, or from 160 μF to 750 μF. The capacitor unit (2803) may include an emergency system (2807) that can cause an emergency discharge of charge from the capacitor unit (2803) in the event of a failure or a measured parameter outside a safe limit in the pulsed field ablation device (101). The emergency system (2807) may include a safety discharge resistor configured to safely discharge the capacitor (2812), thyristor protection and/or a contactor configured, for example, to short circuit the capacitor (2812) if necessary. The operating speed of the back-up system (2807) may be, for example, from 50 ms to 100 ms.

The power supply unit (2800), the capacitor unit (2803), and/or the current source (2802) may be included in a power source (2815).

The pulse generator may further include a switching unit (2804) which may include, for example, at least one switch (2805), for example, a semiconductor switch. The input of the switching unit (2804) may be coupled to the capacitor unit (2803), the output of the switching unit (2804), hence the switch (2805), may be coupled to at least one electrode (109) and may be configured for switching the electrode (109) to the state (mode) of first polarity, state (mode) of second polarity and into a state (mode) of high impedance. The number of switches (2805) may depend on a number of independently switchable electrodes or independently switchable group of electrodes (109). One switch (2805) may be coupled to one electrode (109) or more than one electrode.

The switching unit (2804) may further serve to disconnect the at least one electrode (109) from the power source (2815).

Figure 31:
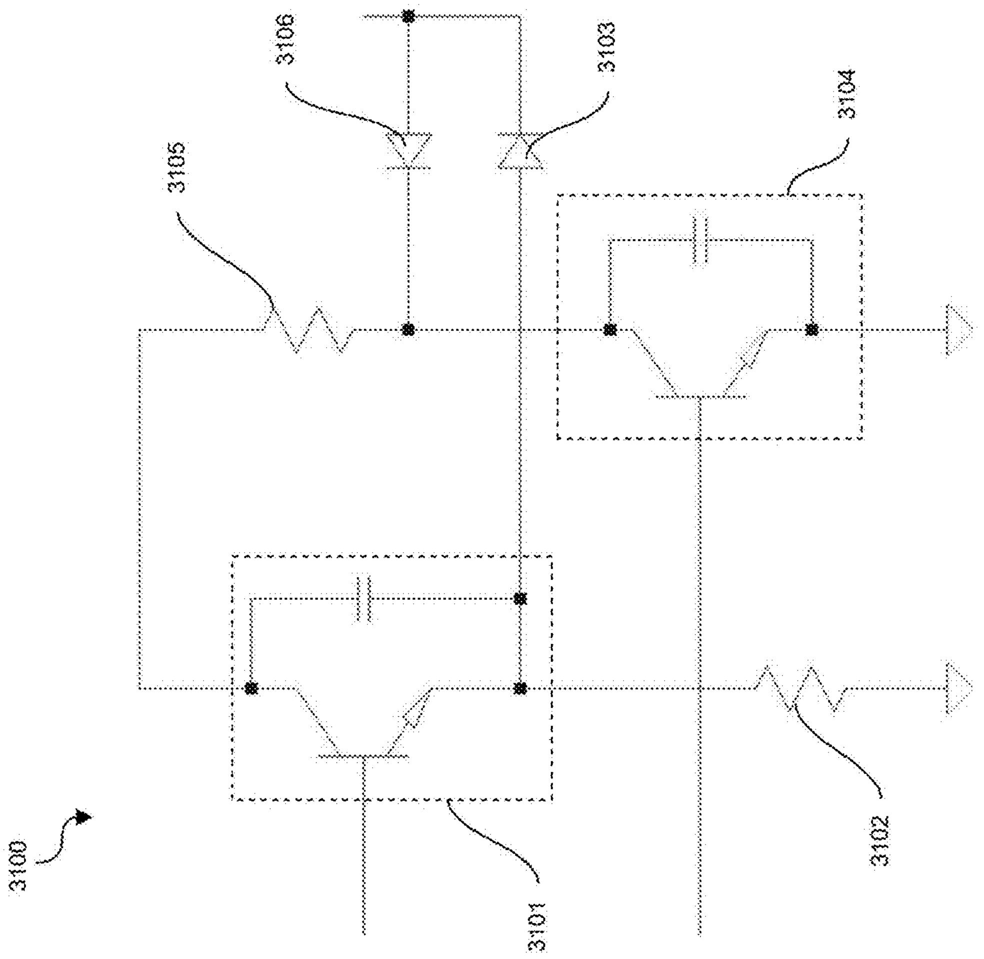
FIG. 31 is a schematic of a modified half-bridge.

The switch (2805) may be a semiconductor switch, for example, a modified half-bridge (3100). A schematic of the modified half-bridge (3100) may be seen in FIG. 31. The modified half-bridge (3100) is an improvement over a classic half-bridge. It solves the problem of parasitic properties of the classic half-bridge, such as leakage current in closed state and output capacitance. The modified half-bridge (3100) may include a top side and a bottom side. The top transistor (3101) is coupled with a common collector. The emitter of the top transistor (3101) is coupled with a top resistor (3102) to ground. Due to the position of the top resistor (3102), the voltage across the top resistor (3102) is close to zero in the closed state of the top transistor (3101). The modified half-bridge (3100) may further include a top diode (3103). The top diode (3103) is coupled via its anode to the emitter of the top transistor (3101) and via its cathode to the output (OUT) of the half-bridge (3100). In the case of a closed top transistor (3101) (high impedance state (mode)) the top diode (3103) may ensure a current from the output of the half-bridge (3100) does not pass through the top resistor (3102). The bottom transistor (3104) has a common emitter, and there is a bottom resistor (3105) coupled to the collector of the bottom transistor (3104). The bottom resistor (3105) is coupled against the positive supply (+). Due to the bottom resistor (3105), the voltage across the bottom resistor (3105) is close to zero in the closed state of the bottom transistor (3104). The bottom diode (3106) is connected in reverse, i.e. the anode of the bottom diode (3106) is coupled to the output (OUT) of the modified half-bridge (3100), and the cathode is coupled to the collector of the bottom transistor (3104), preventing the output (OUT) of the modified half-bridge (3100) from having a permanent output voltage.

In an example where the switching unit (2804) is directly coupled to the capacitor unit (2803) or the power supply unit (2800), the safety of the patient or operator may depend on the reliability of the at least one switch (2805). In the event of failure of the switch (2805), the patient or operator may be faced with uncontrolled discharge of the high capacitance of the capacitor unit (2803) for a period of, for example, 50 ms to 100 ms.

In order to counteract such a danger to the patient or the operator, at least one DC/DC converter unit (2806) may be coupled between the capacitor unit (2803) and the switching unit (2804). The DC/DC converter unit (2806) may have an input voltage of from 100 V to 5000 V or from 250 V to 2000 V or from 500 V to 1000 V and an output voltage of from 150 V to 5000 V or from 500 V to 3000 V or from 1000 V to 2000 V. The DC/DC converter unit (2806) may include, for example, at least one output capacitor (2813) at its output.

The DC/DC converter unit (2806) may include an output capacitor emergency system (2814) which can cause an emergency discharge of capacitance from the output capacitor (2813) and shutdown of a voltage supply from the pulse generator (103) to the electrode (109) in the event of any failure or any measured parameter outside a safe limit in the pulsed field ablation device (101). The output capacitor emergency system (2814) may include a safety discharge resistor configured to safely discharge the output capacitor (2813), thyristor protection and/or a contactor configured, for example, to short the output capacitor (2813) if necessary. The emergency discharge of capacitance from the output capacitor (2813) and the termination of voltage supply from the pulse generator (103) to the electrode (109) may take less than 50 ms or less than 25 ms or less than 15 ms or less than 5 ms or less than 1 ms or less than 100 μs or less than 10 μs.

Figure 32:
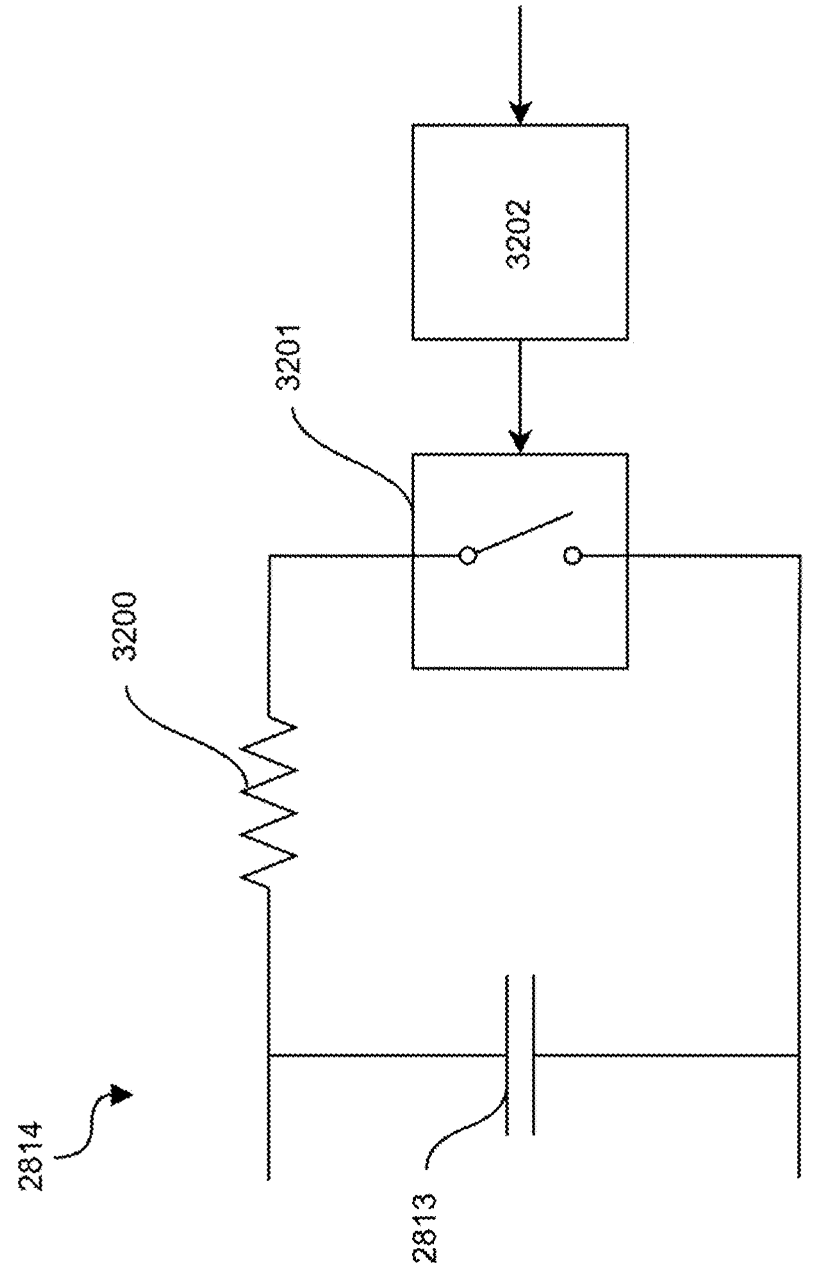
FIG. 32 is a schematic of an output capacitor emergency system.

The output capacitor emergency system (2814) of FIG. 32 may be coupled to the output capacitor (2813), may be configured to short and/or rapidly discharge capacitance from the output capacitor (2813) when necessary, and may include at least one emergency resistive element, such as an emergency resistor (3200), at least one emergency switch element (3201), and a control circuit (3202). The resistor may be coupled between the output capacitor (2813) and the emergency switch element (3201) and may be, for example, a non-inductive resistor. The emergency resistor (3200) may have a resistance of, for example, 1Ω to 1000Ω, or 5Ω to 800Ω, or 10Ω to 600Ω, or 20Ω to 500Ω.

The emergency switch element (3201) may comprise, for example, a thyristor protection, and/or a contactor. The thyristor protection may include, for example, a thyristor, an insulated gate bipolar transistor (IGBT), and/or another power semiconductor device for example a semiconductor switch.

The control circuit (3202) may be coupled to the emergency switch element (3201) and may be configured to receive signals from the ablation system and to send signals to the emergency switch element (3201). For example, upon receiving a signal from the ablation system, e.g., from the ablation device, e.g., from the control circuits, e.g., from any part of the control circuits, or from the user, e.g., via a remote control or any other part of the ablation system, the emergency switch element (3201) may be activated, e.g., the emergency switch element may be switched to a "closed" or a "conducting" state, i.e. a state in which an electrical current may flow through the switch element (3201). For example, the signal received from the ablation system may be a signal indicative of a fault detected in the ablation system, such as a detected failure of a particular part of the ablation system and/or a measured parameter outside a predetermined range. To activate the emergency switch element (3201), the control circuit (3202) may, for example, send an electrical signal having a current in the range of 1 mA to 50 A, or 25 mA to 7 A, or 10 mA to 20 A, or 50 mA to 15 A, or 100 mA to 10 A to the emergency switch element (3201). When the emergency switch element (3201) is activated, the capacitance of the output capacitor (2813) is discharged by the emergency resistor (3200).

The output capacitor (2813) need not be a single capacitor, but may be a plurality of capacitors. The emergency resistor (3200) need not be coupled to a particular side of the emergency switch element (3201), e.g. to an anode of the emergency switch element (3201) in case it includes a power semiconductor device, semiconductor switch, thyristor, and/or the IGBT, but may be coupled to the other side of the emergency switch element (3201), e.g. to a cathode of the emergency switch element (3201) in case it includes a power semiconductor device, semiconductor switch, thyristor and/or the IGBT.

The same arrangement as described above for the output capacitor emergency system (2814) may have the capacitor emergency system (2807) of the capacitor (2812), but instead of being coupled to the output capacitor (2813), it would be coupled to the capacitor (2812).

The capacitance of the output capacitor (2813) may be for example from 1 μF to 200 μF, or from 1.5 μF to 100 μF, or from 2 μF to 50 μF, or from 5 μF to 30 μF. The DC/DC converter unit (2806) may be, for example, a DC/DC converter without feedback.

The DC/DC converter unit (2806) may be configured to convert the high capacitance of the capacitor unit (2803) to a lower capacitance at the output capacitor (2813). The DC/DC converter unit (2806) may further be configured to rapidly discharge the capacitance of the output capacitor (2813). For example, the DC/DC converter unit (2806) may be further configured to limit leakage currents from the power supply unit (2800) to the patient, for example, below a limit of 10 μA. The leakage currents may, for example, be caused by parasitic capacitance on the winding of the power supply unit (2800). The DC/DC converter unit (2806) may comprise two windings and may, for example, be a series resonant converter. The DC/DC converter unit (2806) may, for example, have a conversion ratio of from 1:1 to 1:6, or from 4:5 to 1:4, or from 2:3 to 1:3.

The power supply unit (2800), capacitor unit (2803), DC/DC converter unit (2806), switching unit (2804), and/or current source (2802) may be coupled to one or more electrical control circuits (115). The electrical control circuits (115) may, for example, receive data from and/or send control signals to each of the power supply unit (2800), capacitor unit (2803), DC/DC converter unit (2806), switching unit (2804) and/or current source (2802). The data may comprise, for example, measured parameters at various locations of the pulsed field ablation device (101), the pulse generator (103), the power supply unit (2800), the capacitor unit (2803), the DC/DC converter unit (2806), the switching unit (2804) and/or the current source (2802). The measured parameters may be, for example, a temperature, an impedance, a current, or a voltage. The voltage may, for example, be measured at the output of the power supply unit (2800), capacitor unit (2803), DC/DC converter unit (2806), current source (2802), and/or switching unit (2804), for example at the output of the at least one switch (2805).

The electrical control circuits (115) may be communicatively coupled, evaluate received data, and/or send control signals to the power supply unit (2800), capacitor unit (2803), DC/DC converter unit (2806), current source (2802), switching unit (2804), and/or other parts of the ablation device (101) based on the received data. If at least one of the measured parameters is out of predetermined limits, the electrical control circuits (115) may, for example, send a control signal to the power supply unit (2800), capacitor unit (2803), DC/DC converter unit (2806), switching unit (2804) to activate a safety shutdown of the particular unit or all or a subset of the units. The safety shutdown may include, for example, shutting down the power supply unit (2800), activating the emergency system (2807) in the capacitor unit (2803) (discharging the capacitor (2812) to a safety discharge resistor and/or shorting the capacitor (2812) via a thyristor protection and/or contactor). In the DC/DC converter unit (2806), the safety disconnect may mean activating the output capacitor emergency system (2814) (discharging the output capacitor (2813) to the safety discharge resistor and/or shorting the output capacitor (2813) through a thyristor protection and/or contactor). Safety disconnection in the switching unit (2804) may mean disconnection of at least one switch (2805).

Figure 29:
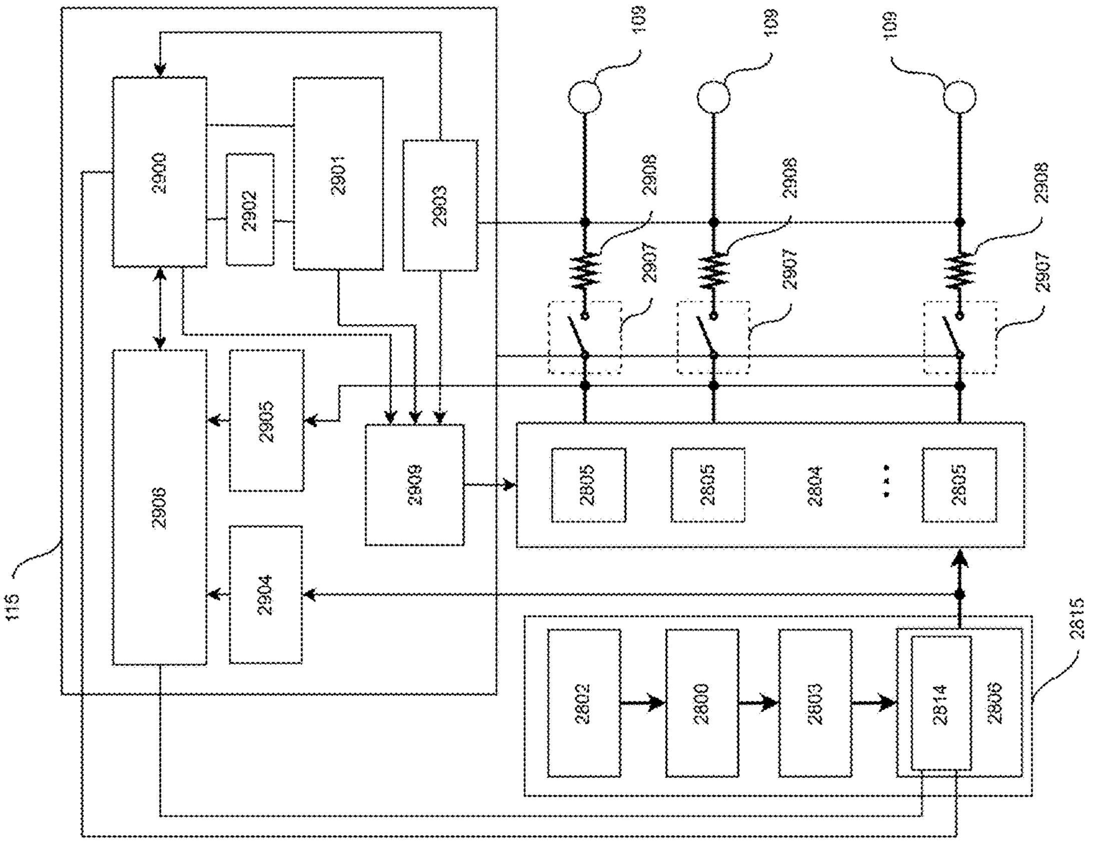
FIG. 29 is a block diagram of electrical control circuits.

Exemplary electrical control circuits (115) are shown in FIG. 29 and may include at least one central processing unit (CPU) (2900), such as a processor, which may be, for example, coupled to a memory (not shown). The electrical control circuits (115) may include a plurality of CPUs. In one example, the electrical control circuits (115) may include the CPU (2900) and at least one CPU control unit (2901). The CPU control unit (2901) may include, for example, a second CPU, a logic circuit, and/or a field programmable gate array (FPGA). For example, the CPU (2900) may be configured to receive and process data from various units and/or sensors of the ablation system, e.g., from the ablation device. The CPU (2900) may also be configured to send an output signal to various units of the ablation device; e.g., the output signals may be based at least in part on the acquired data. For example, it may be configured to generate control signals for a switching unit, e.g., it may be configured to generate control signals for particular switches (2805) in the switching unit (2804). The CPU control unit (2901) may control the work of the CPU (2900). The CPU control unit (2901) may examine at least a portion of the data received by the CPU (2900) and/or at least a portion of the signals sent by the CPU (2900) to the various units, such as the switching unit (2804), for example for each particular switch (2805) included in the switching unit (2804). If the CPU control unit (2901) determines that at least a portion of the data received from the CPU (2900) and/or at least a portion of the signal coming from the CPU (2900) is outside of a predefined value or nominal range, the CPU control unit (2901) may, in response, send a signal to the pulse generator to stop any power supply from the pulse generator (for example from the power source (2815)) to the electrodes or the CPU control unit (2901) may force the CPU (2900) to stop any power supply from the pulse generator (e.g. from the power source (2815)) to the electrodes or to at least one of the electrodes.

The CPU (2900) and the CPU control unit (2901) may be synchronized to each other. The synchronization may include a synchronizing clock circuit (2902), such as a clock generator, such as an electronic oscillator, and may be monitored by the electrical control circuits (115), such as a logic circuit included in the electrical control circuits (115) and configured to monitor the synchronization. When asynchrony beyond a predetermined time range between the CPU (2900) and the CPU control unit (2901) is detected by the electrical control circuits (115) e.g. by the logic circuit, the electrical control circuits (115) may respond by sending a signal to the pulse generator to stop any power supply from the power source (2815) to the at least one of the electrodes (109), or to all of the electrodes (109). The predetermined time range may be, for example, from 1 ns to 1 μs, or from 1 ns to 500 ns, or from 1 ns to 100 ns, or from 1 ns to 50 ns, or from 1 ns to 25 ns, or from 1 ns to 10 ns.

A monitoring frequency of the synchronization (synchronizing clock circuit (2902)) of the CPU (2900) with the CPU control unit (2901) may be at least 1 KHz, or from 1 KHz to 10 GHz, or from 100 KHz to 10 GHz, or from 500 KHz to 10 GHz, or from 600 KHz to 10 GHz, or from 700 KHz to 10 GHz, or from 800 KHz to 10 GHz, or from 1 MHz to 10 GHz.

The CPU (2900) may be coupled to the switching unit (2804) and may generate signals for the at least one switch (2805) included in the switching unit (2804). The coupling of the CPU (2900) to the switching unit may include a logic disconnection circuit (2909). The switch (2805) may switch the electrode (109) to a first polarity state (mode), a second polarity state (mode) or a state (mode) of a high impedance based on the signals from the CPU (2900).

A characteristic of the electrical pulses at the switch (2805), between the switch (2805) and the electrode (109), and/or between the power source (2815) and the electrode (109) may be monitored by the electrical control circuits (115). The monitoring may include measurement of the electrical current by current sensing circuits (2903), measurement of the voltage by voltage sensing circuits (2904), and/or pulse width (pulse length) of the electrical pulse by pulse width sensing circuits (2905) between the power source (2815) and the electrode (109).

The electrical control circuits (115) may include a safety circuit (2906), for example, coupled to at least one of the current sensing circuits (2903), voltage sensing circuits (2904), pulse width sensing circuits (2905), CPU (2900), or power source (2815), for example, to an output capacitor emergency system (2814). The ablation device may have predetermined values of the nominal range of said electrical current, voltage, and/or pulse width between the power source (2815) and the electrode (109). If the measured current, voltage, and/or pulse width is outside the nominal range, the electrical control circuits (115), for example, the safety circuits (2906), may stop any power supply from the power source (2815) to the electrode (109).

The electrical control circuits (115) may include, for example, a logic disconnection circuit (2909) coupled to at least one of the current sensing circuits (2903), the CPU (2900), the CPU control unit (2901), and the switching unit (2804). The disconnection logic circuit (2909) may receive signals from the current sensing circuits (2903), the CPU (2900), and/or the CPU control unit (2901), and based on these signals, the disconnection logic circuit (2909) may send signals to the pulse generator, for example to the switching unit (2804). The signals may, for example, include a signal to stop any power supply to the at least one electrode (109) from the power source (2815).

Each of the individually addressable electrodes or group of electrodes may further be coupled to a resistor (2908). Being addressable may mean being coupled to a switch (2805) and/or being configured to be switched by the switch (2805) to at least one of a state (mode) of a first polarity, state (mode) of a second polarity, or a state (mode) of a high impedance. The resistor (2908) may be coupled between the electrode (109) or group of electrodes (109) and the respective switch (2805) to which the electrode (109) or group of electrodes (109) is coupled.

For example, the voltage of the electrical pulse may be measured between the power source (2815) and the switching unit (2804), in particular between the power source (2815) and the at least one switch (2805). The pulse width and the current may be measured at the switch (2805) and/or between the switch (2805) and the electrode (109), for example, between the switch (2805) and a resistor (2908). The current may be measured between the switch (2805) and the electrode (109), for example, between the resistor (2908) and an electrode (109).

In case the device has a plurality of individually addressable electrodes (or group of electrodes), the switching unit may comprise a plurality of said switches and each of said switches may be configured to switch the individually addressable electrode or the group of individually addressable electrodes. In case the measured current, voltage, and/or pulse width are out of nominal range, the electrical control circuits may stop any power supply from the pulse generator for all the electrodes. The nominal range of current, voltage, and/or pulse width may either be selected by a user of the ablation device, for example, via the remote control unit and/or the graphical user interface unit, or may be selected by the ablation device, for example by the electrical control circuits, based on various input data from the ablation device, and/or may be pre-programmed in the ablation device.

Each of the individually addressable electrodes or group of electrodes may further be coupled to a secondary switch (2907). The secondary switch (2907) may be, for example, a semiconductor switch, a relay, or another type of electric switch. The secondary switch (2907) may be, for example, included in the switching unit (2804). The secondary switch (2907) may serve to disconnect the electrode (109) or a group of electrodes (109) from the power source (2815).

The predetermined nominal electrical pulses can include a wide variety of electrical pulses ranging from monophasic (single polarity) pulses to symmetric and/or asymmetric biphasic pulses. Pulses can be combined with additional pre-pulses for tissue conditioning or additional measurement pulses. Pulses can be single pulses or repeated in trains, where the parameters of the pulses may vary or remain constant. Trains of pulses can also be run in sequence.

A maximum amplitude of the pulses may depend on the target tissue, the size of the electrode, and/or the distance between the electrodes to produce an electric field with a maximum electric field strength of, for example, between 0.1 kV and 10 kV, or between 0.4 kV and 5 kV, or between 0.5 kV and 3 kV per centimeter in a target tissue volume.

A pulse width (pulse length) may be from the nanosecond range to the millisecond range, for example, from 2 ns to 10 ms, or from 10 ns to 5 ms, or from 50 ns to 1 ms, or from 100 ns to 500 μs, or from 250 ns to 200 μs, or from 400 ns to 100 μs.

The shape of the pulse can be, for example, a square, a curve similar to an exponential discharge, a rectangle, a saw, a triangle, or a sinusoidal shape.

Pulses can be monophasic or biphasic. Biphasic pulses can be symmetric or asymmetric. The pulses can be repeated from 1× to 100000×.

The frequency of high-frequency pulses can vary from 0.1 Hz to 10 Hz.

The amplitude of monophasic pulses can vary from 100V to 10 kV, and the peak-to-peak amplitude of biphasic pulses can vary from 200V to 20 kV.

If the measured current of any of the electrodes or group of electrodes is higher than the predetermined range, it may mean, for example, that one of the electrodes is in contact with another electrode. If the measured current is lower than the predetermined range, it may, for example, mean that one of the electrodes or the connection to the electrode has a fault. A measured pulse width outside the predetermined range may indicate a pulse generator failure.

The power supply from the pulse generator (power source (2815)) to the at least one ablation electrode (109) may be stopped in more than one way in different situations. For example, a nominal power stop may occur at the end of ablation and/or at the end of delivery of an ablation protocol comprising one or more electrical pulses. In such an example, the power supply stop may include, for example, the steps of turning off the current source (2802), discharging the at least one capacitor (2812) in the capacitor unit (2803) (for example, via a resistor coupled to the at least one capacitor (2812)), discharging the output capacitor (2813) in the DC/DC converter unit (2806) (for example, via a resistor coupled to the output capacitor (2813)), disconnecting the at least one electrode (109) from the power source (2815) by the switching unit (2804), for example, by turning the at least one secondary switch (2907) and/or the at least one switch (2805) into an "open" or a "non-conducting" state, i.e. a state in which an electrical current cannot flow through the switch. This nominal power supply disconnection procedure can last from about a few ms to a few seconds.

In an abnormal situation, e.g. after detection of disconnection of the catheter from the pulse generator, asynchrony of the CPU (2900) and the CPU control unit (2901), etc., the disconnection of the power supply from the pulse generator (power source (2815)) to the electrode (109) may comprise the steps of turning off the current source (2802), discharging the at least one capacitor (2812) in the capacitor unit (2803) (for example, via a resistor coupled to the at least one capacitor (2812)), discharging the output capacitor (2813) in the DC/DC converter unit (2806) (for example, via a resistor coupled to the output capacitor (2813)), disconnecting the at least one electrode (109) from the power source (2815) by the switching unit (2804), e.g. by turning the at least one secondary switch (2907) and/or the at least one switch (2805) into an "open" or a "non-conducting" state, i.e. a state in which an electrical current cannot flow through the switch. This nominal power supply disconnection procedure may last for approximately a few milliseconds, for example, from 1 ms to 1 s, from 2 ms to 500 ms, from 3 ms to 100 ms, from 4 ms to 50 ms, or from 5 ms to 20 ms.

However, if a specific failure of the ablation device is detected, for example, failure of the switches in the switching unit, measured voltage outside the predetermined range, electrical pulse length outside the predetermined range, . . . , the power supply stop may include all of the previous steps, but also further steps such as activation of the output capacitor emergency system (2814) of the DC/DC converter unit (2806). In this case, the power supply power supply from the pulse generator (power source (2815)) to the electrode (109) may be stopped in less than 50 ms or less than 25 ms or less than 15 ms or less than 5 ms or less than 1 ms or less than 100 μs or less than 10 μs.

The electrodes (109) may be configured to create electric fields. The electric fields may be created among one or more electrodes placed on the catheter distal tip and one indifferent electrode placed in the distance, for example, on the skin of the patient. The indifferent electrode may, in some aspects, have a significantly larger surface than the sum of the surfaces of the active distal tip electrodes. This mode of action is usually called monopolar. Another option for creating an electric field is in a bipolar mode. In this mode, the electric field arises between two or more electrodes, usually closely placed or adjacent to distal tip electrodes with different polarities. In this case, the sum of the surfaces of active electrodes with the first polarity is similar to the sum of the surfaces of the active electrodes with the second polarity.

In some aspects, the electrodes (109) placed on the distal tip (107) may be operated in a hybrid mode of the previous two types. Only the electrodes (109) placed on the distal tip (107) are used for ablation in this mode. There is a first single electrode or group of electrodes operating in a mode with a first polarity and a second single electrode or group of electrodes operating in a mode with a different polarity (which may be an opposite polarity) than the operating mode of the first electrode or group of electrodes. A surface or a sum of the surfaces of the first electrode or the first group of electrodes is significantly smaller than a surface or a sum of the surfaces of the second electrode or group of electrodes. For example, there may be a third electrode or a third group of electrodes operating in a third mode in a state (mode) of high impedance, wherein the impedance of the electrodes in the third group is, for example, higher than 500Ω. The electrodes operating in the third mode may be adjacent to the electrode or group of electrodes operating in the first mode.

One advantage of the operation of electrodes in this hybrid mode is that the generated electric field may have a more homogenous current density in comparison to bipolar mode. Another advantage of the hybrid operation mode is the electric fields created in this mode may, in some aspects, be able to reach deeper into the target tissue compared to bipolar mode. In the case of ablation of a heart cavity, the depth of the ablated target tissue (in one example, the target tissue may comprise a myocardial tissue) may be up to 5 mm.

Examples with a group of electrodes (more than one electrode) operating in a mode with a first polarity can have an advantage over examples with a single electrode operating in the mode with the first polarity, for example, in situations where it is advantageous to reduce the size of the electrodes. Reducing the size of the electrodes can be advantageous or necessary in cases where it is necessary or desirable to increase the number of electrodes. A higher number of electrodes is desirable, for example, where more precise mapping of the treatment site or more precise and/or more homogenous ablation of the target tissue of the treatment site is desired. Because the treatment site can be part of a human's anatomy, the overall size of the pulsed field ablation device, especially the catheter with a catheter distal tip must be restricted according to human anatomy. It follows that if more electrodes are needed for the ablation device, then for a certain number of electrodes, the size of the electrodes must be limited to able to fit into the restricted dimensions of the critical parts of the pulsed field ablation device, for example, the catheter and/or its distal tip, and/or its basket assembly. Another advantage of the smaller size of the electrodes is that such an arrangement may help to increase a depth of the ablation.

The smaller sizes of the electrodes can have other advantages; for example, in examples where the same electrodes are used for ablation and for measurements, it means the same electrode must be configured to deliver high-voltage pulses and record measurements. For example, in measuring of ECG signals, smaller electrodes may be advantageous.

There are, however, some challenges associated with smaller electrodes as well. In examples including pulsed field ablation, the electric fields are, for instance, created among electrodes by electrical pulses, for example, high frequency electrical pulses generated by a pulse generator. For effective ablation of the whole target area of the treatment site, it may be important to create an electric field with a maximum electric field magnitude of several hundred volts to several kilovolts per centimeter in a target tissue volume. Using smaller electrodes means a smaller surface area of the electrodes. With a smaller surface area of the electrodes, the voltage induced on the electrode has to be higher compared to bigger electrodes with a larger surface area to achieve the desired electric field density in a target tissue. Adverse effects of such a configuration may include higher density of the electric field, higher intensity of the electric field, and/or possible sparking on the edges of the electrodes. However, using a chosen group of electrodes (more than one electrode) operating in the mode with the first polarity instead of one electrode operating in the mode with the first polarity can address and overcome some or all of these issues. With a well-chosen first group of electrodes operating in the mode with the first polarity together with the second group of electrodes operating in a mode with different polarity and possibly with a third group of electrodes operating in a third mode in the state (mode) of high impedance, the first group of electrodes and/or the second group of electrodes may act as virtual electrodes. That means the electrodes in the first group may act together as one virtual electrode, and/or the electrodes in the second group may act as another virtual electrode. With such a configuration, the intensity and/or the density of the electric field near the electrodes may be reduced. Other positive effects of this configuration may be a reduced risk of sparking and increased depth of ablation or increased depth of an ablated tissue at the treatment site.

The enlargement of the surface area of the electrodes in the first group and the creation of the resulting virtual electrode may cause a reduction in the voltage needed to be induced in the electrodes and/or elimination of sparking, mainly on the edges of the electrodes. However, the concept of disproportional surface areas of the electrodes in the first and the second groups of electrodes can be preserved, which means the surface area or a sum of the surface areas of the first electrode or the first group of electrodes is significantly smaller than a surface area or a sum of the surface areas of the second electrode or group of electrodes. The ratio of the surface area of the electrode or the sum of the surface areas of the electrodes in the first group to the sum of the surface areas of the electrodes in the second group of electrodes may be between 2:3 to 1:100, or 3:5 to 1:80, or 3:5 to 1:70, or 1:2 to 1:50, or 1:2 to 1:40, or 1:2 to 1:30, or 1:2 to 1:20, or 1:3 to 1:15, or 1:3 to 1:10, or 1:4 to 1:8.

Adding electrodes to the first group of electrodes operating in the mode with the first polarity may significantly reduce the intensity of the electric field near the electrodes. Using four electrodes instead of one, for example, in the first group of electrodes operating in the mode with the first polarity, the intensity of the electric field at the electrode surface decreases by a factor of four, while in examples where three electrodes are used, the intensity of the electric field decreases by a factor of two. This reduction in intensity may allow for the use of lower voltage on the electrodes, compared to a solution with just one electrode operating in the mode with the first polarity. The reduction may additionally or alternatively increase of the depth of the ablated target tissue by increasing an area of the electric field with a certain voltage per cm. The value of the voltage per cm in an area of the electric field may be, for example, from 50 V/cm to 3000 V/cm, from 100 V/cm to 1500 V/cm, or from 250 V/cm to 1000 V/cm.

The particular electrodes on the catheter distal tip can be switched to one or more than one of the modes during the ablation, for example, by the switching unit. They can be switched during one ablation cycle or during several ablation cycles. The electrodes may be switched to one or more of the modes several times during one ablation cycle or during several ablation cycles. In some aspects, it is even possible to have two or more groups of electrodes operating simultaneously in a mode with the first polarity and a group of electrodes operating in a different polarity, with or without electrodes operating in a state (mode) of high impedance.

Particular electrodes may be switched to one of the modes, for example, before or after each pulse, before or after several consecutive pulses within a train of pulses, before or after one train or several trains of pulses within a burst of pulses, or for example, before or after one burst or several burst of pulses.

A layout or spatial pattern of the electrodes on the distal tip may be created in consideration of the hybrid mode of operation of electrodes and/or with the goal of creating virtual electrodes. Because the electrodes may be switched to one or more than one of the modes during the ablation, it is possible the resulting virtual electrodes may have different spatial shapes, which means the electric fields created around and between the virtual electrodes may have different shapes with different structures of the magnetic field and/or different density and intensity of the electric field.

Each of the individually addressable electrodes (109) or group of electrodes (109) may further be coupled to at least one resistor (2908). The resistor (2908) may be coupled between the electrode (109) (group of electrodes) and the switching unit, i.e. the switch (2805). The resistor (2908) may help to increase the effectiveness and safety of the ablation procedure. At least one of the virtual electrodes during ablation may comprise a plurality (a group) of electrodes switched to one of the states (first polarity, second polarity, or a state (mode) of high impedance). While switching the plurality of electrodes included in a first virtual electrode to the first polarity and generating an electric field between e.g. a second virtual electrode with at least one electrode switched to the different polarity, currents at the electrodes included in the first virtual electrode (first group of electrodes switched into a first polarity) or the second virtual electrode (second group of electrodes switched into a second polarity) may vary due to several factors influencing the current at the particular electrodes. The factors may be, for example, an electrode orientation, different distances of the electrodes either from each other or from the second virtual electrode or from the target tissue, and different conditions regarding, for example, the electrical impedance of a tissue and/or blood around certain electrodes.

For example, the described electrical current variance at the different electrodes may occur at the same time, e.g., during a single pulse.

The difference in electrical current at certain electrodes included in the virtual electrodes may cause problems, for example, with respect to the effectiveness of the ablation. For example, electrodes with the highest current within the virtual electrode may cause unwanted thermal damage to tissue, such as a portion of the target tissue. The issue of thermal damage to tissue by the highest current electrodes may arise, for example, if the current difference between a lowest current electrode (electrode with the lowest current flowing through the electrode) and a highest current electrode (electrode with the highest current flowing through the electrode) during an electrical pulse between the respective electrodes included in the virtual electrode exceeds 50%, or 45%, or 40%, or 35%, or 30%, or 25%, or 20%.

The resistance of the resistor used depends on several factors of the ablation device, such as the number of electrodes, the size of the electrodes (e.g., the surface area of the electrodes) used in the device, the current, voltage, length, and number of pulses used in an ablation protocol. In examples where the device comprises a plurality of electrodes, for example, ablation electrodes, and during the ablation protocol, the electrodes are switched to the state (mode) of the first polarity, the state (mode) of the second polarity, and/or the state (mode) of the high impedance. The resistance of the resistors may not even be the same for all of the electrodes, including the resistors, but may vary, for example, based on electrode shape and size or based on the number of electrodes in a group of electrodes coupled to a resistor. The resistance of each of the resistors may be, for example, from 1Ω to 5000Ω, or from 1Ω to 5000Ω, or from 10Ω to 3000Ω, or from 30Ω to 2000Ω, or from 50Ω to 1500Ω, or from 60Ω to 1250Ω, or from 100Ω to 1000Ω.

After consideration of all the factors, the resistance of the particular resistors should be such that the maximum electric current difference between a lowest current electrode (electrode having a lowest current flowing through the electrode) and a highest current electrode (electrode having a highest current flowing through the electrode) during an electric pulse between the particular electrodes included in a virtual electrode (either included in the first group of electrodes switched to the first polarity or in the second group of electrodes switched to the second polarity different from the first polarity) is from 0% to 50%, or from 0% to 45%, or from 0% to 40%, or from 0% to 35%, or from 0% to 30%, or from 0% to 25%, or from 0% to 20%, or from 0% to 15%, or from 0% to 10%.

Figure 30:
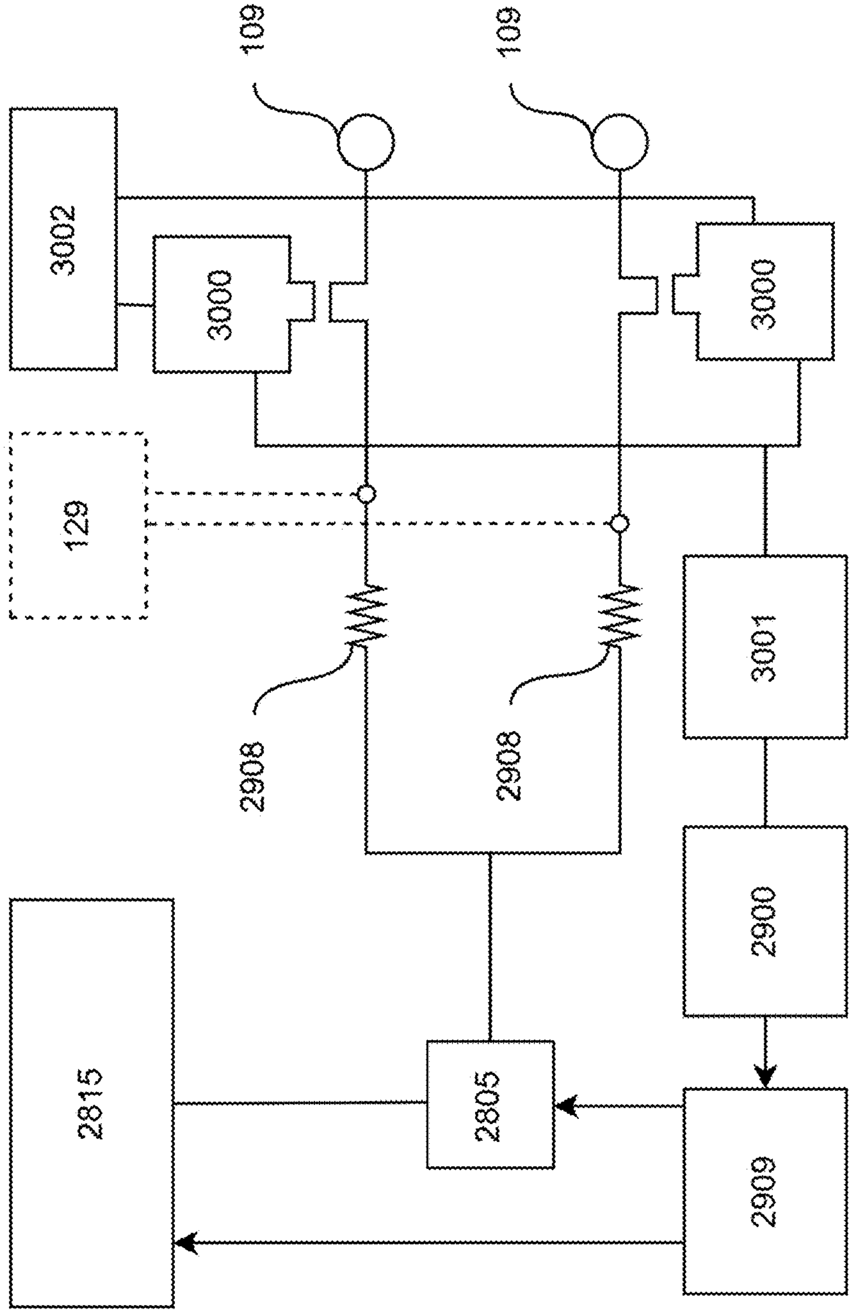
FIG. 30 is a block diagram of a current measurement circuit.

FIG. 30 shows an example where each individually addressable electrode (109) or group of individually addressable electrodes (109) may be coupled to its own electrode processing unit (eCPU) (3000), such as a processor. However, not all electrodes (109) need to be coupled to the eCPU (3000); for example, only a portion of electrodes (109) from a plurality of electrodes (109) included in the ablation system may be coupled to the eCPU (3000). The eCPU (3000) may be included in the electrical control circuits. The eCPU (3000) may further be communicatively coupled to a memory (3001), either a common memory or an individual memory for each eCPU (3000). The eCPU (3000) may be configured to receive data of an electric current measured, for example, between the switch (2805) and the electrode (109), particularly between the resistor (2908) and the electrode (109), and to calculate a statistical value, for example, a minimum, maximum, median, mode, standard deviation, rolling average, arithmetic mean, average and/or a mean from the data of the measured electric current. The eCPU (3000) can store data, such as the measured electric current data and/or the calculated statistical value, in the memory. The eCPU (3000) may be communicatively coupled to, for example, the CPU (2900). In the case of a plurality of the eCPUs (3000), they may be individually coupled to the CPU (2900) or may share a communication coupling to the CPU (2900). If the measured current or pulse width between any of the switches and the electrode and calculated by the particular eCPU (3000) is out of nominal range, the eCPU (3000) may send a signal to electrical control circuits, for example, to the CPU (2900) and/or to the logic disconnection circuit (2909), to stop any power supply from the pulse generator (power source (2815)) to any of the electrodes (109) or to all of the electrodes (109).

The measurements of the characteristics of the electrical pulses (e.g., the electrical current) between the switch and the electrode may be conducted at a predetermined monitoring frequency, and the statistical value may be calculated by the eCPU. The predetermined monitoring frequency may be provided by an eCPU clock synchronization circuit (3002), which may include, for example, at least one clock generator, for example, an electronic oscillator, and/or at least one counter, and which may be coupled to the eCPU. Each of the eCPUs (3000) may be communicatively coupled to its eCPU clock synchronization circuit (3002), or all of the eCPUs (3000) may be coupled to a common eCPU clock synchronization circuit (3002). The eCPUs (3000) may be synchronized to each other by the eCPU clock synchronization circuit (3002).

The predetermined monitoring frequency of the measurement and/or the calculation may be at least 1 KHz, or from 1 KHz to 10 GHz, or from 100 KHz to 500 MHz, or from 500 KHz to 100 MHz, or from 600 KHz to 50 MHz, or from 700 KHz to 30 MHz, or from 800 KHz to 20 MHz, or from 1 MHz to 10 MHz. The frequency may be synchronized to the CPU (2900) and/or to the CPU control unit (2901).

Each of the individually addressable electrodes or group of electrodes may further be coupled to the electrocardiogram (ECG) recording device (129). The ECG recording device may use at least one of the electrodes (109) to sense an intracardiac ECG signal.

The ablation system, for example a part of the ablation system, for example the ECG recording device, may record at least one of the ECG signal, impedance, current or voltage measured by at least one of the individually addressable electrodes. The ablation system may generate a visualization of a tissue, e.g. cardiac tissue, e.g. a three-dimensional map of the tissue, based on the measured values. The ablation system may also generate a visualization of the catheter, e.g. a distal tip of the catheter in space, e.g. in comparison to the tissue. The visualization may be communicated to the user, for example via the graphical user interface unit.

The ablation system may also determine contact of the catheter, for example the distal tip, for example of particular electrodes with the tissue. The system may determine the contact based on the recorded values of the ECG signal, impedance, current or voltage. The contact information may be communicated to the user, for example via the graphical user interface unit.

The ablation system may also determine a quality of the ablation procedure. The system may determine the quality of the ablation procedure based on the recorded values of the ECG signal, impedance, current or voltage at least from the target tissue. The contact information may be communicated to the user via the graphical user interface unit, for example.

The values of the ECG signal, impedance, current or voltage may be measured before, during and/or after the ablation procedure. The values of the signal, impedance, current or voltage may be measured continuously, at a specific frequency or at specific predetermined time intervals. The 3D map, the contact and/or the quality of the ablation procedure may be calculated from the values taken at different times before, during and/or after the ablation procedure.

The values of the ECG signal, impedance, current or voltage may be measured by at least one electrode placed on the distal tip of the catheter. The values may be measured by a plurality of electrodes, such as a plurality of individually addressable electrodes or a group of electrodes placed on the distal tip of the catheter. Values can be measured by all electrodes placed on the distal tip of the catheter. A central electrode, e.g. placed inside the expandable basket contained in the distal tip, may, for example, serve as a measurement ground electrode with respect to at least one measurement electrode placed on the distal tip of the catheter, e.g. on the expandable basket.

The pulsed field ablation device (101) may include or may be coupled to other parts or devices appropriate for performing or for supporting during performance of a method of pulsed field ablation described herein. The other parts or devices may be for example a remote control unit (111), a graphical user interface (GUI) unit (113), electrical control circuits (115), electrocardiogram (ECG) device including ECG triggering circuits (117), an ECG recording device (129), ECG electrodes (125), a pacing device (131), and/or an electro physiology (EP) display device (133), which may include an EP recording system. The EP display device may show and/or record data from other devices connected to the ablation system (100). Further, the ablation system (100) may include a mapping device (135), for example a three-dimensional (3D) mapping device or a real position measurement (RPM) device, and/or indifferent electrodes (127). For example, the pulsed field ablation device (101) may be configured for use in or on a heart of the patient for example for the treatment of the heart tissue, for example for pulsed field ablation of the heart tissue, for example for pulsed field ablation of a myocardial tissue, for example for pulmonary vein isolation. Devices and methods disclosed herein may be used in other locations, for example all tubular tissues, organs or vessels in a body or for example tumor sites.

Moreover, the following aspects are considered to be part of the present invention and the overall disclosure thereof as described herein, with the present invention being, however, not limited thereto:

It may be provided that the ablation system includes a catheter comprising a shaft assembly with a proximal end, a distal end, and a longitudinal axis. The shaft assembly includes an outer elongated shaft having at least one lumen and an inner elongated shaft disposed within the lumen of the outer elongated shaft, wherein the placement of the inner elongated shaft allows for movement of the inner elongated shaft relative to the outer elongated shaft along the longitudinal axis, and the inner elongated shaft comprises at least one of an electrode or a sensor.

It may be provided that the catheter further comprises an expandable basket, wherein a distal end of the expandable basket is coupled adjacent to the distal end of the inner elongated shaft and a proximal end of the expandable basket is coupled adjacent to the distal end of the outer elongated shaft. The expandable basket is deployable into at least one expanded configuration, wherein at least one of the electrode or the sensor is disposed in a portion of the inner elongated shaft that extends distally from the distal end of the outer elongated shaft when the expandable basket is deployed in one of its expanded configurations.

It may be provided that one of the electrode or the sensor is disposed in a portion of the inner elongated shaft that extends distally from the distal end of the outer elongated shaft when the expandable basket is deployed in its fully expanded configuration.

It may be provided that the electrode is one of an ablation electrode, a measurement electrode, or a mapping electrode.

It may be provided that the sensor is one of a position sensor, a temperature sensor, an electronic sensor, or a magnetic sensor.

It may be provided that the electrode is a ground electrode.

It may be provided that the electrode is an ECG measuring electrode.

It may be provided that the ablation system comprises an introducer sheath with an inner liner, wherein the inner liner material comprises at least one of a thermoplastic, a thermoplastic elastomer, a synthetic polymer, or an organic polymer.

It may be provided that the inner liner material comprises at least one of Polyethylene, Ultra high molecular weight polyethylene, High-modulus polyethylene, High-density polyethylene, Polyether block amide, Nylon, or Polyether ether ketone.

It may be provided that the inner liner includes material having an abrasion resistance from 2 times to 20 times higher compared to PTFE.

It may be provided that the inner liner includes material having a coefficient of friction ranging from 0.01 to 0.8.

It may be provided that the system further includes a catheter with a distal tip comprising an expandable basket, wherein the distal tip is deployable from a collapsed configuration to an expanded configuration. The introducer sheath includes a proximal rigid section, a flexible section disposed distally of the proximal rigid section, and a distal rigid section disposed distally of the flexible section. It may be provided that the length of the distal rigid section ranges from 20% to 200% of the length of the distal tip in a collapsed configuration.

It may be provided that the ablation system comprises a catheter, wherein the catheter includes a terminal assembly comprising an inner elongated shaft with first and second protrusions, a ring coupled to the inner elongated shaft between the first and second protrusions, and having an outer edge and an inner edge, and a plurality of filaments coupled to the ring. The inner edge of the ring comprises a plurality of notches.

It may be provided that the filaments of the plurality of filaments are bent around the ring such that a first portion of each filament extends from a proximal direction over the outer edge of the ring, a second portion of each filament extends from a proximal direction over the inner edge of the ring, and a third portion of each filament is bent around a distal edge of the ring.

It may be provided that the second portion of the filament is disposed in the notch.

It may be provided that one of the first, second, or third portions of the filament has a different diameter than the remaining portion of the filament.

It may be provided that the diameter of the first, second, or third portion of the filament is smaller than the diameter of the remaining portion of the filament.

It may be provided that the ablation system comprises a catheter, wherein the catheter includes a terminal assembly comprising an inner elongated shaft having a diameter, a first protrusion, a second protrusion, and a third protrusion with a diameter greater than that of the inner elongated shaft. The second protrusion is formed by a distal additional member, wherein the distal additional member includes a cavity configured to receive at least a portion of the inner elongated shaft. The cavity has a first diameter larger than the diameter of the third protrusion and a second diameter larger than the diameter of the inner elongated shaft but smaller than the diameter of the third protrusion.

It may be provided that the second diameter is distally further than the first diameter.

It may be provided that the distal additional member comprises a tubular structure protruding proximally, including a body and at least a portion of the cavity, wherein the cavity is configured to receive at least a portion of the inner elongated shaft.

It may be provided that the distal additional member comprises a glue opening connecting an outer surface of the distal additional member with the cavity.

It may be provided that the body of the tubular structure comprises at least one aperture.

It may be provided that the aperture is configured to be filled with a glue.

It may be provided that the aperture is configured to allow UV light to reach at least a portion of the glue.

It may be provided that the ablation system comprises a catheter comprising an expandable basket that includes a plurality of filaments, wherein at least a portion of the filaments comprises a lumen including a reinforcement strut. The reinforcement strut is pre-formed before the assembly of the expandable basket, and the pre-formed reinforcement strut includes a first elongated portion and a second elongated portion, wherein the first and second elongated portions are coupled together at their distal ends via a bent portion and have a plane of symmetry between the first and second elongated portions. The bent portion includes a bend of the reinforcement strut, and a bending of the bend takes place in a bending plane.

It may be provided that the ablation system comprises a catheter comprising an expandable basket that includes a plurality of filaments, wherein at least a portion of the filaments comprises a lumen, including a reinforcement strut. The reinforcement strut is pre-formed prior to the assembly of the expandable basket, and the pre-formed reinforcement strut comprises a first elongated portion and a second elongated portion. The first and second elongated portions are coupled together at their distal ends via a bent portion and have a plane of symmetry between the first and second elongated portions. The bent portion includes a bend of the reinforcement strut, and a bending of the bend takes place in a bending plane.

It may be provided that the bending plane is rotated with respect to the plane of symmetry at an angle from 1° to 89°.

It may be provided that the first elongated portion and the second elongated portion conform to a surface envelope of the expandable basket deployed in one of its expandable configurations.

It may be provided that the first elongated portion and the second elongated portion are pre-formed into a helix shape about a longitudinal central axis.

It may be provided that the bend has a peak bend angle from 100° to 150°.

It may be provided that the bend has a center radius from 0.2 mm to 0.7 mm.

It may be provided that the catheter comprises a shaft assembly having a proximal end, a distal end, and a longitudinal axis. The shaft assembly includes an outer elongated shaft having at least one lumen and an inner elongated shaft disposed within the lumen of the outer elongated shaft, wherein the placement of the inner elongated shaft permits movement of the inner elongated shaft relative to the outer elongated shaft along the longitudinal axis. The lumen of the outer elongated shaft further comprises an irrigation shaft, including an irrigation lumen configured to conduct an irrigation fluid and the inner elongated shaft.

It may be provided that the irrigation fluid is conducted between the inner elongated shaft and the irrigation shaft within the lumen of the irrigation shaft.

It may be provided that the shaft assembly further comprises a handle assembly coupled to the proximal end of the shaft assembly.

It may be provided that the proximal end of the irrigation shaft terminates in the shaft assembly.

It may be provided that the proximal end of the irrigation shaft is coupled to a valve, a port, or an irrigation system.

It may be provided that the distal end of the irrigation shaft terminates at the distal end of the outer elongated shaft.

It may be provided that the inner elongated shaft includes a lumen configured to receive a guidewire and/or irrigation fluid.

It may be provided that the inner elongated shaft includes a proximal end and a distal end, wherein the proximal end extends proximally from the proximal end of the outer elongated shaft and wherein the proximal end of the inner elongated shaft terminates in the handle assembly or further proximally outside of the handle assembly, and wherein the proximal end of the inner elongated shaft is coupled to one of a valve, a port, or an irrigation system.

It may be provided that the handle assembly includes at least one valve coupled to the inner elongated shaft.

It may be provided that the valve includes at least one O-ring and allows movement of the inner elongated shaft relative to the valve in the direction of the longitudinal axis.

It may be provided that the valve includes a valve cavity and an inner elongated shaft extending through at least a portion of the valve cavity.

It may be provided that the valve cavity includes the O-ring and that the inner elongated shaft passes through the O-ring, wherein the O-ring seals an irrigation fluid within at least a portion of the valve cavity.

It may be provided that the valve cavity is coupled to a valve inlet, and wherein the valve inlet introduces the irrigation fluid into at least a portion of the valve cavity.

It may be provided that the valve cavity is further coupled to the irrigation shaft by a fluid coupling.

It may be provided that the ablation system includes a filament assembly comprises a filament having an outer diameter and an electrode coupled to the filament. The filament assembly includes an electrode adjacent area, which is defined as an area of the filament lying adjacent to the electrode, wherein the outer diameter of the filament in at least a portion of the electrode adjacent area is greater than the outer diameter of the filament lying outside the electrode adjacent area.

It may be provided that the electrode is a ring electrode having an outer diameter and that the outer diameter of the filament in at least a portion of the electrode adjacent area is equal to the outer diameter of the electrode.

It may be provided that the filament comprises a lumen and has a wall thickness, wherein the filament wall thickness in at least a portion of the electrode adjacent area is greater than the filament wall thickness of the filament lying outside the electrode adjacent area.

It may be provided that the electrode has an outer diameter and that a length of the electrode adjacent area corresponds to the outer diameter of the electrode and falls within a range from 0.1 times the outer diameter to 2 times the outer diameter.

It may be provided that the electrode has an electrode wall thickness and that the filament wall thickness of the remaining portion of the filament equals the sum of the original filament wall thickness and the electrode wall thickness, within a tolerance of ±40%.

It may be provided that a method of manufacturing a filament assembly comprises the steps of providing a filament that includes a fusible material and has a filament wall thickness, providing a ring electrode with an edge, coupling the ring electrode to the filament, heating the filament and/or the electrode to at least the melting temperature of the fusible material, melting at least a portion of the fusible material, and increasing the wall thickness in at least a portion of the electrode adjacent area of the filament compared to the wall thickness of the filament outside the electrode adjacent area.

It may be provided that another method of manufacturing a filament assembly comprises the steps of providing a filament with a filament wall thickness, providing a ring electrode with an edge, coupling the ring electrode to the filament in an electrode fitting area, fitting a tube made of fusible tube material over at least a portion of the electrode fitting area, melting at least a portion of the fusible tube material, and increasing the filament wall thickness in at least a portion of an electrode adjacent area compared to the filament wall thickness outside the electrode adjacent area.

It may be provided that the assembly comprises an introducer sheath and a catheter. The catheter comprises a filament assembly that includes an electrode adjacent area, defined as an area of the filament lying adjacent to the electrode, wherein the outer diameter of the filament in at least a portion of the electrode adjacent area is greater than the outer diameter of the filament lying outside the electrode adjacent area. The introducer sheath comprises an inner liner compatible with the filament assembly.

It may be provided that the inner liner includes a material with a friction coefficient ranging from 0.01 to 0.8.

It may be provided that the inner liner includes a material with an abrasion resistance 2 times to 20 times greater than that of PTFE.

It may be provided that the inner liner includes a material with a Shore hardness ranging from D 55 to D 120.

It may be provided that the ablation system comprises a pulse generator, including a power source, an electrode, and electrical control circuits coupled to the power source. The electrical control circuits include a central processing unit (CPU) configured to receive and process data from the ablation system and to send an output signal to the ablation system. A CPU control unit is coupled to the CPU and is configured to examine at least a portion of either the data received by the CPU or the signals sent by the CPU. The CPU control unit is further configured to send a signal to the pulse generator to stop any power supply from the power source to the electrode in response to determining that at least a portion of the data coming to the CPU or at least a portion of the signal coming from the CPU is outside a predefined value or a nominal range.

It may be provided that the CPU control unit comprises at least one of a second CPU, a logic circuit, or a field programmable gate array (FPGA).

It may be provided that the electrical control circuits include a synchronizing clock circuit, wherein the CPU and the CPU control unit are synchronized to each other via the synchronizing clock circuit.

It may be provided that the synchronizing clock circuit includes one of a clock generator.

It may be provided that the clock generator includes an electronic oscillator.

It may be provided that the electrical control circuits include a logic circuit configured to monitor the synchronization.

It may be provided that the electrical control circuits are configured to send a signal to the pulse generator to stop any power supply from the power source to the electrode when an asynchrony beyond a predetermined time range between the CPU and the CPU control unit is detected by the logic circuit.

It may be provided that the predetermined time range is from 1 ns to 1 µs.

It may be provided that a monitoring frequency of the synchronization of the CPU with the CPU control unit is from 1 KHz to 10 GHz.

It may be provided that the ablation system comprises a pulse generator including a switching unit, wherein the switching unit comprises a switch, an electrode coupled to the switch, and electrical control circuits comprising an electrode processing unit (eCPU). The eCPU is configured to receive data of an electrical current measured between the switch and the electrode and to calculate a statistical value from the data of the electrical current.

It may be provided that the statistical value includes one of a minimum, a maximum, a median, a mode, a standard deviation, a rolling average, an arithmetic mean, an average, or a mean.

It may be provided that the ablation system comprises a plurality of electrodes, wherein the electrical control circuits comprise a plurality of eCPUs, and wherein the plurality of electrodes are coupled to the plurality of eCPUs.

It may be provided that at least one electrode of the plurality of electrodes is coupled to at least one eCPU of the plurality of eCPUs.

It may be provided that each electrode of the plurality of electrodes is coupled to one of the plurality of eCPUs.

It may be provided that the eCPU is configured to receive the data at a predetermined monitoring frequency.

It may be provided that the eCPU is configured to calculate the statistical value at a predetermined monitoring frequency.

It may be provided that the predetermined monitoring frequency is provided by an eCPU clock synchronization circuit coupled to the eCPU.

It may be provided that the eCPU is coupled to a memory and is further configured to store at least one of the data and the statistical value to the memory.

It may be provided that the ablation system comprises a pulse generator that includes at least one capacitor with a capacitance, at least one electrode coupled to the capacitor, and a capacitor emergency system configured to discharge the capacitance from the capacitor. The capacitor emergency system includes an emergency switch element coupled to the capacitor, an emergency resistor coupled between the capacitor and the emergency switch element, and a control circuit coupled to the emergency switch element.

It may be provided that the emergency switch element comprises one of a power semiconductor device or a contactor.

It may be provided that the emergency switch element comprises one of a semiconductor switch, a thyristor, or an insulated gate bipolar transistor.

It may be provided that the control circuit is configured to receive a signal from the ablation system and send a signal to the emergency switch element to activate the emergency switch element.

It may be provided that the signal received from the ablation system is a signal indicative of a fault detected in the ablation system.

It may be provided that the detected fault is a failure of a particular part of the ablation system or a measured parameter outside a predetermined range.

It may be provided that the activation means switching the emergency switch element to a state in which electrical current can flow through the switch element.

It may be provided that the signal sent to the emergency switch is an electrical signal having a current in the range of 1 mA to 50 A.

It may be provided that upon sending the signal to the emergency switch, the capacitor emergency system is configured to discharge the capacitance from the capacitor via the emergency resistor.

It may be provided that the capacitor emergency system is configured to discharge the capacitance from the capacitor via the emergency resistor in less than 100 μs.

It may be provided that the ablation system comprises a pulse generator, a plurality of electrodes coupled to the pulse generator, a switching unit comprising at least one switch, and a resistor, wherein the resistor is coupled between the switching unit and at least one of the plurality of electrodes.

It may be provided that the system comprises a plurality of resistors, wherein each of the plurality of resistors is coupled between the switching unit and the plurality of electrodes.

It may be provided that the switching unit comprises a plurality of switches, and wherein the resistor is coupled between each switch of the plurality of switches and at least one electrode coupled to the switch.

It may be provided that the switching unit includes a plurality of switches, wherein the resistor is coupled between at least one switch of the plurality of switches and at least one electrode coupled to the at least one switch.

It may be provided that the plurality of electrodes includes at least a first group of electrodes configured to be switched to a first polarity and a second group of electrodes configured to be switched to a second polarity, thereby creating electric fields between the first group and the second group from an electric pulse generated by the pulse generator. It may be provided that the maximum electric current difference between an electrode having the lowest current and an electrode having the highest current in the first group, or the maximum electric current difference between an electrode having the lowest current and an electrode having the highest current in the second group during the electric pulse, is from 0% to 50%.

The invention claimed is:

1. A catheter for ablation of a target tissue configured for insertion into a heart of a patient, the catheter having a longitudinal central axis and comprising:
- an outer elongated shaft;
- an inner elongated shaft;
- at least one coupling structure or retaining member, the at least one coupling structure or retaining member being coupled to the inner elongated shaft; and
- a distal tip comprising:
- an expandable basket configured to deploy from a collapsed configuration to at least one expanded configuration, the expandable basket comprising filaments braided into a braided mesh, wherein the one or more filaments are coupled to at least one of the at least one coupling structure or retaining member, and wherein the one or more filaments comprise:
- a first elongated portion comprising a first distal portion having a distal end, and
- a second elongated portion comprising a second distal portion having a distal end,
- wherein the first distal portion and the second distal portion are coupled together at their distal ends via a bent portion, and have a maximum angle between each other as measured on the projection of the first distal portion and the second distal portion coupled to the bent portion to a maximum angle plane, and wherein the maximum angle plane is a plane parallel to the longitudinal central axis where the angle between the first distal portion and the second distal portion is at its maximum, wherein the bent portion comprises a bend of the one or more filaments, and wherein a bending of the bend takes place in a bending plane, and wherein the first elongated portion and the second elongated portion of the one or more filaments are divided by a plane of symmetry therebetween, and wherein the bending plane is rotated with respect to the plane of symmetry at an angle of 1° to 89°.

2. The catheter according to claim 1, wherein the one or more filaments are preformed prior to an assembly of the catheter.

3. The catheter according to claim 1, wherein one or more filaments comprise a reinforcement strut, wherein the reinforcement strut is preformed prior to an assembly of the catheter such that the reinforcement strut, at rest, comprises the first elongated portion, the second elongated portion, and the bent portion.

4. The catheter according to claim 1, wherein the bending plane is rotated at an angle of 0.1° to 90° with respect to the maximum angle plane.

5. The catheter according to claim 1, wherein the first elongated portion and the second elongated portion of the one or more filaments conform to a surface envelope of the expandable basket deployed in one of its expanded configurations.

6. The catheter according to claim 1, wherein the first elongated portion and the second elongated portion of the one or more filaments are pre-formed into a helical shape about the longitudinal central axis.

7. The catheter according to claim 1, wherein the bend of the one or more filaments has a peak bend angle of from 100° to 150°.

8. The catheter according to claim 1, wherein the bend of the one or more filaments has a center radius of from 0.2 mm to 0.7 mm.

9. A catheter for ablation of a target tissue configured for insertion into a heart of a patient, the catheter comprising:
- a distal tip having a distal end, the distal tip comprising:
- one or more filaments, and
- a ring positioned at the distal end, wherein the one or more filaments are coupled to the ring;
- an outer elongated shaft; and
- an inner elongated shaft, wherein the ring is coupled to the inner elongated shaft, and wherein the ring comprises an outer edge, an inner edge, and a distal edge,
- wherein at least one of the outer edge, inner edge or distal edge comprises a plurality of notches, wherein the one or more filaments are bent around the ring such that a first portion of each of the one or more filaments extends from a proximal direction over the outer edge of the ring, a second portion of each of the one or more filaments extends from a proximal direction over the inner edge of the ring, and a third portion of each of the one or more filaments is bent around the distal edge of the ring, and wherein the diameter of the first portion, the second portion, or the third portion of the one or more filaments is less than the diameter of a remaining portion of the one or more filaments.

10. The catheter according to claim 9, wherein the first portion, the second portion or the third portion of each of the one or more filaments is disposed in a notch of the plurality of notches.

11. The catheter according to claim 9, wherein each notch of the plurality of notches has an inner radius which is equal to or greater than an outer radius of a surface of the first portion, the second portion or the third portion of the one or more filaments.

12. The catheter according to claim 9, wherein the diameter of the first portion, the second portion, or the third portion of the one or more filaments is reduced by 10% to 95% compared to a remaining portion of the one or more filaments.

* * * * *